(12) United States Patent
Hsiue et al.

(10) Patent No.: US 11,807,662 B2
(45) Date of Patent: Nov. 7, 2023

(54) MANABODIES AND METHODS OF USING

(71) Applicant: The Johns Hopkins University, Baltimore, MD (US)

(72) Inventors: Emily Han-Chung Hsiue, Baltimore, MD (US); Qing Wang, Owings Mills, MD (US); Bert Vogelstein, Baltimore, MD (US); Kenneth W. Kinzler, Baltimore, MD (US); Shibin Zhou, Owings Mills, MD (US); Jacqueline Douglass, Baltimore, MD (US); Michael S. Hwang, Seattle, WA (US); Nickolas Papadopoulos, Towson, MD (US)

(73) Assignee: The Johns Hopkins University, Baltimore, MD (US)

(*) Notice: Subject to any disclaimer, the term of this patent is extended or adjusted under 35 U.S.C. 154(b) by 648 days.

(21) Appl. No.: 16/614,005

(22) PCT Filed: May 16, 2018

(86) PCT No.: PCT/US2018/032996
§ 371 (c)(1),
(2) Date: Nov. 15, 2019

(87) PCT Pub. No.: WO2018/213467
PCT Pub. Date: Nov. 22, 2018

(65) Prior Publication Data
US 2020/0079854 A1    Mar. 12, 2020

Related U.S. Application Data

(60) Provisional application No. 62/506,674, filed on May 16, 2017.

(51) Int. Cl.
*A61K 39/395* (2006.01)
*C07K 16/28* (2006.01)
(Continued)

(52) U.S. Cl.
CPC ......... *C07K 16/2833* (2013.01); *A61K 35/17* (2013.01); *C07K 14/7051* (2013.01);
(Continued)

(58) Field of Classification Search
None
See application file for complete search history.

(56) References Cited

U.S. PATENT DOCUMENTS 6,750,325 B1   6/2004  Jolliffe et al.
7,655,751 B2 * 2/2010  Itoh .................... A61K 39/0011
                                              530/300

(Continued)

FOREIGN PATENT DOCUMENTS

CN    101228187    8/2008
CN    102675462    9/2012
(Continued)

OTHER PUBLICATIONS

Sun et al., Receptor (TCR) Engineered Therapies for the Treatment of Cancer, Cells, 10:2379, 2021, 19 pages, doi.org/ 10.3390/cells10092379.*
(Continued)

*Primary Examiner* — Claire Kaufman
(74) *Attorney, Agent, or Firm* — Fish & Richardson P.C.

(57) ABSTRACT

This document provides methods and materials for assessing a mammal having or suspected of having cancer and/or for treating a mammal having cancer. For example, molecules including one or more antigen-binding domains (e.g., a single-chain variable fragment (scFv)) that can bind to a modified peptide (e.g., a tumor antigen), as well as method for using such molecules, are provided.

15 Claims, 18 Drawing Sheets
Specification includes a Sequence Listing.

(51) Int. Cl.
    *A61K 35/17*     (2015.01)
    *C07K 14/725*    (2006.01)
    *C07K 14/73*     (2006.01)
    *C07K 14/705*    (2006.01)
    *A61K 38/00*     (2006.01)

(52) U.S. Cl.
    CPC .. *C07K 14/70514* (2013.01); *C07K 14/70517* (2013.01); *C07K 14/70521* (2013.01); *C07K 16/2809* (2013.01); *A61K 38/00* (2013.01); *C07K 2317/24* (2013.01); *C07K 2317/31* (2013.01); *C07K 2317/33* (2013.01); *C07K 2317/622* (2013.01); *C07K 2319/03* (2013.01)

(56) References Cited

U.S. PATENT DOCUMENTS

| | | |
|---|---|---|
| 10,118,964 B2 | 11/2018 | Zhou et al. |
| 11,111,299 B2 | 9/2021 | Huang et al. |
| 2003/0022244 A1 | 1/2003 | Solomon et al. |
| 2005/0042218 A1 | 2/2005 | Zauderer |
| 2006/0177896 A1 | 8/2006 | Mach et al. |
| 2007/0065437 A1 | 3/2007 | Elson et al. |
| 2008/0044413 A1 | 2/2008 | Hammond et al. |
| 2018/0086832 A1 | 3/2018 | Vogelstein et al. |
| 2021/0147572 A1* | 5/2021 | Weidanz ............... C07K 16/30 |
| 2023/0051847 A1 | 2/2023 | Vogelstein et al. |

FOREIGN PATENT DOCUMENTS

| | | | |
|---|---|---|---|
| CN | 103635486 | 3/2014 | |
| JP | 2004187676 | 7/2004 | |
| JP | 2008533986 | 8/2008 | |
| WO | WO 2003070752 | 8/2003 | |
| WO | WO 2005116072 | 12/2005 | |
| WO | WO 2006100681 | 9/2006 | |
| WO | 2012/162067 | 11/2012 | |
| WO | 2014/134165 | 9/2014 | |
| WO | 2015/142675 | 9/2015 | |
| WO | 2015/150526 | 10/2015 | |
| WO | 2016/085904 | 6/2016 | |
| WO | 2016/154047 | 9/2016 | |
| WO | 2016/154246 | 9/2016 | |
| WO | WO-2016166139 A1 * | 10/2016 | ............... A61P 35/00 |
| WO | 2016/187508 | 11/2016 | |
| WO | WO 2016199141 | 12/2016 | |
| WO | WO 2016201124 | 12/2016 | |
| WO | WO 2017021527 | 2/2017 | |
| WO | 2017/048593 | 3/2017 | |
| WO | WO 2017134134 | 8/2017 | |
| WO | WO 2017134158 | 8/2017 | |
| WO | WO 2018071796 | 4/2018 | |
| WO | WO 2018213467 | 11/2018 | |
| WO | WO 2019067242 | 4/2019 | |
| WO | 2019/112941 | 6/2019 | |
| WO | WO 2021127814 | 7/2021 | |

OTHER PUBLICATIONS

Dao et al., Targeting the Intracellular WT1 Oncogene Product with a Therapeutic Human Antibody, Sci. Transl. Med. 5(176): 176ra33, 12 pages, Mar. 13, 2013.*
Dao et al., Therapeutic bispecific T-cell engager antibody targeting the intracellular oncoprotein WT1,Nat. Biotechnol.33:1079-1086, 2015, doi:10.1038/nbt.3349.*
Shtraizent et al., Hot Spot Mutation in TP53 (R248Q) Causes Oncogenic Gain-of-Function Phenotypes in a Breast Cancer Cell Line Derived from an African American Patient, Int. J. Environ. Res. Public Health, 13(1), 22, 2016, 14 pages, doi.org/10.3390/ijerph13010022.*
Sergeeva et al., An anti-PR1/HLA-A2 T-cell receptor-like antibody mediates complement-dependent cytotoxicity against acute myeloid leukemia progenitor cells Blood, 117(160):4262-4272, 2011.*
Ladner, R.C.,Mapping the Epitopes of Antibodies Biotechnol. Genet. Eng. Rev. 24:1-30, 2007.*
Kranz et al., Restricted reassociation of heavy and light chains from hapten-specific monoclonal antibodies, Proc. Natl. Acad. Sci., USA, 78(9):5807-5811, 1981.*
Herold et al., Determinants of the assembly and function of antibody variable domains, Scientific Reports, 7:12276, doi: 10.1038/s41598-017-12519-9, Sep. 2017.*
Extended Search Report and Written Opinion in International Appln. No. PCT/US2018/032996, dated Mar. 15, 2021, 20 pages.
Brischwein et al., "MT110: A novel bispecific single-chain antibody construct with high efficacy eradicating established tumors," Mol Immunol., 2006, 43:1129-43.
Curran et al. "Chimeric antigen receptors for T cell immunotherapy: current understanding and future directions," Gene Med, 2012, 14(6):405-415.
Efremova et al., "Neoantigens Generated by Individual Mutations and Their Role is Cancer Immunity and Immunotherapy," Frontiers in Immunology, 2017, 8(Article 1679):1-8.
Eshhar et al., "Specific activation and targeting of cytotoxic lymphocytes through chimeric single chains consisting of antibody-binding domains and the gamma or zeta subunits of the immunoglobulin and T-cell receptors," Proc. Natl. Acad. Sci. USA, 1993, 90(2):720-724.
Kershaw et al.,"Supernatural T cells: genetic modification of T cells for cancer therapy," Nature Reviews Immunol., 2005, 5(12):928-940.
Kinde et al. "Detection and quantification of rare mutations with massively parallel sequencing," PNAS, 2011, 108:9530-9535.
Li et al., "Construction and characterization of a humanized anti-human CD3 monoclonal antibody 12F6 with effective immunoregulation functions," Immunology, 2005, 116:487-98.
Miller et al., "High somatic mutation and neoantigen burden are correlated with decreased progression-free survival in multiple myeloma," Blood Cancer Journal, 2017, 7:e612, 1-11.
[No Author Listed], "The problem with neoantigen prediction," Nature Biotechnology, 2017, 35(2):97.
PCT International search Report and Written Opinion in International Appln. No. PCT/US2018/32996, dated Aug. 27, 2018, 11 pages.
PCT International Preliminary Report on Patentability in International Appln. No. PCT/US2018/032996, dated Sep. 19, 2019.
Rodrigues et al., "Engineering a humanized bispecific F(ab)2 fragment for improved binding to T cells," Int J Cancer, 1992, Suppl. 7:45-50 (Abstract Only).
Sadelain et al., The promise and potential pitfalls of chimeric antigen receptors, Curr. Opin. Immunol., 2009, 21(2):215-223.
Shalaby et al., "Development of Humanized Bispecitic Antibodies Reactive with Cytotoxic Lymphocytes aud Tumor Cells Overexpressing the HER2 Prostooncogene," J Exp Med., 1992, 175:217-25.
Skora et al., Generation of MANAbodies specific to HLA-restricted epitopes encoded by somatically mutated genes. Proceedings of the National Academy of Science of the USA.2015, Epub Jul. 27, 2015, 112(32):9967-0972, DOI: 10.1073/pnas.1511996112.
Schoenberger et al. the-scientist.com [online], "Neoantigens Enable Personalized Cancer Immunotherapy," Apr. 2017, [retrieved on May 4, 2018], retrieved from: URL>https://www.the-scientist.com?articles.view.articleNo/49000/title/Neoantigens-Enable-Personalized-Cancer-Immunotherapy/>, 5 pages.
European Search Report in Appln. No. 18802867.4, dated Mar. 15, 2021, 7 pages.
Anagnostou et al: "Evolution of Neoantigen Landscape during Immune Checkpoint Blockade in Non-Small Cell Lung Cancer," Cancer Discovery, 2017, 7(3):264-276, DOI: 10.1158/2159-8290. CD-16-0828.
Extended Search Report and Written Opinion in International Appln. No. PCT/US2018/032996, dated Dec. 11, 2020, 22 pages.
Miller et al: "An engineered antibody fragment targeting mutant [beta]-catenin via major histocompatibility complex I neoantigen presentation", Journal of Biological Chemistry, 2019, 29(450):19322-19334.
Wang et al: "Direct Detection and Quantification of Neoantigens," Cancer Immunology Research, 2019, 7 (11):1748-1754.

(56) References Cited

OTHER PUBLICATIONS

Abelin et al., "Mass spectrometry profiling of HLA-associated peptidomes in mono-allelic cells enables more accurate epitope prediction," Immunity, 2017, 46(2):315-26.

Abrams et al., "Generation of stable CD4+ and CD8+ T cell lines from patients immunized with ras oncogene-derived peptides reflecting codon 12 mutations," Cell Immunol, Dec. 1997, 182(2):137-151.

Abrams et al., "Mutant ras epitopes as targets for cancer vaccines," Feb. 1996, Semin Oncol, 23(1):118-134 (Abstract only).

Adair et al., "Humanization of the murine anti-human CD3 monoclonal antibody OKT3," Human Antibodies, 1994, 5(1-2):41-7.

Adderley et al., "KRAS-mutant non-small cell lung cancer: Converging small molecules and immune checkpoint inhibition," EBioMedicine, 2019, 41:711-6.

Aldoss et al., "Correlates of resistance and relapse during blinatumomab therapy for relapsed/refractory acute lymphoblastic leukemia," American journal of hematology, 2017, 92(9):858-65.

Anderson et al., "Intracellular transport of class I MHC molecules in antigen processing mutant cell lines," Oct. 1993, J. Immunology, 151(7):3407-3419.

Andreatta et al., "Gapped sequence alignment using artificial neural networks: application to the MHC class I system," Bioinformatics, 2016, 32(4):511-7.

Apps et al., "A critical look at HLA-G," Trends in Immunol, Jul. 2008, 29(7):313-321.

Asano et al., "Rearranging the domain order of a diabody-based IgG-like bispecific antibody enhances its antitumor activity and improves its degradation resistance and pharmacokinetics," MAbs, 2014, 6(5):1243-1254.

Asano et al., "Structural considerations for functional anti-EGFR× anti-CD3 bispecific diabodies in light of domain order and binding affinity," Oncotarget, 2018, 9(17):13884.

Ataie et al., "Structure of a TCR-mimic antibody with target predicts pharmacogenetics," Journal of molecular biology. 2016, 428(1):194-205.

Ayriss et al., "High-throughput screening of single-chain antibodies using multiplexed flow cytometry," Jan. 2007, Journal of Proteome Research, 6(3):1072-1082, 11 pages.

Azriel-Rosenfeld et al., "A Human Synthetic Combinatorial Library of Arrayable Single-chain antibodies based on Shuffling in Vivo Formed CDRs into General Framework Regions," J. Mol. Biol, 2004, 335:177-192.

Baker et al., "Chromosome 17 deletions and p53 gene mutations in colorectal carcinomas," Science, Apr. 1989, 244(4901):217-21.

Bargou et al., "Tumor regression in cancer patients by very low doses of a T cell-engaging antibody," Science, 2008, 321(5891):974-7.

Barretina et al., "The Cancer Cell Line Encyclopedia enables predictive modelling of anticancer drug sensitivity," Nature, 2012, 483(7391):603-7.

Bedard et al., "Small molecules, big impact: 20 years of targeted therapy in oncology," The Lancet, 2020, 395(10229):1078-88.

Bernal et al., "Implication of the β2-microglobulin gene in the generation of tumor escape phenotypes," Sep. 2012, Cancer Immunol Immunother, 61(9):1359-71.

Beverley et al., "Distinctive functional characteristics of human „T" lymphocytes defined by E rosetting or a monoclonal anti-T cell antibody," European Journal of Immunology, 1981, 11(4):329-34.

Bluemel et al., "Epitope distance to the target cell membrane and antigen size determine the potency of T cell-mediated lysis by BiTE antibodies specific for a large melanoma surface antigen," Cancer immunology, immunotherapy, 2010, 59(8):1197-209.

Bondgaard et al., "High specificity but low sensitivity of mutation-specific antibodies against EGFR mutations in non-small-cell cancer," Dec. 2014, Mod Pathol, 27(12):1590-1598, 9 pages.

Borg et al., "A novel interaction between Rab7b and actomyosin reveals a dual role in intracellular transport and cell migration," Journal of Cell Science, 2014, 127(22):4927-39.

Bossi et al., "Examining the presentation of tumor-associated antigens on peptide-pulsed T2 cells," Oncoimmunology, 2013, 2(11):e26840.

Bostrom et al., "Chapter 2: Design and construction of synthetic phage-displayed fab libraries," May 2009, Methods in Molecular Biology, 562:17-35, 19 pages.

Bouvier et al., "Crystal structures of HLA-A*0201 complexed with antigenic peptides with either the amino- or carboxyl-terminal group substituted by a methyl group," May 1998, Proteins, 33(3):97-106, 10 pages.

Bradbury et al., "Beyond natural antibodies: the power of in vitro display technologies," Nat Biotechnol, Mar. 2011, 29(3):245-254, 28 pages.

Brickner et al., "The PANE1 gene encodes a novel human minor histocompatibility antigen that is selectively expressed in B-lymphoid cells and B-CLL," May 1, 2006, Blood, 107(9):3779-3786, 24 pages.

Brinkmann et al., "The making of bispecific antibodies," MAbs, 2017, 9(2):182-212.

Buhrman et al., "Analysis of binding site hot spots on the surface of Ras GTPase," Journal of Molecular Biology, 2011, 413(4):773-89.

Cameron et al., "Identification of a Titin-derived HLA-A1—presented peptide as a cross-reactive target for engineered MAGE A3-directed T cells," Science Translational Medicine, 2013, 5(197):197ra103.

Canon et al., "The clinical KRAS (G12C) inhibitor AMG 510 drives anti-tumour immunity," Nature, 2019, 575(7781):217-23.

Carosella et al., "Beyond the increasing complexity of the immunomodulatory HLA-G molecule," Blood, May 2008, 111(10):4862-4870.

Carter et al., "Humanization of an anti-p185HER2 antibody for human cancer therapy," May 1992, Proc. Natl. Acad. Sci., 89(10):4285-4289, 5 pages.

Castle et al., "Exploiting the mutanome for tumor vaccination," Mar. 1, 2012, Cancer Res, 72(5):1081-1091, 12 pages.

Caushi et al., "Transcriptional programs of neoantigen-specific TIL in anti-PD-1-treated lung cancers," Nature, Jul. 21, 2021, 596(7870):126-132.

Chang et al., "A therapeutic T cell receptor mimic antibody targets tumor-associated PRAME peptide/HLA-I antigens," The Journal of Clinical Investigation, 2017, 127(7):2705-18.

Chapuis et al., "T cell receptor gene therapy targeting WT1 prevents acute myeloid leukemia relapse post-transplant," Nature Medicine, 2019, 25(7):1064-72.

Chen et al., "A comprehensive survey of genomic alterations in gastric cancer reveals recurrent neoantigens as potential therapeutic targets," BioMed Research International, 2019, Article ID 2183510, 10 pages.

Choudhuri et al., "T-cell receptor triggering is critically dependent on the dimensions of its peptide-MHC ligand," Nature, 2005, 436(7050):578-82.

Coles et al., "TCRs with distinct specificity profiles use different binding modes to engage an identical peptide—HLA complex," The Journal of Immunology, 2020, 204(7):1943-53.

Coordinators, "Database resources of the national center for biotechnology information," Nucleic acids research, 2018, 46(Database issue):D8.

Cottrell et al., "Pathologic features of response to neoadjuvant anti-PD-1 in resected non-small-cell lung carcinoma: a proposal for quantitative immune-related pathologic response criteria (irPRC)," Ann. Oncol., Aug. 1, 2018, 29(8):1853-1860.

D'Angelo et al., "Incidence of EGFR Exon 19 Deletions and L858R in Tumor Specimens From Men and Cigarette Smokers with Lung Adenocarcinomas," May 20, 2011, J. Clin. Oncol., 29(15):2066-2070, 5 pages.

Dao et al., "Approaching untargetable tumor-associated antigens with antibodies," Jul. 2013, OncoImmunology, 2(7):e24678, 2 pages.

De Castro et al., "ScanProsite: detection of PROSITE signature matches and ProRule-associated functional and structural residues in proteins," Nucleic Acids Research, 2006, 34(suppl_2):W362-5.

De Verteuil et al., "Origin and plasticity of MHC I-associated self peptides," Jul. 2012, Autoimmunity Reviews, 11(9):627-635.

(56) References Cited

OTHER PUBLICATIONS

Denkberg et al., "Modification of a tumor-derived peptide at an HLA-A2 anchor residue can alter the conformation of the MHC-peptide complex: probing with TCR-like recombinant antibodies," J. Immunol, 2002, 169:4399-4407.

Digiusto et al., "Preparing clinical grade Ag-specific T cells for adoptive immunotherapy trials," Cytotherapy, 2007, 9(&):613-29.

Dufner et al., "Harnessing phage and ribosome display for antibody optimisation," Trends in Biotechnology, Nov. 2006, 24(11):523-529.

Eigenbrot et al., "X-ray structures of the antigen-binding domains from three variants of humanized anti-p185HER2 antibody 4D5 and comparison with molecular modeling," Feb. 1993, J. Mol. Biol., 229(4):969-995.

Ellis et al., "Frequencies of HLA-A2 alleles in five U.S. population groups: Predominance of A*02011 and identification of HLA-A*0231," Mar. 2000, Human Immunology, 61(3):334-340.

Extended European Search Report in European Application No. 16769561.8, dated Jul. 6, 2018, 9 pages.

Faroudi et al., "Cutting edge: T lymphocyte activation by repeated immunological synapse formation and intermittent signaling," The Journal of Immunology, 2003, 171(3):1128-32.

Fearon et al., "A Genetic Model for Colorectal Tumorigenesis," Cell Press, Jun. 1, 1990, 61(5):759-767, 9 pages.

Fellhouse et al., "High-throughput generation of synthetic antibodies from highly functional minimalist phage-displayed libraries," Aug. 2007, J. Mol. Biol., 373(4):924-940, 17 pages.

Forde et al., "Neoadjuvant PD-1 Blockade in Resectable Lung Cancer," N. Engl. J. Med., May 24, 2018, 378(21):1976-1986.

Gejman et al., "Identification of the Targets of T-cell Receptor Therapeutic Agents and Cells by Use of a High-Throughput Genetic Platform Identifying T-cell Targets Using a High-Throughput Method," Cancer Immunology Research, 2020, 8(5):672-84.

GenBank Accession No. AAH03596.1, "Tumor protein p53 [*Homo sapiens*]," dated Jun. 9, 2008, 2 pages.

Gerstung et al., "The evolutionary history of 2,658 cancers," Nature, 2020, 578(7793):122-8.

Gomez-Eerland et al., "Manufacture of gene-modified human T-cells with a memory stem/central memory phenotype," Human gene therapy methods, 2014, 25(5):277-87.

Gonzalez-Galarza, et al., "Allele frequency net 2015 update: new features for HLA epitopes, KIR and disease and HLA adverse drug reaction associations," Nucleic Acids Research, 2015, 43(D1):D784-8.

Grossman et al., "Toward a shared vision for cancer genomic data," New England Journal of Medicine, 2016, 375(12):1109-12.

Gubin et al., "Checkpoint Blockade Cancer Immunotherapy Targets Tumour-Specific Mutant Antigens," Nov. 27, 2014, Nature, 515(7528):577-581, 32 pages.

Halilovic et al., "Therapeutic strategies for inhibiting oncogenic BRAF signaling," Curr Opin Pharmacol, Aug. 2008, 8(4):419-426.

Ham et al., "TP53gain-of-function mutation promotes inflammation in glioblastoma," Cell Death & Differentiation, May 2018, 26(3):409-425.

Hammond et al., "Selective targeting and potent control of tumor growth using an EphA2/CD3-Bispecific single-chain antibody construct," Cancer research, 2007, 67(8):3927-35.

Harndahl et al., "Peptide binding to HLA class I molecules: homogenous, high-throughput screening, and affinity assays," J. Biomol. Screen, Feb. 2009, 14(2):173-180.

Harper et al., "An approved in vitro approach to preclinical safety and efficacy evaluation of engineered T cell receptor anti-CD3 bispecific (ImmTAC) molecules," PLoS One, 2018, 13(10):e0205491.

Hexham et al., "Influence of relative binding affinity on efficacy in a panel of anti-CD3 scFv immunotoxins," Molecular immunology, 2001, 38(5):397-408.

hla.alleles.org [online], "HLA Nomenclature," retrieved on Mar. 17, 2015, retrieved from URL<http://hla.alleles.org/nomenclature/stat.html>, 2 pages.

Hobbs et al., "RAS isoforms and mutations in cancer at a glance," Journal of Cell Science, 2016, 129(7):1287-92.

Holliger et al., "Diabodies: small bivalent and bispecific antibody fragments," Proceedings of the National Academy of Sciences, 1993, 90(14):6444-8.

Hoof et al., "Proteome sampling by the HLA class I antigen processing pathway," May 2012, Plos Computational Biology, 8(5):e1002517, 9 pages.

Houghton, et al., "Immune recognition of self in immunity against cancer," J. Clin. Invest., 2004, 114(4):468-471.

Hsiue et al., "Targeting a neoantigen derived from a common TP53 mutation," Science, Mar. 1, 2021, 371(6533): eabc8697.

Huang et al., "CD-HIT Suite: a web server for clustering and comparing biological sequences," Bioinformatics, 2010, 26(5):680-2.

Huehls et al., "Bispecific T-cell engagers for cancer immunotherapy," Immunology and cell biology, 2015, 93(3):290-6.

International Preliminary Report on Patentability in International Application No. PCT/US2016/023673, dated Sep. 26, 2017, 8 pages (with English translation).

International Preliminary Report on Patentability in International Application No. PCT/US2020/06561, dated May 17, 2022, 6 pages.

International Search Report and Written Opinion in International Application No. PCT/US2016/023673, dated Jul. 25, 2016, 13 pages.

International Search Report and Written Opinion in International Application No. PCT/US2020/065617, dated Apr. 1, 2021, 8 pages.

Janes et al., "Targeting KRAS mutant cancers with a covalent G12C-specific inhibitor," Cell, 2018, 172(3):578-89.

Jena et al., "Redirecting T-cell specificity by introducing a tumor-specific chimeric antigen receptor," Aug. 2010, Blood, 116(7):1035-1044, 17 pages.

Johnson et al., "Effector cell recruitment with novel Fv-based dual-affinity re-targeting protein leads to potent tumor cytolysis and in vivo B-cell depletion. Journal of molecular biology," 2010, 399(3):436-49.

Jones et al., "Core signaling pathways in human pancreatic cancers revealed by global genomic analyses," Science, 2008, 321(5897):1801-6.

Junttila et al., "Antitumor Efficacy of a Bispecific Antibody That Targets HER2 and Activates T Cells," Cancer research, 2014, 74(19):5561-71.

Kato et al., "A monoclonal antibody IMab-1 specifically recognizes IDH1R132H, the most common glioma-derived mutation," Biochemical and Biophysical Research Communications, 2009, 390(3):547-51.

Kato et al., "Effective screening of T cells recognizing neoantigens and construction of T-cell receptor-engineered T cells," Oncotarget, 2018, 9(13):11009.

Kato et al., "Understanding the function—structure and function—mutation relationships of p53 tumor suppressor protein by high-resolution missense mutation analysis," Proceedings of the National Academy of Sciences, 2003, 100(14): 8424-9.

Kershaw et al., "Clinical application of genetically modified T cells in cancer therapy," Apr. 2014, Clinical & Translational Immunology, 3(5):e16, 7 pages.

Kim et al., "TCR mechanobiology: torques and tunable structures linked to early T cell signaling," Frontiers in immunology, 2012, 3(76):1-8.

Kim et al., "The αβ T cell receptor is an anisotropic mechanosensor," Journal of Biological Chemistry, 2009, 284(45):31028-37.

Kipriyanov et al., "Effect of domain order on the activity of bacterially produced bispecific single-chain Fv antibodies," Journal of molecular biology, 2003, 330(1):99-111.

Koide et al., "The importance of being tyrosine: lessons in molecular recognition from minimalist synthetic binding proteins," May 2009, ACS Chem. Biol., 4(5):325-334, 16 pages.

Kraemer et al., "HLA-E: Presentation of a broader peptide repertoire impacts the cellular immune response-implications on HSCT outcome," Stem Cells Inter, 2015, article ID 346714, pp. 1-12.

Krissinel et al., "Inference of macromolecular assemblies from crystalline state," Journal of Molecular Biology, 2007, 372(3):774-97.

(56) References Cited

OTHER PUBLICATIONS

Kula et al., "T-Scan: a genome-wide method for the systematic discovery of T cell epitopes," Cell, 2019, 178(4):1016-28.
Kunik et al., "Structural consensus among antibodies defines the antigen binding site," Feb. 2012, PLoS Computational Biology, 8(2):e1002388, 12 pages.
Kuroda et al., "Structural classification of CDR-H3 revisited: a lesson in antibody modeling," Nov. 2008, Proteins, 73(3):608-620.
Labrijn et al., "Bispecific antibodies: a mechanistic review of the pipeline," Nature reviews Drug discovery, 2019, 18(8):585-608.
Le et al., "Mismatch repair deficiency predicts response of solid tumors to PD-1 blockade," Science, Jul. 2017, 357(6349):409-413.
Li et al., "A model for RAS mutation patterns in cancers: finding the sweet spot," Nature Reviews Cancer, 2018, 18(12):767-77.
Liddy et al., "Monoclonal TCR-redirected tumor cell killing," Nature Medicine, 2012, 18(6):980-7.
Lin et al., "Enhanced homology-directed human genome engineering by controlled timing of CRISPR/Cas9 delivery," eLife, 2014, 3:e04766.
Link et al., "Anti-CD3-based bispecific antibody designed for therapy of human B-cell malignancy can induce T-cell activation by antigen-dependent and antigen-independent mechanisms," Jul. 1998, Int. J. Cancer, 77(2):251-256, 7 pages.
Lo et al., "Immunologic recognition of a shared p53 mutated neoantigen in a patient with metastatic colorectal cancer," Cancer Immunology Research, 2019, 7(4):534-43.
Low et al., "Targeting mutant p53-expressing tumours with a T cell receptor-like antibody specific for a wild-type antigen," Nature Communications, 2019, 10(1):1-4.
Lowe et al., "TCR-like antibody drug conjugates mediate killing of tumor cells with low peptide/HLA targets," MAbs 2017, 9(4):603-614.
Lu et al., "The effect of variable domain orientation and arrangement on the antigen-binding activity of a recombinant human bispecific diabody," Biochemical and biophysical research communications, 2004, 318(2):507-13.
Luft et al., "Exogenous peptides presented by transporter associated with antigen processing (TAP)-Deficient and TAP-Competent cells: Intracellular loading and kinetics of presentation," Sep. 1, 2017, J. Immunol., 167(5):2529-2537, 10 pages.
Lundegaard et al., "Accurate approximation method for prediction of class I MHC affinities for peptides of length 8, 10 and 11 using prediction tools trained on 9mers," Apr. 2008, Bioinformatics, 24(11):1397-1398, 2 pages.
Lundegaard et al., "NetMHC-3.0: accurate web accessible predictions of human, mouse and monkey MHC class I affinities for peptides of length 8-11," May 7, 2008, Nucleic Acids Research, 36:W509-512, 4 pages.
Maiers et al., "High-resolution HLA alleles and haplotypes in the United States population," Human Immunology, 2007, 68(9):779-88.
Malekzadeh et al., "Neoantigen screening identifies broad TP53 mutant immunogenicity in patients with epithelial cancers," The Journal of Clinical Investigation, 2021, 129(3).
Martayan et al., "Class I HLA folding and antigen presentation in beta 2—microglobulin-defective Daudi cells," Mar. 2009, The Journal of Immunology, 2009, 182:3609-3617.
Marubashi et al., "Rab7B/42 is functionally involved in protein degradation on melanosomes in keratinocytes," Cell structure and function, 2020, 19039.
Maruyama et al., "Increasing the efficiency of precise genome editing with CRISPR-Cas9 by inhibition of nonhomologous end joining," Nature biotechnology, 2015, 33(5):538-42.
Maude et al., "Chimeric antigen receptor T cells for sustained remissions in leukemia," New England Journal of Medicine, 2014, 371(16):1507-17.
McConnell et al., "An integrated approach to extreme thermostablilization and affinity maturation of an antibody," Feb. 2013, PEDS, 26(2):151-163, 13 pages.

Merchant et al., "An efficient route to human bispecific IgG," Nature biotechnology, 1998, 16(7):677-81.
Miller et al., "A human monoclonal antibody neutralizes diverse HIV-1 isolates by binding a critical gp41 epitope," Oct. 11, 2005, Proc. Natl. Acad. Sci., 102(41):14759-14764, 6 pages.
Miller et al., "T Cell Receptor-Like Recognition of Tumor In Vivo by Synthetic Antibody Fragment," Aug. 2012, PLoS One, 7(8):e43746, 14 pages.
Moore et al., "Application of dual affinity retargeting molecules to achieve optimal redirected T-cell killing of B-cell lymphoma," Blood, The Journal of the American Society of Hematology, 2011, 117(17):4542-51.
Morgan et al., "Cancer regression and neurological toxicity following anti-MAGE-A3 TCR gene therapy," Journal of Immunotherapy, 2013, 36(2):133-51.
Muzumdar et al., "Survival of pancreatic cancer cells lacking KRAS function," Nature communications, 2017, 8(1):1-9.
Myszka, "Improving biosensor analysis" 1999, J. Mol. Recognit, 12:279-284.
NCBI.gov [Online], "HLA-F major histocompatibility complex, class I F [*Homo sapiens*(humans)]," Sep. 4, 2016, retrieved on Sep. 29, 2016, retrieved from URL <http://www.ncbi.nlm.nih.gov/gene/3134>, 14 pages.
Nielsen et al., "Reliable prediction of T-cell epitopes using neural networks with novel sequence representations," Feb. 2003, Protein Science, 12(5):1007-1017, 11 pages.
Nolan et al., "Flow cytometry: a versatile tool for all phases of drug discovery," Apr. 1999, Drug Discov Today, 4(4):173-180, 8 pages.
Novak et al., "Selective antibody-mediated targeting of class I MHC to EGFR-expressing tumor cells induces potent antitumor CTL activity in vitro and in vivo," Oct. 2006, International Journal of Cancer, 120:329-336, 8 pages.
Ostrem et al., "K-Ras (G12C) inhibitors allosterically control GTP affinity and effector interactions," Nature, 2013, 503(7477):548-51.
Paix et al., "Precision genome editing using synthesis-dependent repair of Cas9-induced DNA breaks," Proceedings of the National Academy of Sciences, 2017, 114(50):E10745-54.
Park et al., "Long-term follow-up of CD19 CAR therapy in acute lymphoblastic leukemia," New England Journal of Medicine, 2018, 378(5):449-59.
Parkhurst et al., "Unique Neoantigens Arise from Somatic Mutations in Patients with Gastrointestinal Cancers Neoantigens in Patients with Gastrointestinal Cancers," Cancer discovery, 2019, 9(8):1022-35.
PCT International search Report and Written Opinion in International Appln. No. PCT/US2022/022791, dated Nov. 17, 2022, 21 pages.
Petryszak et al., "Expression Atlas update—an integrated database of gene and protein expression in humans, animals and plants," Nucleic acids research, 2016, 44(D1):D746-52.
Porgador et al., "Localization, quantitation, and in situ detection of specific peptide-MHC class I complexes using a monoclonal antibody," Jun. 1997, Immunity, 6(6):715-726, 12 pages.
Prior et al., "A comprehensive survey of Ras mutations in cancer," Cancer Research, 2012, 72(10):2457-67.
Prior et al., "The Frequency of Ras Mutations in Cancer," Cancer Research, 2020, 80(14):2969-74.
Purbhoo et al., "T cell killing does not require the formation of a stable mature immunological synapse," Nature Immunology, 2004, 5(5):524-30.
Puri et al., "Highly efficient selection of epitope specific antibody through competitive yeast display library sorting," Aug. 2013, mAbs, 5(4):533-539, 7 pages.
Rafiq et al., "Engineering strategies to overcome the current roadblocks in CAR T cell therapy," Nature Reviews Clinical Oncology, 2020, 17(3):147-67.
Rafiq et al., "Optimized T-cell receptor-mimic chimeric antigen receptor T cells directed toward the intracellular Wilms Tumor 1 antigen," Leukemia, 2017, 31(8):1788-97.
Rahma et al., "The immunological and clinical effects of mutated ras peptide vaccine in combination with IL-2, GM-CSF, or both in patients with solid tumors," Feb. 2014, Journal of Translational Medicine, 12:55, 12 pages.

(56) References Cited

OTHER PUBLICATIONS

Raman et al., "Direct molecular mimicry enables off-target cardiovascular toxicity by an enhanced affinity TCR designed for cancer immunotherapy," Scientific Reports, 2016, 6(1):1-0.
Richardson et al., "Enhancing homology-directed genome editing by catalytically active and inactive CRISPR-Cas9 using asymmetric donor DNA," Nature biotechnology, 2016, 34(3):339-44.
Rizvi et al., "Cancer immunology. Mutational landscape determines sensitivity to PD-1 blockade in non-small cell lung cancer," Science, Apr. 3, 2015, 348(6230):124-128.
Robbins et al., "Mining exomic sequencing data to identify mutated antigens recognized by adoptively transferred tumor-reactive T cells," Jun. 2013, Nat Med, 19(6):747-752, 14 pages.
Roblek et al., "Monoclonal antibodies specific for disease-associated point-mutants: Lamin A/C R453W and R482W," May 2010, PloS One, 5(5):e10604, 14 pages.
Rosenberg et al., "Adoptive cell transfer as personalized immunotherapy for human cancer," Science, 2015, 348(6230):62-8.
Rosenberg et al., "Use of tumor-infiltrating lymphocytes and interleukin-2 in the immunotherapy of patients with metastatic melanoma," New England Journal of Medicine, 1988, 319(25):1676-80.
Salter et al., "Genes regulating HLA class I antigen expression in T-B lymphoblast hybrids," Mar. 1985, Immunogenetics, 21(3):235-246.
Schmidt et al., "In silico and cell-based analyses reveal strong divergence between prediction and observation of T-cell—recognized tumor antigen T-cell epitopes," Journal of Biological Chemistry, 2017, 292(28):11840-9.
Scholtalbers et al., "TCLP: an online cancer cell line catalogue integrating HLA type, predicted neo-epitopes, virus and gene expression," Genome medicine, 2015, 7(1):1-7.
Schreiber et al., "Cancer Immunoediting: Integrating Immunity's Roles in Cancer Suppression and Promotion," Mar. 2011, Science, 331(6024):1565-1570, 6 pages.
Schumacher et al., "Neoantigens in cancer immunotherapy," Science, 2015, 348(6230):69-74.
Schuster et al., "Tisagenlecleucel in adult relapsed or refractory diffuse large B-cell lymphoma," New England Journal of Medicine, 2019, 380(1):45-56.
Scott et al., "Monoclonal antibodies in cancer therapy," Cancer immunity, 2012, 12(1).
Segal et al., "Epitope landscape in breast and colorectal cancer," Cancer Research, 2008, 68(3):889-92.
Sela-Culang et al., "The structural basis of antibody-antigen recognition," Oct. 2013, Frontiers in Immunology, 4:302, 13 pages.
Sharma et al., "Epidermal growth factor receptor mutations in lung cancer," Mar. 2007, Nat. Rev. Cancer, 7(3):169-181, 13 pages.
Sharma et al., "Recent advances in T-cell engineering for use in immunotherapy," F1000Research, 2016, 5:F1000 Faculty Rev):2344.
Sidhu et al., Phage-displayed Antibody Libraries of Synthetic Heavy Chain Complementarity Determining Regions, Feb. 2004, J. Mol. Biol., 338(2):299-310, 12 pages.
Sliwkowski et al., "Antibody therapeutics in cancer," Science, Sep. 13, 2013, 341(6151):1192-1198.
Snyder et al., "Genetic basis for clinical response to CTLA-4 blockade in melanoma," N. Engl. J. Med., Dec. 4, 2014, 371(23):2189-2199.
Sondek et al., "A general strategy for random insertion and substitution mutagenesis: substoichiometric coupling of trinucleotide phosphoramidites," Proceedings of the National Academy of Sciences, 1992, 89(8):3581-5.
Steinwand et al., "The influence of antibody fragment format on phage display based affinity maturation of IgG," Nov. 26, 2013, mAbs, 6(1):204-218, 16 pages.
Stewart-Jones et al., "Rational development of high-affinity T-cell receptor-like antibodies," Proceedings of the National Academy of Sciences, 2009, 106(14):5784-8.
Stone et al., "A sensitivity scale for targeting T cells with chimeric antigen receptors (CARs) and bispecific T-cell Engagers (BiTEs)," Oncoimmunology, 2012, 1(16):863-73.
Sugiyama et al., "A semi high-throughput method for screening small bispecific antibodies with high cytotoxicity," Scientific reports, 2017, 7(1):1-2.
Sung et al., "Dual-Affinity Re-Targeting proteins direct T cell-mediated cytolysis of latently HIV-infected cells," The Journal of clinical investigation, 2015, 125(11):4077-90.
Taylor et al., "A DNA-based T cell receptor reveals a role for receptor clustering in ligand discrimination," Cell, 2017, 169(1):108-19.
Thakur et al., "Cancer therapy with bispecific antibodies: Clinical experience," Jun. 2010, Curr. Opin. Mol. Ther., 12(3):340-349, 16 pages.
Thomas et al., "Mesothelin-specific CD8+ T cell responses provide evidence of in vivo cross-priming by antigen-presenting cells in vaccinated pancreatic cancer patients," The Journal of experimental medicine, 2004, 200(3):297-306.
Thomsen et al., "Seq2Logo: a method for construction and visualization of amino acid binding motifs and sequence profiles including sequence weighting, pseudo counts and two-sided representation of amino acid enrichment and depletion," Nucleic acids research, 2012, 40(W1):W281-7.
Tran et al., "Cancer immunotherapy based on mutation-specific CD4+ T cells in a patient with epithelial cancer," Science, 2014, 344(6184):641-5.
Tran et al., "T-cell transfer therapy targeting mutant KRAS in cancer," New England Journal of Medicine, 2016, 375(23):2255-62.
Tsai et al., "Discovery of a selective inhibitor of oncogenic B-Raf kinase with potent antimelanoma activity," PNAS, Feb. 26, 2008, 105(8):3041-3046, 6 pages.
Tsukahara et al., "Specific targeting of a naturally presented osteosarcoma antigen, papillomavirus binding factor peptide, using an artificial monoclonal antibody," Aug. 2014, Journal of Biological Chemistry, 289(32):22035-22047, 14 pages.
Tumeh et al., "PD-1 blockade induces responses by inhibiting adaptive immune resistance," Nature, Nov. 27, 2014, 515(7528):568-571.
Uhlen et al., "Tissue-based map of the human proteome," Science, 2015, 347(6220):1260419.
Van Allen et al., "Genomic correlates of response to CTLA-4 blockade in metastatic melanoma," Science, Oct. 2015, 350(6257):207-211.
Van Wauwe et al., "OKT3: a monoclonal anti-human T lymphocyte antibody with potent mitogenic properties," The Journal of Immunology, 1980, 124(6):2708-13.
Vauquelin et al., "Exploring avidity: understanding the potential gains in functional affinity and target residence time of bivalent and heterobivalent ligands," British journal of pharmacology, 2013, 168(8):1771-85.
Verma et al., "TCR mimic monoclonal antibody targets a specific peptide/HLA class I complex and significantly impedes tumor growth in vivo using breast cancer models," Feb. 2010, J. Immunol., 184(4):2156-2165, 11 pages.
Vita et al., "The immune epitope database (IEDB): 2018 update," Nucleic acids research, 2019, 47(D1):D339-43.
Vogelstein et al., "Cancer genome landscapes," Science, 2013, 339(6127):1546-58.
Vonderheide et al., "Engineering T cells for cancer: our synthetic future," Jan. 2014, Immunol Rev., 257(1):7-13, 10 pages.
Wang et al., "A naturally processed peptide presented by HLA-A*0201 is expressed at low abundance and recognized by an alloreactive CD8+ cytotoxic T cell with apparent high affinity," Jun. 1997, J. Immunol., 158(12):5797-5804, 8 pages.
Wang et al., "Identification of T-cell Receptors Targeting KRAS-Mutated Human Tumors," Cancer Immunol Res, 2016, 4:204-214.
Ward et al., "The Role of Neoantigens in Naturally Occurring and Therapeutically Induced Immune Responses to Cancer," Adv Immunol, 2016, 130:25-74.
Warren et al., "A census of predicted mutational epitopes suitable for immunologic cancer control," Human Immunol., 2010, pp. 245-254.

(56) References Cited

OTHER PUBLICATIONS

Watanabe et al., "Expanding the therapeutic window for CAR T cell therapy in solid tumors: the knowns and unknowns of CAR T cell biology," Frontiers in Immunology, 2018, 9:2486.

Webb et al., "Functional and structural characteristics of NY-ESO-1-related HLA A2-restricted epitopes and the design of a novel immunogenic analogue," Journal of Biological Chemistry, 2004, 279(22):23438-46.

Weiner et al., "Antibodies and cancer therapy: versatile platforms for cancer immunotherapy," May 2010, Nature Reviews Immunology, 10(5):317-327, 26 pages.

Wu et al., "Kinetic and structural analysis of mutant CD4 receptors that are defective in HIV gp120 binding," Proceedings of the National Academy of Sciences, 1996, 93(26):15030-5.

Wu et al., "T cell engaging bispecific antibody (T-BsAb): from technology to therapeutics," Pharmacology & Therapeutics, 2018, 182:161-75.

Yadav et al., "Predicting immunogenic tumour mutations by combining mass spectrometry and exome sequencing," Nov. 27, 2014, Nature, 515(7528):572-576, 16 pages.

Yang et al., "Rab7b, a novel lysosome-associated small GTPase, is involved in monocytic differentiation of human acute promyelocytic leukemia cells," Biochemical and biophysical research communications, 2004, 318(3):792-9.

Ylera et al., "Off-rate screening for selection of high-affinity anti-drug antibodies," Oct. 2013, Analytical Biochemistry, 441(2):208-213, 6 pages.

Yossef et al., "Enhanced detection of neoantigen-reactive T cells targeting unique and shared oncogenes for personalized cancer immunotherapy," JCI insight, 2018, 3(19):e122467.

Yu et al., "Mutation-specific antibodies for the detection of EGFR mutations in non-small-cell lung cancer," Clinical Cancer Research, 2009, 15(9):3023-8.

Zacharakis et al., "Immune recognition of somatic mutations leading to complete durable regression in metastatic breast cancer," Nature medicine, 2018, 24(6):724-30.

Zhu et al., "Engineering high affinity humanized anti-p185HER2/anti-CD3 bispecific F (ab') 2 for efficient lysis of p185HER2 overexpressing tumor cells," International Journal of Cancer, 1995, 62(3):319-24.

Zhu et al., "Identification of heavy chain residues in a humanized anti-CD3 antibody important for efficient antigen binding and T cell activation," The Journal of Immunology, 1995, 155(4):1903-10.

Zumrut et al., "Integrating ligand-receptor interactions and in vitro evolution for streamlined discovery of artificial nucleic acid ligands," Molecular Therapy—Nucleic Acids, 2019, 17:150-63.

* cited by examiner

SEQUENCE LISTING

```
<160> NUMBER OF SEQ ID NOS: 420

<210> SEQ ID NO 1
<211> LENGTH: 10
<212> TYPE: PRT
<213> ORGANISM: Artificial
<220> FEATURE:
<223> OTHER INFORMATION: synthetic peptide

<400> SEQUENCE: 1

Ser Pro Asn Gly Thr Ile Gln Asn Ile Leu
1               5                   10

<210> SEQ ID NO 2
<211> LENGTH: 10
<212> TYPE: PRT
<213> ORGANISM: Artificial
<220> FEATURE:
<223> OTHER INFORMATION: synthetic peptide

<400> SEQUENCE: 2

Ser Pro Asn Gly Thr Ile Arg Asn Ile Leu
1               5                   10

<210> SEQ ID NO 3
<211> LENGTH: 243
<212> TYPE: PRT
<213> ORGANISM: Artificial
<220> FEATURE:
```

<223> OTHER INFORMATION: synthetic peptide

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Tyr Ser Pro Pro
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Ser Asp Thr Tyr Ile His Trp Val
145                 150                 155                 160

Arg Gln Ala Pro Gly Lys Gly Leu Glu Trp Val Ala Ser Ile Ser Pro
                165                 170                 175

Arg Thr Gly Tyr Asn Arg Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ala Tyr Tyr
    210                 215                 220

Ser Tyr Ala Tyr Ala Met Asp Val Trp Gly Gln Gly Thr Leu Val Thr
225                 230                 235                 240

Val Ser Ser

<210> SEQ ID NO 4
<211> LENGTH: 242
<212> TYPE: PRT
<213> ORGANISM: Artificial
<220> FEATURE:
<223> OTHER INFORMATION: synthetic peptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Lys Ala Tyr Trp Pro
                85                  90                  95

```
Ala Thr Phe Gly Gln Gly Thr Lys Val Glu Ile Lys Arg Thr Gly Gly
                100                 105                 110

Gly Ser Gly Gly Gly Ser Gly Gly Ala Ser Glu Val Gln Leu
        115                 120                 125

Val Glu Ser Gly Gly Leu Val Gln Pro Gly Gly Ser Leu Arg Leu
    130                 135                 140

Ser Cys Ala Ala Ser Gly Phe Asn Val Gly His Tyr Arg Met His Trp
145                 150                 155                 160

Val Arg Gln Ala Pro Gly Lys Gly Leu Glu Trp Val Ala Met Val Ser
                165                 170                 175

Pro Asn Gly Tyr Tyr Thr Tyr Tyr Ala Asp Ser Val Lys Gly Arg Phe
                180                 185                 190

Thr Ile Ser Ala Asp Thr Ser Lys Asn Thr Ala Tyr Leu Gln Met Asn
                195                 200                 205

Ser Leu Arg Ala Glu Asp Thr Ala Val Tyr Tyr Cys Ser Arg Gly Tyr
    210                 215                 220

Ser Ser Tyr Ala Phe Asp Tyr Trp Gly Gln Gly Thr Leu Val Thr Val
225                 230                 235                 240

Ser Ser

<210> SEQ ID NO 5
<211> LENGTH: 241
<212> TYPE: PRT
<213> ORGANISM: Artificial
<220> FEATURE:
<223> OTHER INFORMATION: synthetic peptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Ser Ser Pro Phe
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Val Lys Tyr Tyr Met Met His Trp Val
145                 150                 155                 160

Arg Gln Ala Pro Gly Lys Gly Leu Glu Trp Val Ala Ala Ile Ser Pro
                165                 170                 175

Gly Tyr Asp Tyr Thr Tyr Tyr Ala Asp Ser Val Lys Gly Arg Phe Thr
                180                 185                 190

Ile Ser Ala Asp Thr Ser Lys Asn Thr Ala Tyr Leu Gln Met Asn Ser
                195                 200                 205

Leu Arg Ala Glu Asp Thr Ala Val Tyr Tyr Cys Ser Arg Ser Tyr Trp
```

```
                210                 215                 220
Arg Tyr Ser Val Asp Val Trp Gly Gln Gly Thr Leu Val Thr Val Ser
225                 230                 235                 240

Ser

<210> SEQ ID NO 6
<211> LENGTH: 245
<212> TYPE: PRT
<213> ORGANISM: Artificial
<220> FEATURE:
<223> OTHER INFORMATION: synthetic peptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Leu Tyr Ser Pro
                85                  90                  95

Met Thr Phe Gly Gln Gly Thr Lys Val Glu Ile Lys Arg Thr Gly Gly
            100                 105                 110

Gly Ser Gly Gly Gly Gly Ser Gly Gly Ala Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ser Phe Leu Ser Ile His Trp Val
145                 150                 155                 160

Arg Gln Ala Pro Gly Lys Gly Leu Glu Trp Val Ala His Ile Phe Pro
                165                 170                 175

Ser Ser Asp Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Gly Lys His
    210                 215                 220

Ser Ser Asp Ser Asn Tyr Tyr Met Asp Tyr Trp Gly Gln Gly Thr Leu
225                 230                 235                 240

Val Thr Val Ser Ser
            245

<210> SEQ ID NO 7

<400> SEQUENCE: 7

000

<210> SEQ ID NO 8
<211> LENGTH: 241
<212> TYPE: PRT
<213> ORGANISM: Artificial
<220> FEATURE:
<223> OTHER INFORMATION: synthetic peptide
```

```
<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Met Pro Phe
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Asn Ile Phe Arg Gly Tyr Met His Trp Val
145                 150                 155                 160

Arg Gln Ala Pro Gly Lys Gly Leu Glu Trp Val Ala Met Ile Ser Pro
                165                 170                 175

His Ser Asp Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Tyr Gly
    210                 215                 220

Trp Ala Ala Phe Asp Tyr Trp Gly Gln Gly Thr Leu Val Thr Val Ser
225                 230                 235                 240

Ser

<210> SEQ ID NO 9
<211> LENGTH: 10
<212> TYPE: PRT
<213> ORGANISM: Artificial
<220> FEATURE:
<223> OTHER INFORMATION: synthetic peptide

<400> SEQUENCE: 9

Arg Pro Ile Pro Ile Lys Tyr Lys Ala Met
1               5                   10

<210> SEQ ID NO 10
<211> LENGTH: 10
<212> TYPE: PRT
<213> ORGANISM: Artificial
<220> FEATURE:
<223> OTHER INFORMATION: synthetic peptide

<400> SEQUENCE: 10

Lys Pro Ile Thr Ile Gly Arg His Ala His
1               5                   10

<210> SEQ ID NO 11
<211> LENGTH: 9
```

-continued

```
<212> TYPE: PRT
<213> ORGANISM: Artificial
<220> FEATURE:
<223> OTHER INFORMATION: synthetic peptide

<400> SEQUENCE: 11

Ala Val Gly Val Gly Lys Ser Ala Leu
1               5

<210> SEQ ID NO 12
<211> LENGTH: 9
<212> TYPE: PRT
<213> ORGANISM: Artificial
<220> FEATURE:
<223> OTHER INFORMATION: synthetic peptide

<400> SEQUENCE: 12

Ala Gly Gly Val Gly Lys Ser Ala Leu
1               5

<210> SEQ ID NO 13
<211> LENGTH: 9
<212> TYPE: PRT
<213> ORGANISM: Artificial
<220> FEATURE:
<223> OTHER INFORMATION: synthetic peptide

<400> SEQUENCE: 13

Ile Met Gln Leu Met Pro Phe Gly Cys
1               5

<210> SEQ ID NO 14
<211> LENGTH: 9
<212> TYPE: PRT
<213> ORGANISM: Artificial
<220> FEATURE:
<223> OTHER INFORMATION: synthetic peptide

<400> SEQUENCE: 14

Ile Thr Gln Leu Met Pro Phe Gly Cys
1               5

<210> SEQ ID NO 15
<211> LENGTH: 10
<212> TYPE: PRT
<213> ORGANISM: Artificial
<220> FEATURE:
<223> OTHER INFORMATION: synthetic peptide

<400> SEQUENCE: 15

Gly Met Asn Gln Arg Pro Ile Leu Thr Ile
1               5                   10

<210> SEQ ID NO 16
<211> LENGTH: 10
<212> TYPE: PRT
<213> ORGANISM: Artificial
<220> FEATURE:
<223> OTHER INFORMATION: synthetic peptide

<400> SEQUENCE: 16

Gly Met Asn Trp Arg Pro Ile Leu Thr Ile
1               5                   10

<210> SEQ ID NO 17
<211> LENGTH: 10
<212> TYPE: PRT
```

<213> ORGANISM: Artificial
<220> FEATURE:
<223> OTHER INFORMATION: synthetic peptide

<400> SEQUENCE: 17

Gly Met Asn Arg Arg Pro Ile Leu Thr Ile
1               5                   10

<210> SEQ ID NO 18
<211> LENGTH: 9
<212> TYPE: PRT
<213> ORGANISM: Artificial
<220> FEATURE:
<223> OTHER INFORMATION: synthetic peptide

<400> SEQUENCE: 18

Leu Val Val Val Gly Ala Val Gly Val
1               5

<210> SEQ ID NO 19
<211> LENGTH: 9
<212> TYPE: PRT
<213> ORGANISM: Artificial
<220> FEATURE:
<223> OTHER INFORMATION: synthetic peptide

<400> SEQUENCE: 19

Leu Val Val Val Gly Ala Gly Gly Val
1               5

<210> SEQ ID NO 20
<211> LENGTH: 10
<212> TYPE: PRT
<213> ORGANISM: Artificial
<220> FEATURE:
<223> OTHER INFORMATION: synthetic peptide

<400> SEQUENCE: 20

Val Val Val Gly Ala Cys Gly Val Gly Lys
1               5                   10

<210> SEQ ID NO 21
<211> LENGTH: 10
<212> TYPE: PRT
<213> ORGANISM: Artificial
<220> FEATURE:
<223> OTHER INFORMATION: synthetic peptide

<400> SEQUENCE: 21

Val Val Val Gly Ala Asp Gly Val Gly Lys
1               5                   10

<210> SEQ ID NO 22
<211> LENGTH: 9
<212> TYPE: PRT
<213> ORGANISM: Artificial
<220> FEATURE:
<223> OTHER INFORMATION: synthetic peptide

<400> SEQUENCE: 22

Val Val Gly Ala Val Gly Val Gly Lys
1               5

<210> SEQ ID NO 23
<211> LENGTH: 10
<212> TYPE: PRT
<213> ORGANISM: Artificial

```
<220> FEATURE:
<223> OTHER INFORMATION: synthetic peptide

<400> SEQUENCE: 23

Val Val Val Gly Ala Gly Gly Val Gly Lys
1               5                   10

<210> SEQ ID NO 24
<211> LENGTH: 9
<212> TYPE: PRT
<213> ORGANISM: Artificial
<220> FEATURE:
<223> OTHER INFORMATION: synthetic peptide

<400> SEQUENCE: 24

Val Val Gly Ala Asp Gly Val Gly Lys
1               5

<210> SEQ ID NO 25
<211> LENGTH: 9
<212> TYPE: PRT
<213> ORGANISM: Artificial
<220> FEATURE:
<223> OTHER INFORMATION: synthetic peptide

<400> SEQUENCE: 25

Val Val Gly Ala Gly Gly Val Gly Lys
1               5

<210> SEQ ID NO 26
<211> LENGTH: 9
<212> TYPE: PRT
<213> ORGANISM: Artificial
<220> FEATURE:
<223> OTHER INFORMATION: synthetic peptide

<400> SEQUENCE: 26

Thr Thr Ala Pro Phe Leu Ser Gly Lys
1               5

<210> SEQ ID NO 27
<211> LENGTH: 9
<212> TYPE: PRT
<213> ORGANISM: Artificial
<220> FEATURE:
<223> OTHER INFORMATION: synthetic peptide

<400> SEQUENCE: 27

Thr Thr Ala Pro Ser Leu Ser Gly Lys
1               5

<210> SEQ ID NO 28
<211> LENGTH: 10
<212> TYPE: PRT
<213> ORGANISM: Artificial
<220> FEATURE:
<223> OTHER INFORMATION: synthetic peptide

<400> SEQUENCE: 28

Ile Leu Asp Thr Ala Gly His Glu Glu Tyr
1               5                   10

<210> SEQ ID NO 29
<211> LENGTH: 10
<212> TYPE: PRT
<213> ORGANISM: Artificial
<220> FEATURE:
```

```
<223> OTHER INFORMATION: synthetic peptide

<400> SEQUENCE: 29

Ile Leu Asp Thr Ala Gly Gln Glu Glu Tyr
1               5                   10

<210> SEQ ID NO 30
<211> LENGTH: 10
<212> TYPE: PRT
<213> ORGANISM: Artificial
<220> FEATURE:
<223> OTHER INFORMATION: synthetic peptide

<400> SEQUENCE: 30

Ile Leu Asp Thr Ala Gly Lys Glu Glu Tyr
1               5                   10

<210> SEQ ID NO 31
<211> LENGTH: 10
<212> TYPE: PRT
<213> ORGANISM: Artificial
<220> FEATURE:
<223> OTHER INFORMATION: synthetic peptide

<400> SEQUENCE: 31

Ile Leu Asp Thr Ala Gly Leu Glu Glu Tyr
1               5                   10

<210> SEQ ID NO 32
<211> LENGTH: 10
<212> TYPE: PRT
<213> ORGANISM: Artificial
<220> FEATURE:
<223> OTHER INFORMATION: synthetic peptide

<400> SEQUENCE: 32

Ile Leu Asp Thr Ala Gly Arg Glu Glu Tyr
1               5                   10

<210> SEQ ID NO 33
<211> LENGTH: 6
<212> TYPE: PRT
<213> ORGANISM: Artificial
<220> FEATURE:
<223> OTHER INFORMATION: synthetic peptide

<400> SEQUENCE: 33

Gln Asp Val Asn Thr Ala
1               5

<210> SEQ ID NO 34
<211> LENGTH: 9
<212> TYPE: PRT
<213> ORGANISM: Artificial
<220> FEATURE:
<223> OTHER INFORMATION: synthetic peptide

<400> SEQUENCE: 34

Gln Gln Tyr Asp Tyr Ala Pro Ile Thr
1               5

<210> SEQ ID NO 35
<211> LENGTH: 11
<212> TYPE: PRT
<213> ORGANISM: Artificial
<220> FEATURE:
<223> OTHER INFORMATION: synthetic peptide
```

```
<400> SEQUENCE: 35

Gln Gln Ser Pro Tyr Tyr Tyr Leu Pro Ile Thr
1               5                   10

<210> SEQ ID NO 36
<211> LENGTH: 9
<212> TYPE: PRT
<213> ORGANISM: Artificial
<220> FEATURE:
<223> OTHER INFORMATION: synthetic peptide

<400> SEQUENCE: 36

Gln Gln Tyr Tyr Tyr Ser Pro Val Thr
1               5

<210> SEQ ID NO 37
<211> LENGTH: 9
<212> TYPE: PRT
<213> ORGANISM: Artificial
<220> FEATURE:
<223> OTHER INFORMATION: synthetic peptide

<400> SEQUENCE: 37

Gln Gln His Tyr Gly Asn Pro Phe Thr
1               5

<210> SEQ ID NO 38
<211> LENGTH: 9
<212> TYPE: PRT
<213> ORGANISM: Artificial
<220> FEATURE:
<223> OTHER INFORMATION: synthetic peptide

<400> SEQUENCE: 38

Gln Gln Ser Tyr Tyr Ser Pro Pro Thr
1               5

<210> SEQ ID NO 39
<211> LENGTH: 9
<212> TYPE: PRT
<213> ORGANISM: Artificial
<220> FEATURE:
<223> OTHER INFORMATION: synthetic peptide

<400> SEQUENCE: 39

Gln Gln Tyr Tyr Ser Tyr Pro Pro Thr
1               5

<210> SEQ ID NO 40
<211> LENGTH: 9
<212> TYPE: PRT
<213> ORGANISM: Artificial
<220> FEATURE:
<223> OTHER INFORMATION: synthetic peptide

<400> SEQUENCE: 40

Gln Gln Tyr Tyr Tyr Tyr Pro Pro Thr
1               5

<210> SEQ ID NO 41
<211> LENGTH: 8
<212> TYPE: PRT
<213> ORGANISM: Artificial
<220> FEATURE:
<223> OTHER INFORMATION: synthetic peptide
```

```
<400> SEQUENCE: 41

Gly Phe Asn Ile Ser Trp Tyr Gln
1               5

<210> SEQ ID NO 42
<211> LENGTH: 8
<212> TYPE: PRT
<213> ORGANISM: Artificial
<220> FEATURE:
<223> OTHER INFORMATION: synthetic peptide

<400> SEQUENCE: 42

Gly Phe Asn Val Ser Trp Ser Tyr
1               5

<210> SEQ ID NO 43
<211> LENGTH: 8
<212> TYPE: PRT
<213> ORGANISM: Artificial
<220> FEATURE:
<223> OTHER INFORMATION: synthetic peptide

<400> SEQUENCE: 43

Gly Phe Asn Ile Ser Trp Asn Gln
1               5

<210> SEQ ID NO 44
<211> LENGTH: 8
<212> TYPE: PRT
<213> ORGANISM: Artificial
<220> FEATURE:
<223> OTHER INFORMATION: synthetic peptide

<400> SEQUENCE: 44

Gly Phe Asn Val Gly Tyr Tyr Gly
1               5

<210> SEQ ID NO 45
<211> LENGTH: 8
<212> TYPE: PRT
<213> ORGANISM: Artificial
<220> FEATURE:
<223> OTHER INFORMATION: synthetic peptide

<400> SEQUENCE: 45

Gly Phe Asn Ile Thr Ser Ser Tyr
1               5

<210> SEQ ID NO 46
<211> LENGTH: 8
<212> TYPE: PRT
<213> ORGANISM: Artificial
<220> FEATURE:
<223> OTHER INFORMATION: synthetic peptide

<400> SEQUENCE: 46

Gly Phe Asn Ile Asn Ser Ser Tyr
1               5

<210> SEQ ID NO 47
<211> LENGTH: 8
<212> TYPE: PRT
<213> ORGANISM: Artificial
<220> FEATURE:
<223> OTHER INFORMATION: synthetic peptide

<400> SEQUENCE: 47
```

Gly Phe Asn Ile Ser Thr Ser Tyr
1               5

<210> SEQ ID NO 48
<211> LENGTH: 8
<212> TYPE: PRT
<213> ORGANISM: Artificial
<220> FEATURE:
<223> OTHER INFORMATION: synthetic peptide

<400> SEQUENCE: 48

Val Thr Pro Tyr Ser Gly Tyr Thr
1               5

<210> SEQ ID NO 49
<211> LENGTH: 8
<212> TYPE: PRT
<213> ORGANISM: Artificial
<220> FEATURE:
<223> OTHER INFORMATION: synthetic peptide

<400> SEQUENCE: 49

Ile Tyr Gly Asp Ser Gly Tyr Thr
1               5

<210> SEQ ID NO 50
<211> LENGTH: 8
<212> TYPE: PRT
<213> ORGANISM: Artificial
<220> FEATURE:
<223> OTHER INFORMATION: synthetic peptide

<400> SEQUENCE: 50

Val Ser Pro Tyr Ser Gly Tyr Thr
1               5

<210> SEQ ID NO 51
<211> LENGTH: 8
<212> TYPE: PRT
<213> ORGANISM: Artificial
<220> FEATURE:
<223> OTHER INFORMATION: synthetic peptide

<400> SEQUENCE: 51

Val Ser Gly Met Glu Gly Tyr Thr
1               5

<210> SEQ ID NO 52
<211> LENGTH: 8
<212> TYPE: PRT
<213> ORGANISM: Artificial
<220> FEATURE:
<223> OTHER INFORMATION: synthetic peptide

<400> SEQUENCE: 52

Ile Ser Pro Ala Asp Gly Tyr Asn
1               5

<210> SEQ ID NO 53
<211> LENGTH: 8
<212> TYPE: PRT
<213> ORGANISM: Artificial
<220> FEATURE:
<223> OTHER INFORMATION: synthetic peptide

<400> SEQUENCE: 53

Ile Ser Pro Thr Asp Gly Tyr Tyr
1               5

<210> SEQ ID NO 54
<211> LENGTH: 8
<212> TYPE: PRT
<213> ORGANISM: Artificial
<220> FEATURE:
<223> OTHER INFORMATION: synthetic peptide

<400> SEQUENCE: 54

Ile Asp Pro Asn Asp Gly Tyr Ser
1               5

<210> SEQ ID NO 55
<211> LENGTH: 10
<212> TYPE: PRT
<213> ORGANISM: Artificial
<220> FEATURE:
<223> OTHER INFORMATION: synthetic peptide

<400> SEQUENCE: 55

Ser Arg Ser Tyr Thr Asp Gly Phe Asp Tyr
1               5                   10

<210> SEQ ID NO 56
<211> LENGTH: 14
<212> TYPE: PRT
<213> ORGANISM: Artificial
<220> FEATURE:
<223> OTHER INFORMATION: synthetic peptide

<400> SEQUENCE: 56

Ser Arg Gly Gln Trp Glu Ala Ser Tyr Tyr Ala Met Asp Tyr
1               5                   10

<210> SEQ ID NO 57
<211> LENGTH: 10
<212> TYPE: PRT
<213> ORGANISM: Artificial
<220> FEATURE:
<223> OTHER INFORMATION: synthetic peptide

<400> SEQUENCE: 57

Ser Arg Ser Asp Tyr Tyr Ala Met Asp Tyr
1               5                   10

<210> SEQ ID NO 58
<211> LENGTH: 11
<212> TYPE: PRT
<213> ORGANISM: Artificial
<220> FEATURE:
<223> OTHER INFORMATION: synthetic peptide

<400> SEQUENCE: 58

Ser Arg Asp Ile Tyr Gly Tyr Ala Met Asp Val
1               5                   10

<210> SEQ ID NO 59
<211> LENGTH: 13
<212> TYPE: PRT
<213> ORGANISM: Artificial
<220> FEATURE:
<223> OTHER INFORMATION: synthetic peptide

<400> SEQUENCE: 59

Ser Arg Thr Asp Ser Thr Ala Tyr Thr Ala Met Asp Val

```
<210> SEQ ID NO 60
<211> LENGTH: 13
<212> TYPE: PRT
<213> ORGANISM: Artificial
<220> FEATURE:
<223> OTHER INFORMATION: synthetic peptide

<400> SEQUENCE: 60

Ser Arg Thr Ser Asp Thr Ser Tyr Ala Ala Met Asp Val
1               5                   10

<210> SEQ ID NO 61
<211> LENGTH: 13
<212> TYPE: PRT
<213> ORGANISM: Artificial
<220> FEATURE:
<223> OTHER INFORMATION: synthetic peptide

<400> SEQUENCE: 61

Ser Arg Thr Asn Asn Thr Ala Ala Asp Ala Met Asp Val
1               5                   10

<210> SEQ ID NO 62
<211> LENGTH: 9
<212> TYPE: PRT
<213> ORGANISM: Artificial
<220> FEATURE:
<223> OTHER INFORMATION: synthetic peptide

<400> SEQUENCE: 62

Gln Gln Tyr Ser Tyr Ser Pro Pro Thr
1               5

<210> SEQ ID NO 63
<211> LENGTH: 10
<212> TYPE: PRT
<213> ORGANISM: Artificial
<220> FEATURE:
<223> OTHER INFORMATION: synthetic peptide

<400> SEQUENCE: 63

Gln Gln Gly Lys Ala Tyr Trp Pro Ala Thr
1               5                   10

<210> SEQ ID NO 64
<211> LENGTH: 9
<212> TYPE: PRT
<213> ORGANISM: Artificial
<220> FEATURE:
<223> OTHER INFORMATION: synthetic peptide

<400> SEQUENCE: 64

Gln Gln Val Tyr Ser Ser Pro Phe Thr
1               5

<210> SEQ ID NO 65
<211> LENGTH: 10
<212> TYPE: PRT
<213> ORGANISM: Artificial
<220> FEATURE:
<223> OTHER INFORMATION: synthetic peptide

<400> SEQUENCE: 65

Gln Gln Tyr Ser Leu Tyr Ser Pro Met Thr
1               5                   10
```

```
<210> SEQ ID NO 66
<211> LENGTH: 9
<212> TYPE: PRT
<213> ORGANISM: Artificial
<220> FEATURE:
<223> OTHER INFORMATION: synthetic peptide

<400> SEQUENCE: 66

Gln Gln Ser Tyr Tyr Met Pro Phe Thr
1               5

<210> SEQ ID NO 67
<211> LENGTH: 8
<212> TYPE: PRT
<213> ORGANISM: Artificial
<220> FEATURE:
<223> OTHER INFORMATION: synthetic peptide

<400> SEQUENCE: 67

Gly Phe Asn Ile Ser Asp Thr Tyr
1               5

<210> SEQ ID NO 68
<211> LENGTH: 8
<212> TYPE: PRT
<213> ORGANISM: Artificial
<220> FEATURE:
<223> OTHER INFORMATION: synthetic peptide

<400> SEQUENCE: 68

Gly Phe Asn Val Gly His Tyr Arg
1               5

<210> SEQ ID NO 69
<211> LENGTH: 8
<212> TYPE: PRT
<213> ORGANISM: Artificial
<220> FEATURE:
<223> OTHER INFORMATION: synthetic peptide

<400> SEQUENCE: 69

Gly Phe Asn Val Lys Tyr Tyr Met
1               5

<210> SEQ ID NO 70
<211> LENGTH: 7
<212> TYPE: PRT
<213> ORGANISM: Artificial
<220> FEATURE:
<223> OTHER INFORMATION: synthetic peptide

<400> SEQUENCE: 70

Gly Phe Asn Ser Phe Leu Ser
1               5

<210> SEQ ID NO 71
<211> LENGTH: 8
<212> TYPE: PRT
<213> ORGANISM: Artificial
<220> FEATURE:
<223> OTHER INFORMATION: synthetic peptide

<400> SEQUENCE: 71

Gly Phe Asn Ile Phe Arg Gly Tyr
1               5
```

<210> SEQ ID NO 72
<211> LENGTH: 8
<212> TYPE: PRT
<213> ORGANISM: Artificial
<220> FEATURE:
<223> OTHER INFORMATION: synthetic peptide

<400> SEQUENCE: 72

Ile Ser Pro Arg Thr Gly Tyr Asn
1               5

<210> SEQ ID NO 73
<211> LENGTH: 8
<212> TYPE: PRT
<213> ORGANISM: Artificial
<220> FEATURE:
<223> OTHER INFORMATION: synthetic peptide

<400> SEQUENCE: 73

Val Ser Pro Asn Gly Tyr Tyr Thr
1               5

<210> SEQ ID NO 74
<211> LENGTH: 8
<212> TYPE: PRT
<213> ORGANISM: Artificial
<220> FEATURE:
<223> OTHER INFORMATION: synthetic peptide

<400> SEQUENCE: 74

Ile Ser Pro Gly Tyr Asp Tyr Thr
1               5

<210> SEQ ID NO 75
<211> LENGTH: 8
<212> TYPE: PRT
<213> ORGANISM: Artificial
<220> FEATURE:
<223> OTHER INFORMATION: synthetic peptide

<400> SEQUENCE: 75

Ile Phe Pro Ser Ser Asp Tyr Thr
1               5

<210> SEQ ID NO 76
<211> LENGTH: 8
<212> TYPE: PRT
<213> ORGANISM: Artificial
<220> FEATURE:
<223> OTHER INFORMATION: synthetic peptide

<400> SEQUENCE: 76

Ile Ser Pro His Ser Asp Tyr Thr
1               5

<210> SEQ ID NO 77
<211> LENGTH: 13
<212> TYPE: PRT
<213> ORGANISM: Artificial
<220> FEATURE:
<223> OTHER INFORMATION: synthetic peptide

<400> SEQUENCE: 77

Ser Arg Ala Tyr Tyr Ser Tyr Ala Tyr Ala Met Asp Val
1               5                   10

-continued

```
<210> SEQ ID NO 78
<211> LENGTH: 11
<212> TYPE: PRT
<213> ORGANISM: Artificial
<220> FEATURE:
<223> OTHER INFORMATION: synthetic peptide

<400> SEQUENCE: 78

Ser Arg Gly Tyr Ser Ser Tyr Ala Phe Asp Tyr
1               5                   10

<210> SEQ ID NO 79
<211> LENGTH: 11
<212> TYPE: PRT
<213> ORGANISM: Artificial
<220> FEATURE:
<223> OTHER INFORMATION: synthetic peptide

<400> SEQUENCE: 79

Ser Arg Ser Tyr Trp Arg Tyr Ser Val Asp Val
1               5                   10

<210> SEQ ID NO 80
<211> LENGTH: 15
<212> TYPE: PRT
<213> ORGANISM: Artificial
<220> FEATURE:
<223> OTHER INFORMATION: synthetic peptide

<400> SEQUENCE: 80

Ser Arg Gly Lys His Ser Ser Asp Ser Asn Tyr Tyr Met Asp Tyr
1               5                   10                  15

<210> SEQ ID NO 81
<211> LENGTH: 11
<212> TYPE: PRT
<213> ORGANISM: Artificial
<220> FEATURE:
<223> OTHER INFORMATION: synthetic peptide

<400> SEQUENCE: 81

Ser Arg Ser Tyr Gly Trp Ala Ala Phe Asp Tyr
1               5                   10

<210> SEQ ID NO 82
<211> LENGTH: 9
<212> TYPE: PRT
<213> ORGANISM: Artificial
<220> FEATURE:
<223> OTHER INFORMATION: synthetic peptide

<400> SEQUENCE: 82

Gln Gln Ser Gly Tyr Ala Pro Ile Thr
1               5

<210> SEQ ID NO 83
<211> LENGTH: 9
<212> TYPE: PRT
<213> ORGANISM: Artificial
<220> FEATURE:
<223> OTHER INFORMATION: synthetic peptide

<400> SEQUENCE: 83

Gln Gln Tyr Ser Tyr Ala Pro Ile Thr
1               5

<210> SEQ ID NO 84
```

```
<211> LENGTH: 9
<212> TYPE: PRT
<213> ORGANISM: Artificial
<220> FEATURE:
<223> OTHER INFORMATION: synthetic peptide

<400> SEQUENCE: 84

Gln Gln Ser Leu Tyr Gly Pro Phe Thr
1               5

<210> SEQ ID NO 85
<211> LENGTH: 9
<212> TYPE: PRT
<213> ORGANISM: Artificial
<220> FEATURE:
<223> OTHER INFORMATION: synthetic peptide

<400> SEQUENCE: 85

Gln Gln Tyr Ser Tyr Ser Pro Ile Thr
1               5

<210> SEQ ID NO 86
<211> LENGTH: 9
<212> TYPE: PRT
<213> ORGANISM: Artificial
<220> FEATURE:
<223> OTHER INFORMATION: synthetic peptide

<400> SEQUENCE: 86

Gln Gln Ser Gly Tyr Gln Pro Asp Thr
1               5

<210> SEQ ID NO 87
<211> LENGTH: 9
<212> TYPE: PRT
<213> ORGANISM: Artificial
<220> FEATURE:
<223> OTHER INFORMATION: synthetic peptide

<400> SEQUENCE: 87

Gln Gln Tyr Leu Tyr Gln Pro Trp Thr
1               5

<210> SEQ ID NO 88
<211> LENGTH: 9
<212> TYPE: PRT
<213> ORGANISM: Artificial
<220> FEATURE:
<223> OTHER INFORMATION: synthetic peptide

<400> SEQUENCE: 88

Gln Gln Gly Leu Tyr Tyr Pro Trp Thr
1               5

<210> SEQ ID NO 89
<211> LENGTH: 8
<212> TYPE: PRT
<213> ORGANISM: Artificial
<220> FEATURE:
<223> OTHER INFORMATION: synthetic peptide

<400> SEQUENCE: 89

Gly Phe Asn Ile Ser Tyr Tyr Ser
1               5

<210> SEQ ID NO 90
<211> LENGTH: 8
```

```
<212> TYPE: PRT
<213> ORGANISM: Artificial
<220> FEATURE:
<223> OTHER INFORMATION: synthetic peptide

<400> SEQUENCE: 90

Gly Phe Asn Ile Gly Tyr Tyr Thr
1               5

<210> SEQ ID NO 91
<211> LENGTH: 8
<212> TYPE: PRT
<213> ORGANISM: Artificial
<220> FEATURE:
<223> OTHER INFORMATION: synthetic peptide

<400> SEQUENCE: 91

Gly Phe Asn Ile Ala Tyr Glu Tyr
1               5

<210> SEQ ID NO 92
<211> LENGTH: 8
<212> TYPE: PRT
<213> ORGANISM: Artificial
<220> FEATURE:
<223> OTHER INFORMATION: synthetic peptide

<400> SEQUENCE: 92

Gly Phe Asn Leu Phe Gly Tyr Gly
1               5

<210> SEQ ID NO 93
<211> LENGTH: 8
<212> TYPE: PRT
<213> ORGANISM: Artificial
<220> FEATURE:
<223> OTHER INFORMATION: synthetic peptide

<400> SEQUENCE: 93

Gly Phe Asn Ile Ser Trp Tyr Ala
1               5

<210> SEQ ID NO 94
<211> LENGTH: 8
<212> TYPE: PRT
<213> ORGANISM: Artificial
<220> FEATURE:
<223> OTHER INFORMATION: synthetic peptide

<400> SEQUENCE: 94

Gly Phe Asn Ile Asp Tyr Tyr Gly
1               5

<210> SEQ ID NO 95
<211> LENGTH: 8
<212> TYPE: PRT
<213> ORGANISM: Artificial
<220> FEATURE:
<223> OTHER INFORMATION: synthetic peptide

<400> SEQUENCE: 95

Gly Phe Asn Val Ser Tyr Ser Ser
1               5

<210> SEQ ID NO 96
<211> LENGTH: 8
<212> TYPE: PRT
```

```
<213> ORGANISM: Artificial
<220> FEATURE:
<223> OTHER INFORMATION: synthetic peptide

<400> SEQUENCE: 96

Val Asp Pro Asp Ser Asp Tyr Thr
1               5

<210> SEQ ID NO 97
<211> LENGTH: 8
<212> TYPE: PRT
<213> ORGANISM: Artificial
<220> FEATURE:
<223> OTHER INFORMATION: synthetic peptide

<400> SEQUENCE: 97

Val Ser Pro Trp Ser Tyr Ser Thr
1               5

<210> SEQ ID NO 98
<211> LENGTH: 8
<212> TYPE: PRT
<213> ORGANISM: Artificial
<220> FEATURE:
<223> OTHER INFORMATION: synthetic peptide

<400> SEQUENCE: 98

Ile Gly Pro Asp Ser Gly Tyr Thr
1               5

<210> SEQ ID NO 99
<211> LENGTH: 8
<212> TYPE: PRT
<213> ORGANISM: Artificial
<220> FEATURE:
<223> OTHER INFORMATION: synthetic peptide

<400> SEQUENCE: 99

Ile Gly Pro Tyr Tyr Tyr Tyr Thr
1               5

<210> SEQ ID NO 100
<211> LENGTH: 8
<212> TYPE: PRT
<213> ORGANISM: Artificial
<220> FEATURE:
<223> OTHER INFORMATION: synthetic peptide

<400> SEQUENCE: 100

Ile Trp Pro Asp Ser Asp Trp Thr
1               5

<210> SEQ ID NO 101
<211> LENGTH: 8
<212> TYPE: PRT
<213> ORGANISM: Artificial
<220> FEATURE:
<223> OTHER INFORMATION: synthetic peptide

<400> SEQUENCE: 101

Leu Tyr Gly Gly Ser Asp Ser Thr
1               5

<210> SEQ ID NO 102
<211> LENGTH: 8
<212> TYPE: PRT
<213> ORGANISM: Artificial
```

```
<220> FEATURE:
<223> OTHER INFORMATION: synthetic peptide

<400> SEQUENCE: 102

Ile Trp Pro Asp Ser Gly Gln Thr
1               5

<210> SEQ ID NO 103
<211> LENGTH: 12
<212> TYPE: PRT
<213> ORGANISM: Artificial
<220> FEATURE:
<223> OTHER INFORMATION: synthetic peptide

<400> SEQUENCE: 103

Ser Arg Ser Trp Ile His Met Phe Ser Met Asp Tyr
1               5                   10

<210> SEQ ID NO 104
<211> LENGTH: 11
<212> TYPE: PRT
<213> ORGANISM: Artificial
<220> FEATURE:
<223> OTHER INFORMATION: synthetic peptide

<400> SEQUENCE: 104

Ser Arg Asp His Trp Asp Glu Ala Phe Asp Val
1               5                   10

<210> SEQ ID NO 105
<211> LENGTH: 13
<212> TYPE: PRT
<213> ORGANISM: Artificial
<220> FEATURE:
<223> OTHER INFORMATION: synthetic peptide

<400> SEQUENCE: 105

Ser Arg Val Trp Tyr Tyr Ser Thr Tyr Gly Met Asp Tyr
1               5                   10

<210> SEQ ID NO 106
<211> LENGTH: 11
<212> TYPE: PRT
<213> ORGANISM: Artificial
<220> FEATURE:
<223> OTHER INFORMATION: synthetic peptide

<400> SEQUENCE: 106

Ser Arg Glu Asn Tyr Asp Met Ala Met Asp Tyr
1               5                   10

<210> SEQ ID NO 107
<211> LENGTH: 11
<212> TYPE: PRT
<213> ORGANISM: Artificial
<220> FEATURE:
<223> OTHER INFORMATION: synthetic peptide

<400> SEQUENCE: 107

Ser Arg Tyr Tyr Tyr Ser Ser Ala Phe Asp Val
1               5                   10

<210> SEQ ID NO 108
<211> LENGTH: 10
<212> TYPE: PRT
<213> ORGANISM: Artificial
<220> FEATURE:
```

```
<223> OTHER INFORMATION: synthetic peptide

<400> SEQUENCE: 108

Ser Arg Gln Tyr Ser Ala Tyr Phe Asp Tyr
1               5                   10

<210> SEQ ID NO 109
<211> LENGTH: 11
<212> TYPE: PRT
<213> ORGANISM: Artificial
<220> FEATURE:
<223> OTHER INFORMATION: synthetic peptide

<400> SEQUENCE: 109

Ser Arg Ser Ser Tyr Phe Asp Ala Met Asp Tyr
1               5                   10

<210> SEQ ID NO 110
<211> LENGTH: 9
<212> TYPE: PRT
<213> ORGANISM: Artificial
<220> FEATURE:
<223> OTHER INFORMATION: synthetic peptide

<400> SEQUENCE: 110

Gln Gln Trp Tyr Ser Ser Pro Val Thr
1               5

<210> SEQ ID NO 111
<211> LENGTH: 8
<212> TYPE: PRT
<213> ORGANISM: Artificial
<220> FEATURE:
<223> OTHER INFORMATION: synthetic peptide

<400> SEQUENCE: 111

Gly Phe Asn Ile Asn Trp Ala Asn
1               5

<210> SEQ ID NO 112
<211> LENGTH: 8
<212> TYPE: PRT
<213> ORGANISM: Artificial
<220> FEATURE:
<223> OTHER INFORMATION: synthetic peptide

<400> SEQUENCE: 112

Gly Phe Asn Ile Asn Trp Ala Asn
1               5

<210> SEQ ID NO 113
<211> LENGTH: 8
<212> TYPE: PRT
<213> ORGANISM: Artificial
<220> FEATURE:
<223> OTHER INFORMATION: synthetic peptide

<400> SEQUENCE: 113

Gly Phe Asn Ile Tyr Leu His Asp
1               5

<210> SEQ ID NO 114
<211> LENGTH: 8
<212> TYPE: PRT
<213> ORGANISM: Artificial
<220> FEATURE:
<223> OTHER INFORMATION: synthetic peptide
```

```
<400> SEQUENCE: 114

Gly Phe Asn Ile Tyr Trp Ser His
1               5

<210> SEQ ID NO 115
<211> LENGTH: 8
<212> TYPE: PRT
<213> ORGANISM: Artificial
<220> FEATURE:
<223> OTHER INFORMATION: synthetic peptide

<400> SEQUENCE: 115

Ile Ser Pro Pro Tyr Asp Tyr Thr
1               5

<210> SEQ ID NO 116
<211> LENGTH: 8
<212> TYPE: PRT
<213> ORGANISM: Artificial
<220> FEATURE:
<223> OTHER INFORMATION: synthetic peptide

<400> SEQUENCE: 116

Ile Ile Pro Ala Ile Asp Tyr Thr
1               5

<210> SEQ ID NO 117
<211> LENGTH: 8
<212> TYPE: PRT
<213> ORGANISM: Artificial
<220> FEATURE:
<223> OTHER INFORMATION: synthetic peptide

<400> SEQUENCE: 117

Ile Ser Ser Phe Glu Gly Tyr Thr
1               5

<210> SEQ ID NO 118
<211> LENGTH: 10
<212> TYPE: PRT
<213> ORGANISM: Artificial
<220> FEATURE:
<223> OTHER INFORMATION: synthetic peptide

<400> SEQUENCE: 118

Ser Arg Ser Tyr Ser Tyr Tyr Phe Asp Tyr
1               5                   10

<210> SEQ ID NO 119
<211> LENGTH: 10
<212> TYPE: PRT
<213> ORGANISM: Artificial
<220> FEATURE:
<223> OTHER INFORMATION: synthetic peptide

<400> SEQUENCE: 119

Ser Arg Arg Asp Gly Tyr Tyr Phe Asp Tyr
1               5                   10

<210> SEQ ID NO 120
<211> LENGTH: 10
<212> TYPE: PRT
<213> ORGANISM: Artificial
<220> FEATURE:
<223> OTHER INFORMATION: synthetic peptide
```

```
<400> SEQUENCE: 120

Ser Arg Ser Tyr Ser Tyr Tyr Met Asp Tyr
1               5                   10

<210> SEQ ID NO 121
<211> LENGTH: 11
<212> TYPE: PRT
<213> ORGANISM: Artificial
<220> FEATURE:
<223> OTHER INFORMATION: synthetic peptide

<400> SEQUENCE: 121

Gln Gln Ser Tyr Gly Ser Gly Ser Pro Trp Thr
1               5                   10

<210> SEQ ID NO 122
<211> LENGTH: 9
<212> TYPE: PRT
<213> ORGANISM: Artificial
<220> FEATURE:
<223> OTHER INFORMATION: synthetic peptide

<400> SEQUENCE: 122

Gln Gln Thr Tyr Tyr Ser Pro Trp Thr
1               5

<210> SEQ ID NO 123
<211> LENGTH: 9
<212> TYPE: PRT
<213> ORGANISM: Artificial
<220> FEATURE:
<223> OTHER INFORMATION: synthetic peptide

<400> SEQUENCE: 123

Gln Gln Tyr Tyr Tyr Pro Pro Ile Thr
1               5

<210> SEQ ID NO 124
<211> LENGTH: 8
<212> TYPE: PRT
<213> ORGANISM: Artificial
<220> FEATURE:
<223> OTHER INFORMATION: synthetic peptide

<400> SEQUENCE: 124

Gly Phe Asn Ile Val Gly Gly Gly
1               5

<210> SEQ ID NO 125
<211> LENGTH: 8
<212> TYPE: PRT
<213> ORGANISM: Artificial
<220> FEATURE:
<223> OTHER INFORMATION: synthetic peptide

<400> SEQUENCE: 125

Gly Phe Asn Ile Arg Ser Tyr Ala
1               5

<210> SEQ ID NO 126
<211> LENGTH: 8
<212> TYPE: PRT
<213> ORGANISM: Artificial
<220> FEATURE:
<223> OTHER INFORMATION: synthetic peptide

<400> SEQUENCE: 126
```

```
Gly Phe Asn Val Ser His Thr Gly
1               5
```

<210> SEQ ID NO 127
<211> LENGTH: 8
<212> TYPE: PRT
<213> ORGANISM: Artificial
<220> FEATURE:
<223> OTHER INFORMATION: synthetic peptide

<400> SEQUENCE: 127

```
Ile Tyr Pro Gln Gly Asp Tyr Thr
1               5
```

<210> SEQ ID NO 128
<211> LENGTH: 8
<212> TYPE: PRT
<213> ORGANISM: Artificial
<220> FEATURE:
<223> OTHER INFORMATION: synthetic peptide

<400> SEQUENCE: 128

```
Val Gly Pro Gly Lys Gly Tyr Thr
1               5
```

<210> SEQ ID NO 129
<211> LENGTH: 11
<212> TYPE: PRT
<213> ORGANISM: Artificial
<220> FEATURE:
<223> OTHER INFORMATION: synthetic peptide

<400> SEQUENCE: 129

```
Ser Arg Asp Ser Ser Tyr Leu Ala Phe Asp Tyr
1               5                   10
```

<210> SEQ ID NO 130
<211> LENGTH: 13
<212> TYPE: PRT
<213> ORGANISM: Artificial
<220> FEATURE:
<223> OTHER INFORMATION: synthetic peptide

<400> SEQUENCE: 130

```
Ser Arg Asn Phe Gln Ser Thr Ser His Ala Phe Asp Tyr
1               5                   10
```

<210> SEQ ID NO 131
<211> LENGTH: 10
<212> TYPE: PRT
<213> ORGANISM: Artificial
<220> FEATURE:
<223> OTHER INFORMATION: synthetic peptide

<400> SEQUENCE: 131

```
Ser Arg Lys Thr Tyr Tyr Ala Phe Asp Tyr
1               5                   10
```

<210> SEQ ID NO 132
<211> LENGTH: 11
<212> TYPE: PRT
<213> ORGANISM: Artificial
<220> FEATURE:
<223> OTHER INFORMATION: synthetic peptide

<400> SEQUENCE: 132

Gln Gln Ser Tyr Tyr Tyr Phe Arg Pro Ile Thr
1               5                   10

<210> SEQ ID NO 133
<211> LENGTH: 10
<212> TYPE: PRT
<213> ORGANISM: Artificial
<220> FEATURE:
<223> OTHER INFORMATION: synthetic peptide

<400> SEQUENCE: 133

Gln Gln Ala Ser Tyr Tyr Tyr Pro Leu Thr
1               5                   10

<210> SEQ ID NO 134
<211> LENGTH: 10
<212> TYPE: PRT
<213> ORGANISM: Artificial
<220> FEATURE:
<223> OTHER INFORMATION: synthetic peptide

<400> SEQUENCE: 134

Gln Gln Lys Ser Glu Tyr Ser Pro Trp Thr
1               5                   10

<210> SEQ ID NO 135
<211> LENGTH: 9
<212> TYPE: PRT
<213> ORGANISM: Artificial
<220> FEATURE:
<223> OTHER INFORMATION: synthetic peptide

<400> SEQUENCE: 135

Gln Gln Ser Gly Tyr Ile Pro Phe Thr
1               5

<210> SEQ ID NO 136
<211> LENGTH: 10
<212> TYPE: PRT
<213> ORGANISM: Artificial
<220> FEATURE:
<223> OTHER INFORMATION: synthetic peptide

<400> SEQUENCE: 136

Gln Gln Gly Ala Tyr Tyr Arg Pro Phe Thr
1               5                   10

<210> SEQ ID NO 137
<211> LENGTH: 8
<212> TYPE: PRT
<213> ORGANISM: Artificial
<220> FEATURE:
<223> OTHER INFORMATION: synthetic peptide

<400> SEQUENCE: 137

Gly Phe Asn Leu Ser Tyr Ser Asp
1               5

<210> SEQ ID NO 138
<211> LENGTH: 8
<212> TYPE: PRT
<213> ORGANISM: Artificial
<220> FEATURE:
<223> OTHER INFORMATION: synthetic peptide

<400> SEQUENCE: 138

Gly Phe Asn Ile Ser Ala Ser Gly 1               5

<210> SEQ ID NO 139
<211> LENGTH: 8
<212> TYPE: PRT
<213> ORGANISM: Artificial
<220> FEATURE:
<223> OTHER INFORMATION: synthetic peptide

<400> SEQUENCE: 139

Gly Phe Asn Ile Tyr Arg Tyr Gly
1               5

<210> SEQ ID NO 140
<211> LENGTH: 8
<212> TYPE: PRT
<213> ORGANISM: Artificial
<220> FEATURE:
<223> OTHER INFORMATION: synthetic peptide

<400> SEQUENCE: 140

Gly Phe Asn Ile Tyr Gly Thr Met
1               5

<210> SEQ ID NO 141
<211> LENGTH: 8
<212> TYPE: PRT
<213> ORGANISM: Artificial
<220> FEATURE:
<223> OTHER INFORMATION: synthetic peptide

<400> SEQUENCE: 141

Gly Phe Asn Ile Ser Tyr Ser Tyr
1               5

<210> SEQ ID NO 142
<211> LENGTH: 8
<212> TYPE: PRT
<213> ORGANISM: Artificial
<220> FEATURE:
<223> OTHER INFORMATION: synthetic peptide

<400> SEQUENCE: 142

Val Met Pro Asp Ser Gly His Thr
1               5

<210> SEQ ID NO 143
<211> LENGTH: 8
<212> TYPE: PRT
<213> ORGANISM: Artificial
<220> FEATURE:
<223> OTHER INFORMATION: synthetic peptide

<400> SEQUENCE: 143

Ile His Pro Leu Lys Pro Tyr Thr
1               5

<210> SEQ ID NO 144
<211> LENGTH: 8
<212> TYPE: PRT
<213> ORGANISM: Artificial
<220> FEATURE:
<223> OTHER INFORMATION: synthetic peptide

<400> SEQUENCE: 144

Leu Tyr Pro Tyr Gly Tyr Ser Thr
1               5

```
<210> SEQ ID NO 145
<211> LENGTH: 8
<212> TYPE: PRT
<213> ORGANISM: Artificial
<220> FEATURE:
<223> OTHER INFORMATION: synthetic peptide

<400> SEQUENCE: 145

Phe Lys Pro Asp Ser Tyr Asn Thr
1               5

<210> SEQ ID NO 146
<211> LENGTH: 8
<212> TYPE: PRT
<213> ORGANISM: Artificial
<220> FEATURE:
<223> OTHER INFORMATION: synthetic peptide

<400> SEQUENCE: 146

Leu Leu Pro Tyr Asp Gly Asn Thr
1               5

<210> SEQ ID NO 147
<211> LENGTH: 13
<212> TYPE: PRT
<213> ORGANISM: Artificial
<220> FEATURE:
<223> OTHER INFORMATION: synthetic peptide

<400> SEQUENCE: 147

Ser Arg Ala Thr Asn Ile Pro Val Tyr Ala Phe Asp Tyr
1               5                   10

<210> SEQ ID NO 148
<211> LENGTH: 13
<212> TYPE: PRT
<213> ORGANISM: Artificial
<220> FEATURE:
<223> OTHER INFORMATION: synthetic peptide

<400> SEQUENCE: 148

Ser Arg Tyr Ser Ser Met Tyr Tyr Tyr Tyr Phe Asp Tyr
1               5                   10

<210> SEQ ID NO 149
<211> LENGTH: 11
<212> TYPE: PRT
<213> ORGANISM: Artificial
<220> FEATURE:
<223> OTHER INFORMATION: synthetic peptide

<400> SEQUENCE: 149

Ser Arg Ser Tyr Ala Tyr Gly Tyr Phe Ala Tyr
1               5                   10

<210> SEQ ID NO 150
<211> LENGTH: 13
<212> TYPE: PRT
<213> ORGANISM: Artificial
<220> FEATURE:
<223> OTHER INFORMATION: synthetic peptide

<400> SEQUENCE: 150

Ser Arg Gly Glu Val Tyr His Tyr Tyr Ala Phe Asp Tyr
1               5                   10
```

<210> SEQ ID NO 151
<211> LENGTH: 10
<212> TYPE: PRT
<213> ORGANISM: Artificial
<220> FEATURE:
<223> OTHER INFORMATION: synthetic peptide

<400> SEQUENCE: 151

Ser Arg Ala Ala Tyr Ser Ser Met Asp Val
1               5                   10

<210> SEQ ID NO 152
<211> LENGTH: 9
<212> TYPE: PRT
<213> ORGANISM: Artificial
<220> FEATURE:
<223> OTHER INFORMATION: synthetic peptide

<400> SEQUENCE: 152

Gln Gln Tyr Met Tyr Ser Pro Val Thr
1               5

<210> SEQ ID NO 153
<211> LENGTH: 9
<212> TYPE: PRT
<213> ORGANISM: Artificial
<220> FEATURE:
<223> OTHER INFORMATION: synthetic peptide

<400> SEQUENCE: 153

Gln Gln Ser Ser Ser Ser Pro Ile Thr
1               5

<210> SEQ ID NO 154
<211> LENGTH: 9
<212> TYPE: PRT
<213> ORGANISM: Artificial
<220> FEATURE:
<223> OTHER INFORMATION: synthetic peptide

<400> SEQUENCE: 154

Gln Gln Ser Ser Ala Ser Pro Leu Thr
1               5

<210> SEQ ID NO 155
<211> LENGTH: 9
<212> TYPE: PRT
<213> ORGANISM: Artificial
<220> FEATURE:
<223> OTHER INFORMATION: synthetic peptide

<400> SEQUENCE: 155

Gln Gln Tyr Ala Tyr Ser Pro Leu Thr
1               5

<210> SEQ ID NO 156
<211> LENGTH: 8
<212> TYPE: PRT
<213> ORGANISM: Artificial
<220> FEATURE:
<223> OTHER INFORMATION: synthetic peptide

<400> SEQUENCE: 156

Gly Phe Asn Val Ser Ala Tyr Trp
1               5

```
<210> SEQ ID NO 157
<211> LENGTH: 8
<212> TYPE: PRT
<213> ORGANISM: Artificial
<220> FEATURE:
<223> OTHER INFORMATION: synthetic peptide

<400> SEQUENCE: 157

Gly Phe Asn Ile Ser Gly Tyr Gly
1               5

<210> SEQ ID NO 158
<211> LENGTH: 8
<212> TYPE: PRT
<213> ORGANISM: Artificial
<220> FEATURE:
<223> OTHER INFORMATION: synthetic peptide

<400> SEQUENCE: 158

Gly Phe Asn Val Ser Ser Val Gly
1               5

<210> SEQ ID NO 159
<211> LENGTH: 8
<212> TYPE: PRT
<213> ORGANISM: Artificial
<220> FEATURE:
<223> OTHER INFORMATION: synthetic peptide

<400> SEQUENCE: 159

Gly Phe Asn Val Ser Ser Tyr Gly
1               5

<210> SEQ ID NO 160
<211> LENGTH: 8
<212> TYPE: PRT
<213> ORGANISM: Artificial
<220> FEATURE:
<223> OTHER INFORMATION: synthetic peptide

<400> SEQUENCE: 160

Ile Tyr Gly Gly Ser Gly Tyr Thr
1               5

<210> SEQ ID NO 161
<211> LENGTH: 8
<212> TYPE: PRT
<213> ORGANISM: Artificial
<220> FEATURE:
<223> OTHER INFORMATION: synthetic peptide

<400> SEQUENCE: 161

Leu Tyr Gly Gly Ser Asp Tyr Thr
1               5

<210> SEQ ID NO 162
<211> LENGTH: 8
<212> TYPE: PRT
<213> ORGANISM: Artificial
<220> FEATURE:
<223> OTHER INFORMATION: synthetic peptide

<400> SEQUENCE: 162

Ile Tyr Gly Thr Ser Asp Tyr Thr
1               5

<210> SEQ ID NO 163
```

```
<211> LENGTH: 8
<212> TYPE: PRT
<213> ORGANISM: Artificial
<220> FEATURE:
<223> OTHER INFORMATION: synthetic peptide

<400> SEQUENCE: 163

Ile Ala Pro Arg Arg Asp Tyr Thr
1               5

<210> SEQ ID NO 164
<211> LENGTH: 12
<212> TYPE: PRT
<213> ORGANISM: Artificial
<220> FEATURE:
<223> OTHER INFORMATION: synthetic peptide

<400> SEQUENCE: 164

Ser Arg Thr His Ser Tyr Trp Ser Ala Phe Asp Tyr
1               5                   10

<210> SEQ ID NO 165
<211> LENGTH: 10
<212> TYPE: PRT
<213> ORGANISM: Artificial
<220> FEATURE:
<223> OTHER INFORMATION: synthetic peptide

<400> SEQUENCE: 165

Ser Arg Thr Val Arg Tyr Ala Phe Asp Tyr
1               5                   10

<210> SEQ ID NO 166
<211> LENGTH: 10
<212> TYPE: PRT
<213> ORGANISM: Artificial
<220> FEATURE:
<223> OTHER INFORMATION: synthetic peptide

<400> SEQUENCE: 166

Ser Arg Ser Ser Arg Tyr Ser Met Asp Tyr
1               5                   10

<210> SEQ ID NO 167
<211> LENGTH: 10
<212> TYPE: PRT
<213> ORGANISM: Artificial
<220> FEATURE:
<223> OTHER INFORMATION: synthetic peptide

<400> SEQUENCE: 167

Ser Arg Lys Ser Ser Tyr Tyr Phe Asp Tyr
1               5                   10

<210> SEQ ID NO 168
<211> LENGTH: 9
<212> TYPE: PRT
<213> ORGANISM: Artificial
<220> FEATURE:
<223> OTHER INFORMATION: synthetic peptide

<400> SEQUENCE: 168

Gln Gln Tyr Ser Tyr Tyr Pro Ile Thr
1               5

<210> SEQ ID NO 169
<211> LENGTH: 9
```

```
<212> TYPE: PRT
<213> ORGANISM: Artificial
<220> FEATURE:
<223> OTHER INFORMATION: synthetic peptide

<400> SEQUENCE: 169

Gln Gln Tyr Ser Tyr Thr Pro Val Thr
1               5

<210> SEQ ID NO 170
<211> LENGTH: 9
<212> TYPE: PRT
<213> ORGANISM: Artificial
<220> FEATURE:
<223> OTHER INFORMATION: synthetic peptide

<400> SEQUENCE: 170

Gln Gln Tyr Ser Tyr Glu Pro Val Thr
1               5

<210> SEQ ID NO 171
<211> LENGTH: 10
<212> TYPE: PRT
<213> ORGANISM: Artificial
<220> FEATURE:
<223> OTHER INFORMATION: synthetic peptide

<400> SEQUENCE: 171

Gln Gln Tyr Ala Tyr Tyr Ser Pro Val Thr
1               5                   10

<210> SEQ ID NO 172
<211> LENGTH: 9
<212> TYPE: PRT
<213> ORGANISM: Artificial
<220> FEATURE:
<223> OTHER INFORMATION: synthetic peptide

<400> SEQUENCE: 172

Gln Gln Tyr Glu Tyr Tyr Pro Met Thr
1               5

<210> SEQ ID NO 173
<211> LENGTH: 8
<212> TYPE: PRT
<213> ORGANISM: Artificial
<220> FEATURE:
<223> OTHER INFORMATION: synthetic peptide

<400> SEQUENCE: 173

Gly Phe Asn Phe Ser Tyr Gly Tyr
1               5

<210> SEQ ID NO 174
<211> LENGTH: 8
<212> TYPE: PRT
<213> ORGANISM: Artificial
<220> FEATURE:
<223> OTHER INFORMATION: synthetic peptide

<400> SEQUENCE: 174

Gly Phe Asn Val Trp Gly Pro Gly
1               5

<210> SEQ ID NO 175
<211> LENGTH: 8
<212> TYPE: PRT
```

```
<213> ORGANISM: Artificial
<220> FEATURE:
<223> OTHER INFORMATION: synthetic peptide

<400> SEQUENCE: 175

Gly Phe Asn Val Ser Gly Ser Gln
1               5

<210> SEQ ID NO 176
<211> LENGTH: 8
<212> TYPE: PRT
<213> ORGANISM: Artificial
<220> FEATURE:
<223> OTHER INFORMATION: synthetic peptide

<400> SEQUENCE: 176

Gly Phe Asn Ile Tyr Gly Gln Met
1               5

<210> SEQ ID NO 177
<211> LENGTH: 8
<212> TYPE: PRT
<213> ORGANISM: Artificial
<220> FEATURE:
<223> OTHER INFORMATION: synthetic peptide

<400> SEQUENCE: 177

Gly Phe Asn Val Met Tyr Ser Thr
1               5

<210> SEQ ID NO 178
<211> LENGTH: 8
<212> TYPE: PRT
<213> ORGANISM: Artificial
<220> FEATURE:
<223> OTHER INFORMATION: synthetic peptide

<400> SEQUENCE: 178

Ile Ser Gly Tyr Thr Gly Asn Thr
1               5

<210> SEQ ID NO 179
<211> LENGTH: 8
<212> TYPE: PRT
<213> ORGANISM: Artificial
<220> FEATURE:
<223> OTHER INFORMATION: synthetic peptide

<400> SEQUENCE: 179

Ile His Pro Phe Ser Gly Asn Thr
1               5

<210> SEQ ID NO 180
<211> LENGTH: 8
<212> TYPE: PRT
<213> ORGANISM: Artificial
<220> FEATURE:
<223> OTHER INFORMATION: synthetic peptide

<400> SEQUENCE: 180

Ile Pro Gly Trp Ser Gly Tyr Thr
1               5

<210> SEQ ID NO 181
<211> LENGTH: 8
<212> TYPE: PRT
<213> ORGANISM: Artificial
```

```
<220> FEATURE:
<223> OTHER INFORMATION: synthetic peptide

<400> SEQUENCE: 181

Leu Ser Pro Phe Ser Gly Asn Thr
1               5

<210> SEQ ID NO 182
<211> LENGTH: 8
<212> TYPE: PRT
<213> ORGANISM: Artificial
<220> FEATURE:
<223> OTHER INFORMATION: synthetic peptide

<400> SEQUENCE: 182

Ile Tyr Ser Trp Ser Asp Tyr Thr
1               5

<210> SEQ ID NO 183
<211> LENGTH: 16
<212> TYPE: PRT
<213> ORGANISM: Artificial
<220> FEATURE:
<223> OTHER INFORMATION: synthetic peptide

<400> SEQUENCE: 183

Ser Arg Ala Ala Ser Leu Ser Ser Ser Tyr Tyr Ser Ala Phe Asp Val
1               5                   10                  15

<210> SEQ ID NO 184
<211> LENGTH: 11
<212> TYPE: PRT
<213> ORGANISM: Artificial
<220> FEATURE:
<223> OTHER INFORMATION: synthetic peptide

<400> SEQUENCE: 184

Ser Arg Gly Tyr Ser Tyr Ser Ala Met Asp Tyr
1               5                   10

<210> SEQ ID NO 185
<211> LENGTH: 11
<212> TYPE: PRT
<213> ORGANISM: Artificial
<220> FEATURE:
<223> OTHER INFORMATION: synthetic peptide

<400> SEQUENCE: 185

Ser Arg Gly Tyr Ser Tyr Phe Ala Met Asp Tyr
1               5                   10

<210> SEQ ID NO 186
<211> LENGTH: 14
<212> TYPE: PRT
<213> ORGANISM: Artificial
<220> FEATURE:
<223> OTHER INFORMATION: synthetic peptide

<400> SEQUENCE: 186

Ser Arg Asn Ile Ser Tyr Glu Gln Ser Ser Ala Phe Asp Tyr
1               5                   10

<210> SEQ ID NO 187
<211> LENGTH: 11
<212> TYPE: PRT
<213> ORGANISM: Artificial
<220> FEATURE:
```

```
<223> OTHER INFORMATION: synthetic peptide

<400> SEQUENCE: 187

Ser Arg Gly Tyr Ala His Asn Ser Phe Asp Tyr
1               5                   10

<210> SEQ ID NO 188
<211> LENGTH: 9
<212> TYPE: PRT
<213> ORGANISM: Artificial
<220> FEATURE:
<223> OTHER INFORMATION: synthetic peptide

<400> SEQUENCE: 188

Gln Gln Tyr Ser Phe Tyr Pro Phe Thr
1               5

<210> SEQ ID NO 189
<211> LENGTH: 11
<212> TYPE: PRT
<213> ORGANISM: Artificial
<220> FEATURE:
<223> OTHER INFORMATION: synthetic peptide

<400> SEQUENCE: 189

Gln Gln Tyr Ser Ala Tyr Tyr Gln Pro Ile Thr
1               5                   10

<210> SEQ ID NO 190
<211> LENGTH: 9
<212> TYPE: PRT
<213> ORGANISM: Artificial
<220> FEATURE:
<223> OTHER INFORMATION: synthetic peptide

<400> SEQUENCE: 190

Gln Gln Tyr Glu Tyr Val Pro His Thr
1               5

<210> SEQ ID NO 191
<211> LENGTH: 9
<212> TYPE: PRT
<213> ORGANISM: Artificial
<220> FEATURE:
<223> OTHER INFORMATION: synthetic peptide

<400> SEQUENCE: 191

Gln Gln Tyr Ser Tyr Met Pro Ile Thr
1               5

<210> SEQ ID NO 192
<211> LENGTH: 9
<212> TYPE: PRT
<213> ORGANISM: Artificial
<220> FEATURE:
<223> OTHER INFORMATION: synthetic peptide

<400> SEQUENCE: 192

Gln Gln Tyr Ala Tyr Tyr Pro Val Thr
1               5

<210> SEQ ID NO 193
<211> LENGTH: 9
<212> TYPE: PRT
<213> ORGANISM: Artificial
<220> FEATURE:
<223> OTHER INFORMATION: synthetic peptide
```

<400> SEQUENCE: 193

Gln Gln Tyr Asp Tyr Arg Pro Val Thr
1               5

<210> SEQ ID NO 194
<211> LENGTH: 9
<212> TYPE: PRT
<213> ORGANISM: Artificial
<220> FEATURE:
<223> OTHER INFORMATION: synthetic peptide

<400> SEQUENCE: 194

Gln Gln Tyr Asp Phe Thr Pro Met Thr
1               5

<210> SEQ ID NO 195
<211> LENGTH: 10
<212> TYPE: PRT
<213> ORGANISM: Artificial
<220> FEATURE:
<223> OTHER INFORMATION: synthetic peptide

<400> SEQUENCE: 195

Gln Gln Tyr Ser Ser Ser Ser Pro Val Thr
1               5                   10

<210> SEQ ID NO 196
<211> LENGTH: 7
<212> TYPE: PRT
<213> ORGANISM: Artificial
<220> FEATURE:
<223> OTHER INFORMATION: synthetic peptide

<400> SEQUENCE: 196

Gly Phe Asn Phe Gly Ser Tyr
1               5

<210> SEQ ID NO 197
<211> LENGTH: 8
<212> TYPE: PRT
<213> ORGANISM: Artificial
<220> FEATURE:
<223> OTHER INFORMATION: synthetic peptide

<400> SEQUENCE: 197

Gly Phe Asn Ile Ser Asp Ser Tyr
1               5

<210> SEQ ID NO 198
<211> LENGTH: 8
<212> TYPE: PRT
<213> ORGANISM: Artificial
<220> FEATURE:
<223> OTHER INFORMATION: synthetic peptide

<400> SEQUENCE: 198

Gly Phe Asn Ile Phe Ser Asp Gln
1               5

<210> SEQ ID NO 199
<211> LENGTH: 8
<212> TYPE: PRT
<213> ORGANISM: Artificial
<220> FEATURE:
<223> OTHER INFORMATION: synthetic peptide

```
<400> SEQUENCE: 199

Gly Phe Asn Leu Ser Tyr Ser Tyr
1               5

<210> SEQ ID NO 200
<211> LENGTH: 8
<212> TYPE: PRT
<213> ORGANISM: Artificial
<220> FEATURE:
<223> OTHER INFORMATION: synthetic peptide

<400> SEQUENCE: 200

Gly Phe Asn Ile Ser Tyr Gly Tyr
1               5

<210> SEQ ID NO 201
<211> LENGTH: 8
<212> TYPE: PRT
<213> ORGANISM: Artificial
<220> FEATURE:
<223> OTHER INFORMATION: synthetic peptide

<400> SEQUENCE: 201

Gly Phe Asn Ile Ser Tyr Gln His
1               5

<210> SEQ ID NO 202
<211> LENGTH: 8
<212> TYPE: PRT
<213> ORGANISM: Artificial
<220> FEATURE:
<223> OTHER INFORMATION: synthetic peptide

<400> SEQUENCE: 202

Gly Phe Asn Leu Ser Gly Tyr Tyr
1               5

<210> SEQ ID NO 203
<211> LENGTH: 8
<212> TYPE: PRT
<213> ORGANISM: Artificial
<220> FEATURE:
<223> OTHER INFORMATION: synthetic peptide

<400> SEQUENCE: 203

Gly Phe Asn Val Ser Gly Gln Tyr
1               5

<210> SEQ ID NO 204
<211> LENGTH: 8
<212> TYPE: PRT
<213> ORGANISM: Artificial
<220> FEATURE:
<223> OTHER INFORMATION: synthetic peptide

<400> SEQUENCE: 204

Gly Phe Asn Val Ser Thr Ser Gly
1               5

<210> SEQ ID NO 205
<211> LENGTH: 8
<212> TYPE: PRT
<213> ORGANISM: Artificial
<220> FEATURE:
<223> OTHER INFORMATION: synthetic peptide

<400> SEQUENCE: 205
```

```
Gly Phe Asn Ile Ser Tyr Ala Lys
1               5

<210> SEQ ID NO 206
<211> LENGTH: 8
<212> TYPE: PRT
<213> ORGANISM: Artificial
<220> FEATURE:
<223> OTHER INFORMATION: synthetic peptide

<400> SEQUENCE: 206

Gly Phe Asn Phe Ser Ser Tyr Val
1               5

<210> SEQ ID NO 207
<211> LENGTH: 8
<212> TYPE: PRT
<213> ORGANISM: Artificial
<220> FEATURE:
<223> OTHER INFORMATION: synthetic peptide

<400> SEQUENCE: 207

Ile Ser Gly Tyr Ser Gly Asn Thr
1               5

<210> SEQ ID NO 208
<211> LENGTH: 8
<212> TYPE: PRT
<213> ORGANISM: Artificial
<220> FEATURE:
<223> OTHER INFORMATION: synthetic peptide

<400> SEQUENCE: 208

Phe Ser Pro Tyr Ser Ser Asn Thr
1               5

<210> SEQ ID NO 209
<211> LENGTH: 9
<212> TYPE: PRT
<213> ORGANISM: Artificial
<220> FEATURE:
<223> OTHER INFORMATION: synthetic peptide

<400> SEQUENCE: 209

Phe Met Pro Tyr Asp Ser Tyr Tyr Thr
1               5

<210> SEQ ID NO 210
<211> LENGTH: 8
<212> TYPE: PRT
<213> ORGANISM: Artificial
<220> FEATURE:
<223> OTHER INFORMATION: synthetic peptide

<400> SEQUENCE: 210

Ile Ser Gly Phe Ser Gly Asn Thr
1               5

<210> SEQ ID NO 211
<211> LENGTH: 8
<212> TYPE: PRT
<213> ORGANISM: Artificial
<220> FEATURE:
<223> OTHER INFORMATION: synthetic peptide

<400> SEQUENCE: 211
```

```
Phe His Tyr Gly Ser Gly Asn Thr
1               5

<210> SEQ ID NO 212
<211> LENGTH: 8
<212> TYPE: PRT
<213> ORGANISM: Artificial
<220> FEATURE:
<223> OTHER INFORMATION: synthetic peptide

<400> SEQUENCE: 212

Phe Met Pro Tyr Gln Gly Ser Thr
1               5

<210> SEQ ID NO 213
<211> LENGTH: 8
<212> TYPE: PRT
<213> ORGANISM: Artificial
<220> FEATURE:
<223> OTHER INFORMATION: synthetic peptide

<400> SEQUENCE: 213

Phe Ser Pro Tyr Ser Gly Tyr Thr
1               5

<210> SEQ ID NO 214
<211> LENGTH: 8
<212> TYPE: PRT
<213> ORGANISM: Artificial
<220> FEATURE:
<223> OTHER INFORMATION: synthetic peptide

<400> SEQUENCE: 214

Ile Ser Pro Val Ser Gly Asn Thr
1               5

<210> SEQ ID NO 215
<211> LENGTH: 8
<212> TYPE: PRT
<213> ORGANISM: Artificial
<220> FEATURE:
<223> OTHER INFORMATION: synthetic peptide

<400> SEQUENCE: 215

Ile Tyr Gly Ala Tyr Ser Gly Thr
1               5

<210> SEQ ID NO 216
<211> LENGTH: 8
<212> TYPE: PRT
<213> ORGANISM: Artificial
<220> FEATURE:
<223> OTHER INFORMATION: synthetic peptide

<400> SEQUENCE: 216

Leu Thr Tyr Trp Gly Gly Tyr Thr
1               5

<210> SEQ ID NO 217
<211> LENGTH: 8
<212> TYPE: PRT
<213> ORGANISM: Artificial
<220> FEATURE:
<223> OTHER INFORMATION: synthetic peptide

<400> SEQUENCE: 217

Val Tyr Pro Asp Ser Gly Gly Thr
```

```
1               5
```

<210> SEQ ID NO 218
<211> LENGTH: 13
<212> TYPE: PRT
<213> ORGANISM: Artificial
<220> FEATURE:
<223> OTHER INFORMATION: synthetic peptide

<400> SEQUENCE: 218

```
Ser Arg Ser Asn Gln Ser Ala Tyr Ser Tyr Met Asp Tyr
1               5                   10
```

<210> SEQ ID NO 219
<211> LENGTH: 13
<212> TYPE: PRT
<213> ORGANISM: Artificial
<220> FEATURE:
<223> OTHER INFORMATION: synthetic peptide

<400> SEQUENCE: 219

```
Ser Arg Ser Gln Phe Thr Phe Tyr Gln Tyr Phe Asp Tyr
1               5                   10
```

<210> SEQ ID NO 220
<211> LENGTH: 11
<212> TYPE: PRT
<213> ORGANISM: Artificial
<220> FEATURE:
<223> OTHER INFORMATION: synthetic peptide

<400> SEQUENCE: 220

```
Ser Arg Met Ser Val Arg Asn Ala Phe Asp Tyr
1               5                   10
```

<210> SEQ ID NO 221
<211> LENGTH: 12
<212> TYPE: PRT
<213> ORGANISM: Artificial
<220> FEATURE:
<223> OTHER INFORMATION: synthetic peptide

<400> SEQUENCE: 221

```
Ser Arg Ser Asp Ser Tyr Tyr Thr Ala Met Asp Tyr
1               5                   10
```

<210> SEQ ID NO 222
<211> LENGTH: 10
<212> TYPE: PRT
<213> ORGANISM: Artificial
<220> FEATURE:
<223> OTHER INFORMATION: synthetic peptide

<400> SEQUENCE: 222

```
Ser Arg Ser Asn Tyr Tyr Tyr Leu Asp Tyr
1               5                   10
```

<210> SEQ ID NO 223
<211> LENGTH: 14
<212> TYPE: PRT
<213> ORGANISM: Artificial
<220> FEATURE:
<223> OTHER INFORMATION: synthetic peptide

<400> SEQUENCE: 223

```
Ser Arg Ala Asn Ile Tyr Ser Ser His Ser Phe Phe Asp Tyr
1               5                   10
```

<210> SEQ ID NO 224
<211> LENGTH: 13
<212> TYPE: PRT
<213> ORGANISM: Artificial
<220> FEATURE:
<223> OTHER INFORMATION: synthetic peptide

<400> SEQUENCE: 224

Ser Arg Thr His Ser Ser Ile Tyr His Ser Phe Asp Tyr
1               5                   10

<210> SEQ ID NO 225
<211> LENGTH: 14
<212> TYPE: PRT
<213> ORGANISM: Artificial
<220> FEATURE:
<223> OTHER INFORMATION: synthetic peptide

<400> SEQUENCE: 225

Ser Arg Pro Met Lys Thr Ser Tyr Tyr Gly Ala Phe Asp Tyr
1               5                   10

<210> SEQ ID NO 226
<211> LENGTH: 14
<212> TYPE: PRT
<213> ORGANISM: Artificial
<220> FEATURE:
<223> OTHER INFORMATION: synthetic peptide

<400> SEQUENCE: 226

Ser Arg Ser Gln Ser Tyr Thr Tyr Trp Ser Ala Met Asp Tyr
1               5                   10

<210> SEQ ID NO 227
<211> LENGTH: 11
<212> TYPE: PRT
<213> ORGANISM: Artificial
<220> FEATURE:
<223> OTHER INFORMATION: synthetic peptide

<400> SEQUENCE: 227

Ser Arg Gly Glu Tyr Gly Thr Tyr Met Asp Tyr
1               5                   10

<210> SEQ ID NO 228
<211> LENGTH: 11
<212> TYPE: PRT
<213> ORGANISM: Artificial
<220> FEATURE:
<223> OTHER INFORMATION: synthetic peptide

<400> SEQUENCE: 228

Ser Arg Thr Ser Ser Tyr Tyr Ala Phe Asp Tyr
1               5                   10

<210> SEQ ID NO 229
<211> LENGTH: 8
<212> TYPE: PRT
<213> ORGANISM: Artificial
<220> FEATURE:
<223> OTHER INFORMATION: synthetic peptide

<400> SEQUENCE: 229

Gln Gln Ser Ser Tyr Thr Pro Ile
1               5

<210> SEQ ID NO 230
<211> LENGTH: 9
<212> TYPE: PRT
<213> ORGANISM: Artificial
<220> FEATURE:
<223> OTHER INFORMATION: synthetic peptide

<400> SEQUENCE: 230

Gln Gln Tyr Ala Tyr Tyr Pro Ile Thr
1               5

<210> SEQ ID NO 231
<211> LENGTH: 9
<212> TYPE: PRT
<213> ORGANISM: Artificial
<220> FEATURE:
<223> OTHER INFORMATION: synthetic peptide

<400> SEQUENCE: 231

Gln Gln Tyr Glu Tyr Tyr Pro Ile Thr
1               5

<210> SEQ ID NO 232
<211> LENGTH: 9
<212> TYPE: PRT
<213> ORGANISM: Artificial
<220> FEATURE:
<223> OTHER INFORMATION: synthetic peptide

<400> SEQUENCE: 232

Gln Gln Tyr Thr Tyr Tyr Pro Ile Thr
1               5

<210> SEQ ID NO 233
<211> LENGTH: 9
<212> TYPE: PRT
<213> ORGANISM: Artificial
<220> FEATURE:
<223> OTHER INFORMATION: synthetic peptide

<400> SEQUENCE: 233

Gln Gln Ser Ser Val Glu Pro Trp Thr
1               5

<210> SEQ ID NO 234
<211> LENGTH: 8
<212> TYPE: PRT
<213> ORGANISM: Artificial
<220> FEATURE:
<223> OTHER INFORMATION: synthetic peptide

<400> SEQUENCE: 234

Gly Phe Asn Ile Ser Gln Gly Gly
1               5

<210> SEQ ID NO 235
<211> LENGTH: 8
<212> TYPE: PRT
<213> ORGANISM: Artificial
<220> FEATURE:
<223> OTHER INFORMATION: synthetic peptide

<400> SEQUENCE: 235

Gly Phe Asn Ile Ser Ser Thr Gly
1               5

```
<210> SEQ ID NO 236
<211> LENGTH: 8
<212> TYPE: PRT
<213> ORGANISM: Artificial
<220> FEATURE:
<223> OTHER INFORMATION: synthetic peptide

<400> SEQUENCE: 236

Gly Phe Asn Phe Phe Ser Thr Val
1               5

<210> SEQ ID NO 237
<211> LENGTH: 8
<212> TYPE: PRT
<213> ORGANISM: Artificial
<220> FEATURE:
<223> OTHER INFORMATION: synthetic peptide

<400> SEQUENCE: 237

Gly Phe Asn Leu His Gly Tyr Leu
1               5

<210> SEQ ID NO 238
<211> LENGTH: 8
<212> TYPE: PRT
<213> ORGANISM: Artificial
<220> FEATURE:
<223> OTHER INFORMATION: synthetic peptide

<400> SEQUENCE: 238

Gly Phe Asn Leu Ser Thr His Val
1               5

<210> SEQ ID NO 239
<211> LENGTH: 8
<212> TYPE: PRT
<213> ORGANISM: Artificial
<220> FEATURE:
<223> OTHER INFORMATION: synthetic peptide

<400> SEQUENCE: 239

Gly Phe Asn Val Ser Tyr Tyr Ser
1               5

<210> SEQ ID NO 240
<211> LENGTH: 8
<212> TYPE: PRT
<213> ORGANISM: Artificial
<220> FEATURE:
<223> OTHER INFORMATION: synthetic peptide

<400> SEQUENCE: 240

Val Tyr Pro Gly Gly Gly Gln Thr
1               5

<210> SEQ ID NO 241
<211> LENGTH: 8
<212> TYPE: PRT
<213> ORGANISM: Artificial
<220> FEATURE:
<223> OTHER INFORMATION: synthetic peptide

<400> SEQUENCE: 241

Leu Leu Gly Gly Ser Gly Asn Thr
1               5

<210> SEQ ID NO 242
```

```
<211> LENGTH: 8
<212> TYPE: PRT
<213> ORGANISM: Artificial
<220> FEATURE:
<223> OTHER INFORMATION: synthetic peptide

<400> SEQUENCE: 242

Ile Tyr Pro Trp Ser Gly Ser Thr
1               5

<210> SEQ ID NO 243
<211> LENGTH: 8
<212> TYPE: PRT
<213> ORGANISM: Artificial
<220> FEATURE:
<223> OTHER INFORMATION: synthetic peptide

<400> SEQUENCE: 243

Ile Tyr Pro Pro Asn Gly Tyr Thr
1               5

<210> SEQ ID NO 244
<211> LENGTH: 8
<212> TYPE: PRT
<213> ORGANISM: Artificial
<220> FEATURE:
<223> OTHER INFORMATION: synthetic peptide

<400> SEQUENCE: 244

Phe Tyr Pro Tyr Val Gly Tyr Thr
1               5

<210> SEQ ID NO 245
<211> LENGTH: 8
<212> TYPE: PRT
<213> ORGANISM: Artificial
<220> FEATURE:
<223> OTHER INFORMATION: synthetic peptide

<400> SEQUENCE: 245

Ile Tyr Pro Trp Asn Asp Tyr Thr
1               5

<210> SEQ ID NO 246
<211> LENGTH: 11
<212> TYPE: PRT
<213> ORGANISM: Artificial
<220> FEATURE:
<223> OTHER INFORMATION: synthetic peptide

<400> SEQUENCE: 246

Ser Arg Gly Tyr Asp Tyr Ser Ala Phe Asp Tyr
1               5                   10

<210> SEQ ID NO 247
<211> LENGTH: 11
<212> TYPE: PRT
<213> ORGANISM: Artificial
<220> FEATURE:
<223> OTHER INFORMATION: synthetic peptide

<400> SEQUENCE: 247

Ser Arg Gly Leu Gln Tyr Ser Ala Met Asp Tyr
1               5                   10

<210> SEQ ID NO 248
<211> LENGTH: 12
```

```
<212> TYPE: PRT
<213> ORGANISM: Artificial
<220> FEATURE:
<223> OTHER INFORMATION: synthetic peptide

<400> SEQUENCE: 248

Ser Arg Ser Arg Ser Ser Asn Tyr Tyr Phe Asp Val
1               5                   10

<210> SEQ ID NO 249
<211> LENGTH: 11
<212> TYPE: PRT
<213> ORGANISM: Artificial
<220> FEATURE:
<223> OTHER INFORMATION: synthetic peptide

<400> SEQUENCE: 249

Ser Arg Gly Val Asp Tyr Ala Tyr Leu Asp Tyr
1               5                   10

<210> SEQ ID NO 250
<211> LENGTH: 11
<212> TYPE: PRT
<213> ORGANISM: Artificial
<220> FEATURE:
<223> OTHER INFORMATION: synthetic peptide

<400> SEQUENCE: 250

Ser Arg Gly Tyr Arg Tyr Gln Tyr Met Asp Val
1               5                   10

<210> SEQ ID NO 251
<211> LENGTH: 10
<212> TYPE: PRT
<213> ORGANISM: Artificial
<220> FEATURE:
<223> OTHER INFORMATION: synthetic peptide

<400> SEQUENCE: 251

Ser Arg Gly Ser Tyr Tyr Ser Phe Asp Tyr
1               5                   10

<210> SEQ ID NO 252
<211> LENGTH: 9
<212> TYPE: PRT
<213> ORGANISM: Artificial
<220> FEATURE:
<223> OTHER INFORMATION: synthetic peptide

<400> SEQUENCE: 252

Gln Gln Ile Tyr Thr Ser Pro Ile Thr
1               5

<210> SEQ ID NO 253
<211> LENGTH: 9
<212> TYPE: PRT
<213> ORGANISM: Artificial
<220> FEATURE:
<223> OTHER INFORMATION: synthetic peptide

<400> SEQUENCE: 253

Gln Gln Arg Ala Tyr Phe Pro Ile Thr
1               5

<210> SEQ ID NO 254
<211> LENGTH: 10
<212> TYPE: PRT
```

```
<213> ORGANISM: Artificial
<220> FEATURE:
<223> OTHER INFORMATION: synthetic peptide

<400> SEQUENCE: 254

Gln Gln Gln Tyr Ala Tyr Thr Pro Ile Thr
1               5                   10

<210> SEQ ID NO 255
<211> LENGTH: 9
<212> TYPE: PRT
<213> ORGANISM: Artificial
<220> FEATURE:
<223> OTHER INFORMATION: synthetic peptide

<400> SEQUENCE: 255

Gln Gln Ile His Tyr Lys Pro Leu Thr
1               5

<210> SEQ ID NO 256
<211> LENGTH: 8
<212> TYPE: PRT
<213> ORGANISM: Artificial
<220> FEATURE:
<223> OTHER INFORMATION: synthetic peptide

<400> SEQUENCE: 256

Gly Phe Asn Ile Asn Asn Thr Tyr
1               5

<210> SEQ ID NO 257
<211> LENGTH: 8
<212> TYPE: PRT
<213> ORGANISM: Artificial
<220> FEATURE:
<223> OTHER INFORMATION: synthetic peptide

<400> SEQUENCE: 257

Gly Phe Asn Phe Ile Thr Thr Gly
1               5

<210> SEQ ID NO 258
<211> LENGTH: 8
<212> TYPE: PRT
<213> ORGANISM: Artificial
<220> FEATURE:
<223> OTHER INFORMATION: synthetic peptide

<400> SEQUENCE: 258

Gly Phe Asn Phe Ser Asp Tyr Gly
1               5

<210> SEQ ID NO 259
<211> LENGTH: 8
<212> TYPE: PRT
<213> ORGANISM: Artificial
<220> FEATURE:
<223> OTHER INFORMATION: synthetic peptide

<400> SEQUENCE: 259

Gly Phe Asn Val Trp Ser Tyr Gly
1               5

<210> SEQ ID NO 260
<211> LENGTH: 8
<212> TYPE: PRT
<213> ORGANISM: Artificial
```

```
<220> FEATURE:
<223> OTHER INFORMATION: synthetic peptide

<400> SEQUENCE: 260

Gly Phe Asn Val Ala Trp Tyr Ser
1               5

<210> SEQ ID NO 261
<211> LENGTH: 8
<212> TYPE: PRT
<213> ORGANISM: Artificial
<220> FEATURE:
<223> OTHER INFORMATION: synthetic peptide

<400> SEQUENCE: 261

Ile Gly Pro Gly Ser Asp Tyr Thr
1               5

<210> SEQ ID NO 262
<211> LENGTH: 8
<212> TYPE: PRT
<213> ORGANISM: Artificial
<220> FEATURE:
<223> OTHER INFORMATION: synthetic peptide

<400> SEQUENCE: 262

Leu Ile Pro Ala Ser Gly Tyr Thr
1               5

<210> SEQ ID NO 263
<211> LENGTH: 8
<212> TYPE: PRT
<213> ORGANISM: Artificial
<220> FEATURE:
<223> OTHER INFORMATION: synthetic peptide

<400> SEQUENCE: 263

Val Thr Pro Asp Gly Ser Tyr Thr
1               5

<210> SEQ ID NO 264
<211> LENGTH: 8
<212> TYPE: PRT
<213> ORGANISM: Artificial
<220> FEATURE:
<223> OTHER INFORMATION: synthetic peptide

<400> SEQUENCE: 264

Val Tyr Gly Gly Ser Ser Tyr Thr
1               5

<210> SEQ ID NO 265
<211> LENGTH: 13
<212> TYPE: PRT
<213> ORGANISM: Artificial
<220> FEATURE:
<223> OTHER INFORMATION: synthetic peptide

<400> SEQUENCE: 265

Ser Arg Thr Tyr Tyr Ser Tyr Tyr Ser Ala Met Asp Val
1               5                   10

<210> SEQ ID NO 266
<211> LENGTH: 11
<212> TYPE: PRT
<213> ORGANISM: Artificial
<220> FEATURE:
```

```
<223> OTHER INFORMATION: synthetic peptide

<400> SEQUENCE: 266

Ser Arg Tyr Tyr Tyr Ala Ser Ala Leu Asp Tyr
1               5                   10

<210> SEQ ID NO 267
<211> LENGTH: 10
<212> TYPE: PRT
<213> ORGANISM: Artificial
<220> FEATURE:
<223> OTHER INFORMATION: synthetic peptide

<400> SEQUENCE: 267

Ser Arg Gly Trp Ser Tyr Tyr Met Asp Tyr
1               5                   10

<210> SEQ ID NO 268
<211> LENGTH: 10
<212> TYPE: PRT
<213> ORGANISM: Artificial
<220> FEATURE:
<223> OTHER INFORMATION: synthetic peptide

<400> SEQUENCE: 268

Ser Arg Ser Tyr Gly Trp Ala Met Asp Tyr
1               5                   10

<210> SEQ ID NO 269
<211> LENGTH: 11
<212> TYPE: PRT
<213> ORGANISM: Artificial
<220> FEATURE:
<223> OTHER INFORMATION: synthetic peptide

<400> SEQUENCE: 269

Ser Arg Asp Phe Tyr Ser Ser Gly Met Asp Tyr
1               5                   10

<210> SEQ ID NO 270
<211> LENGTH: 9
<212> TYPE: PRT
<213> ORGANISM: Artificial
<220> FEATURE:
<223> OTHER INFORMATION: synthetic peptide

<400> SEQUENCE: 270

Gln Gln Glu Trp Arg Leu Pro Ile Thr
1               5

<210> SEQ ID NO 271
<211> LENGTH: 9
<212> TYPE: PRT
<213> ORGANISM: Artificial
<220> FEATURE:
<223> OTHER INFORMATION: synthetic peptide

<400> SEQUENCE: 271

Gln Gln Gly Thr Ser Thr Pro Phe Thr
1               5

<210> SEQ ID NO 272
<211> LENGTH: 9
<212> TYPE: PRT
<213> ORGANISM: Artificial
<220> FEATURE:
<223> OTHER INFORMATION: synthetic peptide
```

<400> SEQUENCE: 272

Gln Gln Ser Trp Arg Tyr Pro Met Thr
1               5

<210> SEQ ID NO 273
<211> LENGTH: 9
<212> TYPE: PRT
<213> ORGANISM: Artificial
<220> FEATURE:
<223> OTHER INFORMATION: synthetic peptide

<400> SEQUENCE: 273

Gln Gln Ser Tyr Ser Tyr Pro Val Thr
1               5

<210> SEQ ID NO 274
<211> LENGTH: 10
<212> TYPE: PRT
<213> ORGANISM: Artificial
<220> FEATURE:
<223> OTHER INFORMATION: synthetic peptide

<400> SEQUENCE: 274

Gln Gln Gly Trp Leu Tyr Ser Pro Phe Thr
1               5                   10

<210> SEQ ID NO 275
<211> LENGTH: 8
<212> TYPE: PRT
<213> ORGANISM: Artificial
<220> FEATURE:
<223> OTHER INFORMATION: synthetic peptide

<400> SEQUENCE: 275

Gly Phe Asn Val Tyr Gly Asn Gln
1               5

<210> SEQ ID NO 276
<211> LENGTH: 8
<212> TYPE: PRT
<213> ORGANISM: Artificial
<220> FEATURE:
<223> OTHER INFORMATION: synthetic peptide

<400> SEQUENCE: 276

Gly Phe Asn Ile Ser Arg Tyr Gly
1               5

<210> SEQ ID NO 277
<211> LENGTH: 8
<212> TYPE: PRT
<213> ORGANISM: Artificial
<220> FEATURE:
<223> OTHER INFORMATION: synthetic peptide

<400> SEQUENCE: 277

Gly Phe Asn Ile Tyr Ser Ser Trp
1               5

<210> SEQ ID NO 278
<211> LENGTH: 8
<212> TYPE: PRT
<213> ORGANISM: Artificial
<220> FEATURE:
<223> OTHER INFORMATION: synthetic peptide

```
<400> SEQUENCE: 278

Ile Tyr Pro Tyr Ser Gly Ser Thr
1               5

<210> SEQ ID NO 279
<211> LENGTH: 8
<212> TYPE: PRT
<213> ORGANISM: Artificial
<220> FEATURE:
<223> OTHER INFORMATION: synthetic peptide

<400> SEQUENCE: 279

Ile Tyr Pro Asp Ser Gly Tyr Thr
1               5

<210> SEQ ID NO 280
<211> LENGTH: 8
<212> TYPE: PRT
<213> ORGANISM: Artificial
<220> FEATURE:
<223> OTHER INFORMATION: synthetic peptide

<400> SEQUENCE: 280

Phe Tyr Pro Ser Ser Ser Tyr Thr
1               5

<210> SEQ ID NO 281
<211> LENGTH: 8
<212> TYPE: PRT
<213> ORGANISM: Artificial
<220> FEATURE:
<223> OTHER INFORMATION: synthetic peptide

<400> SEQUENCE: 281

Phe Gln Pro Tyr Ser Gly Tyr Thr
1               5

<210> SEQ ID NO 282
<211> LENGTH: 8
<212> TYPE: PRT
<213> ORGANISM: Artificial
<220> FEATURE:
<223> OTHER INFORMATION: synthetic peptide

<400> SEQUENCE: 282

Val Tyr Gly Gly Ser Gly Tyr Thr
1               5

<210> SEQ ID NO 283
<211> LENGTH: 13
<212> TYPE: PRT
<213> ORGANISM: Artificial
<220> FEATURE:
<223> OTHER INFORMATION: synthetic peptide

<400> SEQUENCE: 283

Ser Arg Ser Ala Tyr Val Ala Tyr Ser Tyr Phe Asp Tyr
1               5                   10

<210> SEQ ID NO 284
<211> LENGTH: 11
<212> TYPE: PRT
<213> ORGANISM: Artificial
<220> FEATURE:
<223> OTHER INFORMATION: synthetic peptide

<400> SEQUENCE: 284
```

```
Ser Arg Ala Tyr Leu Tyr Tyr Leu Ala Tyr
1               5                   10
```

<210> SEQ ID NO 285
<211> LENGTH: 10
<212> TYPE: PRT
<213> ORGANISM: Artificial
<220> FEATURE:
<223> OTHER INFORMATION: synthetic peptide

<400> SEQUENCE: 285

```
Ser Arg Lys Tyr Tyr Glu Ala Met Asp Tyr
1               5                   10
```

<210> SEQ ID NO 286
<211> LENGTH: 10
<212> TYPE: PRT
<213> ORGANISM: Artificial
<220> FEATURE:
<223> OTHER INFORMATION: synthetic peptide

<400> SEQUENCE: 286

```
Ser Arg Glu Tyr Thr Tyr Tyr Phe Asp Tyr
1               5                   10
```

<210> SEQ ID NO 287
<211> LENGTH: 11
<212> TYPE: PRT
<213> ORGANISM: Artificial
<220> FEATURE:
<223> OTHER INFORMATION: synthetic peptide

<400> SEQUENCE: 287

```
Ser Arg Ala His Ser Ser Tyr Tyr Val Asp Tyr
1               5                   10
```

<210> SEQ ID NO 288
<211> LENGTH: 10
<212> TYPE: PRT
<213> ORGANISM: Artificial
<220> FEATURE:
<223> OTHER INFORMATION: synthetic peptide

<400> SEQUENCE: 288

```
Gln Gln Gly Tyr Phe Tyr Tyr Pro Asn Thr
1               5                   10
```

<210> SEQ ID NO 289
<211> LENGTH: 8
<212> TYPE: PRT
<213> ORGANISM: Artificial
<220> FEATURE:
<223> OTHER INFORMATION: synthetic peptide

<400> SEQUENCE: 289

```
Gly Phe Asn Ile Gly Tyr Tyr Gly
1               5
```

<210> SEQ ID NO 290
<211> LENGTH: 8
<212> TYPE: PRT
<213> ORGANISM: Artificial
<220> FEATURE:
<223> OTHER INFORMATION: synthetic peptide

<400> SEQUENCE: 290

Val Tyr Pro Gly Gly Gly Tyr Thr
1               5

<210> SEQ ID NO 291
<211> LENGTH: 10
<212> TYPE: PRT
<213> ORGANISM: Artificial
<220> FEATURE:
<223> OTHER INFORMATION: synthetic peptide

<400> SEQUENCE: 291

Ser Arg Tyr Tyr Tyr Tyr Gly Phe Asp Tyr
1               5                   10

<210> SEQ ID NO 292
<211> LENGTH: 9
<212> TYPE: PRT
<213> ORGANISM: Artificial
<220> FEATURE:
<223> OTHER INFORMATION: synthetic peptide

<400> SEQUENCE: 292

Gln Gln His Tyr Tyr Ser Pro Val Thr
1               5

<210> SEQ ID NO 293
<211> LENGTH: 9
<212> TYPE: PRT
<213> ORGANISM: Artificial
<220> FEATURE:
<223> OTHER INFORMATION: synthetic peptide

<400> SEQUENCE: 293

Gln Gln His Tyr Tyr Ser Pro Val Thr
1               5

<210> SEQ ID NO 294
<211> LENGTH: 8
<212> TYPE: PRT
<213> ORGANISM: Artificial
<220> FEATURE:
<223> OTHER INFORMATION: synthetic peptide

<400> SEQUENCE: 294

Ile Tyr Pro Asp Tyr Asp Tyr Thr
1               5

<210> SEQ ID NO 295
<211> LENGTH: 10
<212> TYPE: PRT
<213> ORGANISM: Artificial
<220> FEATURE:
<223> OTHER INFORMATION: synthetic peptide

<400> SEQUENCE: 295

Ser Arg Thr Tyr Ser Val Tyr Met Asp Tyr
1               5                   10

<210> SEQ ID NO 296
<211> LENGTH: 9
<212> TYPE: PRT
<213> ORGANISM: Artificial
<220> FEATURE:
<223> OTHER INFORMATION: synthetic peptide

<400> SEQUENCE: 296

Gln Gln Tyr Ala Tyr Ala Pro Phe Thr

```
1               5
```

<210> SEQ ID NO 297
<211> LENGTH: 8
<212> TYPE: PRT
<213> ORGANISM: Artificial
<220> FEATURE:
<223> OTHER INFORMATION: synthetic peptide

<400> SEQUENCE: 297

```
Gly Phe Asn Val Ser Tyr Ser Met
1               5
```

<210> SEQ ID NO 298
<211> LENGTH: 8
<212> TYPE: PRT
<213> ORGANISM: Artificial
<220> FEATURE:
<223> OTHER INFORMATION: synthetic peptide

<400> SEQUENCE: 298

```
Val Trp Gly Asp Gly Gly Val Thr
1               5
```

<210> SEQ ID NO 299
<211> LENGTH: 10
<212> TYPE: PRT
<213> ORGANISM: Artificial
<220> FEATURE:
<223> OTHER INFORMATION: synthetic peptide

<400> SEQUENCE: 299

```
Ser Arg Gly Ser Tyr Tyr Ala Phe Asp Tyr
1               5                   10
```

<210> SEQ ID NO 300
<211> LENGTH: 9
<212> TYPE: PRT
<213> ORGANISM: Artificial
<220> FEATURE:
<223> OTHER INFORMATION: synthetic peptide

<400> SEQUENCE: 300

```
Gln Gln Ala His Met Ile Pro Ile Thr
1               5
```

<210> SEQ ID NO 301
<211> LENGTH: 9
<212> TYPE: PRT
<213> ORGANISM: Artificial
<220> FEATURE:
<223> OTHER INFORMATION: synthetic peptide

<400> SEQUENCE: 301

```
Gln Gln Ser Val Tyr Asp Pro Ile Thr
1               5
```

<210> SEQ ID NO 302
<211> LENGTH: 9
<212> TYPE: PRT
<213> ORGANISM: Artificial
<220> FEATURE:
<223> OTHER INFORMATION: synthetic peptide

<400> SEQUENCE: 302

```
Gln Gln Ser Tyr Thr Ser Pro Leu Thr
1               5
```

<210> SEQ ID NO 303
<211> LENGTH: 9
<212> TYPE: PRT
<213> ORGANISM: Artificial
<220> FEATURE:
<223> OTHER INFORMATION: synthetic peptide

<400> SEQUENCE: 303

Gln Gln Gly Gln Tyr Ser Pro Phe Thr
1               5

<210> SEQ ID NO 304

<400> SEQUENCE: 304

000

<210> SEQ ID NO 305
<211> LENGTH: 8
<212> TYPE: PRT
<213> ORGANISM: Artificial
<220> FEATURE:
<223> OTHER INFORMATION: synthetic peptide

<400> SEQUENCE: 305

Gly Phe Asn Phe Ser Phe Pro Gly
1               5

<210> SEQ ID NO 306
<211> LENGTH: 8
<212> TYPE: PRT
<213> ORGANISM: Artificial
<220> FEATURE:
<223> OTHER INFORMATION: synthetic peptide

<400> SEQUENCE: 306

Gly Phe Asn Ile Ser Gly Ser Trp
1               5

<210> SEQ ID NO 307
<211> LENGTH: 8
<212> TYPE: PRT
<213> ORGANISM: Artificial
<220> FEATURE:
<223> OTHER INFORMATION: synthetic peptide

<400> SEQUENCE: 307

Gly Phe Asn Ile Tyr Tyr Gly Val
1               5

<210> SEQ ID NO 308
<211> LENGTH: 8
<212> TYPE: PRT
<213> ORGANISM: Artificial
<220> FEATURE:
<223> OTHER INFORMATION: synthetic peptide

<400> SEQUENCE: 308

Gly Phe Asn Val Ser Tyr Glu Tyr
1               5

<210> SEQ ID NO 309

<400> SEQUENCE: 309

000

<210> SEQ ID NO 310
<211> LENGTH: 8
<212> TYPE: PRT
<213> ORGANISM: Artificial
<220> FEATURE:
<223> OTHER INFORMATION: synthetic peptide

<400> SEQUENCE: 310

Phe Val Gly Tyr Asp Gly Tyr Thr
1               5

<210> SEQ ID NO 311
<211> LENGTH: 8
<212> TYPE: PRT
<213> ORGANISM: Artificial
<220> FEATURE:
<223> OTHER INFORMATION: synthetic peptide

<400> SEQUENCE: 311

Leu Tyr Pro Asp Ser Asp Tyr Thr
1               5

<210> SEQ ID NO 312
<211> LENGTH: 8
<212> TYPE: PRT
<213> ORGANISM: Artificial
<220> FEATURE:
<223> OTHER INFORMATION: synthetic peptide

<400> SEQUENCE: 312

Ile Tyr Pro Asp Ser Ser Trp Thr
1               5

<210> SEQ ID NO 313
<211> LENGTH: 8
<212> TYPE: PRT
<213> ORGANISM: Artificial
<220> FEATURE:
<223> OTHER INFORMATION: synthetic peptide

<400> SEQUENCE: 313

Ile Tyr Gly Gly Ser Asp Asn Thr
1               5

<210> SEQ ID NO 314

<400> SEQUENCE: 314

000

<210> SEQ ID NO 315

<400> SEQUENCE: 315

000

<210> SEQ ID NO 316
<211> LENGTH: 11
<212> TYPE: PRT
<213> ORGANISM: Artificial
<220> FEATURE:
<223> OTHER INFORMATION: synthetic peptide

<400> SEQUENCE: 316

Ser Arg Asp Tyr Tyr Ser Phe Ser Met Asp Tyr
1               5                   10

<210> SEQ ID NO 317
<211> LENGTH: 10
<212> TYPE: PRT
<213> ORGANISM: Artificial
<220> FEATURE:
<223> OTHER INFORMATION: synthetic peptide

<400> SEQUENCE: 317

Ser Arg Ala His Thr Tyr Ala Phe Asp Tyr
1               5                   10

<210> SEQ ID NO 318
<211> LENGTH: 19
<212> TYPE: PRT
<213> ORGANISM: Artificial
<220> FEATURE:
<223> OTHER INFORMATION: synthetic peptide

<400> SEQUENCE: 318

Ser Arg Asp Gln Asp Phe His Tyr Met Asn Tyr Leu Ser Tyr Ala
1               5                   10                  15

Leu Asp Tyr

<210> SEQ ID NO 319
<211> LENGTH: 10
<212> TYPE: PRT
<213> ORGANISM: Artificial
<220> FEATURE:
<223> OTHER INFORMATION: synthetic peptide

<400> SEQUENCE: 319

Ser Arg Pro Leu Gly Ser Tyr Phe Asp Tyr
1               5                   10

<210> SEQ ID NO 320
<211> LENGTH: 9
<212> TYPE: PRT
<213> ORGANISM: Artificial
<220> FEATURE:
<223> OTHER INFORMATION: synthetic peptide

<400> SEQUENCE: 320

Gln Gln Tyr Trp Tyr Leu Pro Thr Thr
1               5

<210> SEQ ID NO 321
<211> LENGTH: 8
<212> TYPE: PRT
<213> ORGANISM: Artificial
<220> FEATURE:
<223> OTHER INFORMATION: synthetic peptide

<400> SEQUENCE: 321

Gly Phe Asn Ile Ser Trp Tyr Asp
1               5

<210> SEQ ID NO 322
<211> LENGTH: 8
<212> TYPE: PRT
<213> ORGANISM: Artificial
<220> FEATURE:
<223> OTHER INFORMATION: synthetic peptide

<400> SEQUENCE: 322

Ile Glu Pro Ser Val Gly Tyr Thr

```
<210> SEQ ID NO 323
<211> LENGTH: 11
<212> TYPE: PRT
<213> ORGANISM: Artificial
<220> FEATURE:
<223> OTHER INFORMATION: synthetic peptide

<400> SEQUENCE: 323

Ser Arg Ser Tyr Pro Tyr Tyr Phe Asp Tyr
1               5                   10

<210> SEQ ID NO 324
<211> LENGTH: 240
<212> TYPE: PRT
<213> ORGANISM: Artificial
<220> FEATURE:
<223> OTHER INFORMATION: synthetic peptide

<400> SEQUENCE: 324

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Tyr Ala Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Ser Trp Tyr Gln Met His Trp Val
145                 150                 155                 160

Arg Gln Ala Pro Gly Lys Gly Leu Glu Trp Val Ala Leu Val Thr Pro
                165                 170                 175

Tyr Ser Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Tyr Thr
    210                 215                 220

Asp Gly Phe Asp Tyr Trp Gly Gln Gly Thr Leu Val Thr Val Ser Ser
225                 230                 235                 240

<210> SEQ ID NO 325
<211> LENGTH: 246
<212> TYPE: PRT
<213> ORGANISM: Artificial
<220> FEATURE:
<223> OTHER INFORMATION: synthetic peptide

<400> SEQUENCE: 325
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Pro Tyr Tyr Tyr Leu
                85                  90                  95

Pro Ile Thr Phe Gly Gln Gly Thr Lys Val Glu Ile Lys Arg Thr Gly
                100                 105                 110

Gly Gly Ser Gly Gly Gly Gly Ser Gly Gly Ala Ser Glu Val Gln
            115                 120                 125

Leu Val Glu Ser Gly Gly Gly Leu Val Gln Pro Gly Gly Ser Leu Arg
            130                 135                 140

Leu Ser Cys Ala Ala Ser Gly Phe Asn Val Ser Trp Ser Tyr Met His
145                 150                 155                 160

Trp Val Arg Gln Ala Pro Gly Lys Gly Leu Glu Trp Val Ala Asn Ile
                165                 170                 175

Tyr Gly Asp Ser Gly Tyr Thr His Tyr Ala Asp Ser Val Lys Gly Arg
            180                 185                 190

Phe Thr Ile Ser Ala Asp Thr Ser Lys Asn Thr Ala Tyr Leu Gln Met
            195                 200                 205

Asn Ser Leu Arg Ala Glu Asp Thr Ala Val Tyr Tyr Cys Ser Arg Gly
210                 215                 220

Gln Trp Glu Ala Ser Tyr Tyr Ala Met Asp Tyr Trp Gly Gln Gly Thr
225                 230                 235                 240

Leu Val Thr Val Ser Ser
                245

<210> SEQ ID NO 326
<211> LENGTH: 240
<212> TYPE: PRT
<213> ORGANISM: Artificial
<220> FEATURE:
<223> OTHER INFORMATION: synthetic peptide

<400> SEQUENCE: 326

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Ser Pro Val
                85                  90                  95

Thr Phe Gly Gln Gly Thr Lys Val Glu Ile Lys Arg Thr Gly Gly Gly
                100                 105                 110

```
Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Ser Trp Asn Gln Met His Trp Val
145                 150                 155                 160

Arg Gln Ala Pro Gly Lys Gly Leu Glu Trp Val Ala Leu Val Ser Pro
                165                 170                 175

Tyr Ser Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Asp Tyr
    210                 215                 220

Tyr Ala Met Asp Tyr Trp Gly Gln Gly Thr Leu Val Thr Val Ser Ser
225                 230                 235                 240

<210> SEQ ID NO 327
<211> LENGTH: 241
<212> TYPE: PRT
<213> ORGANISM: Artificial
<220> FEATURE:
<223> OTHER INFORMATION: synthetic peptide

<400> SEQUENCE: 327

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Asn Pro Phe
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Val Gly Tyr Tyr Gly Met His Trp Val
145                 150                 155                 160

Arg Gln Ala Pro Gly Lys Gly Leu Glu Trp Val Ala Phe Val Ser Gly
                165                 170                 175

Met Glu Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Asp Ile Tyr
    210                 215                 220

Gly Tyr Ala Met Asp Val Trp Gly Gln Gly Thr Leu Val Thr Val Ser
225                 230                 235                 240
```

Ser

```
<210> SEQ ID NO 328
<211> LENGTH: 243
<212> TYPE: PRT
<213> ORGANISM: Artificial
<220> FEATURE:
<223> OTHER INFORMATION: synthetic peptide

<400> SEQUENCE: 328

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Ser Pro Pro
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Asn Ile Thr Ser Ser Tyr Ile His Trp Val
145                 150                 155                 160

Arg Gln Ala Pro Gly Lys Gly Leu Glu Trp Val Ala Tyr Ile Ser Pro
                165                 170                 175

Ala Asp Gly Tyr Asn Arg Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Thr Asp Ser
210                 215                 220

Thr Ala Tyr Thr Ala Met Asp Val Trp Gly Gln Gly Thr Leu Val Thr
225                 230                 235                 240

Val Ser Ser

<210> SEQ ID NO 329
<211> LENGTH: 243
<212> TYPE: PRT
<213> ORGANISM: Artificial
<220> FEATURE:
<223> OTHER INFORMATION: synthetic peptide

<400> SEQUENCE: 329

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Pro
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Asn Ser Ser Tyr Ile His Trp Val
145                 150                 155                 160

Arg Gln Ala Pro Gly Lys Gly Leu Glu Trp Val Ala Tyr Ile Ser Pro
                165                 170                 175

Thr Asp Gly Tyr Tyr Arg Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Thr Ser Asp
    210                 215                 220

Thr Ser Tyr Ala Ala Met Asp Val Trp Gly Gln Gly Thr Leu Val Thr
225                 230                 235                 240

Val Ser Ser

<210> SEQ ID NO 330
<211> LENGTH: 243
<212> TYPE: PRT
<213> ORGANISM: Artificial
<220> FEATURE:
<223> OTHER INFORMATION: synthetic peptide

<400> SEQUENCE: 330

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Tyr Pro Pro
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Ser Thr Ser Tyr Ile His Trp Val
145                 150                 155                 160

Arg Gln Ala Pro Gly Lys Gly Leu Glu Trp Val Ala Thr Ile Asp Pro
```

```
                    165                 170                 175
Asn Asp Gly Tyr Ser Arg Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Thr Asn Asn
        210                 215                 220

Thr Ala Ala Asp Ala Met Asp Val Trp Gly Gln Gly Thr Leu Val Thr
225                 230                 235                 240

Val Ser Ser

<210> SEQ ID NO 331
<211> LENGTH: 242
<212> TYPE: PRT
<213> ORGANISM: Artificial
<220> FEATURE:
<223> OTHER INFORMATION: synthetic peptide

<400> SEQUENCE: 331

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Tyr Ala Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Asn Ile Ser Tyr Tyr Ser Met His Trp Val
145                 150                 155                 160

Arg Gln Ala Pro Gly Lys Gly Leu Glu Trp Val Ala Asp Val Asp Pro
                165                 170                 175

Asp Ser Asp Tyr Thr Glu Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Trp Ile
    210                 215                 220

His Met Phe Ser Met Asp Tyr Trp Gly Gln Gly Thr Leu Val Thr Val
225                 230                 235                 240

Ser Ser

<210> SEQ ID NO 332
<211> LENGTH: 241
<212> TYPE: PRT
<213> ORGANISM: Artificial
<220> FEATURE:
```

<223> OTHER INFORMATION: synthetic peptide

<400> SEQUENCE: 332

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Tyr Ala Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Gly Tyr Tyr Thr Met His Trp Val
145                 150                 155                 160

Arg Gln Ala Pro Gly Lys Gly Leu Glu Trp Val Ala Glu Val Ser Pro
                165                 170                 175

Trp Ser Tyr Ser Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Asp His Trp
    210                 215                 220

Asp Glu Ala Phe Asp Val Trp Gly Gln Gly Thr Leu Val Thr Val Ser
225                 230                 235                 240

Ser

<210> SEQ ID NO 333
<211> LENGTH: 243
<212> TYPE: PRT
<213> ORGANISM: Artificial
<220> FEATURE:
<223> OTHER INFORMATION: synthetic peptide

<400> SEQUENCE: 333

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Tyr Gly Pro Phe
                85                  90                  95

```
Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Ala Tyr Glu Tyr Met His Trp Val
145                 150                 155                 160

Arg Gln Ala Pro Gly Lys Gly Leu Glu Trp Val Ala Leu Ile Gly Pro
                165                 170                 175

Asp Ser Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Val Trp Tyr
    210                 215                 220

Tyr Ser Thr Tyr Gly Met Asp Tyr Trp Gly Gln Gly Thr Leu Val Thr
225                 230                 235                 240

Val Ser Ser

<210> SEQ ID NO 334
<211> LENGTH: 241
<212> TYPE: PRT
<213> ORGANISM: Artificial
<220> FEATURE:
<223> OTHER INFORMATION: synthetic peptide

<400> SEQUENCE: 334

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Tyr Ser Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Leu Phe Gly Tyr Gly Met His Trp Val
145                 150                 155                 160

Arg Gln Ala Pro Gly Lys Gly Leu Glu Trp Val Ala Glu Ile Gly Pro
                165                 170                 175

Tyr Tyr Tyr Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Glu Asn Tyr
```

```
                210                 215                 220
Asp Met Ala Met Asp Tyr Trp Gly Gln Gly Thr Leu Val Thr Val Ser
225                 230                 235                 240

Ser
```

```
<210> SEQ ID NO 335
<211> LENGTH: 241
<212> TYPE: PRT
<213> ORGANISM: Artificial
<220> FEATURE:
<223> OTHER INFORMATION: synthetic peptide

<400> SEQUENCE: 335

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Tyr Gln Pro Asp
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Asn Ile Ser Trp Tyr Ala Met His Trp Val
145                 150                 155                 160

Arg Gln Ala Pro Gly Lys Gly Leu Glu Trp Val Ala Glu Ile Trp Pro
                165                 170                 175

Asp Ser Asp Trp Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Tyr Tyr Tyr
210                 215                 220

Ser Ser Ala Phe Asp Val Trp Gly Gln Gly Thr Leu Val Thr Val Ser
225                 230                 235                 240

Ser
```

```
<210> SEQ ID NO 336
<211> LENGTH: 240
<212> TYPE: PRT
<213> ORGANISM: Artificial
<220> FEATURE:
<223> OTHER INFORMATION: synthetic peptide

<400> SEQUENCE: 336

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30
```

```
Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
         50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr Gln Pro Trp
                 85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Asn Ile Asp Tyr Tyr Gly Met His Trp Val
145                 150                 155                 160

Arg Gln Ala Pro Gly Lys Gly Leu Glu Trp Val Ala Ser Leu Tyr Gly
                165                 170                 175

Gly Ser Asp Ser Thr Asp Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Gln Tyr Ser
    210                 215                 220

Ala Tyr Phe Asp Tyr Trp Gly Gln Gly Thr Leu Val Thr Val Ser Ser
225                 230                 235                 240

<210> SEQ ID NO 337
<211> LENGTH: 241
<212> TYPE: PRT
<213> ORGANISM: Artificial
<220> FEATURE:
<223> OTHER INFORMATION: synthetic peptide

<400> SEQUENCE: 337

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
         50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Leu Tyr Tyr Pro Trp
                 85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Asn Val Ser Tyr Ser Ser Ile His Trp Val
145                 150                 155                 160
```

Arg Gln Ala Pro Gly Lys Gly Leu Glu Trp Val Ala Glu Ile Trp Pro
                165                 170                 175

Asp Ser Gly Gln Thr Trp Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Ser Tyr
    210                 215                 220

Phe Asp Ala Met Asp Tyr Trp Gly Gln Gly Thr Leu Val Thr Val Ser
225                 230                 235                 240

Ser

<210> SEQ ID NO 338
<211> LENGTH: 240
<212> TYPE: PRT
<213> ORGANISM: Artificial
<220> FEATURE:
<223> OTHER INFORMATION: synthetic peptide

<400> SEQUENCE: 338

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Tyr Ser Ser Pro Val
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Asn Trp Ala Asn Met His Trp Val
145                 150                 155                 160

Arg Gln Ala Pro Gly Lys Gly Leu Glu Trp Val Ala Gln Ile Ser Pro
                165                 170                 175

Pro Tyr Asp Tyr Thr Asn Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Tyr Ser
    210                 215                 220

Tyr Tyr Phe Asp Tyr Trp Gly Gln Gly Thr Leu Val Thr Val Ser Ser
225                 230                 235                 240

<210> SEQ ID NO 339
<211> LENGTH: 240
<212> TYPE: PRT
<213> ORGANISM: Artificial
<220> FEATURE:

<223> OTHER INFORMATION: synthetic peptide

<400> SEQUENCE: 339

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Arg Pro Val
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Tyr Leu His Asp Met His Trp Val
145                 150                 155                 160

Arg Gln Ala Pro Gly Lys Gly Leu Glu Trp Val Ala Gln Ile Ile Pro
                165                 170                 175

Ala Ile Asp Tyr Thr Asn Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Arg Asp Gly
    210                 215                 220

Tyr Tyr Phe Asp Tyr Trp Gly Gln Gly Thr Leu Val Thr Val Ser Ser
225                 230                 235                 240

<210> SEQ ID NO 340
<211> LENGTH: 240
<212> TYPE: PRT
<213> ORGANISM: Artificial
<220> FEATURE:
<223> OTHER INFORMATION: synthetic peptide

<400> SEQUENCE: 340

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Tyr Ser Ser Pro Val
                85                  90                  95

Thr Phe Gly Gln Gly Thr Lys Val Glu Ile Lys Arg Thr Gly Gly Gly
            100                 105                 110

```
Ser Gly Gly Gly Ser Gly Gly Ala Ser Glu Val Gln Leu Val
    115             120             125

Glu Ser Gly Gly Gly Leu Val Gln Pro Gly Gly Ser Leu Arg Leu Ser
130             135                 140

Cys Ala Ala Ser Gly Phe Asn Ile Tyr Trp Ser His Met His Trp Val
145             150                 155                 160

Arg Gln Ala Pro Gly Lys Gly Leu Glu Trp Val Ala Ile Ile Ser Ser
                165             170                 175

Phe Glu Gly Tyr Thr Tyr Tyr Ala Asp Ser Val Lys Gly Arg Phe Thr
            180             185                 190

Ile Ser Ala Asp Thr Ser Lys Asn Thr Ala Tyr Leu Gln Met Asn Ser
        195             200             205

Leu Arg Ala Glu Asp Thr Ala Val Tyr Tyr Cys Ser Arg Ser Tyr Ser
    210             215                 220

Tyr Tyr Met Asp Tyr Trp Gly Gln Gly Thr Leu Val Thr Val Ser Ser
225             230             235                 240
```

<210> SEQ ID NO 341
<211> LENGTH: 243
<212> TYPE: PRT
<213> ORGANISM: Artificial
<220> FEATURE:
<223> OTHER INFORMATION: synthetic peptide

<400> SEQUENCE: 341

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65              70                  75                  80

Glu Asp Phe Ala Thr Tyr Tyr Cys Gln Gln Ser Tyr Gly Ser Gly Ser
                85                  90                  95

Pro Trp Thr Phe Gly Gln Gly Thr Lys Val Glu Ile Lys Arg Thr Gly
            100                 105                 110

Gly Gly Ser Gly Gly Gly Gly Ser Gly Gly Ala Ser Glu Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Asn Ile Val Gly Gly Gly Ile His
145                 150                 155                 160

Trp Val Arg Gln Ala Pro Gly Lys Gly Leu Glu Trp Val Ala Lys Ile
                165                 170                 175

Tyr Pro Gln Gly Asp Tyr Thr Tyr Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Ser Arg Asp
    210                 215                 220

Ser Ser Tyr Leu Ala Phe Asp Tyr Trp Gly Gln Gly Thr Leu Val Thr
225                 230                 235                 240
```

Val Ser Ser

<210> SEQ ID NO 342
<211> LENGTH: 243
<212> TYPE: PRT
<213> ORGANISM: Artificial
<220> FEATURE:
<223> OTHER INFORMATION: synthetic peptide

<400> SEQUENCE: 342

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Tyr Ser Pro Trp
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
            130                 135                 140

Cys Ala Ala Ser Gly Phe Asn Ile Arg Ser Tyr Ala Met His Trp Val
145                 150                 155                 160

Arg Gln Ala Pro Gly Lys Gly Leu Glu Trp Val Ala Gln Val Gly Pro
                165                 170                 175

Gly Lys Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Asn Phe Gln
        210                 215                 220

Ser Thr Ser His Ala Phe Asp Tyr Trp Gly Gln Gly Thr Leu Val Thr
225                 230                 235                 240

Val Ser Ser

<210> SEQ ID NO 343
<211> LENGTH: 240
<212> TYPE: PRT
<213> ORGANISM: Artificial
<220> FEATURE:
<223> OTHER INFORMATION: synthetic peptide

<400> SEQUENCE: 343

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Pro Pro Ile
                85                  90                  95

Thr Phe Gly Gln Gly Thr Lys Val Glu Ile Lys Arg Thr Gly Gly
                100                 105                 110

Ser Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Asn Val Ser His Thr Gly Met His Trp Val
145                 150                 155                 160

Arg Gln Ala Pro Gly Lys Gly Leu Glu Trp Val Ala Val Val Gly Pro
                165                 170                 175

Gly Lys Gly Tyr Thr Tyr Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Lys Thr Tyr
210                 215                 220

Tyr Ala Phe Asp Tyr Trp Gly Gln Gly Thr Leu Val Thr Val Ser Ser
225                 230                 235                 240

<210> SEQ ID NO 344
<211> LENGTH: 245
<212> TYPE: PRT
<213> ORGANISM: Artificial
<220> FEATURE:
<223> OTHER INFORMATION: synthetic peptide

<400> SEQUENCE: 344

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Tyr Phe Arg
                85                  90                  95

Pro Ile Thr Phe Gly Gln Gly Thr Lys Val Glu Ile Lys Arg Thr Gly
                100                 105                 110

Gly Gly Ser Gly Gly Gly Gly Ser Gly Gly Ala Ser Glu Val Gln
            115                 120                 125

Leu Val Glu Ser Gly Gly Gly Leu Val Gln Pro Gly Gly Ser Leu Arg
            130                 135                 140

Leu Ser Cys Ala Ala Ser Gly Phe Asn Leu Ser Tyr Ser Asp Ile His
145                 150                 155                 160

Trp Val Arg Gln Ala Pro Gly Lys Gly Leu Glu Trp Val Ala Val Val
                165                 170                 175

```
Met Pro Asp Ser Gly His Thr Asn Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Ser Arg Ala
    210                 215                 220

Thr Asn Ile Pro Val Tyr Ala Phe Asp Tyr Trp Gly Gln Gly Thr Leu
225                 230                 235                 240

Val Thr Val Ser Ser
                245

<210> SEQ ID NO 345
<211> LENGTH: 244
<212> TYPE: PRT
<213> ORGANISM: Artificial
<220> FEATURE:
<223> OTHER INFORMATION: synthetic peptide

<400> SEQUENCE: 345

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Tyr Tyr Tyr Pro
                85                  90                  95

Leu Thr Phe Gly Gln Gly Thr Lys Val Glu Ile Lys Arg Thr Gly Gly
            100                 105                 110

Gly Ser Gly Gly Gly Gly Ser Gly Gly Ala Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ile Ser Ala Ser Gly Met His Trp
145                 150                 155                 160

Val Arg Gln Ala Pro Gly Lys Gly Leu Glu Trp Val Ala Asp Ile His
                165                 170                 175

Pro Leu Lys Pro Tyr Thr Asn Tyr Ala Asp Ser Val Lys Gly Arg Phe
            180                 185                 190

Thr Ile Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Ser Arg Tyr Ser
    210                 215                 220

Ser Met Tyr Tyr Tyr Tyr Phe Asp Tyr Trp Gly Gln Gly Thr Leu Val
225                 230                 235                 240

Thr Val Ser Ser

<210> SEQ ID NO 346
<211> LENGTH: 242
<212> TYPE: PRT
<213> ORGANISM: Artificial
<220> FEATURE:
<223> OTHER INFORMATION: synthetic peptide
```

<400> SEQUENCE: 346

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Ser Glu Tyr Ser Pro
                85                  90                  95

Trp Thr Phe Gly Gln Gly Thr Lys Val Glu Ile Lys Arg Thr Gly Gly
            100                 105                 110

Gly Ser Gly Gly Gly Ser Gly Gly Ala Ser Glu Val Gln Leu
        115                 120                 125

Val Glu Ser Gly Gly Gly Leu Val Gln Pro Gly Gly Ser Leu Arg Leu
130                 135                 140

Ser Cys Ala Ala Ser Gly Phe Asn Ile Tyr Arg Tyr Gly Ile His Trp
145                 150                 155                 160

Val Arg Gln Ala Pro Gly Lys Gly Leu Glu Trp Val Ala Val Leu Tyr
                165                 170                 175

Pro Tyr Gly Tyr Ser Thr Ser Tyr Ala Asp Ser Val Lys Gly Arg Phe
            180                 185                 190

Thr Ile Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Ser Arg Ser Tyr
210                 215                 220

Ala Tyr Gly Tyr Phe Ala Tyr Trp Gly Gln Gly Thr Leu Val Thr Val
225                 230                 235                 240

Ser Ser

<210> SEQ ID NO 347
<211> LENGTH: 243
<212> TYPE: PRT
<213> ORGANISM: Artificial
<220> FEATURE:
<223> OTHER INFORMATION: synthetic peptide

<400> SEQUENCE: 347

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Tyr Ile Pro Phe
                85                  90                  95

Thr Phe Gly Gln Gly Thr Lys Val Glu Ile Lys Arg Thr Gly Gly Gly

```
            100                 105                 110
Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
            130                 135                 140

Cys Ala Ala Ser Gly Phe Asn Ile Tyr Gly Thr Met Met His Trp Val
145                 150                 155                 160

Arg Gln Ala Pro Gly Lys Gly Leu Glu Trp Val Ala Gln Phe Lys Pro
                165                 170                 175

Asp Ser Tyr Asn Thr Tyr Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Gly Glu Val
            210                 215                 220

Tyr His Tyr Tyr Ala Phe Asp Tyr Trp Gly Gln Gly Thr Leu Val Thr
225                 230                 235                 240

Val Ser Ser

<210> SEQ ID NO 348
<211> LENGTH: 241
<212> TYPE: PRT
<213> ORGANISM: Artificial
<220> FEATURE:
<223> OTHER INFORMATION: synthetic peptide

<400> SEQUENCE: 348

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Tyr Tyr Arg Pro
                85                  90                  95

Phe Thr Phe Gly Gln Gly Thr Lys Val Glu Ile Lys Arg Thr Gly Gly
            100                 105                 110

Gly Ser Gly Gly Gly Gly Ser Gly Gly Gly Ala Ser Glu Val Gln Leu
            115                 120                 125

Val Glu Ser Gly Gly Gly Leu Val Gln Pro Gly Gly Ser Leu Arg Leu
            130                 135                 140

Ser Cys Ala Ala Ser Gly Phe Asn Ile Ser Tyr Ser Tyr Met His Trp
145                 150                 155                 160

Val Arg Gln Ala Pro Gly Lys Gly Leu Glu Trp Val Ala Thr Leu Leu
                165                 170                 175

Pro Tyr Asp Gly Asn Thr Tyr Tyr Ala Asp Ser Val Lys Gly Arg Phe
                180                 185                 190

Thr Ile Ser Ala Asp Thr Ser Lys Asn Thr Ala Tyr Leu Gln Met Asn
            195                 200                 205

Ser Leu Arg Ala Glu Asp Thr Ala Val Tyr Tyr Cys Ser Arg Ala Ala
            210                 215                 220
```

```
Tyr Ser Ser Met Asp Val Trp Gly Gln Gly Thr Leu Val Thr Val Ser
225                 230                 235                 240

Ser

<210> SEQ ID NO 349
<211> LENGTH: 242
<212> TYPE: PRT
<213> ORGANISM: Artificial
<220> FEATURE:
<223> OTHER INFORMATION: synthetic peptide

<400> SEQUENCE: 349

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Tyr Ser Pro Val
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Asn Val Ser Ala Tyr Trp Met His Trp Val
145                 150                 155                 160

Arg Gln Ala Pro Gly Lys Gly Leu Glu Trp Val Ala Gln Ile Tyr Gly
                165                 170                 175

Gly Ser Gly Tyr Thr Met Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Thr His Ser
210                 215                 220

Tyr Trp Ser Ala Phe Asp Tyr Trp Gly Gln Gly Thr Leu Val Thr Val
225                 230                 235                 240

Ser Ser

<210> SEQ ID NO 350
<211> LENGTH: 240
<212> TYPE: PRT
<213> ORGANISM: Artificial
<220> FEATURE:
<223> OTHER INFORMATION: synthetic peptide

<400> SEQUENCE: 350

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30
```

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Pro Ile
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Ala Ser Glu Val Gln Leu Val
                115                 120                 125

Glu Ser Gly Gly Gly Leu Val Gln Pro Gly Gly Ser Leu Arg Leu Ser
130                 135                 140

Cys Ala Ala Ser Gly Phe Asn Ile Ser Gly Tyr Gly Met His Trp Val
145                 150                 155                 160

Arg Gln Ala Pro Gly Lys Gly Leu Glu Trp Val Ala Tyr Leu Tyr Gly
                165                 170                 175

Gly Ser Asp Tyr Thr Asn Tyr Ala Asp Ser Val Lys Gly Arg Phe Thr
                180                 185                 190

Ile Ser Ala Asp Thr Ser Lys Asn Thr Ala Tyr Leu Gln Met Asn Ser
                195                 200                 205

Leu Arg Ala Glu Asp Thr Ala Val Tyr Tyr Cys Ser Arg Thr Val Arg
                210                 215                 220

Tyr Ala Phe Asp Tyr Trp Gly Gln Gly Thr Leu Val Thr Val Ser Ser
225                 230                 235                 240

<210> SEQ ID NO 351
<211> LENGTH: 240
<212> TYPE: PRT
<213> ORGANISM: Artificial
<220> FEATURE:
<223> OTHER INFORMATION: synthetic peptide

<400> SEQUENCE: 351

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ala Ser Pro Leu
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Ala Ser Glu Val Gln Leu Val
                115                 120                 125

Glu Ser Gly Gly Gly Leu Val Gln Pro Gly Gly Ser Leu Arg Leu Ser
130                 135                 140

Cys Ala Ala Ser Gly Phe Asn Val Ser Ser Val Gly Met His Trp Val
145                 150                 155                 160

Arg Gln Ala Pro Gly Lys Gly Leu Glu Trp Val Ala Tyr Ile Tyr Gly
            165                 170                 175

Thr Ser Asp Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Ser Ser Arg
            210                 215                 220

Tyr Ser Met Asp Tyr Trp Gly Gln Gly Thr Leu Val Thr Val Ser Ser
225                 230                 235                 240

<210> SEQ ID NO 352
<211> LENGTH: 240
<212> TYPE: PRT
<213> ORGANISM: Artificial
<220> FEATURE:
<223> OTHER INFORMATION: synthetic peptide

<400> SEQUENCE: 352

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ala Tyr Ser Pro Leu
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
        130                 135                 140

Cys Ala Ala Ser Gly Phe Asn Val Ser Ser Tyr Gly Met His Trp Val
145                 150                 155                 160

Arg Gln Ala Pro Gly Lys Gly Leu Glu Trp Val Ala Phe Ile Ala Pro
            165                 170                 175

Arg Arg Asp Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Lys Ser Ser
            210                 215                 220

Tyr Tyr Phe Asp Tyr Trp Gly Gln Gly Thr Leu Val Thr Val Ser Ser
225                 230                 235                 240

<210> SEQ ID NO 353
<211> LENGTH: 246
<212> TYPE: PRT
<213> ORGANISM: Artificial
<220> FEATURE:
<223> OTHER INFORMATION: synthetic peptide

<400> SEQUENCE: 353

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Tyr Tyr Pro Ile
                 85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Ala Ser Glu Val Gln Leu Val
             115                 120                 125

Glu Ser Gly Gly Gly Leu Val Gln Pro Gly Gly Ser Leu Arg Leu Ser
    130                 135                 140

Cys Ala Ala Ser Gly Phe Asn Phe Ser Tyr Gly Tyr Met His Trp Val
145                 150                 155                 160

Arg Gln Ala Pro Gly Lys Gly Leu Glu Trp Val Ala Trp Ile Ser Gly
                165                 170                 175

Tyr Thr Gly Asn Thr Tyr Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Ala Ala Ser
    210                 215                 220

Leu Ser Ser Ser Tyr Tyr Ser Ala Phe Asp Val Trp Gly Gln Gly Thr
225                 230                 235                 240

Leu Val Thr Val Ser Ser
                245

<210> SEQ ID NO 354
<211> LENGTH: 241
<212> TYPE: PRT
<213> ORGANISM: Artificial
<220> FEATURE:
<223> OTHER INFORMATION: synthetic peptide

<400> SEQUENCE: 354

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Tyr Thr Pro Val
                 85                  90                  95

Thr Phe Gly Gln Gly Thr Lys Val Glu Ile Lys Arg Thr Gly Gly Gly
                100                 105                 110
```

```
Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Asn Val Trp Gly Pro Gly Met His Trp Val
145                 150                 155                 160

Arg Gln Ala Pro Gly Lys Gly Leu Glu Trp Val Ala Arg Ile His Pro
                165                 170                 175

Phe Ser Gly Asn Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Gly Tyr Ser
    210                 215                 220

Tyr Ser Ala Met Asp Tyr Trp Gly Gln Gly Thr Leu Val Thr Val Ser
225                 230                 235                 240

Ser
```

```
<210> SEQ ID NO 355
<211> LENGTH: 241
<212> TYPE: PRT
<213> ORGANISM: Artificial
<220> FEATURE:
<223> OTHER INFORMATION: synthetic peptide

<400> SEQUENCE: 355

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Tyr Glu Pro Val
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Asn Val Ser Gly Ser Gln Met His Trp Val
145                 150                 155                 160

Arg Gln Ala Pro Gly Lys Gly Leu Glu Trp Val Ala Arg Ile Pro Gly
                165                 170                 175

Trp Ser Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Gly Tyr Ser
    210                 215                 220
```

```
Tyr Phe Ala Met Asp Tyr Trp Gly Gln Gly Thr Leu Val Thr Val Ser
225                 230                 235                 240

Ser

<210> SEQ ID NO 356
<211> LENGTH: 245
<212> TYPE: PRT
<213> ORGANISM: Artificial
<220> FEATURE:
<223> OTHER INFORMATION: synthetic peptide

<400> SEQUENCE: 356

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ala Tyr Tyr Ser Pro
                85                  90                  95

Val Thr Phe Gly Gln Gly Thr Lys Val Glu Ile Lys Arg Thr Gly Gly
            100                 105                 110

Gly Ser Gly Gly Gly Gly Ser Gly Gly Gly Ala Ser Glu Val Gln Leu
        115                 120                 125

Val Glu Ser Gly Gly Gly Leu Val Gln Pro Gly Gly Ser Leu Arg Leu
130                 135                 140

Ser Cys Ala Ala Ser Gly Phe Asn Ile Tyr Gly Gln Met Met His Trp
145                 150                 155                 160

Val Arg Gln Ala Pro Gly Lys Gly Leu Glu Trp Val Ala Phe Leu Ser
                165                 170                 175

Pro Phe Ser Gly Asn Thr Tyr Tyr Ala Asp Ser Val Lys Gly Arg Phe
            180                 185                 190

Thr Ile Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Ser Arg Asn Ile
    210                 215                 220

Ser Tyr Glu Gln Ser Ser Ala Phe Asp Tyr Trp Gly Gln Gly Thr Leu
225                 230                 235                 240

Val Thr Val Ser Ser
                245

<210> SEQ ID NO 357
<211> LENGTH: 241
<212> TYPE: PRT
<213> ORGANISM: Artificial
<220> FEATURE:
<223> OTHER INFORMATION: synthetic peptide

<400> SEQUENCE: 357

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30
```

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Glu Tyr Tyr Pro Met
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Val Met Tyr Ser Thr Met His Trp Val
145                 150                 155                 160

Arg Gln Ala Pro Gly Lys Gly Leu Glu Trp Val Ala Ser Ile Tyr Ser
                165                 170                 175

Trp Ser Asp Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Gly Tyr Ala
    210                 215                 220

His Asn Ser Phe Asp Tyr Trp Gly Gln Gly Thr Leu Val Thr Val Ser
225                 230                 235                 240

Ser

<210> SEQ ID NO 358
<211> LENGTH: 242
<212> TYPE: PRT
<213> ORGANISM: Artificial
<220> FEATURE:
<223> OTHER INFORMATION: synthetic peptide

<400> SEQUENCE: 358

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Phe Tyr Pro Phe
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Phe Gly Ser Tyr Ile His Trp Val Arg

```
145                 150                 155                 160
Gln Ala Pro Gly Lys Gly Leu Glu Trp Val Ala Ile Ile Ser Gly Tyr
            165                 170                 175

Ser Gly Asn Thr Tyr Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
            195                 200                 205

Arg Ala Glu Asp Thr Ala Val Tyr Tyr Cys Ser Arg Ser Asn Gln Ser
210                 215                 220

Ala Tyr Ser Tyr Met Asp Tyr Trp Gly Gln Gly Thr Leu Val Thr Val
225                 230                 235                 240

Ser Ser

<210> SEQ ID NO 359
<211> LENGTH: 243
<212> TYPE: PRT
<213> ORGANISM: Artificial
<220> FEATURE:
<223> OTHER INFORMATION: synthetic peptide

<400> SEQUENCE: 359

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Tyr Ser Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Ser Asp Ser Tyr Met His Trp Val
145                 150                 155                 160

Arg Gln Ala Pro Gly Lys Gly Leu Glu Trp Val Ala Thr Phe Ser Pro
                165                 170                 175

Tyr Ser Ser Asn Thr Trp Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Gln Phe
    210                 215                 220

Thr Phe Tyr Gln Tyr Phe Asp Tyr Trp Gly Gln Gly Thr Leu Val Thr
225                 230                 235                 240

Val Ser Ser

<210> SEQ ID NO 360
<211> LENGTH: 244
```

```
<212> TYPE: PRT
<213> ORGANISM: Artificial
<220> FEATURE:
<223> OTHER INFORMATION: synthetic peptide

<400> SEQUENCE: 360
```

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Asp | Val | Asn | Thr | Ala |
| | | | 20 | | | | | 25 | | | | | 30 | | |

| Val | Ala | Trp | Tyr | Gln | Gln | Lys | Pro | Gly | Lys | Ala | Pro | Lys | Leu | Leu | Ile |
| | | | 35 | | | | | 40 | | | | | 45 | | |

| Tyr | Ser | Ala | Tyr | Phe | Leu | Tyr | Ser | Gly | Val | Pro | Ser | Arg | Phe | Ser | Gly |
| | 50 | | | | | 55 | | | | | 60 | | | | |

| Ser | Arg | Ser | Gly | Thr | Asp | Phe | Thr | Leu | Thr | Ile | Ser | Ser | Leu | Gln | Pro |
| 65 | | | | | 70 | | | | | 75 | | | | | 80 |

| Glu | Asp | Phe | Ala | Thr | Tyr | Tyr | Cys | Gln | Gln | Tyr | Ser | Ala | Tyr | Tyr | Gln |
| | | | | 85 | | | | | 90 | | | | | 95 | |

| Pro | Ile | Thr | Phe | Gly | Gln | Gly | Thr | Lys | Val | Glu | Ile | Lys | Arg | Thr | Gly |
| | | | 100 | | | | | 105 | | | | | 110 | | |

| Gly | Gly | Ser | Gly | Gly | Gly | Ser | Gly | Gly | Gly | Ala | Ser | Glu | Val | Gln |
| | | 115 | | | | | 120 | | | | | 125 | | |

| Leu | Val | Glu | Ser | Gly | Gly | Gly | Leu | Val | Gln | Pro | Gly | Gly | Ser | Leu | Arg |
| | 130 | | | | | 135 | | | | | 140 | | | | |

| Leu | Ser | Cys | Ala | Ala | Ser | Gly | Phe | Asn | Ile | Phe | Ser | Asp | Gln | Met | His |
| 145 | | | | | 150 | | | | | 155 | | | | | 160 |

| Trp | Val | Arg | Gln | Ala | Pro | Gly | Lys | Gly | Leu | Glu | Trp | Val | Ala | Gly | Phe |
| | | | | 165 | | | | | 170 | | | | | 175 | |

| Met | Pro | Tyr | Asp | Ser | Tyr | Tyr | Thr | Asn | Tyr | Ala | Asp | Ser | Val | Lys | Gly |
| | | | 180 | | | | | 185 | | | | | 190 | | |

| Arg | Phe | Thr | Ile | Ser | Ala | Asp | Thr | Ser | Lys | Asn | Thr | Ala | Tyr | Leu | Gln |
| | | | 195 | | | | | 200 | | | | | 205 | | |

| Met | Asn | Ser | Leu | Arg | Ala | Glu | Asp | Thr | Ala | Val | Tyr | Tyr | Cys | Ser | Arg |
| 210 | | | | | 215 | | | | | 220 | | | | | |

| Met | Ser | Val | Arg | Asn | Ala | Phe | Asp | Tyr | Trp | Gly | Gln | Gly | Thr | Leu | Val |
| 225 | | | | | 230 | | | | | 235 | | | | | 240 |

| Thr | Val | Ser | Ser |
|---|---|---|---|

```
<210> SEQ ID NO 361
<211> LENGTH: 242
<212> TYPE: PRT
<213> ORGANISM: Artificial
<220> FEATURE:
<223> OTHER INFORMATION: synthetic peptide

<400> SEQUENCE: 361
```

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Asp | Val | Asn | Thr | Ala |
| | | | 20 | | | | | 25 | | | | | 30 | | |

| Val | Ala | Trp | Tyr | Gln | Gln | Lys | Pro | Gly | Lys | Ala | Pro | Lys | Leu | Leu | Ile |
| | | | 35 | | | | | 40 | | | | | 45 | | |

| Tyr | Ser | Ala | Ser | Phe | Leu | Tyr | Ser | Gly | Val | Pro | Ser | Arg | Phe | Ser | Gly |
| | 50 | | | | | 55 | | | | | 60 | | | | |

| Ser | Arg | Ser | Gly | Thr | Asp | Phe | Thr | Leu | Thr | Ile | Ser | Ser | Leu | Gln | Pro |
| 65 | | | | | 70 | | | | | 75 | | | | | 80 |

```
Glu Asp Phe Ala Thr Tyr Tyr Cys Gln Gln Tyr Ser Tyr Tyr Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Asn Leu Ser Tyr Tyr Met His Trp Val
145                 150                 155                 160

Arg Gln Ala Pro Gly Lys Gly Leu Glu Trp Val Ala Val Ile Ser Gly
                165                 170                 175

Phe Ser Gly Asn Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Asp Ser
    210                 215                 220

Tyr Tyr Thr Ala Met Asp Tyr Trp Gly Gln Gly Thr Leu Val Thr Val
225                 230                 235                 240

Ser Ser
```

<210> SEQ ID NO 362
<211> LENGTH: 240
<212> TYPE: PRT
<213> ORGANISM: Artificial
<220> FEATURE:
<223> OTHER INFORMATION: synthetic peptide

<400> SEQUENCE: 362

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Glu Tyr Val Pro His
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Asn Ile Ser Tyr Gly Tyr Met His Trp Val
145                 150                 155                 160

Arg Gln Ala Pro Gly Lys Gly Leu Glu Trp Val Ala Lys Phe His Tyr
                165                 170                 175

Gly Ser Gly Asn Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
```

```
                195                 200                 205
Leu Arg Ala Glu Asp Thr Ala Val Tyr Tyr Cys Ser Arg Ser Asn Tyr
    210                 215                 220

Tyr Tyr Leu Asp Tyr Trp Gly Gln Gly Thr Leu Val Thr Val Ser Ser
225                 230                 235                 240

<210> SEQ ID NO 363
<211> LENGTH: 244
<212> TYPE: PRT
<213> ORGANISM: Artificial
<220> FEATURE:
<223> OTHER INFORMATION: synthetic peptide

<400> SEQUENCE: 363

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Tyr Met Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Asn Ile Ser Tyr Gln His Ile His Trp Val
145                 150                 155                 160

Arg Gln Ala Pro Gly Lys Gly Leu Glu Trp Val Ala Val Phe Met Pro
                165                 170                 175

Tyr Gln Gly Ser Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ala Asn Ile
    210                 215                 220

Tyr Ser Ser His Ser Phe Phe Asp Tyr Trp Gly Gln Gly Thr Leu Val
225                 230                 235                 240

Thr Val Ser Ser

<210> SEQ ID NO 364
<211> LENGTH: 243
<212> TYPE: PRT
<213> ORGANISM: Artificial
<220> FEATURE:
<223> OTHER INFORMATION: synthetic peptide

<400> SEQUENCE: 364

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
```

```
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ala Tyr Tyr Pro Val
                85                  90                  95
Thr Phe Gly Gln Gly Thr Lys Val Glu Ile Lys Arg Thr Gly Gly Gly
                100                 105                 110
Ser Gly Gly Gly Gly Ser Gly Gly Ala Ser Glu Val Gln Leu Val
            115                 120                 125
Glu Ser Gly Gly Gly Leu Val Gln Pro Gly Gly Ser Leu Arg Leu Ser
        130                 135                 140
Cys Ala Ala Ser Gly Phe Asn Leu Ser Gly Tyr Tyr Met His Trp Val
145                 150                 155                 160
Arg Gln Ala Pro Gly Lys Gly Leu Glu Trp Val Ala Trp Phe Ser Pro
                165                 170                 175
Tyr Ser Gly Tyr Thr Tyr Tyr Ala Asp Ser Val Lys Gly Arg Phe Thr
                180                 185                 190
Ile Ser Ala Asp Thr Ser Lys Asn Thr Ala Tyr Leu Gln Met Asn Ser
            195                 200                 205
Leu Arg Ala Glu Asp Thr Ala Val Tyr Tyr Cys Ser Arg Thr His Ser
        210                 215                 220
Ser Ile Tyr His Ser Phe Asp Tyr Trp Gly Gln Gly Thr Leu Val Thr
225                 230                 235                 240
Val Ser Ser

<210> SEQ ID NO 365
<211> LENGTH: 244
<212> TYPE: PRT
<213> ORGANISM: Artificial
<220> FEATURE:
<223> OTHER INFORMATION: synthetic peptide

<400> SEQUENCE: 365

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Tyr Met Pro Ile
                85                  90                  95
Thr Phe Gly Gln Gly Thr Lys Val Glu Ile Lys Arg Thr Gly Gly Gly
                100                 105                 110
Ser Gly Gly Gly Gly Ser Gly Gly Ala Ser Glu Val Gln Leu Val
            115                 120                 125
Glu Ser Gly Gly Gly Leu Val Gln Pro Gly Gly Ser Leu Arg Leu Ser
        130                 135                 140
```

```
Cys Ala Ala Ser Gly Phe Asn Val Ser Gly Gln Tyr Met His Trp Val
145                 150                 155                 160

Arg Gln Ala Pro Gly Lys Gly Leu Glu Trp Val Ala Val Ile Ser Pro
                165                 170                 175

Val Ser Gly Asn Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Pro Met Lys
    210                 215                 220

Thr Ser Tyr Tyr Gly Ala Phe Asp Tyr Trp Gly Gln Gly Thr Leu Val
225                 230                 235                 240

Thr Val Ser Ser

<210> SEQ ID NO 366
<211> LENGTH: 244
<212> TYPE: PRT
<213> ORGANISM: Artificial
<220> FEATURE:
<223> OTHER INFORMATION: synthetic peptide

<400> SEQUENCE: 366

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Tyr Arg Pro Val
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Asn Val Ser Thr Ser Gly Met His Trp Val
145                 150                 155                 160

Arg Gln Ala Pro Gly Lys Gly Leu Glu Trp Val Ala Phe Ile Tyr Gly
                165                 170                 175

Ala Tyr Ser Gly Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Gln Ser
    210                 215                 220

Tyr Thr Tyr Trp Ser Ala Met Asp Tyr Trp Gly Gln Gly Thr Leu Val
225                 230                 235                 240

Thr Val Ser Ser
```

```
<210> SEQ ID NO 367
<211> LENGTH: 241
<212> TYPE: PRT
<213> ORGANISM: Artificial
<220> FEATURE:
<223> OTHER INFORMATION: synthetic peptide

<400> SEQUENCE: 367

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Phe Thr Pro Met
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Asn Ile Ser Tyr Ala Lys Met His Trp Val
145                 150                 155                 160

Arg Gln Ala Pro Gly Lys Gly Leu Glu Trp Val Ala Tyr Leu Thr Tyr
                165                 170                 175

Trp Gly Gly Tyr Thr Asn Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Gly Glu Tyr
210                 215                 220

Gly Thr Tyr Met Asp Tyr Trp Gly Gln Gly Thr Leu Val Thr Val Ser
225                 230                 235                 240

Ser

<210> SEQ ID NO 368
<211> LENGTH: 242
<212> TYPE: PRT
<213> ORGANISM: Artificial
<220> FEATURE:
<223> OTHER INFORMATION: synthetic peptide

<400> SEQUENCE: 368

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Tyr Ser Ser Ser Pro
                    85                  90                  95
Val Thr Phe Gly Gln Gly Thr Lys Val Glu Ile Lys Arg Thr Gly Gly
                100                 105                 110
Gly Ser Gly Gly Gly Ser Gly Gly Ala Ser Glu Val Gln Leu
                115                 120                 125
Val Glu Ser Gly Gly Leu Val Gln Pro Gly Gly Ser Leu Arg Leu
                130                 135                 140
Ser Cys Ala Ala Ser Gly Phe Asn Phe Ser Ser Tyr Val Met His Trp
145                 150                 155                 160
Val Arg Gln Ala Pro Gly Lys Gly Leu Glu Trp Val Ala Val Tyr
                165                 170                 175
Pro Asp Ser Gly Gly Thr Tyr Tyr Ala Asp Ser Val Lys Gly Arg Phe
                180                 185                 190
Thr Ile Ser Ala Asp Thr Ser Lys Asn Thr Ala Tyr Leu Gln Met Asn
                195                 200                 205
Ser Leu Arg Ala Glu Asp Thr Ala Val Tyr Tyr Cys Ser Arg Thr Ser
                210                 215                 220
Ser Tyr Tyr Ala Phe Asp Tyr Trp Gly Gln Gly Thr Leu Val Thr Val
225                 230                 235                 240

Ser Ser

<210> SEQ ID NO 369
<211> LENGTH: 241
<212> TYPE: PRT
<213> ORGANISM: Artificial
<220> FEATURE:
<223> OTHER INFORMATION: synthetic peptide

<400> SEQUENCE: 369

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
65              70                  75                  80

Glu Asp Phe Ala Thr Tyr Tyr Cys Gln Gln Ser Ser Tyr Thr Pro Ile
                    85                  90                  95

Thr Phe Gly Gln Gly Thr Lys Val Glu Ile Lys Arg Thr Gly Gly Gly
                100                 105                 110

Ser Gly Gly Gly Ser Gly Gly Ala Ser Glu Val Gln Leu Val
                115                 120                 125

Glu Ser Gly Gly Gly Leu Val Gln Pro Gly Gly Ser Leu Arg Leu Ser
                130                 135                 140

Cys Ala Ala Ser Gly Phe Asn Ile Ser Gln Gly Gly Ile His Trp Val
145                 150                 155                 160

Arg Gln Ala Pro Gly Lys Gly Leu Glu Trp Val Ala Tyr Val Tyr Pro
                165                 170                 175

Gly Gly Gly Gln Thr Asn Tyr Ala Asp Ser Val Lys Gly Arg Phe Thr
                180                 185                 190
```

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Gly Tyr Asp
            210                 215                 220

Tyr Ser Ala Phe Asp Tyr Trp Gly Gln Gly Thr Leu Val Thr Val Ser
225                 230                 235                 240

Ser

<210> SEQ ID NO 370
<211> LENGTH: 241
<212> TYPE: PRT
<213> ORGANISM: Artificial
<220> FEATURE:
<223> OTHER INFORMATION: synthetic peptide

<400> SEQUENCE: 370

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ala Tyr Tyr Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Asn Ile Ser Ser Thr Gly Met His Trp Val
145                 150                 155                 160

Arg Gln Ala Pro Gly Lys Gly Leu Glu Trp Val Ala Glu Leu Leu Gly
                165                 170                 175

Gly Ser Gly Asn Thr Asn Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Gly Leu Gln
            210                 215                 220

Tyr Ser Ala Met Asp Tyr Trp Gly Gln Gly Thr Leu Val Thr Val Ser
225                 230                 235                 240

Ser

<210> SEQ ID NO 371
<211> LENGTH: 242
<212> TYPE: PRT
<213> ORGANISM: Artificial
<220> FEATURE:
<223> OTHER INFORMATION: synthetic peptide

<400> SEQUENCE: 371

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Glu Tyr Tyr Pro Ile
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Asn Phe Phe Ser Thr Val Ile His Trp Val
145                 150                 155                 160

Arg Gln Ala Pro Gly Lys Gly Leu Glu Trp Val Ala Glu Ile Tyr Pro
                165                 170                 175

Trp Ser Gly Ser Thr Tyr Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Ser Arg Ser
    210                 215                 220

Ser Asn Tyr Tyr Phe Asp Val Trp Gly Gln Gly Thr Leu Val Thr Val
225                 230                 235                 240

Ser Ser

<210> SEQ ID NO 372
<211> LENGTH: 241
<212> TYPE: PRT
<213> ORGANISM: Artificial
<220> FEATURE:
<223> OTHER INFORMATION: synthetic peptide

<400> SEQUENCE: 372

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Thr Tyr Tyr Pro Ile
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Gly Ala Ser Glu Val Gln Leu Val

```
                115                 120                 125
Glu Ser Gly Gly Gly Leu Val Gln Pro Gly Gly Ser Leu Arg Leu Ser
        130                 135                 140

Cys Ala Ala Ser Gly Phe Asn Leu His Gly Tyr Leu Met His Trp Val
145                 150                 155                 160

Arg Gln Ala Pro Gly Lys Gly Leu Glu Trp Val Ala Phe Ile Tyr Pro
                165                 170                 175

Pro Asn Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Gly Val Asp
    210                 215                 220

Tyr Ala Tyr Leu Asp Tyr Trp Gly Gln Gly Thr Leu Val Thr Val Ser
225                 230                 235                 240

Ser

<210> SEQ ID NO 373
<211> LENGTH: 241
<212> TYPE: PRT
<213> ORGANISM: Artificial
<220> FEATURE:
<223> OTHER INFORMATION: synthetic peptide

<400> SEQUENCE: 373

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Tyr Tyr Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
        130                 135                 140

Cys Ala Ala Ser Gly Phe Asn Leu Ser Thr His Val Met His Trp Val
145                 150                 155                 160

Arg Gln Ala Pro Gly Lys Gly Leu Glu Trp Val Ala Glu Phe Tyr Pro
                165                 170                 175

Tyr Val Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Gly Tyr Arg
    210                 215                 220

Tyr Gln Tyr Met Asp Val Trp Gly Gln Gly Thr Leu Val Thr Val Ser
225                 230                 235                 240
```

Ser

<210> SEQ ID NO 374
<211> LENGTH: 240
<212> TYPE: PRT
<213> ORGANISM: Artificial
<220> FEATURE:
<223> OTHER INFORMATION: synthetic peptide

<400> SEQUENCE: 374

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Ser Val Glu Pro Trp
                85                  90                  95
Thr Phe Gly Gln Gly Thr Lys Val Glu Ile Lys Arg Thr Gly Gly Gly
            100                 105                 110
Ser Gly Gly Gly Gly Ser Gly Gly Ala Ser Glu Val Gln Leu Val
        115                 120                 125
Glu Ser Gly Gly Gly Leu Val Gln Pro Gly Gly Ser Leu Arg Leu Ser
    130                 135                 140
Cys Ala Ala Ser Gly Phe Asn Val Ser Tyr Tyr Ser Ile His Trp Val
145                 150                 155                 160
Arg Gln Ala Pro Gly Lys Gly Leu Glu Trp Val Ala Tyr Ile Tyr Pro
                165                 170                 175
Trp Asn Asp Tyr Thr Tyr Tyr Ala Asp Ser Val Lys Gly Arg Phe Thr
            180                 185                 190
Ile Ser Ala Asp Thr Ser Lys Asn Thr Ala Tyr Leu Gln Met Asn Ser
        195                 200                 205
Leu Arg Ala Glu Asp Thr Ala Val Tyr Tyr Cys Ser Arg Gly Ser Tyr
    210                 215                 220
Tyr Ser Phe Asp Tyr Trp Gly Gln Gly Thr Leu Val Thr Val Ser Ser
225                 230                 235                 240
```

<210> SEQ ID NO 375
<211> LENGTH: 238
<212> TYPE: PRT
<213> ORGANISM: Artificial
<220> FEATURE:
<223> OTHER INFORMATION: synthetic peptide

<400> SEQUENCE: 375

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Tyr Ser Pro Pro
                 85                  90                  95

Thr Phe Gly Gln Gly Thr Lys Val Glu Ile Lys Arg Thr Gly Gly Gly
            100                 105                 110

Ser Gly Gly Gly Ala Ser Glu Val Gln Leu Val Glu Ser Gly Gly Gly
            115                 120                 125

Leu Val Gln Pro Gly Gly Ser Leu Arg Leu Ser Cys Ala Ala Ser Gly
            130                 135                 140

Phe Asn Ile Asn Asn Thr Tyr Ile His Trp Val Arg Gln Ala Pro Gly
145                 150                 155                 160

Lys Gly Leu Glu Trp Val Ala Ser Ile Tyr Pro Thr Asp Gly Tyr Thr
                165                 170                 175

Arg Tyr Ala Asp Ser Val Lys Gly Arg Phe Thr Ile Ser Ala Asp Thr
                180                 185                 190

Ser Lys Asn Thr Ala Tyr Leu Gln Met Asn Ser Leu Arg Ala Glu Asp
                195                 200                 205

Thr Ala Val Tyr Tyr Cys Ser Arg Thr Tyr Tyr Ser Tyr Tyr Ser Ala
            210                 215                 220

Met Asp Val Trp Gly Gln Gly Thr Leu Val Thr Val Ser Ser
225                 230                 235

<210> SEQ ID NO 376
<211> LENGTH: 241
<212> TYPE: PRT
<213> ORGANISM: Artificial
<220> FEATURE:
<223> OTHER INFORMATION: synthetic peptide

<400> SEQUENCE: 376

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
             35                  40                  45

Tyr Ser Ala Tyr Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ile Tyr Thr Ser Pro Ile
                 85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Gly Ala Ser Glu Val Gln Leu Val
            115                 120                 125

Glu Ser Gly Gly Gly Leu Val Gln Pro Gly Gly Ser Leu Arg Leu Ser
            130                 135                 140

Cys Ala Ala Ser Gly Phe Asn Phe Ile Thr Thr Gly Met His Trp Val
145                 150                 155                 160

Arg Gln Ala Pro Gly Lys Gly Leu Glu Trp Val Ala Arg Ile Gly Pro
                165                 170                 175

Gly Ser Asp Tyr Thr Asn Tyr Ala Asp Ser Val Lys Gly Arg Phe Thr
                180                 185                 190
```

```
Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Tyr Tyr Tyr
        210                 215                 220

Ala Ser Ala Leu Asp Tyr Trp Gly Gln Gly Thr Leu Val Thr Val Ser
225                 230                 235                 240

Ser

<210> SEQ ID NO 377
<211> LENGTH: 240
<212> TYPE: PRT
<213> ORGANISM: Artificial
<220> FEATURE:
<223> OTHER INFORMATION: synthetic peptide

<400> SEQUENCE: 377

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Ala Tyr Phe Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Asn Phe Ser Asp Tyr Gly Met His Trp Val
145                 150                 155                 160

Arg Gln Ala Pro Gly Lys Gly Leu Glu Trp Val Ala Met Leu Ile Pro
                165                 170                 175

Ala Ser Gly Tyr Thr Asn Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Gly Trp Ser
        210                 215                 220

Tyr Tyr Met Asp Tyr Trp Gly Gln Gly Thr Leu Val Thr Val Ser Ser
225                 230                 235                 240

<210> SEQ ID NO 378
<211> LENGTH: 241
<212> TYPE: PRT
<213> ORGANISM: Artificial
<220> FEATURE:
<223> OTHER INFORMATION: synthetic peptide

<400> SEQUENCE: 378

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gln Tyr Ala Tyr Thr Pro
                85                  90                  95

Ile Thr Phe Gly Gln Gly Thr Lys Val Glu Ile Lys Arg Thr Gly Gly
            100                 105                 110

Gly Ser Gly Gly Gly Ser Gly Gly Ala Ser Glu Val Gln Leu
        115                 120                 125

Val Glu Ser Gly Gly Gly Leu Val Gln Pro Gly Gly Ser Leu Arg Leu
130                 135                 140

Ser Cys Ala Ala Ser Gly Phe Asn Val Trp Ser Tyr Gly Ile His Trp
145                 150                 155                 160

Val Arg Gln Ala Pro Gly Lys Gly Leu Glu Trp Val Ala Gly Val Thr
            165                 170                 175

Pro Asp Gly Ser Tyr Thr Tyr Tyr Ala Asp Ser Val Lys Gly Arg Phe
        180                 185                 190

Thr Ile Ser Ala Asp Thr Ser Lys Asn Thr Ala Tyr Leu Gln Met Asn
    195                 200                 205

Ser Leu Arg Ala Glu Asp Thr Ala Val Tyr Tyr Cys Ser Arg Ser Tyr
210                 215                 220

Gly Trp Ala Met Asp Tyr Trp Gly Gln Gly Thr Leu Val Thr Val Ser
225                 230                 235                 240

Ser

<210> SEQ ID NO 379
<211> LENGTH: 241
<212> TYPE: PRT
<213> ORGANISM: Artificial
<220> FEATURE:
<223> OTHER INFORMATION: synthetic peptide

<400> SEQUENCE: 379

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Tyr Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ile His Tyr Lys Pro Leu
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

```
Glu Ser Gly Gly Gly Leu Val Gln Pro Gly Gly Ser Leu Arg Leu Ser
    130                 135                 140

Cys Ala Ala Ser Gly Phe Asn Val Ala Trp Tyr Ser Ile His Trp Val
145                 150                 155                 160

Arg Gln Ala Pro Gly Lys Gly Leu Glu Trp Val Ala Gln Val Tyr Gly
                165                 170                 175

Gly Ser Ser Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Asp Phe Tyr
    210                 215                 220

Ser Ser Gly Met Asp Tyr Trp Gly Gln Gly Thr Leu Val Thr Val Ser
225                 230                 235                 240

Ser
```

<210> SEQ ID NO 380
<211> LENGTH: 243
<212> TYPE: PRT
<213> ORGANISM: Artificial
<220> FEATURE:
<223> OTHER INFORMATION: synthetic peptide

<400> SEQUENCE: 380

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Trp Arg Leu Pro Ile
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Val Tyr Gly Asn Gln Ile His Trp Val
145                 150                 155                 160

Arg Gln Ala Pro Gly Lys Gly Leu Glu Trp Val Ala Arg Ile Tyr Pro
                165                 170                 175

Tyr Ser Gly Ser Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Ala Tyr
    210                 215                 220

Val Ala Tyr Ser Tyr Phe Asp Tyr Trp Gly Gln Gly Thr Leu Val Thr
225                 230                 235                 240

Val Ser Ser
```

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390
<211> LENGTH: 241
<212> TYPE: PRT
<213> ORGANISM: Artificial
<220> FEATURE:
<223> OTHER INFORMATION: synthetic peptide

<400> SEQUENCE: 390

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Thr Ser Thr Pro Phe
                 85                  90                  95

Thr Phe Gly Gln Gly Thr Lys Val Glu Ile Lys Arg Thr Gly Gly Gly
             100                 105                 110

Ser Gly Gly Gly Gly Ser Gly Gly Ala Ser Glu Val Gln Leu Val
             115                 120                 125

Glu Ser Gly Gly Gly Leu Val Gln Pro Gly Gly Ser Leu Arg Leu Ser
        130                 135                 140

Cys Ala Ala Ser Gly Phe Asn Leu Ser Tyr Tyr Gly Met His Trp Val
145                 150                 155                 160

Arg Gln Ala Pro Gly Lys Gly Leu Glu Trp Val Ala Thr Ile Tyr Pro
                 165                 170                 175

Asp Ser Gly Tyr Thr Lys Tyr Ala Asp Ser Val Lys Gly Arg Phe Thr
             180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ala Tyr Leu
    210                 215                 220

Tyr Tyr Tyr Leu Ala Tyr Trp Gly Gln Gly Thr Leu Val Thr Val Ser
225                 230                 235                 240

Ser

<210> SEQ ID NO 391
<211> LENGTH: 240
<212> TYPE: PRT
<213> ORGANISM: Artificial
<220> FEATURE:
<223> OTHER INFORMATION: synthetic peptide

<400> SEQUENCE: 391

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Arg Tyr Pro Met
                 85                  90                  95

Thr Phe Gly Gln Gly Thr Lys Val Glu Ile Lys Arg Thr Gly Gly Gly
             100                 105                 110

Ser Gly Gly Gly Gly Ser Gly Gly Ala Ser Glu Val Gln Leu Val
             115                 120                 125

Glu Ser Gly Gly Gly Leu Val Gln Pro Gly Gly Ser Leu Arg Leu Ser
        130                 135                 140

```
Cys Ala Ala Ser Gly Phe Asn Ile Ser Arg Tyr Gly Met His Trp Val
145                 150                 155                 160

Arg Gln Ala Pro Gly Lys Gly Leu Glu Trp Val Ala Val Phe Tyr Pro
                165                 170                 175

Ser Ser Ser Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Lys Tyr Tyr
    210                 215                 220

Glu Ala Met Asp Tyr Trp Gly Gln Gly Thr Leu Val Thr Val Ser Ser
225                 230                 235                 240

<210> SEQ ID NO 392
<211> LENGTH: 240
<212> TYPE: PRT
<213> ORGANISM: Artificial
<220> FEATURE:
<223> OTHER INFORMATION: synthetic peptide

<400> SEQUENCE: 392

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Tyr Pro Val
                85                  90                  95

Thr Phe Gly His Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Asn Ile Tyr Ser Ser Trp Met His Trp Val
145                 150                 155                 160

Arg Gln Ala Pro Gly Lys Gly Leu Glu Trp Val Ala Tyr Phe Gln Pro
                165                 170                 175

Tyr Ser Gly Tyr Thr Lys Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Glu Tyr Thr
    210                 215                 220

Tyr Tyr Phe Asp Tyr Trp Gly Gln Gly Thr Leu Val Thr Val Ser Ser
225                 230                 235                 240

<210> SEQ ID NO 393
<211> LENGTH: 242
<212> TYPE: PRT
<213> ORGANISM: Artificial
<220> FEATURE:
```

<223> OTHER INFORMATION: synthetic peptide

<400> SEQUENCE: 393

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Leu Tyr Ser Pro
                85                  90                  95

Phe Thr Phe Gly Gln Gly Thr Lys Val Glu Ile Lys Arg Thr Gly Gly
            100                 105                 110

Gly Ser Gly Gly Gly Gly Ser Gly Gly Ala Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ile Ser Gly Tyr Gly Met His Trp
145                 150                 155                 160

Val Arg Gln Ala Pro Gly Lys Gly Leu Glu Trp Val Ala Arg Val Tyr
                165                 170                 175

Gly Gly Ser Gly Tyr Thr Tyr Tyr Ala Asp Ser Val Lys Gly Arg Phe
            180                 185                 190

Thr Ile Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Ser Arg Ala His
    210                 215                 220

Ser Ser Tyr Tyr Val Asp Tyr Trp Gly Gln Gly Thr Leu Val Thr Val
225                 230                 235                 240

Ser Ser

<210> SEQ ID NO 394
<211> LENGTH: 241
<212> TYPE: PRT
<213> ORGANISM: Artificial
<220> FEATURE:
<223> OTHER INFORMATION: synthetic peptide

<400> SEQUENCE: 394

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Phe Tyr Tyr Pro
                85                  90                  95

```
Asn Thr Phe Gly Gln Gly Thr Lys Val Glu Ile Lys Arg Thr Gly Gly
                100                 105                 110

Gly Ser Gly Gly Gly Ser Gly Gly Ala Ser Glu Val Gln Leu
        115                 120                 125

Val Glu Ser Gly Gly Gly Leu Val Gln Pro Gly Gly Ser Leu Arg Leu
130                 135                 140

Ser Cys Ala Ala Ser Gly Phe Asn Ile Gly Tyr Tyr Gly Met His Trp
145                 150                 155                 160

Val Arg Gln Ala Pro Gly Lys Gly Leu Glu Trp Val Ala Thr Val Tyr
                165                 170                 175

Pro Gly Gly Gly Tyr Thr Ser Tyr Ala Asp Ser Val Lys Gly Arg Phe
                180                 185                 190

Thr Ile Ser Ala Asp Thr Ser Lys Asn Thr Ala Tyr Leu Gln Met Asn
                195                 200                 205

Ser Leu Arg Ala Glu Asp Thr Ala Val Tyr Tyr Cys Ser Arg Tyr Tyr
210                 215                 220

Tyr Tyr Gly Phe Asp Tyr Trp Gly Gln Gly Thr Leu Val Thr Val Ser
225                 230                 235                 240

Ser

<210> SEQ ID NO 395
<211> LENGTH: 240
<212> TYPE: PRT
<213> ORGANISM: Artificial
<220> FEATURE:
<223> OTHER INFORMATION: synthetic peptide

<400> SEQUENCE: 395

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Tyr Ser Pro Val
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Asn Ile Phe Tyr Gln Asp Met His Trp Val
145                 150                 155                 160

Arg Gln Ala Pro Gly Lys Gly Leu Glu Trp Val Ala Met Ile Tyr Pro
                165                 170                 175

Asp Tyr Asp Tyr Thr Tyr Tyr Ala Asp Ser Val Lys Gly Arg Phe Thr
                180                 185                 190

Ile Ser Ala Asp Thr Ser Lys Asn Thr Ala Tyr Leu Gln Met Asn Ser
                195                 200                 205

Leu Arg Ala Glu Asp Thr Ala Val Tyr Tyr Cys Ser Arg Thr Tyr Ser
```

```
Val Tyr Met Asp Tyr Trp Gly Gln Gly Thr Leu Val Thr Val Ser Ser
225                 230                 235                 240
```

<210> SEQ ID NO 396
<211> LENGTH: 240
<212> TYPE: PRT
<213> ORGANISM: Artificial
<220> FEATURE:
<223> OTHER INFORMATION: synthetic peptide

<400> SEQUENCE: 396

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ala Tyr Ala Pro Phe
                85                  90                  95

Thr Phe Gly Gln Gly Thr Lys Val Glu Ile Lys Arg Thr Gly Gly Gly
            100                 105                 110

Ser Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Asn Val Ser Tyr Ser Met Ile His Trp Val
145                 150                 155                 160

Arg Gln Ala Pro Gly Lys Gly Leu Glu Trp Val Ala Arg Val Trp Gly
                165                 170                 175

Asp Gly Gly Val Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Gly Ser Tyr
    210                 215                 220

Tyr Ala Phe Asp Tyr Trp Gly Gln Gly Thr Leu Val Thr Val Ser Ser
225                 230                 235                 240
```

<210> SEQ ID NO 397
<211> LENGTH: 241
<212> TYPE: PRT
<213> ORGANISM: Artificial
<220> FEATURE:
<223> OTHER INFORMATION: synthetic peptide

<400> SEQUENCE: 397

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Met Ile Pro Ile
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Ala Ser Glu Val Gln Leu Val
                115                 120                 125

Glu Ser Gly Gly Gly Leu Val Gln Pro Gly Gly Ser Leu Arg Leu Ser
130                 135                 140

Cys Ala Ala Ser Gly Phe Asn Phe Ser Phe Pro Gly Met His Trp Val
145                 150                 155                 160

Arg Gln Ala Pro Gly Lys Gly Leu Glu Trp Val Ala Trp Phe Val Gly
                165                 170                 175

Tyr Asp Gly Tyr Thr Tyr Ala Asp Ser Val Lys Gly Arg Phe Thr
                180                 185                 190

Ile Ser Ala Asp Thr Ser Lys Asn Thr Ala Tyr Leu Gln Met Asn Ser
    195                 200                 205

Leu Arg Ala Glu Asp Thr Ala Val Tyr Tyr Cys Ser Arg Asp Tyr Tyr
    210                 215                 220

Ser Phe Ser Met Asp Tyr Trp Gly Gln Gly Thr Leu Val Thr Val Ser
225                 230                 235                 240

Ser

<210> SEQ ID NO 398
<211> LENGTH: 240
<212> TYPE: PRT
<213> ORGANISM: Artificial
<220> FEATURE:
<223> OTHER INFORMATION: synthetic peptide

<400> SEQUENCE: 398

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Tyr Asp Pro Ile
                85                  90                  95

Thr Phe Gly Gln Gly Thr Lys Val Glu Ile Lys Arg Thr Gly Gly Gly
                100                 105                 110

Ser Gly Gly Gly Gly Ser Gly Gly Ala Ser Glu Val Gln Leu Val
                115                 120                 125

Glu Ser Gly Gly Gly Leu Val Gln Pro Gly Gly Ser Leu Arg Leu Ser
130                 135                 140

Cys Ala Ala Ser Gly Phe Asn Ile Ser Gly Ser Trp Ile His Trp Val
145                 150                 155                 160

Arg Gln Ala Pro Gly Lys Gly Leu Glu Trp Val Ala Trp Leu Tyr Pro
```

```
                165                 170                 175
Asp Ser Asp Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ala His Thr
    210                 215                 220

Tyr Ala Phe Asp Tyr Trp Gly Gln Gly Thr Leu Val Thr Val Ser Ser
225                 230                 235                 240

<210> SEQ ID NO 399
<211> LENGTH: 249
<212> TYPE: PRT
<213> ORGANISM: Artificial
<220> FEATURE:
<223> OTHER INFORMATION: synthetic peptide

<400> SEQUENCE: 399

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Leu
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Asn Ile Tyr Tyr Gly Val Met His Trp Val
145                 150                 155                 160

Arg Gln Ala Pro Gly Lys Gly Leu Glu Trp Val Ala Met Ile Tyr Pro
                165                 170                 175

Asp Ser Ser Trp Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Asp Gln Asp
    210                 215                 220

Phe His Tyr Met Asn Tyr Tyr Leu Ser Tyr Ala Leu Asp Tyr Trp Gly
225                 230                 235                 240

Gln Gly Thr Leu Val Thr Val Ser Ser
                245

<210> SEQ ID NO 400
<211> LENGTH: 240
<212> TYPE: PRT
<213> ORGANISM: Artificial
<220> FEATURE:
<223> OTHER INFORMATION: synthetic peptide
```

<400> SEQUENCE: 400

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Tyr Ser Pro Phe
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Asn Val Ser Tyr Glu Tyr Met His Trp Val
145                 150                 155                 160

Arg Gln Ala Pro Gly Lys Gly Leu Glu Trp Val Ala Glu Ile Tyr Gly
                165                 170                 175

Gly Ser Asp Asn Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Pro Leu Gly
    210                 215                 220

Ser Tyr Phe Asp Tyr Trp Gly Gln Gly Thr Leu Val Thr Val Ser Ser
225                 230                 235                 240

<210> SEQ ID NO 401
<211> LENGTH: 241
<212> TYPE: PRT
<213> ORGANISM: Artificial
<220> FEATURE:
<223> OTHER INFORMATION: synthetic peptide

<400> SEQUENCE: 401

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Tyr Leu Pro Thr
                85                  90                  95

Thr Phe Gly Gln Gly Thr Lys Val Glu Ile Lys Arg Thr Gly Gly Gly
            100                 105                 110

Ser Gly Gly Gly Gly Ser Gly Gly Ala Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Asn Ile Ser Trp Tyr Asp Ile His Trp Val
145                 150                 155                 160

Arg Gln Ala Pro Gly Lys Gly Leu Glu Trp Val Ala Asp Ile Glu Pro
                165                 170                 175

Ser Val Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Ser Tyr Pro
    210                 215                 220

Tyr Tyr Tyr Phe Asp Tyr Trp Gly Gln Gly Thr Leu Val Thr Val Ser
225                 230                 235                 240

Ser

<210> SEQ ID NO 402
<211> LENGTH: 8
<212> TYPE: PRT
<213> ORGANISM: Artificial
<220> FEATURE:
<223> OTHER INFORMATION: synthetic peptide

<400> SEQUENCE: 402

Gly Phe Asn Leu Ser Tyr Tyr Gly
1               5

<210> SEQ ID NO 403
<211> LENGTH: 10
<212> TYPE: PRT
<213> ORGANISM: Artificial
<220> FEATURE:
<223> OTHER INFORMATION: synthetic peptide

<400> SEQUENCE: 403

Glu Leu Ala Gly Ile Gly Ile Leu Thr Val
1               5                   10

<210> SEQ ID NO 404
<211> LENGTH: 244
<212> TYPE: PRT
<213> ORGANISM: Artificial
<220> FEATURE:
<223> OTHER INFORMATION: synthetic peptide

<400> SEQUENCE: 404

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Ser
                100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Tyr Ser Phe Thr Gly Tyr Thr Met Asn Trp Val Arg
145                 150                 155                 160

Gln Ala Pro Gly Lys Gly Leu Glu Trp Val Ala Leu Ile Asn Pro Tyr
                165                 170                 175

Lys Gly Val Ser Thr Tyr Asn Gln Lys Phe Lys Asp Arg Phe Thr Ile
                180                 185                 190

Ser Val Asp Lys Ser Lys Asn Thr Ala Tyr Leu Gln Met Asn Ser Leu
                195                 200                 205

Arg Ala Glu Asp Thr Ala Val Tyr Tyr Cys Ala Arg Ser Gly Tyr Tyr
                210                 215                 220

Gly Asp Ser Asp Trp Tyr Phe Asp Val Trp Gly Gln Gly Thr Leu Val
225                 230                 235                 240

Thr Val Ser Ser

<210> SEQ ID NO 405
<211> LENGTH: 244
<212> TYPE: PRT
<213> ORGANISM: Artificial
<220> FEATURE:
<223> OTHER INFORMATION: synthetic peptide

<400> SEQUENCE: 405

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Lys Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Ala Gly Gly Thr Lys Leu Glu Ile Lys Gly Gly Gly Gly Ser
                100                 105                 110

Gly Gly Gly Gly Ser Gly Gly Gly Gly Ser Glu Val Gln Leu Gln Gln
            115                 120                 125

Ser Gly Pro Glu Leu Val Lys Pro Gly Ala Ser Met Lys Ile Ser Cys
130                 135                 140

Lys Ala Ser Gly Tyr Ser Phe Thr Gly Tyr Thr Met Asn Trp Val Lys
145                 150                 155                 160

Gln Ser His Gly Lys Asn Leu Glu Trp Met Gly Leu Ile Asn Pro Tyr
                165                 170                 175

Lys Gly Val Ser Thr Tyr Asn Gln Lys Phe Lys Asp Lys Ala Thr Leu
                180                 185                 190

Thr Val Asp Lys Ser Ser Ser Thr Ala Tyr Met Glu Leu Leu Ser Leu
                195                 200                 205

```
Thr Ser Glu Asp Ser Ala Val Tyr Tyr Cys Ala Arg Ser Gly Tyr Tyr
            210                 215                 220

Gly Asp Ser Asp Trp Tyr Phe Asp Val Trp Gly Ala Gly Thr Thr Val
225                 230                 235                 240

Thr Val Ser Ser

<210> SEQ ID NO 406
<211> LENGTH: 240
<212> TYPE: PRT
<213> ORGANISM: Artificial
<220> FEATURE:
<223> OTHER INFORMATION: synthetic peptide

<400> SEQUENCE: 406

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Val Ala Ser Gly Val Pro Ala Arg Phe Ser Gly Ser
    50                  55                  60

Gly Ser Gly Thr Asp Tyr Ser Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys Gly Gly Gly Gly Ser Gly
            100                 105                 110

Gly Gly Gly Ser Gly Gly Gly Ser Asp Val Gln Leu Val Gln Ser
        115                 120                 125

Gly Ala Glu Val Lys Lys Pro Gly Ala Ser Val Lys Val Ser Cys Lys
    130                 135                 140

Ala Ser Gly Tyr Thr Phe Thr Arg Tyr Thr Met His Trp Val Arg Gln
145                 150                 155                 160

Ala Pro Gly Gln Gly Leu Glu Trp Ile Gly Tyr Ile Asn Pro Ser Arg
                165                 170                 175

Gly Tyr Thr Asn Tyr Ala Asp Ser Val Lys Gly Arg Phe Thr Ile Thr
            180                 185                 190

Thr Asp Lys Ser Thr Ser Thr Ala Tyr Met Glu Leu Ser Ser Leu Arg
        195                 200                 205

Ser Glu Asp Thr Ala Thr Tyr Tyr Cys Ala Arg Tyr Tyr Asp His
    210                 215                 220

Tyr Cys Leu Asp Tyr Trp Gly Gln Gly Thr Thr Val Thr Val Ser Ser
225                 230                 235                 240

<210> SEQ ID NO 407
<211> LENGTH: 249
<212> TYPE: PRT
<213> ORGANISM: Artificial
<220> FEATURE:
<223> OTHER INFORMATION: synthetic peptide

<400> SEQUENCE: 407

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30
```

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly Gly Gly
                100                 105                 110

Gly Ser Gly Gly Gly Gly Ser Gly Gly Gly Ser Glu Val Gln Leu
                115                 120                 125

Val Glu Ser Gly Gly Gly Leu Val Gln Pro Gly Gly Ser Leu Arg Leu
130                 135                 140

Ser Cys Ala Ala Ser Gly Phe Thr Phe Asn Thr Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
                180                 185                 190

Arg Phe Thr Ile Ser Arg Asp Asp Ser Lys Asn Ser Leu Tyr Leu Gln
                195                 200                 205

Met Asn Ser Leu Lys Thr Glu Asp Thr Ala Val Tyr Tyr Cys Val Arg
210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ser
                245

<210> SEQ ID NO 408
<211> LENGTH: 240
<212> TYPE: PRT
<213> ORGANISM: Artificial
<220> FEATURE:
<223> OTHER INFORMATION: synthetic peptide

<400> SEQUENCE: 408

Asp Ile Gln Leu Thr Gln Ser Pro Ala Ile Met Ser Ala Ser Pro Gly
 1               5                  10                  15

Glu Lys Val Thr Met Thr Cys Arg Ala Ser Ser Ser Val Ser Tyr Met
                 20                  25                  30

Asn Trp Tyr Gln Gln Lys Ser Gly Thr Ser Pro Lys Arg Trp Ile Tyr
            35                  40                  45

Asp Thr Ser Lys Val Ala Ser Gly Val Pro Tyr Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Leu Lys Gly Gly Gly Gly Ser Gly
                100                 105                 110

Gly Gly Gly Ser Gly Gly Gly Ser Asp Ile Lys Leu Gln Gln Ser
                115                 120                 125

Gly Ala Glu Leu Ala Arg Pro Gly Ala Ser Val Lys Met Ser Cys Lys
            130                 135                 140

Thr Ser Gly Tyr Thr Phe Thr Arg Tyr Thr Met His Trp Val Lys Gln
145                 150                 155                 160

Arg Pro Gly Gln Gly Leu Glu Trp Ile Gly Tyr Ile Asn Pro Ser Arg
                165                 170                 175

Gly Tyr Thr Asn Tyr Asn Gln Lys Phe Lys Asp Lys Ala Thr Leu Thr
            180                 185                 190

Thr Asp Lys Ser Ser Ser Thr Ala Tyr Met Gln Leu Ser Ser Leu Thr
        195                 200                 205

Ser Glu Asp Ser Ala Val Tyr Tyr Cys Ala Arg Tyr Tyr Asp Asp His
    210                 215                 220

Tyr Cys Leu Asp Tyr Trp Gly Gln Gly Thr Thr Leu Thr Val Ser Ser
225                 230                 235                 240

<210> SEQ ID NO 409
<211> LENGTH: 240
<212> TYPE: PRT
<213> ORGANISM: Artificial
<220> FEATURE:
<223> OTHER INFORMATION: synthetic peptide

<400> SEQUENCE: 409

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Gly Gly Gly Ser Gly
            100                 105                 110

Gly Gly Gly Ser Gly Gly Gly Ser Gln Val Gln Leu Gln Gln Ser
        115                 120                 125

Gly Ala Glu Leu Ala Arg Pro Gly Ala Ser Val Lys Met Ser Cys Lys
    130                 135                 140

Ala Ser Gly Tyr Thr Phe Thr Arg Tyr Thr Met His Trp Val Lys Gln
145                 150                 155                 160

Arg Pro Gly Gln Gly Leu Glu Trp Ile Gly Tyr Ile Asn Pro Ser Arg
                165                 170                 175

Gly Tyr Thr Asn Tyr Asn Gln Lys Phe Lys Asp Lys Ala Thr Leu Thr
            180                 185                 190

Thr Asp Lys Ser Ser Ser Thr Ala Tyr Met Gln Leu Ser Ser Leu Thr
        195                 200                 205

Ser Glu Asp Ser Ala Val Tyr Tyr Cys Ala Arg Tyr Tyr Asp Asp His
    210                 215                 220

Tyr Cys Leu Asp Tyr Trp Gly Gln Gly Thr Thr Leu Thr Val Ser Ser
225                 230                 235                 240

<210> SEQ ID NO 410
<211> LENGTH: 249
<212> TYPE: PRT
<213> ORGANISM: Artificial
<220> FEATURE:

<223> OTHER INFORMATION: synthetic peptide

<400> SEQUENCE: 410

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu Gly Gly Gly
            100                 105                 110

Gly Ser Gly Gly Gly Gly Ser Gly Gly Gly Ser Glu Val Gln Leu
        115                 120                 125

Val Glu Ser Gly Gly Gly Leu Val Gln Pro Gly Gly Ser Leu Lys Leu
130                 135                 140

Ser Cys Ala Ala Ser Gly Phe Thr Phe Asn Lys Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Asn Thr Ala Tyr Leu Gln
        195                 200                 205

Met Asn Asn Leu Lys Thr Glu Asp Thr Ala Val Tyr Tyr Cys Val Arg
    210                 215                 220

His Gly Asn Phe Gly Asn Ser Tyr Ile Ser Tyr Trp Ala Tyr Trp Gly
225                 230                 235                 240

Gln Gly Thr Leu Val Thr Val Ser Ser
                245

<210> SEQ ID NO 411
<211> LENGTH: 241
<212> TYPE: PRT
<213> ORGANISM: Artificial
<220> FEATURE:
<223> OTHER INFORMATION: synthetic peptide

<400> SEQUENCE: 411

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

```
Leu Thr Phe Gly Gly Gly Thr Lys Val Glu Ile Lys Gly Gly Gly
                100                 105                 110

Ser Gly Gly Gly Gly Ser Gly Gly Gly Ser Gln Val Gln Leu Val
                115                 120                 125

Glu Ser Gly Gly Gly Val Val Gln Pro Gly Arg Ser Leu Arg Leu Ser
    130                 135                 140

Cys Ala Ala Ser Gly Phe Lys Phe Ser Gly Tyr Gly Met His Trp Val
145                 150                 155                 160

Arg Gln Ala Pro Gly Lys Gly Leu Glu Trp Val Ala Val Ile Trp Tyr
                165                 170                 175

Asp Gly Ser Lys Lys Tyr Tyr Val Asp Ser Val Lys Gly Arg Phe Thr
                180                 185                 190

Ile Ser Arg Asp Asn Ser Lys Asn Thr Leu Tyr Leu Gln Met Asn Ser
                195                 200                 205

Leu Arg Ala Glu Asp Thr Ala Val Tyr Tyr Cys Ala Arg Gln Met Gly
                210                 215                 220

Tyr Trp His Phe Asp Leu Trp Gly Arg Gly Thr Leu Val Thr Val Ser
225                 230                 235                 240

Ser

<210> SEQ ID NO 412
<211> LENGTH: 241
<212> TYPE: PRT
<213> ORGANISM: Artificial
<220> FEATURE:
<223> OTHER INFORMATION: synthetic peptide

<400> SEQUENCE: 412

Glu Ile Val Leu Thr Gln Ser Pro Arg Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Asp
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys Gly Gly Gly Gly
                100                 105                 110

Ser Gly Gly Gly Gly Ser Gly Gly Gly Ser Gln Val Gln Leu Val
                115                 120                 125

Glu Ser Gly Gly Gly Val Val Gln Pro Gly Arg Ser Leu Arg Leu Ser
    130                 135                 140

Cys Ala Ala Ser Gly Phe Thr Phe Arg Ser Tyr Gly Met His Trp Val
145                 150                 155                 160

Arg Gln Ala Pro Gly Lys Gly Leu Glu Trp Val Ala Ile Ile Trp Tyr
                165                 170                 175

Asp Gly Ser Lys Lys Asn Tyr Ala Asp Ser Val Lys Gly Arg Phe Thr
                180                 185                 190

Ile Ser Arg Asp Asn Ser Lys Asn Thr Leu Tyr Leu Gln Met Asn Ser
                195                 200                 205
```

```
Leu Arg Ala Glu Asp Thr Ala Val Tyr Tyr Cys Ala Arg Gly Thr Gly
    210                 215                 220

Tyr Asn Trp Phe Asp Pro Trp Gly Gln Gly Thr Leu Val Thr Val Ser
225                 230                 235                 240

Ser

<210> SEQ ID NO 413
<211> LENGTH: 239
<212> TYPE: PRT
<213> ORGANISM: Artificial
<220> FEATURE:
<223> OTHER INFORMATION: synthetic peptide

<400> SEQUENCE: 413

Asp Ile Leu Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Tyr Ala Ser Ser Leu Gln Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Leu Thr
                85                  90                  95

Phe Gly Gly Gly Thr Lys Val Glu Ile Lys Gly Gly Gly Gly Ser Gly
            100                 105                 110

Gly Gly Gly Ser Gly Gly Gly Gly Ser Gln Val Gln Leu Val Glu Ser
        115                 120                 125

Gly Gly Gly Val Val Gln Pro Gly Arg Ser Leu Arg Leu Ser Cys Ala
130                 135                 140

Ala Ser Gly Phe Thr Phe Arg Ser Tyr Gly Met His Trp Val Arg Gln
145                 150                 155                 160

Ala Pro Gly Lys Gly Leu Glu Trp Val Ala Ile Ile Trp Tyr Asp Gly
                165                 170                 175

Ser Lys Lys Asn Tyr Ala Asp Ser Val Lys Gly Arg Phe Thr Ile Ser
            180                 185                 190

Arg Asp Asn Ser Lys Asn Thr Leu Tyr Leu Gln Met Asn Ser Leu Arg
        195                 200                 205

Ala Glu Asp Thr Ala Val Tyr Tyr Cys Ala Arg Gly Thr Gly Tyr Asn
210                 215                 220

Trp Phe Asp Pro Trp Gly Gln Gly Thr Leu Val Thr Val Ser Ser
225                 230                 235

<210> SEQ ID NO 414
<211> LENGTH: 241
<212> TYPE: PRT
<213> ORGANISM: Artificial
<220> FEATURE:
<223> OTHER INFORMATION: synthetic peptide

<400> SEQUENCE: 414

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30
```

```
Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Leu Thr Phe Gly Gly Gly Thr Lys Val Glu Ile Lys Gly Gly Gly Gly
                100                 105                 110

Ser Gly Gly Gly Gly Ser Gly Gly Gly Ser Gln Val Gln Leu Val
            115                 120                 125

Gln Ser Gly Gly Gly Val Val Gln Ser Gly Arg Ser Leu Arg Leu Ser
130                 135                 140

Cys Ala Ala Ser Gly Phe Lys Phe Ser Gly Tyr Gly Met His Trp Val
145                 150                 155                 160

Arg Gln Ala Pro Gly Lys Gly Leu Glu Trp Val Ala Val Ile Trp Tyr
                165                 170                 175

Asp Gly Ser Lys Lys Tyr Tyr Val Asp Ser Val Lys Gly Arg Phe Thr
            180                 185                 190

Ile Ser Arg Asp Asn Ser Lys Asn Thr Leu Tyr Leu Gln Met Asn Ser
        195                 200                 205

Leu Arg Gly Glu Asp Thr Ala Val Tyr Tyr Cys Ala Arg Gln Met Gly
    210                 215                 220

Tyr Trp His Phe Asp Leu Trp Gly Arg Gly Thr Leu Val Thr Val Ser
225                 230                 235                 240

Ser

<210> SEQ ID NO 415
<211> LENGTH: 240
<212> TYPE: PRT
<213> ORGANISM: Artificial
<220> FEATURE:
<223> OTHER INFORMATION: synthetic peptide

<400> SEQUENCE: 415

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Trp
                 85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Gln Val Gln Leu Val Gln
            115                 120                 125

Ser Gly Gly Gly Val Val Gln Pro Gly Arg Ser Leu Arg Leu Ser Cys
130                 135                 140

Val Ala Ser Gly Phe Thr Phe Ser Ser Tyr Gly Met His Trp Val Arg
```

```
145                 150                 155                 160
Gln Ala Pro Gly Lys Gly Leu Glu Trp Val Ala Ala Ile Trp Tyr Asn
                165                 170                 175
Gly Arg Lys Gln Asp Tyr Ala Asp Ser Val Lys Gly Arg Phe Thr Ile
                180                 185                 190
Ser Arg Asp Asn Ser Lys Asn Thr Leu Tyr Leu Gln Met Asn Ser Leu
                195                 200                 205
Arg Ala Glu Asp Thr Ala Val Tyr Tyr Cys Thr Arg Gly Thr Gly Tyr
210                 215                 220
Asn Trp Phe Asp Pro Trp Gly Gln Gly Thr Leu Val Thr Val Ser Ser
225                 230                 235                 240

<210> SEQ ID NO 416
<211> LENGTH: 240
<212> TYPE: PRT
<213> ORGANISM: Artificial
<220> FEATURE:
<223> OTHER INFORMATION: synthetic peptide

<400> SEQUENCE: 416

Ala Ile Gln Leu Thr Gln Ser Pro Ser Ser Leu Ser Ala Ser Val Gly
1               5                   10                  15
Asp Arg Val Thr Ile Thr Cys Arg Ala Ser Gln Gly Ile Ser Ser Ala
                20                  25                  30
Leu Ala Trp Tyr Gln Gln Lys Pro Gly Lys Ala Pro Lys Leu Leu Ile
            35                  40                  45
Tyr Asp Ala Ser Ser Leu Glu Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Asn Ser Tyr Pro Ile
                85                  90                  95
Thr Phe Gly Gln Gly Thr Arg Leu Glu Ile Lys Gly Gly Gly Gly Ser
                100                 105                 110
Gly Gly Gly Gly Ser Gly Gly Gly Ser Gln Val Gln Leu Val Gln
            115                 120                 125
Ser Gly Gly Gly Val Val Gln Pro Gly Arg Ser Leu Arg Leu Ser Cys
130                 135                 140
Val Ala Ser Gly Phe Thr Phe Ser Ser Tyr Gly Met His Trp Val Arg
145                 150                 155                 160
Gln Ala Pro Gly Lys Gly Leu Glu Trp Val Ala Ala Ile Trp Tyr Asn
                165                 170                 175
Gly Arg Lys Gln Asp Tyr Ala Asp Ser Val Lys Gly Arg Phe Thr Ile
                180                 185                 190
Ser Arg Asp Asn Ser Lys Asn Thr Leu Tyr Leu Gln Met Asn Ser Leu
                195                 200                 205
Arg Ala Glu Asp Thr Ala Val Tyr Tyr Cys Thr Arg Gly Thr Gly Tyr
210                 215                 220
Asn Trp Phe Asp Pro Trp Gly Gln Gly Thr Leu Val Thr Val Ser Ser
225                 230                 235                 240

<210> SEQ ID NO 417
<211> LENGTH: 241
<212> TYPE: PRT
<213> ORGANISM: Artificial
<220> FEATURE:
<223> OTHER INFORMATION: synthetic peptide
```

<400> SEQUENCE: 417

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Thr Lys Arg Gly Gly Gly Gly Ser
            100                 105                 110

Gly Gly Gly Gly Ser Gly Gly Gly Gly Ser Gln Val Gln Leu Gln Gln
        115                 120                 125

Ser Gly Ala Glu Leu Ala Arg Pro Gly Ala Ser Val Lys Met Ser Cys
    130                 135                 140

Lys Ala Ser Gly Tyr Thr Phe Thr Ser Tyr Thr Met His Trp Val Lys
145                 150                 155                 160

Gln Arg Pro Gly Gln Gly Leu Glu Trp Ile Gly Tyr Ile Asn Pro Ser
                165                 170                 175

Ser Gly Tyr Thr Lys Tyr Asn Gln Lys Phe Lys Asp Lys Ala Thr Leu
            180                 185                 190

Thr Ala Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Trp Gln Asp Tyr
    210                 215                 220

Asp Val Tyr Phe Asp Tyr Trp Gly Gln Gly Thr Thr Leu Thr Val Ser
225                 230                 235                 240

Ser

<210> SEQ ID NO 418
<211> LENGTH: 10
<212> TYPE: PRT
<213> ORGANISM: Artificial
<220> FEATURE:
<223> OTHER INFORMATION: synthetic peptide

<400> SEQUENCE: 418

Ser Pro Gly Ala Ala Asn Lys Arg Pro Ile
1               5                   10

<210> SEQ ID NO 419
<211> LENGTH: 9
<212> TYPE: PRT
<213> ORGANISM: Artificial
<220> FEATURE:
<223> OTHER INFORMATION: synthetic peptide

<400> SEQUENCE: 419

Val Val Gly Ala Cys Gly Val Gly Lys
1               5

<210> SEQ ID NO 420
<211> LENGTH: 9

```
<212> TYPE: PRT
<213> ORGANISM: Artificial
<220> FEATURE:
<223> OTHER INFORMATION: synthetic peptide

<400> SEQUENCE: 420

Val Val Gly Ala Asp Gly Val Gly Lys
1               5
```

MANABODIES AND METHODS OF USING

CROSS-REFERENCE TO RELATED APPLICATIONS

This application is a National Stage application under 35 U.S.C. § 371 of International Application No. PCT/US2018/032996, having an International Filing Date of May 16, 2018, which claims the benefit of U.S. Patent Application Ser. No. 62/506,674, filed on May 16, 2017. The disclosures of the prior application are considered part of, and are incorporated by reference in, the disclosure of this application.

SEQUENCE LISTING

This document contains a sequence listing that has been submitted electronically as an ASCII text file. The ASCII text file, created on Jun. 29, 2018, is 244000 bytes in size. The material in the ASCII text file is hereby incorporated by reference in its entirety.

BACKGROUND

1. Technical Field

This document relates to methods and materials for assessing a mammal having or suspected of having cancer and/or for treating a mammal having cancer. For example, this document provides methods and materials for using a molecule including one or more antigen-binding domains (e.g., a single-chain variable fragment (scFv)) that can bind to a modified peptide (e.g., a tumor antigen) to treat a mammal having a cancer.

2. Background Information

Somatic mutations in cancer are ideal targets for cancer therapy as they are uniquely expressed only in tumor cells and not normal cells. In particular, targeting driver gene proteins (broadly subdivided into oncogene proteins and tumor suppressor proteins) have added benefits. First, the tumor's dependence on their oncogenic-endowing capacity makes resistance less likely. Second, these mutations typically occur early during the development of the tumor, thus essentially all daughter cancer cells will contain the mutation. Finally, driver gene proteins tend to have hotspot mutations shared among many patients, thus a therapy targeting a single mutation could be applied to a broad patient population.

Most mutant proteins, including most mutant driver gene proteins, are intracellular. While small molecules can target intracellular proteins, developing small molecules that can specifically inhibit the activity of a mutant driver gene and not its wild-type (wt) counterpart has remained out of reach for the majority of such driver gene proteins. Antibodies, which can have the capacity to distinguish a single amino acid mutation, can typically only target extracellular epitopes.

The immune system samples the intracellular contents of cells through antigen processing and presentation. Following protein proteolysis, a fraction of the resulting peptides are loaded onto human leukocyte antigen (HLA) and sent to the cell surface where they serve as a way for T cells, via their T cell receptor (TCR), to distinguish self from non-self peptides. For example, a virally-infected cell will present viral peptides in its HLA, triggering T cells to kill that cell. Similarly, in cancer, mutant peptides can be presented in HLA on the cancer cell surface, referred to as MANAs, for Mutation-Associated Neo-Antigens. In some cases, and to varying degrees, patients may mount an anti-cancer T cell response against these mutant-peptide-HLA neoantigens, and checkpoint blockade antibodies can further augment this response. However, many patients, particularly those with a low mutational burden, cannot mount a sufficient anti-cancer T cell response. A therapy or diagnostic specifically targeting MANAs could therefore provide a truly tumor-specific method to diagnose or treat cancer.

HLA class I proteins are present on all nucleated cells. There are three classical HLA class I genes, A, B, and C, each of which are highly polymorphic. Each HLA allele has a particular peptide-binding motif, and as a result, only certain peptides will bind to certain HLA alleles.

There is a continuing need in the art to develop new methods to diagnose, monitor, and effectively treat cancers.

SUMMARY

This document provides methods and materials for treating a mammal having cancer. For example, this document provides methods and materials for using one or more molecules including one or more antigen-binding domains (e.g., scFvs) that can bind to a modified peptide (e.g., a modified peptide present in a peptide-HLA-b2M complex) to treat a mammal having a cancer (e.g., a cancer expressing the modified peptide). In some cases, one or more molecules including one or more antigen-binding domains (e.g., scFvs) that can bind to a modified peptide (e.g., a modified peptide present in a peptide-HLA-b2M complex) can be administered to a mammal having a cancer (e.g., a cancer expressing the modified peptide) to treat the mammal.

As demonstrated herein, scFvs were identified that target (e.g., bind to) numerous Mutation-Associated Neo-Antigens (MANAs) present in a peptide-HLA-b2M complex in many acute myeloid leukemia (AML) cases. Also as demonstrated herein, the scFvs were used to design both chimeric antigen receptor (CAR) T cells (CARTs; also abbreviated as CAR Ts or CAR-Ts) and bispecific antibodies capable of recognizing and killing cells expressing MANAs. The ability to specifically target MANAs provides a tumor-specific method to diagnose and/or treat cancer. For example, scFvs specifically targeting MANAs can be used in full-length antibodies or fragments thereof, antibody drug conjugates (ADCs), antibody radionuclide conjugates, CARTs, or bispecific antibodies to diagnose and/or treat a mammal having cancer.

In general, one aspect of this document a molecule comprising an antigen-binding domain that can bind to a peptide-HLA-beta-2 microglobulin complex, where the peptide includes a modified peptide, where the HLA is a class I HLA, and where the antigen-binding domain does not bind to a complex that includes a wild-type version of the modified peptide. The modified peptide can include from 7 amino acids to 15 amino acids (e.g., 10 amino acids). The modified peptide can be derived from a modified IDH2 polypeptide, a modified EGFR polypeptide, a modified p53 polypeptide, a modified KRAS polypeptide, a modified HRAS polypeptide, a modified NRAS polypeptide, or a modified CTNNB polypeptide. The modified peptide can include an amino acid sequence set forth SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, or SEQ ID NO:32. When the modified peptide includes SEQ ID NO:1, the class I HLA can be an HLA-B7, and the antigen binding fragment can include an amino acid sequence set forth in SEQ ID NO:3, SEQ ID NO:4, SEQ ID NO:5, SEQ ID NO:6, or SEQ ID NO:8. When the modified peptide includes SEQ ID NO:11, the class I HLA can be an HLA-B7, and the antigen binding fragment can include an amino acid sequence set forth in SEQ ID NO:380, SEQ ID NO:390, SEQ ID NO:391, SEQ ID NO:392, or SEQ ID NO:393. When the modified peptide includes SEQ ID NO:13, the class I HLA can be an HLA-A2, and the antigen binding fragment can include an amino acid sequence set forth in SEQ ID NO:324, SEQ ID NO:325, SEQ ID NO:326, SEQ ID NO:327, SEQ ID NO:328, SEQ ID NO:329, or SEQ ID NO:330. When the modified peptide includes SEQ ID NO:15, the class I HLA can be an HLA-A2, and the antigen binding fragment can include an amino acid sequence set forth in SEQ ID NO:331, SEQ ID NO:333, SEQ ID NO:336, or SEQ ID NO:337. When the modified peptide includes SEQ ID NO:16, the class I HLA can be an HLA-A2, and the antigen binding fragment can include an amino acid sequence set forth in SEQ ID NO:332, SEQ ID NO:334, SEQ ID NO:335, SEQ ID NO:336, or SEQ ID NO:337. When the modified peptide includes SEQ ID NO:18, the class I HLA can be an HLA-A2, and the antigen binding fragment can include an amino acid sequence set forth in SEQ ID NO:338, SEQ ID NO:339, or SEQ ID NO:340. When the modified peptide includes SEQ ID NO:20, the class I HLA can be an HLA-A3, and the antigen binding fragment can include an amino acid sequence set forth in SEQ ID NO:341, SEQ ID NO:342, or SEQ ID NO:343. When the modified peptide includes SEQ ID NO:21, the class I HLA can be an HLA-A3, and the antigen binding fragment can include an amino acid sequence set forth in SEQ ID NO:342, SEQ ID NO:343, SEQ ID NO:349, SEQ ID NO:350, SEQ ID NO:351, SEQ ID NO:352, SEQ ID NO:353, SEQ ID NO:354, SEQ ID NO:355, SEQ ID NO:356, or SEQ ID NO:357. When the modified peptide includes SEQ ID NO:22, the class I HLA can be an HLA-A3, and the antigen binding fragment can include an amino acid sequence set forth in SEQ ID NO:338, SEQ ID NO:339, SEQ ID NO:340, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:369, SEQ ID NO:370, SEQ ID NO:371, SEQ ID NO:372, SEQ ID NO:373, or SEQ ID NO:374. When the modified peptide includes SEQ ID NO:24, the class I HLA can be an HLA-A11, and the antigen binding fragment can include an amino acid sequence set forth in SEQ ID NO:358, SEQ ID NO:359, SEQ ID NO:360, SEQ ID NO:361, SEQ ID NO:362, SEQ ID NO:363, SEQ ID NO:364, SEQ ID NO:365, SEQ ID NO:366, SEQ ID NO:367, or SEQ ID NO:368. When the modified peptide includes SEQ ID NO:26, the class I HLA can be an HLA-A3, and the antigen binding fragment can include an amino acid sequence set forth in SEQ ID NO:375, SEQ ID NO:376, SEQ ID NO:377, SEQ ID NO:378, or SEQ ID NO:379. When the modified peptide includes SEQ ID NO:28, the class I HLA can be an HLA-A1, and the antigen binding fragment can include an amino acid sequence set forth in SEQ ID NO:394. When the modified peptide includes SEQ ID NO:30, the class I HLA can be an HLA-A1, and the antigen binding fragment can include an amino acid sequence set forth in SEQ ID NO:395. When the modified peptide includes SEQ ID NO:31, the class I HLA can be an HLA-A1, and the antigen binding fragment can include an amino acid sequence set forth in SEQ ID NO:396. When the modified peptide includes SEQ ID NO:32, the class I HLA can be an HLA-A1, and the antigen binding fragment can include an amino acid sequence set forth in SEQ ID NO:397, SEQ ID NO:398, SEQ ID NO:399, SEQ ID NO:400, or SEQ ID NO:401. The molecule can be an antibody, an antibody fragment, a scFv, a CAR, a TCR, a TCR mimic, a tandem scFv, a bispecific T cell engager, a diabody, a single-chain diabody, an scFv-Fc, a bispecific antibody, or a dual-affinity re-targeting antibody (DART). For example, the molecule can be a single-chain diabody. The molecule also can include an antigen-binding domain that can bind to an effector cell receptor (e.g., CD3, CD28, CD4, CD8, CD16a, NKG2D, PD-1, CTLA-4, 4-1BB, OX40, ICOS, or CD27). When the antigen-binding domain that can bind to an effector cell can bind to CD3, the antigen-binding domain can include an amino acid sequence set forth in SEQ ID NO:404, SEQ ID NO:405, SEQ ID NO:406, SEQ ID NO:407, SEQ ID NO:408, SEQ ID NO:409, SEQ ID NO:410, SEQ ID NO:411, SEQ ID NO:412, SEQ ID NO:413, SEQ ID NO:414, SEQ ID NO:415, SEQ ID NO:416, or SEQ ID NO:417.

In another aspect, this document features a CAR. The CAR can include an extracellular domain that includes any antigen-binding domain described herein (e.g., an antigen-binding domain that can bind to a peptide-HLA-beta-2 microglobulin complex, where the peptide includes a modified peptide, where the HLA is a class I HLA, and where the antigen-binding domain does not bind to a complex that includes a wild-type version of the modified peptide), a transmembrane domain, and an intracellular domain. The transmembrane domain can include a transmembrane domain of CD4, CD8, or CD28. The intracellular domain can include one or more costimulatory domains from CD28, DAP10, ICOS, OX40, and/or 4-1BB. The intracellular domain can include a signaling domain from CD3-zeta.

In another aspect, this document features a T cell expressing any CAR described herein (e.g., a CAR including an extracellular domain that includes any antigen-binding domain described herein, a transmembrane domain, and an intracellular domain). The T cell can express a CAR including an extracellular domain that includes an antigen-binding domain that can bind to a peptide-HLA-beta-2 microglobulin complex, where the peptide includes a modified peptide, where the HLA is a class I HLA, and where the antigen-binding domain does not bind to a complex that includes a wild-type version of the modified peptide), a transmembrane domain, and an intracellular domain.

In another aspect, this document features methods for treating a mammal having a cancer. The methods can include, or consist essentially of, administering to a mammal one or more molecules that include any antigen-binding domain described herein (e.g., an antigen-binding domain that can bind to a peptide-HLA-beta-2 microglobulin complex, where the peptide includes a modified peptide, where the HLA is a class I HLA, and where the antigen-binding domain does not bind to a complex that includes a wild-type version of the modified peptide), wherein the cancer includes cancer cells expressing a modified peptide. The mammal can be a human. The cancer can be Hodgkin's lymphoma, non-Hodgkin's lymphoma, AML, a lung cancer, a pancreatic cancer, a gastric cancer, a colorectal cancer, an ovarian cancer, an endometrial cancer, a biliary tract cancer, a liver cancer, myeloma, a breast cancer, a prostate cancer, an esophageal cancer, a stomach cancer, a kidney cancer, a bone cancer, a soft tissue cancer, a head and neck cancer, a glioblastoma multiforme, or an astrocytoma.

In another aspect, this document features methods for treating a mammal having a cancer. The methods can include, or consist essentially of, administering to a mammal one or more T cells expressing any one of the CARs described herein (e.g., a CAR including an extracellular domain that includes any antigen-binding domain described herein, a transmembrane domain, and an intracellular domain), where the cancer includes cancer cells expressing a modified peptide. The mammal can be a human. The cancer can be Hodgkin's lymphoma, non-Hodgkin's lymphoma, AML, a lung cancer, a pancreatic cancer, a gastric cancer, a colorectal cancer, an ovarian cancer, an endometrial cancer, a biliary tract cancer, a liver cancer, myeloma, a breast cancer, a prostate cancer, an esophageal cancer, a stomach cancer, a kidney cancer, a bone cancer, a soft tissue cancer, a head and neck cancer, a glioblastoma multiforme, or an astrocytoma.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 15A: IDH2 R140Q(134-143)-B7 cl.1 MANA-CAR-T cells were co-cultured for 4 hours at 37° C. with COS-7 cells co-transfected with plasmids encoding various combinations of HLA-B7, IDH2 (WT), and IDH2(R140Q). Following co-culture, conditioned media was collected and assayed for secreted IFNγ by ELISA. FIG. 15B: KRAS G12V(7-16)-A3 cl.2 MANA-CAR-T cells were co-cultured for 4 hours at 37° C. with COS-7 cells transfected with plasmids encoding various combinations of HLA-A3, KRAS(WT), and KRAS(G12V). Following co-culture, conditioned media was collected and assayed for secreted IFNγ by ELISA.

FIG. 16A: IDH2 R140Q(134-143)-B7 cl.29, cl.1, and cl.3 scDbs, containing either the anti-CD3 clone mUCHT1 or hUCHT1v9, were incubated at the specified concentrations with T cells and COS-7 cells co-transfected with plasmids encoding various combinations of HLA-B7, IDH2(WT), IDH2 (R140Q), and GFP for 24 hours at 37° C. Following co-culture, plates was snap frozen and conditioned media was collected and assayed for secreted IFNγ by ELISA. FIG. 16B: KRAS G12V(7-16)-A3 cl.2 mUCHT1 scDb was incubated at the specified concentrations with or without T cells and either 1) no target cells, 2) COS-7 cells co-transfected with plasmids encoding HLA-A3 and KRAS(WT) or HLA-A3 and KRAS(G12V), or 3) with NCI-H441 parental or HLA-A3 knockout cells for 24 hours at 37° C. Following co-culture, plates was snap frozen and conditioned media was collected and assayed for secreted IFNγ by ELISA.

DETAILED DESCRIPTION

Figure 1:
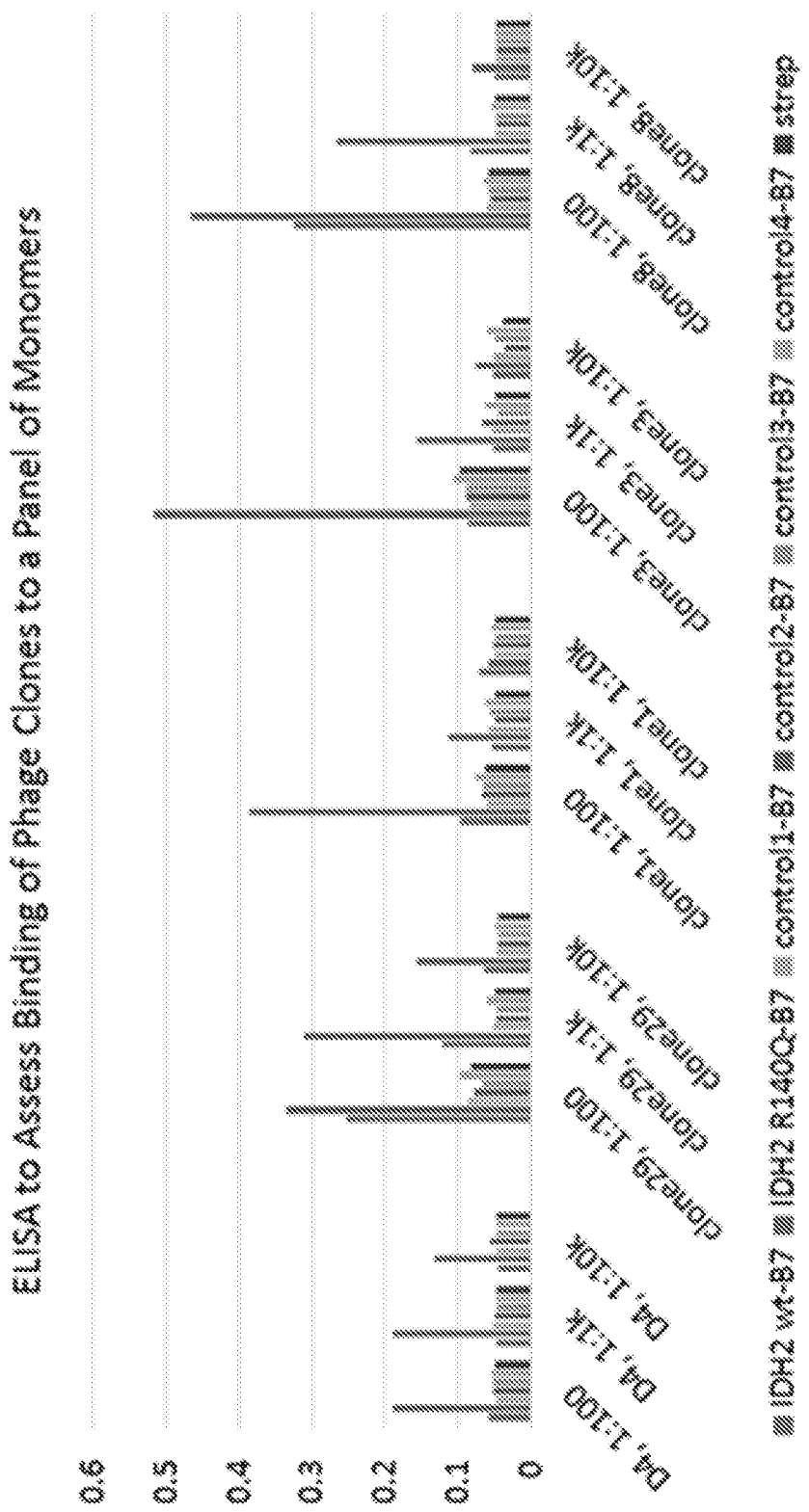
FIG. 1 contains ELISA results showing specificity of IDH2 R140Q HLA-B7 scFvs. Peptide-HLA biotinylated monomers were coated on a streptavidin plate, including the wild type (wt) version of an IDH2 peptide (SPNGTIRNIL; SEQ ID NO:2), an IDH2 peptide containing the R140Q mutation (SPNGTIQNIL; SEQ ID NO:1), and four control HLA-B7 monomers containing the following control peptides: control 1 peptide is SPGAANKRPI (an artificial sequence; SEQ ID NO:418), control 2 peptide is RPIPIKYKAM (from mutant MyD88 L265P; SEQ ID NO:9), control 3 peptide is KPITIGRHAH (from a different peptide from wt IDH2; SEQ ID NO:10), and control 4 peptide is AVGVGKSAL (from mutant KRAS G12V; SEQ ID NO:11). The five clones identified in panning were incubated in the wells at the specified dilutions, followed by a rabbit anti-phage antibody, then anti-Rabbit-HRP antibody.
Figure 2:
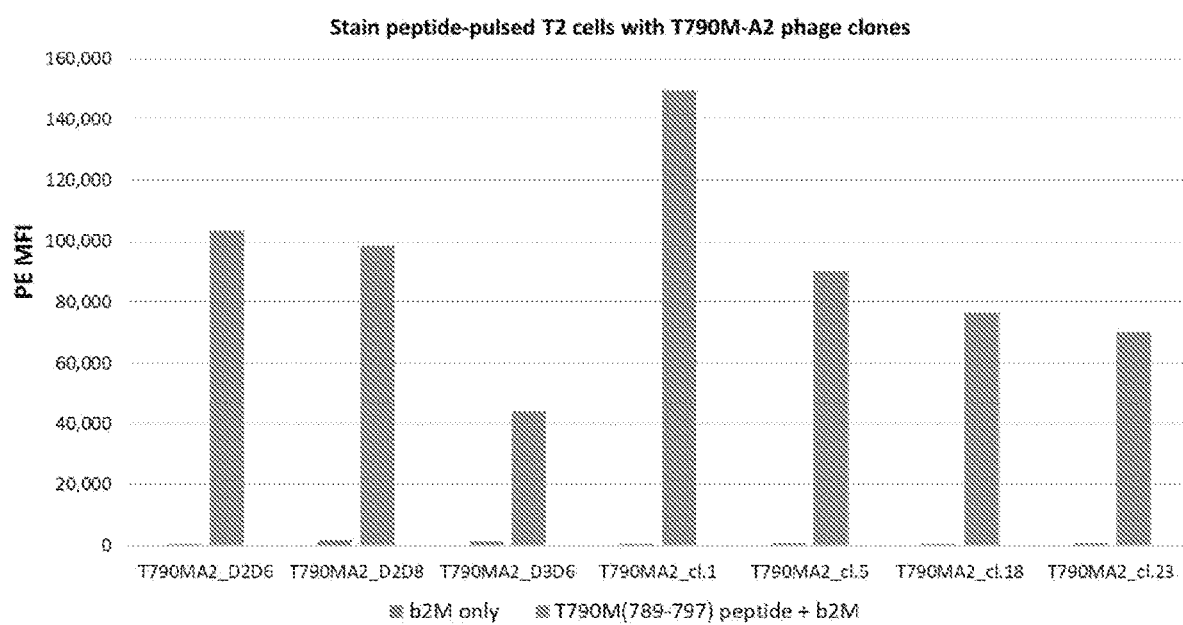
FIG. 2 contains a graph showing flow cytometry on peptide-pulsed A2+ cells. T2 cells were peptide-pulsed overnight at 37° C. in serum-free media with beta-2 microglobulin (b2M) protein only, or b2M with a EGFR T790M (789-797) peptide (IMQLMPFGC; SEQ ID NO:13). The EGFR wt(789-797) peptide (ITQLMPFGC; SEQ ID NO:14) did not bind to HLA-A2. Cells were stained with 10 µL of precipitated phage per 100 µL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 3:
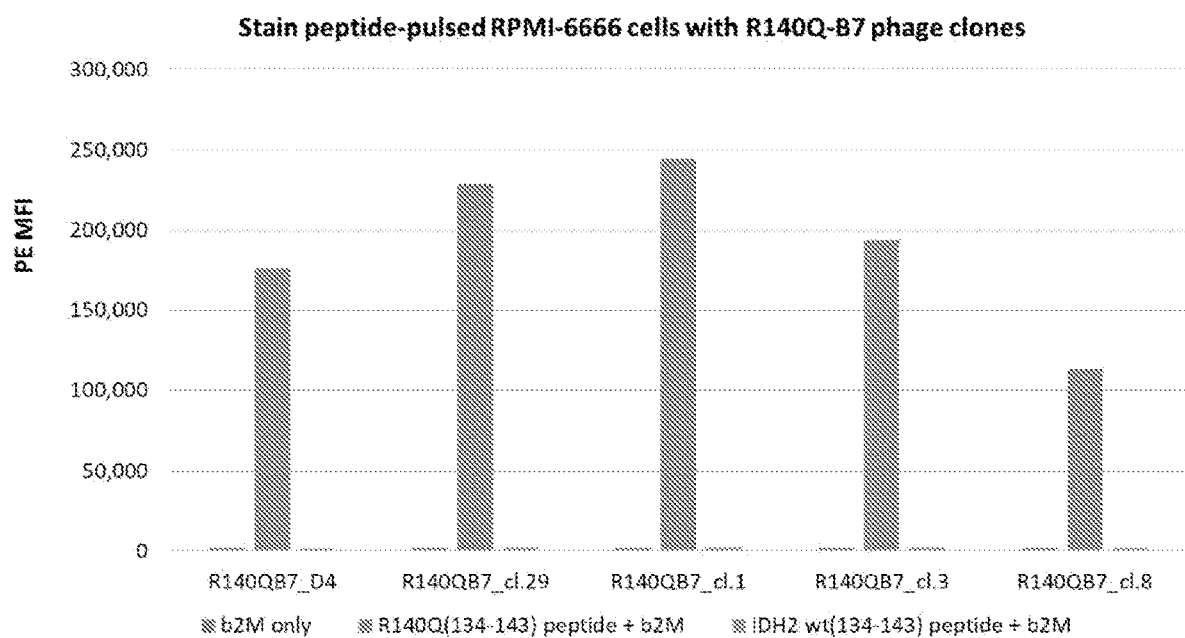
FIG. 3 contains a graph showing flow cytometry on peptide-pulsed B7+ cells. RPMI-6666 cells were peptide pulsed overnight at 37° C. in serum-free media with b2M protein only, b2M protein with an IDH2 mutant R140Q peptide (SPNGTIQNIL; SEQ ID NO:1), or b2M with the IDH2 wt peptide (SPNGTIRNIL; SEQ ID NO:2). Cells were stained with 10 µL of precipitated phage per 100 µL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 4:
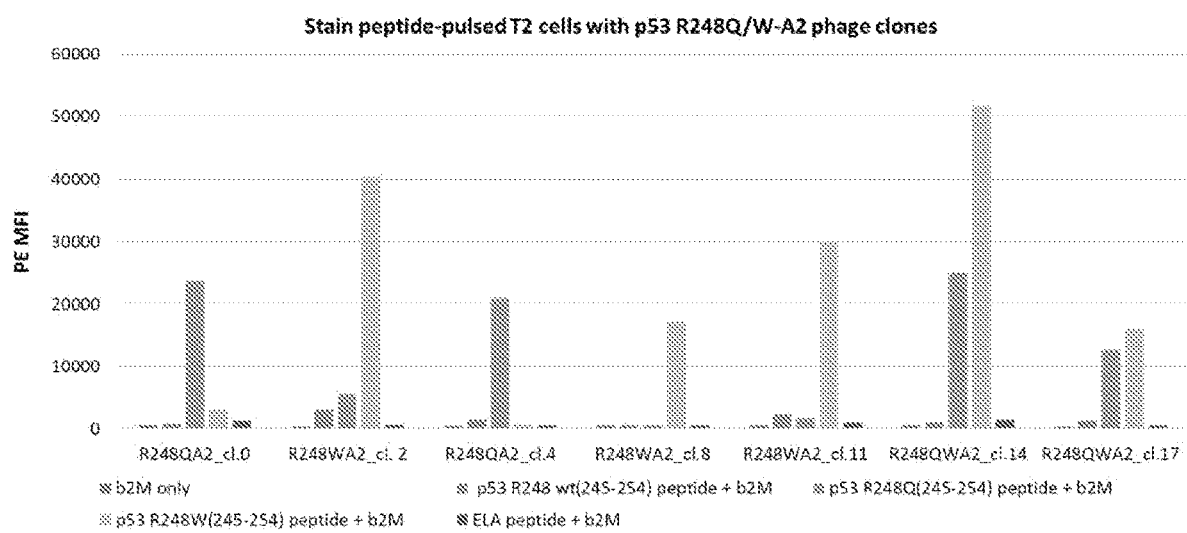
FIG. 4 contains a graph showing flow cytometry on peptide-pulsed A2+ cells. T2 cells were peptide-pulsed overnight at 37° C. in serum-free media with b2M only, b2M with a p53 mutant R248Q(245-254) peptide (GMNQRPILTI; SEQ ID NO:15), b2M with a p53 mutant R248W(245-254) peptide (GMNWRPILTI; SEQ ID NO:16), b2M with the p53 wt(245-254) peptide (GMNRRPILTI; SEQ ID NO:17), or b2M with an HLA-A2 control peptide ELA (ELAGIGILTV; SEQ ID NO:403). Cells were stained with 10 µL of precipitated phage per 100 µL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 5:
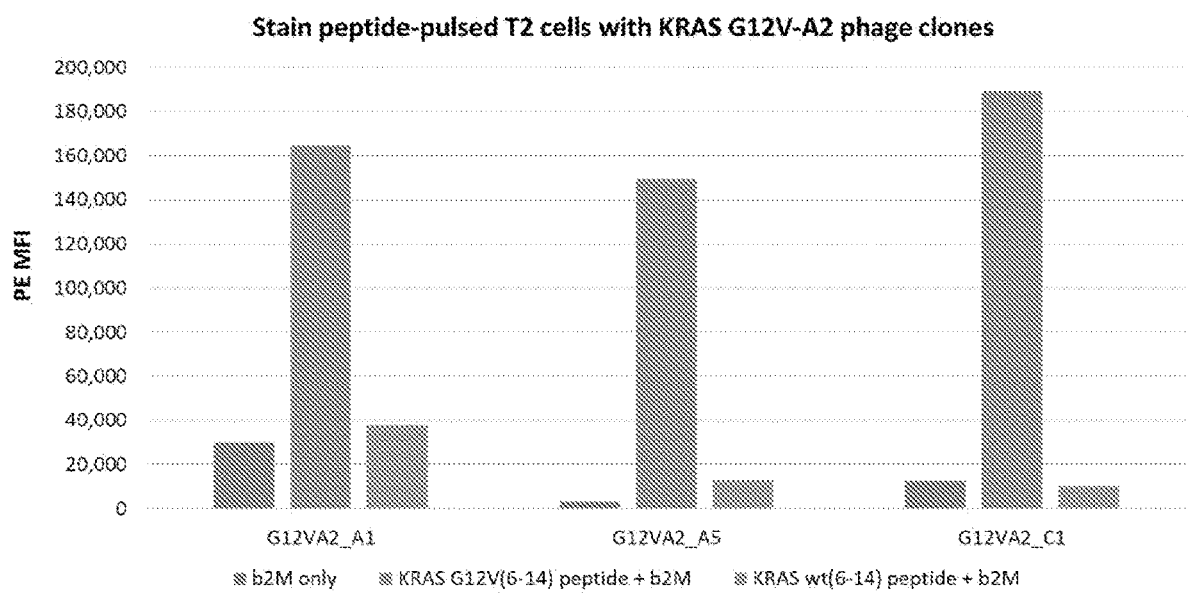
FIG. 5 contains a graph showing flow cytometry on peptide-pulsed A2+ cells. T2 cells were peptide-pulsed overnight at 37° C. in serum-free media with b2M only, b2M with a KRAS mutant G12V(6-14) peptide (LVVVGAVGV; SEQ ID NO:18), or b2M with the KRAS wt(6-14) peptide (LVVVGAGGV; SEQ ID NO:19). Cells were stained with 10 µL of precipitated phage per 100 µL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 6:
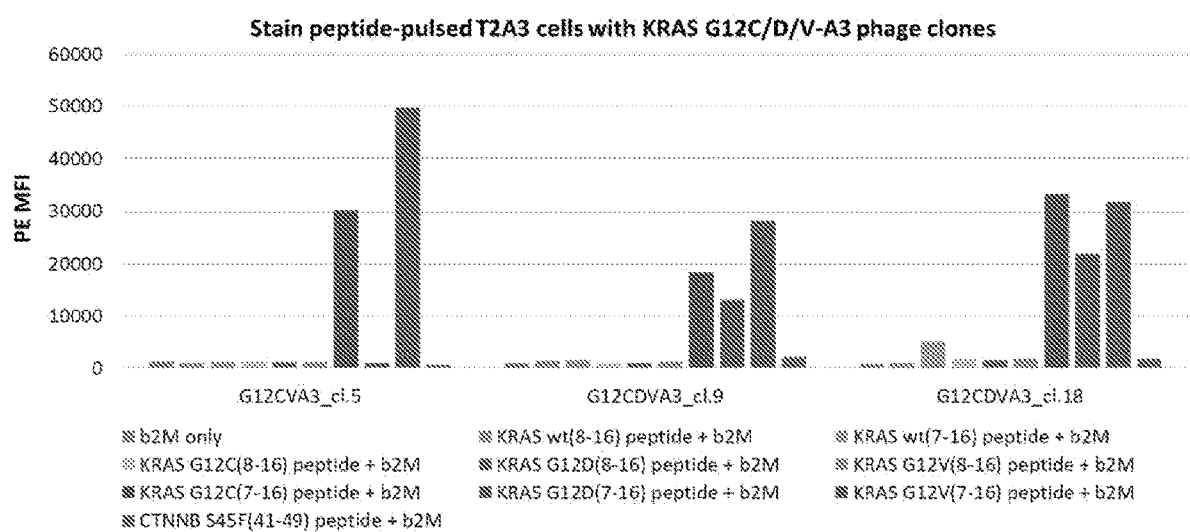
FIG. 6 contains a graph showing flow cytometry on peptide-pulsed A3+ cells. T2A3 cells were peptide-pulsed overnight at 37° C. in serum-free media with b2M only, b2M with a KRAS mutant G12C(8-16) peptide (VVGACGVGK; SEQ ID NO:419), b2M with a KRAS mutant G12D(8-16) peptide (VVGADGVGK; SEQ ID NO:420), b2M with a KRAS mutant G12V(8-16) peptide (VVGAVGVGK; SEQ ID NO:22), b2M with a KRAS mutant G12C(7-16) peptide (VVVGACGVGK; SEQ ID NO:20), b2M with a KRAS mutant G12D(7-16) peptide (VVVGADGVGK; SEQ ID NO:21), b2M with a KRAS mutant G12V(7-16) peptide (VVVGAVGVGK; SEQ ID NO:22), b2M with the KRAS wt(8-16) peptide (VVGAGGVGK; SEQ ID NO:25), b2M with the KRAS wt(7-16) peptide (VVVGAGGVGK; SEQ ID NO:23), or the CTNNB S45F(41-49) peptide (TTAPFLSGK; SEQ ID NO:26). Cells were stained with 10 µL of precipitated phage per 100 µL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 7:
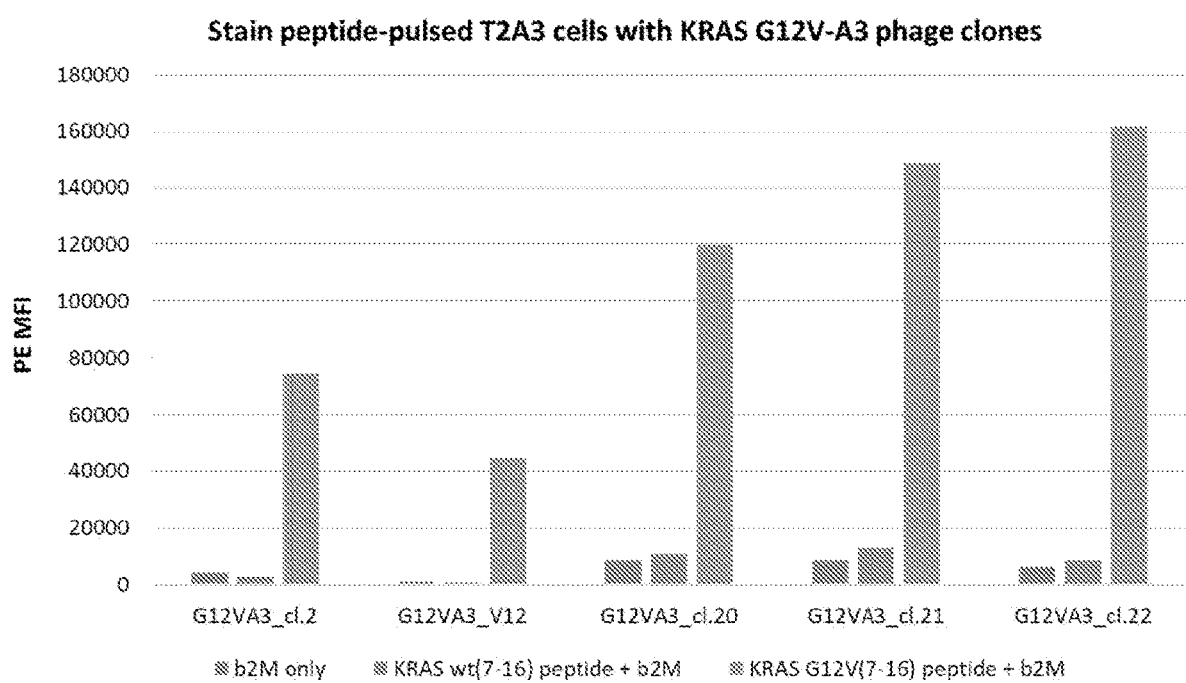
FIG. 7 contains a graph showing flow cytometry on peptide-pulsed A3+ cells. T2A3 cells were peptide-pulsed overnight at 37° C. in serum-free media with b2M only, b2M with a KRAS mutant G12V(7-16) peptide (VVVGAVGVGK; SEQ ID NO:22), or b2M with the KRAS wt(7-16) peptide (VVVGAGGVGK; SEQ ID NO:23). Cells were stained with 10 of precipitated phage per 100 µL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 8:
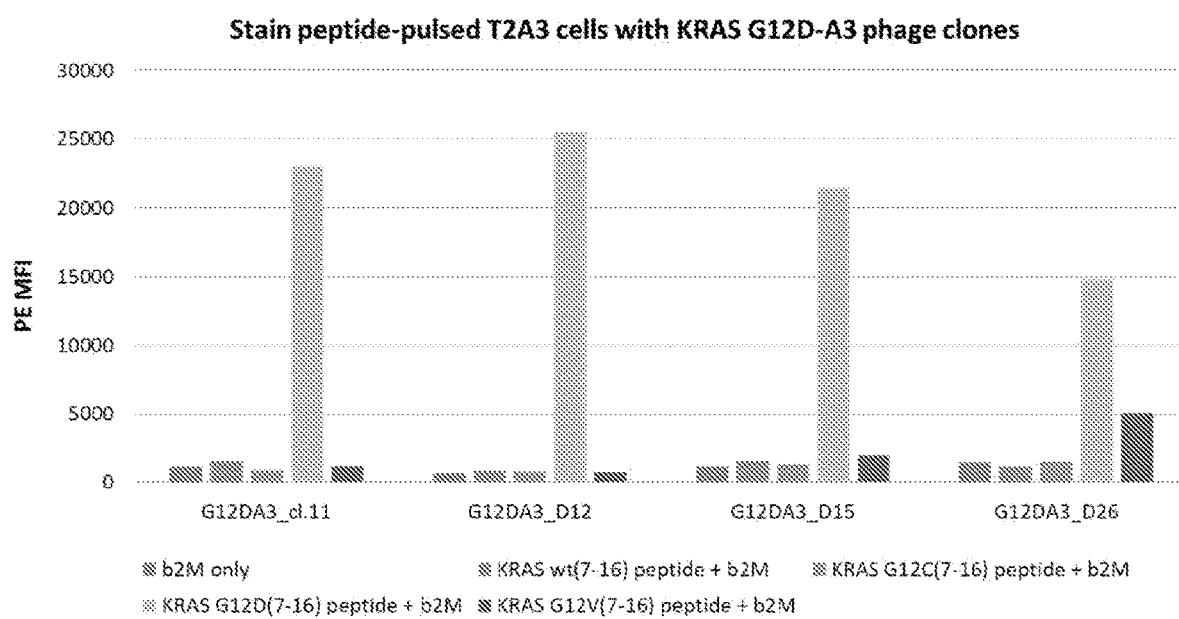
FIG. 8 contains a graph showing flow cytometry on peptide-pulsed A3+ cells. T2A3 cells were peptide-pulsed overnight at 37° C. in serum-free media with b2M only, b2M with a KRAS mutant G12C(7-16) peptide (VVVGACGVGK; SEQ ID NO:20), b2M with a KRAS mutant G12D(7-16) peptide (VVVGADGVGK; SEQ ID NO:21), b2M with a KRAS mutant G12V(7-16) peptide (VVVGAVGVGK; SEQ ID NO:22), or b2M with the KRAS wt(7-16) peptide (VVVGAGGVGK; SEQ ID NO:23). Cells were stained with 10 µL of precipitated phage per 100 µL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 9:
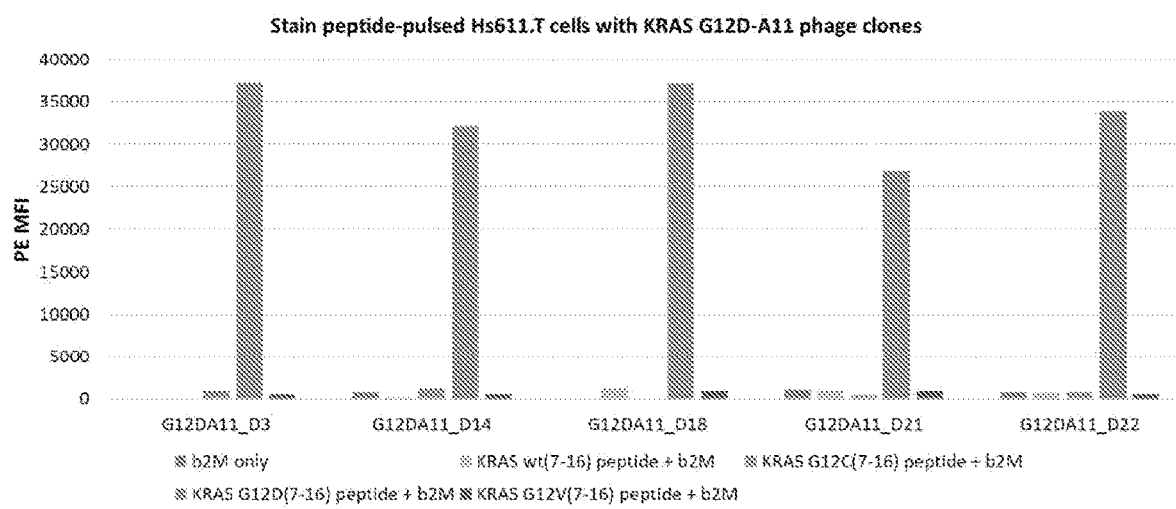
FIG. 9 contains a graph showing flow cytometry on peptide-pulsed A11+ cells. Hs611.T cells were peptide-pulsed overnight at 37° C. in serum-free media with b2M only, b2M with a KRAS mutant G12C(7-16) peptide (VVVGACGVGK; SEQ ID NO:20), b2M with a KRAS mutant G12D(7-16) peptide (VVVGADGVGK; SEQ ID NO:21), b2M with a KRAS mutant G12V(7-16) peptide (VVVGAVGVGK; SEQ ID NO:22), or b2M with the KRAS wt(7-16) peptide (VVVGAGGVGK; SEQ ID NO:23). Cells were stained with 10 µL of precipitated phage per 100 µL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 10:
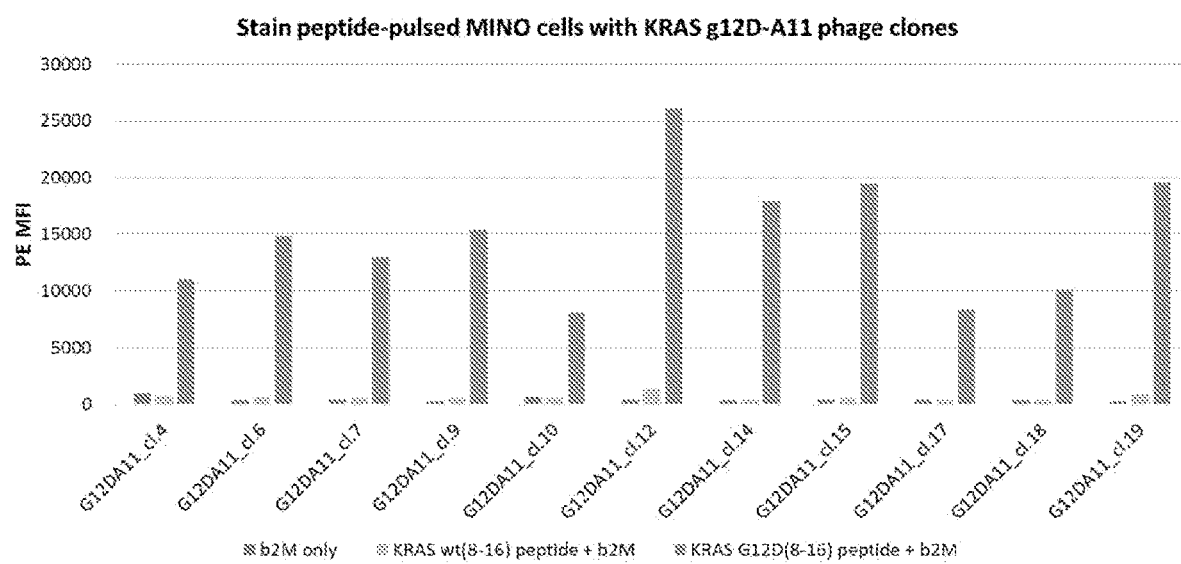
FIG. 10 contains a graph showing flow cytometry on peptide-pulsed A11+ cells. MINO cells were peptide-pulsed overnight at 37° C. in serum-free media with b2M only, b2M with a KRAS mutant G12D(8-16) peptide (VVGADGVGK; SEQ ID NO:24), or b2M with the KRAS wt(8-16) peptide (VVGAGGVGK; SEQ ID NO:25). Cells were stained with 10 µL of precipitated phage per 100 µL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 11:
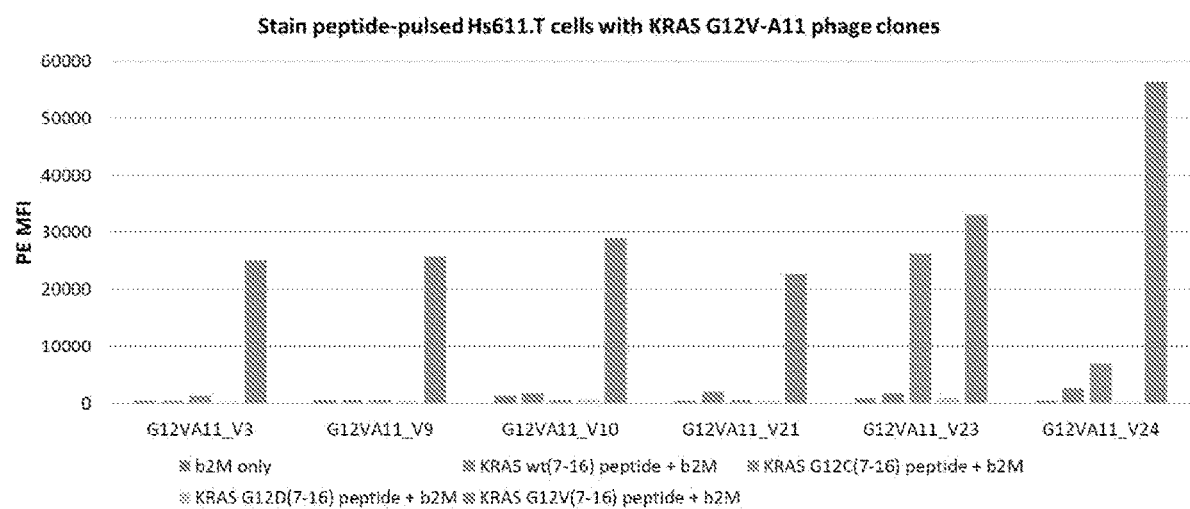
FIG. 11 contains a graph showing flow cytometry on peptide-pulsed A11+ cells. Hs611.T cells were peptide-pulsed overnight at 37° C. in serum-free media with b2M only, b2M with a KRAS mutant G12C(7-16) peptide (VVVGACGVGK; SEQ ID NO:20), b2M with a KRAS mutant G12D(7-16) peptide (VVVGADGVGK; SEQ ID NO:21), b2M with a KRAS mutant G12V(7-16) peptide (VVVGAVGVGK; SEQ ID NO:22), or b2M with the KRAS wt(7-16) peptide (VVVGAGGVGK; SEQ ID NO:23). Cells were stained with 10 µL of precipitated phage per 100 µL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 12:
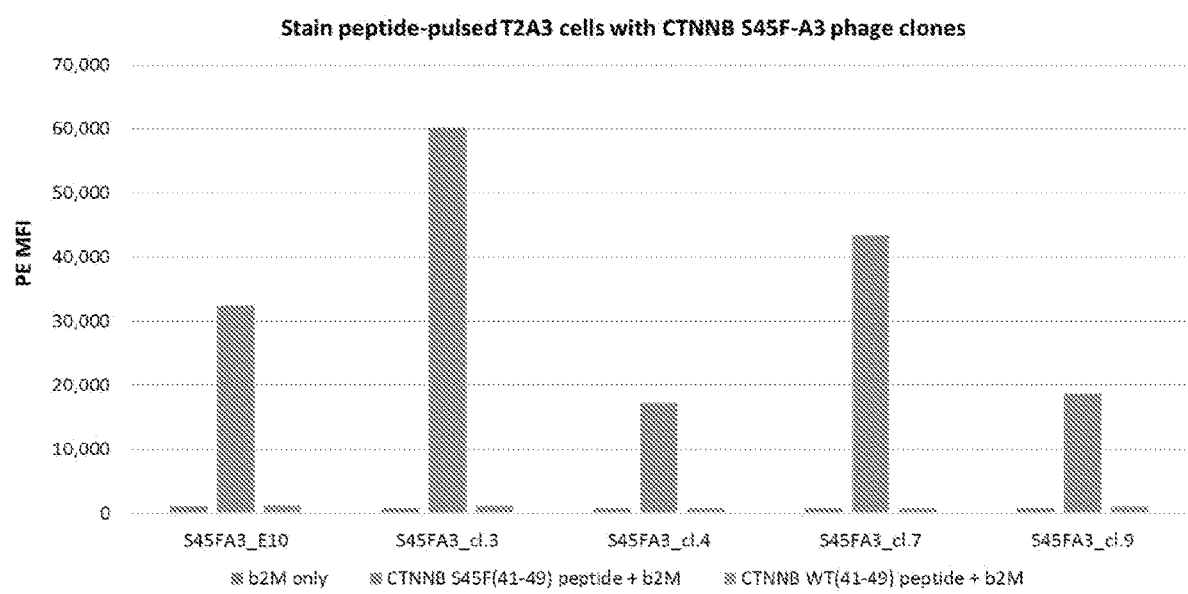
FIG. 12 contains a graph showing flow cytometry on peptide-pulsed A3+ cells. T2A3 cells were peptide-pulsed overnight at 37° C. in serum-free media with b2M only, b2M with a CTNNB mutant S45F(41-49) peptide (TTAPFLSGK; SEQ ID NO:26), or b2M with CTNNB wt(41-49) peptide (TTAPSLSGK; SEQ ID NO:27). Cells were stained with 10 µL of precipitated phage per 100 µL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 13:
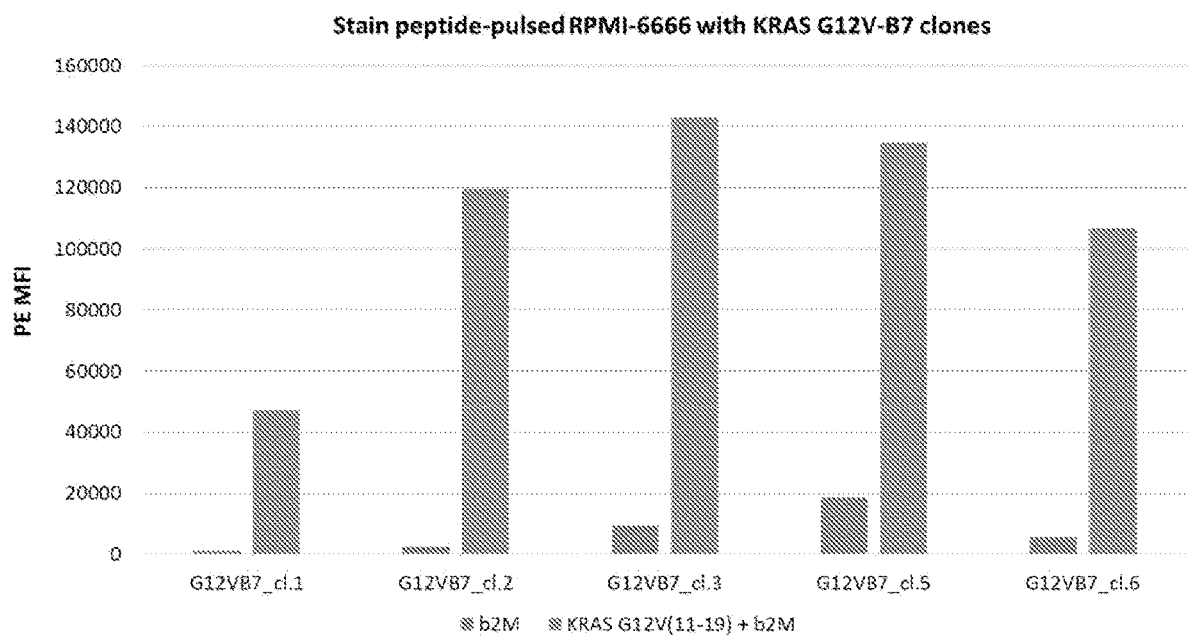
FIG. 13 contains a graph showing flow cytometry on peptide-pulsed B7+ cells. RPMI-6666 cells were peptide-pulsed overnight at 37° C. in serum-free media shows cells pulsed with b2M only, b2M with a KRAS mutant G12V(11-19) peptide (AVGVGKSAL; SEQ ID NO:11). The KRAS wt(11-19) peptide (AGGVGKSAL; SEQ ID NO:12) did not bind to HLA-B7. Cells were stained with 10 µL of precipitated phage per 100 µL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 14:
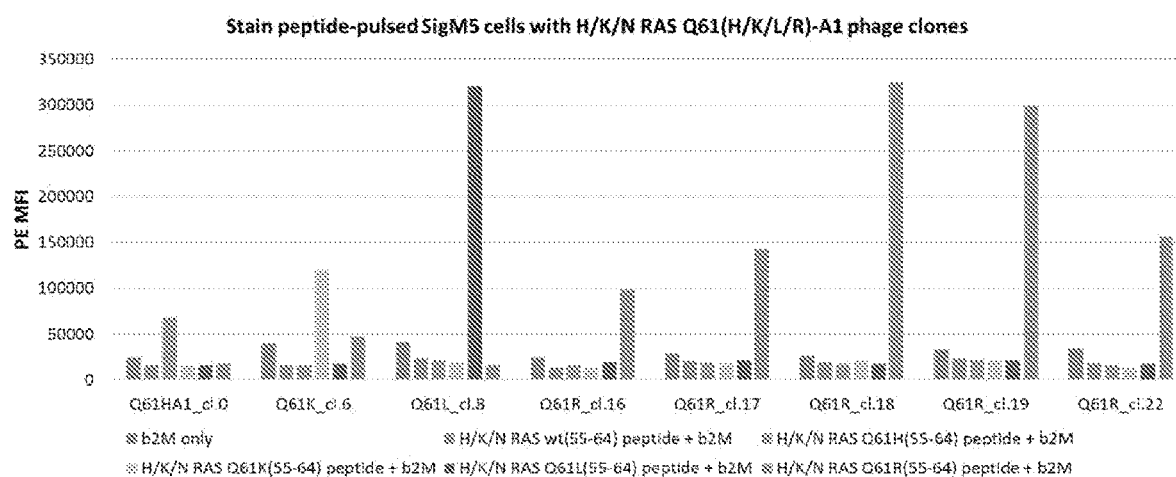
FIG. 14 contains a graph showing flow cytometry on peptide-pulsed A1+ cells. SigM5 cells were peptide-pulsed overnight at 37° C. in serum-free media shows cells pulsed with b2M only, b2M with a H/K/N RAS mutant Q61H(55-64) peptide (ILDTAGHEEY; SEQ ID NO:28), b2M with a H/K/N RAS mutant Q61K(55-64) peptide (ILDTAGKEEY; SEQ ID NO:30), b2M with a H/K/N RAS mutant Q61L(55-64) peptide (ILDTAGLEEY; SEQ ID NO:31), b2M with a H/K/N RAS mutant Q61R(55-64) peptide (ILDTAGREEY; SEQ ID NO:32), or b2M with the H/K/N RAS wt(55-64) peptide (ILDTAGQEEY; SEQ ID NO:29). Cells were stained with 10 µL of precipitated phage per 100 µL of cells, washed and stained with rabbit anti-M13 antibody, then washed and stained with anti-Rabbit-PE antibody. Cells were stained with a live/dead Near-IR dye, washed, and analyzed by an LSRII flow cytometer.

This document provides methods and materials for assessing a mammal having cancer or suspected of having cancer and/or treating a mammal having cancer. For example, one or more molecules including one or more antigen-binding domains (e.g., scFvs) that can target (e.g., bind to) one or more modified peptides (e.g., peptides present in a peptide-HLA complex such as a peptide-HLA-b2M complex) can be used to assess a mammal having cancer or suspected of having cancer and/or to treat a mammal having a cancer (e.g., a cancer expressing one or more modified peptides). In some cases, one or more molecules includes one or more antigen-binding domains that can bind to a modified peptide can be used to detect the presence or absence of one or more modified peptides in a sample obtained from a mammal having cancer or suspected of having cancer. In some cases, one or more molecules including one or more antigen-binding domains that can bind to a modified peptide can be administered to a mammal having a cancer (e.g., a cancer expressing the modified peptide) to treat the mammal.

As used herein, a modified peptide is a peptide derived from a modified polypeptide. A modified polypeptide can be any appropriate modified polypeptide (e.g., a polypeptide having a disease causing mutation such as an oncogenic mutation). A modified peptide can have one or more amino acid modifications (e.g., substitutions) relative to a wild type (wt) peptide (e.g., a peptide derived from a wt polypeptide from which the modified polypeptide is derived). A modified peptide also can be referred to as a mutant peptide. In some cases, a modified peptide can be a tumor antigen. Examples of tumor antigens include, without limitation, mutation-associated neo-antigens (MANAs), tumor-associated antigen, and tumor-specific antigens. A modified peptide can be any appropriate length. In some cases, a modified peptide can be from about 7 amino acids to about 15 amino acids (e.g., from about 8 amino acids to about 15 amino acids, from about 9 amino acids to about 15 amino acids, from about 10 amino acids to about 15 amino acids, from about 11 amino acids to about 15 amino acids, from about 12 amino acids to about 15 amino acids, from about 13 amino acids to about 15 amino acids, from about 7 amino acids to about 14 amino acids, from about 7 amino acids to about 13 amino acids, from about 7 amino acids to about 12 amino acids, from about 7 amino acids to about 11 amino acids, from about 7 amino acids to about 10 amino acids, from about 7 amino acids to about 9 amino acids, or from about 9 amino acids to about 10 amino acids) in length. For example, a modified peptide can be about 9 amino acids in length. For example, a modified peptide can be about 10 amino acids in length. A modified peptide can be derived from any modified (e.g., oncogenic) polypeptide. Examples of modified polypeptides from which modified peptides described herein can be derived include, without limitation, epidermal growth factor receptor (EGFR), isocitrate dehydrogenase 2 (IDH2), p53, RAS (e.g., KRAS, HRAS, and NRAS), and CTNNB. A modified peptide can include any appropriate modification. In some cases, modified peptides described herein can include one or more modifications (e.g., mutations) shown in Table 1.

TABLE 1

Modified peptides.

| Protein of origin | Mutation | Mutant Peptide(s) | SEQ ID NO: | WT Peptide | SEQ ID NO: | Peptide Codons | HLA Allele |
|---|---|---|---|---|---|---|---|
| EGFR | T790M | IMQLMPFGC | 13 | ITQLMPFGC | 14 | 789-797 | A2 |
| IDH2 | R140Q | SPNGTIQNIL | 1 | SPNGTIRNIL | 2 | 134-143 | B7 |
| p53 | R248Q, R248W | GMNQRPILTI, GMNWRPILTI | 15, 16 | GMNRRPILTI | 17 | 245-254 | A2 |
| KRAS | G12V | LVVVGAVGV | 18 | LVVVGAGGV | 19 | 6-14 | A2 |
| KRAS | G12C, G12D, G12V | VVVGACGVGK, VVVGADGVGK, VVVGAVGVGK | 20, 21, 22 | VVVGAGGVGK | 23 | 7-16 | A3 |
| KRAS | G12V | VVVGAVGVGK | 22 | VVVGAGGVGK | 23 | 7-16 | A3 |
| KRAS | G12D | VVVGADGVGK | 21 | VVVGAGGVGK | 23 | 7-16 | A3 |
| KRAS | G12D | VVVGADGVGK | 21 | VVVGAGGVGK | 23 | 7-16 | A11 |
| KRAS | G12D | VVGADGVGK | 24 | VVGAGGVGK | 25 | 8-16 | A11 |
| KRAS | G12V | VVVGAVGVGK | 22 | VVVGAGGVGK | 23 | 7-16 | A11 |
| CTNNB | S45F | TTAPFLSGK | 26 | TTAPSLSGK | 27 | 41-49 | A3 |
| KRAS | G12V | AVGVGKSAL | 11 | AGGVGKSAL | 12 | 11-19 | B7 |
| H/K/N RAS | Q61H | ILDTAGHEEY | 28 | ILDTAGQEEY | 29 | 55-64 | A1 |
| H/K/N RAS | Q61K | ILDTAGKEEY | 30 | ILDTAGQEEY | 29 | 55-64 | A1 |
| H/K/N RAS | Q61L | ILDTAGLEEY | 31 | ILDTAGQEEY | 29 | 55-64 | A1 |
| H/K/N RAS | Q61R | ILDTAGREEY | 32 | ILDTAGQEEY | 29 | 55-64 | A1 |

A modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be in a complex with any appropriate HLA. An HLA can be any appropriate HLA allele. In some cases, an HLA can be a class I HLA (e.g., HLA-A, HLA-B, and HLA-C) allele. Examples of HLA alleles that a modified peptide described herein can complex with include, without limitation, HLA-A1, HLA-A2, HLA-A3, HLA-11, and HLA-B7. Exemplary HLA alleles for particular modified peptides are shown in Table 1. For example, a modified peptide derived from a modified EGFR polypeptide (e.g., IMQLMPFGC (SEQ ID NO:13)) can be in a complex with HLA-A2 and b2M. For example a modified peptide derived from a modified IDH2 polypeptide (e.g., SPNGTIQNIL (SEQ ID NO:1)) can be in a complex with HLA-B7 and b2M. For example a modified peptide derived from a modified p53 polypeptide (e.g., GMNQRPILTI (SEQ ID NO:15) or GMNWRPILTI 1 (SEQ ID NO:16)) can be in a complex with HLA-A2 and b2M. For example a modified peptide derived from a modified KRAS polypeptide (e.g., LVVVGAVGV (SEQ ID NO:18), VVVGACGVGK (SEQ ID NO:20), VVVGADGVGK (SEQ ID NO:21), VVVGAVGVGK (SEQ ID NO:22), and VVGADGVGK (SEQ ID NO:24)) can be in a complex with HLA-A2, HLA-A3, and/or HLA-A11, and b2M. For example a modified peptide derived from a modified CTNNB polypeptide (e.g., TTAPFLSGK (SEQ ID NO:26)) can be in a complex with HLA-A3 and b2M. For example a modified peptide derived from a modified KRAS polypeptide (e.g., AVGVGKSAL (SEQ ID NO:11)) can be in a complex with HLA-B7 and b2M. For example a modified peptide derived from a modified H/K/N RAS polypeptide (e.g., ILDTAGHEEY (SEQ ID NO:28), ILDTAGKEEY (SEQ ID NO:30), ILDTAGLEEY (SEQ ID NO:31), ILDTAGREEY (SEQ ID NO:32)) can be in a complex with HLA-A1 and b2M.

This document provides molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32). In some cases, a molecule including one or more antigen-binding domains that can bind to a modified peptide described herein does not target (e.g., does not bind to) a modified peptide described herein that is not present in a complex (e.g., a peptide-HLA-b2M complex). In some cases, a molecule including one or more antigen-binding domains that can bind to a modified peptide described herein does not target (e.g., does not bind to) a wt peptide (e.g., a peptide derived from a wt polypeptide from which the modified polypeptide is derived).

A molecule including one or more antigen-binding domains (e.g., scFvs) that can bind to a modified peptide described herein can be any appropriate type of molecule. In some cases, a molecule can be a monovalent molecule (e.g., containing a single antigen-binding domain). In some cases, a molecule can be a multivalent molecule (e.g., containing two or more antigen-binding domains and simultaneously targeting two or more antigens). For example, a bispecific molecule can include two antigen-binding domains, a trispecific molecule can include three antigen-binding domains, a quadspecific molecule can include four antigen-binding domains, etc. Examples of molecules that contain antigen-binding domains include, without limitation, antibodies, antibody fragments, scFvs, CARs, T cell receptors (TCRs), TCR mimics, tandem scFvs, bispecific T cell engagers, diabodies, scDbs, scFv-Fcs, bispecific antibodies, dual-affinity re-targeting antibodies (DARTs), and any other molecule that includes at least one variable heavy chain (VH) and at least one variable light chain (VL). Any of these molecules can be used in accordance with materials and methods described herein. In some cases, an antigen-binding domain can be a scFv. For example, a molecule including one or more antigen-binding domains (e.g., one or more scFvs) that can bind to a modified peptide described herein can be a CAR. For example, a molecule including two scFvs that can bind to a modified peptide described herein can be a single-chain diabody (scDb).

In some cases, when a molecule including one or more antigen-binding domains (e.g., one or more scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) is a CAR, the CAR can be any appropriate CAR. A CAR provided herein can include an extracellular domain having at least one antigen-binding domain that can bind to a modified peptide described herein, a transmembrane domain, and an intracellular domain (e.g., an intracellular signaling domain such as a costimulatory domain). A CAR can include any appropriate extracellular domain. For example, a CAR can include a molecule (e.g., a scFv) having an antigen binding domain that can bind to a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32. A CAR can include any appropriate transmembrane domain. A transmembrane domain can be derived from any appropriate polypeptide. Examples of transmembrane domains that can be used in CAR described herein include, without limitation, transmembrane domains of CD4, CD8 (e.g., CD8-alpha and CD8-beta), CD28, CD3 epsilon, CD5, CD6, CD9, CD16, CD22, CD33, CD37, CD45, CD64, CD80, CD86, CD134, 4-1BB, and CD154. In some cases, a CAR described herein can include a CD28 transmembrane domain. A CAR can include any appropriate intracellular domain. An intracellular domain can be derived from any appropriate polypeptide. An intracellular domain can include a costimulatory domain (e.g., a single costimulatory domain or multiple costimulatory domains). In cases where a CAR includes multiple costimulatory domains, the CAR can include multiple costimulatory domains of the same type or multiple costimulatory domains of different types. An intracellular domain can include a signaling domain. Examples of intracellular domains that can be used in CAR described herein include, without limitation, intracellular domains of CD3 (e.g., a CD3-zeta), CD28, DAP10, inducible T-cell costimulator (ICOS), OX40, 4-1BB, CD2, CD4, CD8, CD5, CD22, DAP-12, CD22, and CD79. A CAR can be made using any appropriate method. In some cases, a CAR also can include a hinge sequence (e.g., positioned between the extracellular domain and the transmembrane domain). In some cases, a CAR can be made as described elsewhere (see, Curran et al., 2012 *J. Gene Med* 14:405-415; Kershaw et al., 2005 *Nature Reviews Immunol.* 5(12):928-940; Eshhar et al., 1993 *Proc. Natl. Acad. Sci. U.S.A.* 90(2):720-724; Sadelain et al., 2009 *Curr. Opin. Immunol.* 21(2): 215-223; WO 2015/142675; WO 2015/150526; and WO 2014/134165). Also provided here are CARTs expressing one or more CARs, which CARs can target (e.g., bind to) one or more modified peptides described herein (e.g., CARs having two or more antigen-binding domains). Also provided here are CARTs expressing one or more CARs, which CARTs can target (e.g., bind to) one or more modified peptides described herein.

In some cases, when a molecule including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) is a multivalent molecule (e.g., a bispecific molecule), a first antigen-binding domain can bind to a modified peptide described herein and a second antigen-binding domain can bind to an effector cell (e.g., an antigen present on an effector cell). Examples of effector cells include, without limitation, T cells, natural killer (NK) cells, natural killer T (NKT) cells, B cells, plasma cells, macrophages, monocytes, microglia, dendritic cells, neutrophils, fibroblasts, and mast cells. Examples of antigens present on effector cells include, without limitation, CD3, CD4, CD8, CD28, CD16a, NKG2D, PD-1, CTLA-4, 4-1BB, OX40, ICOS, CD27, and any other effector cell surface receptors. In some cases, a molecule described herein can include a first antigen-binding domain that can bind to a modified peptide described herein and a second antigen-binding domain that can bind to an antigen present on a T cell (e.g., CD3). In some cases, sequences (e.g., scFv sequences) that can bind to CD3 can be as shown in Table 4. In some cases, sequences (e.g., scFv sequences) that can bind to CD3 can be as described elsewhere (see, e.g., Rodrigues et al., 1992 *Int J Cancer Suppl.* 7:45-50; Shalaby et al., 1992 *J Exp Med.* 175:217-25; Brischwein et al., 2006 *Mol Immunol.* 43:1129-43; Li et al., 2005 *Immunology.* 116:487-98; WO2012162067; US20070065437; US20070065437; US20070065437; US20070065437; US20070065437; and US20070065437). In some cases, a molecule described herein can include a first antigen-binding domain that can bind to a modified peptide described herein and a second antigen-binding domain that can bind to an antigen present on a NK cell (e.g., CD16a or NKG2D). By binding both the modified peptide and the effector cell, the multivalent molecule can bring the cell expressing the modified peptide (e.g., as part of the HLA complex) into proximity with the effector cell, permitting the effector cell to act on the cell expressing the modified peptide.

In some cases, when a molecule including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) is a multivalent molecule (e.g., a bispecific molecule), a molecule can be in any appropriate format which includes at least one VH and at least one VL. For example, a VH and a VL can be in any appropriate orientation. In some cases, a VH can be N-terminal to the VL. In some cases, a VH can be C-terminal to the VL. In some cases, a linker amino acid sequence can be positioned between the VH and VL.

In some cases, when a bispecific molecule is a tandem scFv, the tandem scFv can be in any appropriate orientation. Examples of tandem scFv orientations including scFv-A and scFv-B include, without limitation, VLA-LL-VHA-SL-VLB-LL-VHB, VLA-LL-VHA-SL-VHB-LL-VLB, VHA-LL-VLA-SL-VLB-LL-VHB, VHA-LL-VLA-SL-VHB-LL-VLB, VLB-LL-VHB-SL-VLA-LL-VHA, VLB-LL-VHB-SL-VHA-LL-VLA, VHB-LL-VLB-SL-VLA-LL-VHA, and VHB-LL-VLB-SL-VHA-LL-VLA, where SL is a short linker and LL is a long linker. A short linker can be from about 3 amino acids to about 10 amino acids in length. A short linker can include any appropriate amino acids (e.g., glycines and serines) in any appropriate combination. A long linker can be from about 10 amino acids to about 25 amino acids in length. A long linker can include any appropriate amino acids (e.g., glycines and serines) in any appropriate combination.

In some cases, when a bispecific molecule is a diabody, the diabody can be in any appropriate orientation. Examples of diabody orientations including scFv-A and scFv-B include, without limitation, VLA-SL-VHB and VLB-SL-VHA, VLA-SL-VLB and VHB-SL-VHA, VHA-SL-VLB and VHB-SL-VLA, VLB-SL-VHA and VLA-SL-VHB, VLB-SL-VLA and VHA-SL-VHB, and VHB-SL-VLA and VHA-SL-VLB, where SL is a short linker. A short linker can be from about 3 amino acids to about 10 amino acids in length. A short linker can include any appropriate amino acids (e.g., glycines and serines) in any appropriate combination.

In some cases, when a bispecific molecule is a scDb, the scDb can be in any appropriate orientation. Examples of scDb orientations including scFv-A and scFv-B include, without limitation, VLA-SL-VHB-LL-VLB-SL-VHA, VHA-SL-VLB-LL-VHB-SL-VLA, VLA-SL-VLB-LL-VHB-SL-VHA, VHA-SL-VHB-LL-VLB-SL-VLA, VLB-SL-VHA-LL-VLA-SL-VHB, VHB-SL-VLA-LL-VHA-SL-VLB, VLB-SL-VLA-LL-VHA-SL-VHB, and VHB-SL-VHA-LL-VLA-SL-VLB, where SL is a short linker and LL is a long linker. A short linker can be from about 3 amino acids to about 10 amino acids in length. A short linker can include any appropriate amino acids (e.g., glycines and serines) in any appropriate combination. A long linker can be from about 10 amino acids to about 25 amino acids in length. A long linker can include any appropriate amino acids (e.g., glycines and serines) in any appropriate combination.

In some cases, when a bispecific molecule is a scFv-Fc, the scFv-Fc can be in any appropriate orientation. Examples of scFv-Fc orientations including scFv-Fc-A, scFv-Fc-B, and an Fc domain include, without limitation, VLA-LL-VHA-hinge-Fc and VLB-LL-VHB-hinge-Fc, VHA-LL-VLA-hinge-Fc and VHB-LL-VLB-hinge-Fc, VLA-LL-VHA-hinge-Fc and VHB-LL-VLB-hinge-Fc, VHA-LL-VLA-hinge-Fc and VLB-LL-VHB-hinge-Fc, where LL is a long linker. A long linker can be from about 10 amino acids to about 25 amino acids in length. A long linker can include any appropriate amino acids (e.g., glycines and serines) in any appropriate combination. In some cases, an Fc domain in a scFv-Fc can include one or more modifications to increase heterodimerization and/or to decrease homodimerization of the scFv-Fc. In some cases, an Fc domain in a scFv-Fc can exclude a hinge domain. In some cases, an Fc domain in a scFv-Fc can be at the N-terminus of the scFv.

A molecule including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can include any appropriate complementarity determining regions (CDRs). For example, a molecule including one or more antigen-binding domains that can bind to a modified peptide described herein can include a variable heavy chain (VH) having three VH complementarity determining regions (CDR-VHs) and a variable light chain (VL) having three VL CDRs (CDR-VLs). For example, a molecule that can bind to a modified peptide derived from a modified EGFR polypeptide (e.g., IMQLMPFGC (SEQ ID NO:13)) can include one of each of the CDRs set forth below:

```
CDR-VL1:
                                         (SEQ ID NO: 33)
    QDVNTA;

CDR-VL2:
    SAS;

CDR-VL3:
                                         (SEQ ID NO: 34)
    QQYDYAPIT, (SEQ ID NO: 35)
    QQSPYYYLPIT, (SEQ ID NO: 36)
    QQYYYSPVT, (SEQ ID NO: 37)
    QQHYGNPFT, (SEQ ID NO: 38)
    QQSYYSPPT, (SEQ ID NO: 39)
    QQYYSYPPT, (SEQ ID NO: 40)
    QQYYYYPPT;

CDR-VH1:
                                         (SEQ ID NO: 41)
    GFNISWYQ, (SEQ ID NO: 42)
    GFNVSWSY, (SEQ ID NO: 43)
    GFNISWNQ, (SEQ ID NO: 44)
    GFNVGYYG, (SEQ ID NO: 45)
    GFNITSSY, (SEQ ID NO: 46)
    GFNINSSY, (SEQ ID NO: 47)
    GFNISTSY;

CDR-VH2:
                                         (SEQ ID NO: 48)
    VTPYSGYT, (SEQ ID NO: 49)
    IYGDSGYT, (SEQ ID NO: 50)
    VSPYSGYT, (SEQ ID NO: 51)
    VSGMEGYT, (SEQ ID NO: 52)
    ISPADGYN, (SEQ ID NO: 53)
    ISPTDGYY, (SEQ ID NO: 54)
    IDPNDGYS;
and CDR-VH3:
                                         (SEQ ID NO: 55)
    SRSYTDGFDY, (SEQ ID NO: 56)
    SRGQWEASYYAMDY, (SEQ ID NO: 57)
    SRSDYYAMDY, (SEQ ID NO: 58)
    SRDIYGYAMDV, (SEQ ID NO: 59)
    SRTDSTAYTAMDV, (SEQ ID NO: 60)
    SRTSDTSYAAMDV, (SEQ ID NO: 61)
    SRTNNTAADAMDV.
```

For example, a molecule that can bind to a modified peptide derived from a modified IDH2 polypeptide (e.g., SPNGTIQNIL (SEQ ID NO:1)) can include one of each of the CDRs set forth below:

```
CDR-VL1:
                                         (SEQ ID NO: 33)
    QDVNTA;

CDR-VL2:
    SAS;

CDR-VL3:
                                         (SEQ ID NO: 62)
    QQYSYSPPT, (SEQ ID NO: 63)
    QQGKAYWPAT, (SEQ ID NO: 64)
    QQVYSSPFT, (SEQ ID NO: 65)
    QQYSLYSPMT, (SEQ ID NO: 66)
    QQSYYMPFT;

CDR-VH1:
                                         (SEQ ID NO: 67)
    GFNISDTY, (SEQ ID NO: 68)
    GFNVGHYR, (SEQ ID NO: 69)
    GFNVKYYM, (SEQ ID NO: 70)
    GFNSFLS, (SEQ ID NO: 71)
    GFNIFRGY;

CDR-VH2:
                                         (SEQ ID NO: 72)
    ISPRTGYN,
```

```
                                    (SEQ ID NO: 73)
VSPNGYYT, (SEQ ID NO: 74)
ISPGYDYT, (SEQ ID NO: 75)
IFPSSDYT, (SEQ ID NO: 76)
ISPHSDYT;
and

CDR-VH3:
                                    (SEQ ID NO: 77)
SRAYYSYAYAMDV, (SEQ ID NO: 78)
SRGYSSYAFDY, (SEQ ID NO: 79)
SRSYWRYSVDV, (SEQ ID NO: 80)
SRGKHSSDSNYYMDY, (SEQ ID NO: 81)
SRSYGWAAFDY.
```

For example, a molecule that can bind to a modified peptide derived from a modified p53 polypeptide (e.g., GMNQRPILTI (SEQ ID NO:15) and GMNWRPILTI (SEQ ID NO:16)) can include one of each of the CDRs set forth below:

```
CDR-VL1:
                                    (SEQ ID NO: 33)
QDVNTA;

CDR-VL2:
SAS;

CDR-VL3:
                                    (SEQ ID NO: 82)
QQSGYAPIT, (SEQ ID NO: 83)
QQYSYAPIT, (SEQ ID NO: 84)
QQSLYGPFT, (SEQ ID NO: 85)
QQYSYSPIT, (SEQ ID NO: 86)
QQSGYQPDT, (SEQ ID NO: 87)
QQYLYQPWT;

CDR-VH1:
                                    (SEQ ID NO: 89)
GFNISYYS, (SEQ ID NO: 90)
GFNIGYYT, (SEQ ID NO: 91)
GFNIAYEY, (SEQ ID NO: 92)
GFNLFGYG, (SEQ ID NO: 93)
GFNISWYA, (SEQ ID NO: 94)
GFNIDYYG;

CDR-VH2:
                                    (SEQ ID NO: 96)
VDPDSDYT, (SEQ ID NO: 97)
VSPWSYST, (SEQ ID NO: 98)
IGPDSGYT, (SEQ ID NO: 99)
IGPYYYYT, (SEQ ID NO: 100)
IWPDSDWT, (SEQ ID NO: 101)
LYGGSDST;
and

CDR-VH3:
                                    (SEQ ID NO: 103)
SRSWIHMFSMDY, (SEQ ID NO: 104)
SRDHWDEAFDV, (SEQ ID NO: 105)
SRVWYYSTYGMDY, (SEQ ID NO: 106)
SRENYDMAMDY, (SEQ ID NO: 107)
SRYYYSSAFDV, (SEQ ID NO: 108)
SRQYSAYFDY.
```

For example, a molecule that can bind to a modified peptide derived from a modified KRAS polypeptide (e.g., LVVVGAVGV (SEQ ID NO:18), VVVGACGVGK (SEQ ID NO:20), VVVGADGVGK (SEQ ID NO:21), VVVGAVGVGK (SEQ ID NO:22), and VVGADGVGK (SEQ ID NO:24)) can include one of each of the CDRs set forth below:

```
CDR-VL1:
                                    (SEQ ID NO: 33)
QDVNTA;

CDR-VL2:
SAS and SAY;

CDR-VL3:
                                    (SEQ ID NO: 110)
QQWYSSPVT, (SEQ ID NO: 111)
QQYSRPVT, (SEQ ID NO: 121)
QQSYGSGSPWT, (SEQ ID NO: 122)
QQTYYSPWT, (SEQ ID NO: 123)
QQYYYPPIT, (SEQ ID NO: 132)
QQSYYFRPIT, (SEQ ID NO: 133)
QQASYYYPLT,
```

-continued

QQKSEYSPWT, (SEQ ID NO: 134)

QQSGYIPFT, (SEQ ID NO: 135)

QQGAYYRPFT, (SEQ ID NO: 136)

QQYMYSPVT, (SEQ ID NO: 152)

QQSSSSPIT, (SEQ ID NO: 153)

QQSSASPLT, (SEQ ID NO: 154)

QQYAYSPLT, (SEQ ID NO: 155)

QQYSYYPIT, (SEQ ID NO: 168)

QQYSYTPVT, (SEQ ID NO: 169)

QQYSYEPVT, (SEQ ID NO: 170)

QQYAYYSPVT, (SEQ ID NO: 171)

QQYEYYPMT, (SEQ ID NO: 172)

QQYSFYPFT, (SEQ ID NO: 188)

QQYSYSPIT, (SEQ ID NO: 85)

QQYSAYYQPIT, (SEQ ID NO: 189)

QQYSYYPIT, (SEQ ID NO: 168)

QQYEYVPHT, (SEQ ID NO: 190)

QQYSYMPIT, (SEQ ID NO: 191)

QQYAYYPVT, (SEQ ID NO: 192)

QQYSYMPIT, (SEQ ID NO: 191)

QQYDYRPVT, (SEQ ID NO: 193)

QQYDFTPMT, (SEQ ID NO: 194)

QQYSSSSPVT, (SEQ ID NO: 195)

QQSSYTPIT, (SEQ ID NO: 229)

QQYAYYPIT, (SEQ ID NO: 230)

QQYEYYPIT, (SEQ ID NO: 231)

QQYTYYPIT, (SEQ ID NO: 232)

-continued

QQYSYYPIT, (SEQ ID NO: 168)

QQSSVEPWT; (SEQ ID NO: 233)

CDR-VH1:

GFNINWAN, (SEQ ID NO: 112)

GFNIYLHD, (SEQ ID NO: 113)

GFNIYWSH, (SEQ ID NO: 114)

GFNIVGGG, (SEQ ID NO: 124)

GFNIRSYA, (SEQ ID NO: 125)

GFNVSHTG, (SEQ ID NO: 126)

GFNLSYSD, (SEQ ID NO: 137)

GFNISASG, (SEQ ID NO: 138)

GFNIYRYG, (SEQ ID NO: 139)

GFNIYGTM, (SEQ ID NO: 140)

GFNISYSY, (SEQ ID NO: 141)

GFNVSAYW, (SEQ ID NO: 156)

GFNISGYG, (SEQ ID NO: 157)

GFNVSSVG, (SEQ ID NO: 158)

GFNVSSYG, (SEQ ID NO: 159)

GFNFSYGY, (SEQ ID NO: 173)

GFNVWGPG, (SEQ ID NO: 174)

GFNVSGSQ, (SEQ ID NO: 175)

GFNIYGQM, (SEQ ID NO: 176)

GFNVMYST, (SEQ ID NO: 177)

GFNFGSY, (SEQ ID NO: 196)

GFNISDSY, (SEQ ID NO: 197)

GFNIFSDQ, (SEQ ID NO: 198)

GFNLSYSY, (SEQ ID NO: 199)

GFNISYGY, (SEQ ID NO: 200)

-continued

GFNISYQH, (SEQ ID NO: 201)

GFNLSGYY, (SEQ ID NO: 202)

GFNVSGQY, (SEQ ID NO: 203)

GFNVSTSG, (SEQ ID NO: 204)

GFNISYAK, (SEQ ID NO: 205)

GFNFSSYV, (SEQ ID NO: 206)

GFNISQGG, (SEQ ID NO: 234)

GFNISSTG, (SEQ ID NO: 235)

GFNFFSTV, (SEQ ID NO: 236)

GFNLHGYL, (SEQ ID NO: 237)

GFNLSTHV, (SEQ ID NO: 238)

GFNVSYYS; (SEQ ID NO: 239)

CDR-VH2:

ISPPYDYT, (SEQ ID NO: 115)

IIPAIDYT, (SEQ ID NO: 116)

ISSFEGYT, (SEQ ID NO: 117)

IYPQGDYT, (SEQ ID NO: 127)

VGPGKGYT, (SEQ ID NO: 128)

VGPGKGYT, (SEQ ID NO: 128)

VMPDSGHT, (SEQ ID NO: 142)

IHPLKPYT, (SEQ ID NO: 143)

LYPYGYST, (SEQ ID NO: 144)

FKPDSYNT, (SEQ ID NO: 145)

LLPYDGNT, (SEQ ID NO: 146)

IYGGSGYT, (SEQ ID NO: 160)

LYGGSDYT, (SEQ ID NO: 161)

IYGTSDYT, (SEQ ID NO: 162)

-continued

IAPRRDYT, (SEQ ID NO: 163)

ISGYTGNT, (SEQ ID NO: 178)

IHPFSGNT, (SEQ ID NO: 179)

IPGWSGYT, (SEQ ID NO: 180)

LSPFSGNT, (SEQ ID NO: 181)

IYSWSDYT, (SEQ ID NO: 182)

ISGYSGNT, (SEQ ID NO: 207)

FSPYSSNT, (SEQ ID NO: 208)

FNIPYDSYYT, (SEQ ID NO: 209)

ISGFSGNT, (SEQ ID NO: 210)

FHYGSGNT, (SEQ ID NO: 211)

FMPYQGST, (SEQ ID NO: 212)

FSPYSGYT, (SEQ ID NO: 213)

ISPVSGNT, (SEQ ID NO: 214)

IYGAYSGT, (SEQ ID NO: 215)

LTYWGGYT, (SEQ ID NO: 216)

VYPDSGGT, (SEQ ID NO: 217)

VYPGGGQT, (SEQ ID NO: 240)

LLGGSGNT, (SEQ ID NO: 241)

IYPWSGST, (SEQ ID NO: 242)

IYPPNGYT, (SEQ ID NO: 243)

FYPYVGYT, (SEQ ID NO: 244)

IYPWNDYT; (SEQ ID NO: 245)
and

CDR-VH3:

SRSYSYYFDY, (SEQ ID NO: 118)

SRRDGYYFDY, (SEQ ID NO: 119)

SRSYSYYMDY, (SEQ ID NO: 120)

SRDSSYLAFDY, (SEQ ID NO: 129)

SRNFQSTSHAFDY, (SEQ ID NO: 130)

SRKTYYAFDY, (SEQ ID NO: 131)

SRATNIPVYAFDY, (SEQ ID NO: 147)

SRYSSMYYYFDY, (SEQ ID NO: 148)

SRSYAYGYFAY, (SEQ ID NO: 149)

SRGEVYHYYAFDY, (SEQ ID NO: 150)

SRAAYSSMDV, (SEQ ID NO: 151)

SRTHSYWSAFDY, (SEQ ID NO: 164)

SRTVRYAFDY, (SEQ ID NO: 165)

SRSSRYSMDY, (SEQ ID NO: 166)

SRKSSYYFDY, (SEQ ID NO: 167)

SRAASLSSSYYSAFDV, (SEQ ID NO: 183)

SRGYSYSAMDY, (SEQ ID NO: 184)

SRGYSYFAMDY, (SEQ ID NO: 185)

SRNISYEQSSAFDY, (SEQ ID NO: 186)

SRGYAHNSFDY, (SEQ ID NO: 187)

SRSNQSAYSYMDY, (SEQ ID NO: 218)

SRSQFTFYQYFDY, (SEQ ID NO: 219)

SRMSVRNAFDY, (SEQ ID NO: 220)

SRSDSYYTAMDY, (SEQ ID NO: 221)

SRSNYYYLDY, (SEQ ID NO: 222)

SRANIYSSHSFFDY, (SEQ ID NO: 223)

SRTHSSIYHSFDY, (SEQ ID NO: 224)

SRPMKTSYYGAFDY, (SEQ ID NO: 225)

SRSQSYTYWSAMDY, (SEQ ID NO: 226)

SRGEYGTYMDY, (SEQ ID NO: 227)

SRTSSYYAFDY, (SEQ ID NO: 228)

SRGYDYSAFDY, (SEQ ID NO: 246)

SRGLQYSAMDY, (SEQ ID NO: 247)

SRSRSSNYYFDV, (SEQ ID NO: 248)

SRGVDYAYLDY, (SEQ ID NO: 249)

SRGYRYQYMDV, (SEQ ID NO: 250)

SRGSYYSFDY. (SEQ ID NO: 251)

For example, a molecule that can bind to a modified peptide derived from a modified CTNNB polypeptide (e.g., TTAP-FLSGK (SEQ ID NO:26)) can include one of each of the CDRs set forth below:

CDR-VL1:
QDVNTA; (SEQ ID NO: 33)

CDR-VL2:
SAS and SAY;

CDR-VL3:
QQSYYSPPT, (SEQ ID NO: 38)

QQIYTSPIT, (SEQ ID NO: 252)

QQRAYFPIT, (SEQ ID NO: 253)

QQQYAYTPIT, (SEQ ID NO: 254)

QQIHYKPLT; (SEQ ID NO: 255)

CDR-VH1:
GFNINNTY, (SEQ ID NO: 256)

GFNFITTG, (SEQ ID NO: 257)

GFNFSDYG, (SEQ ID NO: 258)

GFNVWSYG, (SEQ ID NO: 259)

GFNVAWYS; (SEQ ID NO: 260)

CDR-VH2:
IYPTDGYT, (SEQ ID NO: 260)

IGPGSDYT, (SEQ ID NO: 261)

LIPASGYT, (SEQ ID NO: 262)

VTPDGSYT, (SEQ ID NO: 263)

-continued

VYGGSSYT; (SEQ ID NO: 264)
and

CDR-VH3:
SRTYYSYYSAMDV, (SEQ ID NO: 265)

SRYYYASALDY, (SEQ ID NO: 266)

SRGWSYYMDY, (SEQ ID NO: 267)

SRSYGWAMDY, (SEQ ID NO: 268)

SRDFYSSGMDY. (SEQ ID NO: 269)

For example, a molecule that can bind to a modified peptide derived from a modified KRAS polypeptide (e.g., AVGVGKSAL (SEQ ID NO:11)) can include one of each of the CDRs set forth below:

```
CDR-VL1:
                        (SEQ ID NO: 33)
QDVNTA;

CDR-VL2:
SAS;

CDR-VL3:
                        (SEQ ID NO: 270)
QQEWRLPIT, (SEQ ID NO: 271)
QQGTSTPFT, (SEQ ID NO: 272)
QQSWRYPMT, (SEQ ID NO: 273)
QQSYSYPVT, (SEQ ID NO: 274)
QQGWLYSPFT;

CDR-VH1:
                        (SEQ ID NO: 275),
GFNVYGNQ, (SEQ ID NO: 402)
GFNLSYYG, (SEQ ID NO: 276)
GFNISRYG, (SEQ ID NO: 277)
GFNIYSSW, (SEQ ID NO: 157)
GFNISGYG;

CDR-VH2:
                        (SEQ ID NO: 278)
IYPYSGST, (SEQ ID NO: 279)
IYPDSGYT, (SEQ ID NO: 280)
FYPSSSYT, (SEQ ID NO: 281)
FQPYSGYT, (SEQ ID NO: 282)
VYGGSGYT;
```

-continued
and

CDR-VH3:
SRSAYVAYSYFDY, (SEQ ID NO: 283)

SRAYLYYYLAY, (SEQ ID NO: 284)

SRKYYEAMDY, (SEQ ID NO: 285)

SREYTYYFDY, (SEQ ID NO: 286)

SRAHSSYYVDY. (SEQ ID NO: 287)

For example, a molecule that can bind to a modified peptide derived from a modified H/K/N RAS polypeptide (e.g., ILDTAGKEEY (SEQ ID NO:28), ILDTAGKEEY (SEQ ID NO:30), ILDTAGLEEY (SEQ ID NO:31), ILDTAGREEY (SEQ ID NO:32)) can include one of each of the CDRs set forth below:

```
CDR-VL1:
                        (SEQ ID NO: 33)
QDVNTA;

CDR-VL2:
SAS;

CDR-VL3:
                        (SEQ ID NO: 292)
QQHYYSPVT, (SEQ ID NO: 296)
QQYAYAPFT, (SEQ ID NO: 300)
QQAHMIPIT, (SEQ ID NO: 301)
QQSVYDPIT, (SEQ ID NO: 302)
QQSYTSPLT, (SEQ ID NO: 303)
QQGQYSPFT, (SEQ ID NO: 320)
QQYWYLPTT;

CDR-VH1:
                        (SEQ ID NO: 289)
GFNIGYYG, (SEQ ID NO: 293)
GFNIFYQD, (SEQ ID NO: 297)
GFNVSYSM, (SEQ ID NO: 305)
GFNFSFPG, (SEQ ID NO: 306)
GFNISGSW, (SEQ ID NO: 307),
GFNIYYGV, (SEQ ID NO: 308)
GFNVSYEY, (SEQ ID NO: 321)
GFNISWYD;
```

```
CDR-VH2:
                                     (SEQ ID NO: 290)
VYPGGGYT, (SEQ ID NO: 294)
IYPDYDYT, (SEQ ID NO: 298)
VWGDGGVT, (SEQ ID NO: 310)
FVGYDGYT, (SEQ ID NO: 311)
LYPDSDYT, (SEQ ID NO: 312)
IYPDSSWT, (SEQ ID NO: 313)
IYGGSDNT, (SEQ ID NO: 322)
IEPSVGYT;
and

CDR-VH3:
                                     (SEQ ID NO: 291)
SRYYYYGFDY, (SEQ ID NO: 295)
SRTYSVYMDY, (SEQ ID NO: 299)
SRGSYYAFDY, (SEQ ID NO: 316)
SRDYYSFSMDY, (SEQ ID NO: 317)
SRAHTYAFDY, (SEQ ID NO: 318)
SRDQDFHYMNYYLSYALDY, (SEQ ID NO: 319)
SRPLGSYFDY, (SEQ ID NO: 323)
SRSYPYYYFDY.
```

Examples of CDRs (e.g., particular combinations of a CDR-VL1, a CDR-VL2, a CDR-VL3, a CDR-VH1, a CDR-VH2, and a CDR-VH3) that can bind to particular modified peptides are shown in Table 2. In some cases, a molecule including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can include any appropriate set of CDR sequences (e.g., any of the CDR sequence sets described herein).

A molecule including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can include any appropriate sequence. For example, a molecule that can bind to a modified peptide derived from a modified EGFR polypeptide (e.g., IMQLMPFGC (SEQ ID NO:13)) can include, without limitation, the scFv sequence set forth in any one of SEQ ID NO:324, SEQ ID NO:325, SEQ ID NO:326, SEQ ID NO:327, SEQ ID NO:328, SEQ ID NO:329, and SEQ ID NO:330. For example, a molecule that can bind to a modified peptide derived from a modified IDH2 polypeptide (e.g., SPNGTIQNIL (SEQ ID NO:1)) can include, without limitation, the scFv sequence set forth in any one of SEQ ID NO:3, SEQ ID NO:4, SEQ ID NO:5, SEQ ID NO:6, and SEQ ID NO:8. For example, a molecule that can bind to a modified peptide derived from a modified p53 polypeptide (e.g., GMNQRPILTI (SEQ ID NO:15) and GMNWRPILTI 1 (SEQ ID NO:16)) can include, without limitation, the scFv sequence set forth in any one of SEQ ID NO:331, SEQ ID NO:332, SEQ ID NO:333, SEQ ID NO:334, SEQ ID NO:335, SEQ ID NO:336, and SEQ ID NO:337. For example, a molecule that can bind to a modified peptide derived from a modified KRAS polypeptide (e.g., LVVVGAVGV (SEQ ID NO:18), VVVGACGVGK (SEQ ID NO:20), VVVGADGVGK (SEQ ID NO:21), VVVGAVGVGK (SEQ ID NO:22), and VVGADGVGK (SEQ ID NO:24)) can include, without limitation, the scFv sequence set forth in any one of SEQ ID NO:338, SEQ ID NO:339, SEQ ID NO:340, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:350, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:361, SEQ ID NO:362, SEQ ID NO:363, SEQ ID NO:364, SEQ ID NO:365, SEQ ID NO:366, SEQ ID NO:367, SEQ ID NO:368, SEQ ID NO:369, SEQ ID NO:370, SEQ ID NO:371, SEQ ID NO:372, SEQ ID NO:373, and SEQ ID NO:374. For example, a molecule that can bind to a modified peptide derived from a modified CTNNB polypeptide (e.g., TTAPFLSGK (SEQ ID NO:26)) can include, without limitation, the scFv sequence set forth in any one of SEQ ID NO:375, SEQ ID NO:376, SEQ ID NO:377, SEQ ID NO:378, SEQ ID NO:379. For example, a molecule that can bind to a modified peptide derived from a modified KRAS polypeptide (e.g., AVGVGKSAL (SEQ ID NO:11)) can include, without limitation, the scFv sequence set forth in any one of SEQ ID NO:380, SEQ ID NO:390, SEQ ID NO:391, SEQ ID NO:392, and SEQ ID NO:393. For example, a molecule that can bind to a modified peptide derived from a modified H/K/N RAS polypeptide (e.g., ILDTAGKEEY (SEQ ID NO:28), ILDTAGKEEY (SEQ ID NO:30), ILDTAGLEEY (SEQ ID NO:31), ILDTAGREEY (SEQ ID NO:32)) can include, without limitation, the scFv sequence set forth in any one of SEQ ID NO:394, SEQ ID NO:395, SEQ ID NO:396, SEQ ID NO:397, SEQ ID NO:398, SEQ ID NO:399, and SEQ ID NO:400. Examples of sequences (e.g., scFv sequences) that can bind to particular modified peptides are shown in Table 3. In some cases, a molecule including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can have a sequence that deviates from a sequence shown in Table 3, sometimes referred to as a variant sequence. For example, a molecule including one or more antigen-binding domains that can bind to a modified peptide described herein can have at least 75% sequence identity (e.g., at least 80% sequence identity, at least 85% sequence identity, at least 90% sequence identity, at least 95% sequence identity, at least 96% sequence identity, at least 97% sequence identity, at least 98% sequence identity, at least 99% sequence identity, or more) to any of the sequences shown in Table 3, provided the variant sequence maintains the ability to bind to a modified peptide described herein. In some cases, a molecule including one or more antigen-binding domains that can bind to a modified peptide described herein can include any appropriate set of CDR sequences described herein, and any sequence deviations from a sequence shown in Table 3 can be in the scaffold sequence(s).

A molecule including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be attached (e.g., covalently or non-covalently attached) to a label (e.g., a detectable label). A detectable label can be any appropriate label. In some cases, a label can be used to assist in detecting the presence or absence of one or more modified peptides described herein. For example, a molecule described herein that is labelled can be used in vitro to detect cancer cells (e.g., cancer cells expressing a modified peptide described herein) in a sample obtained from a mammal. In some cases, a label (e.g., a detectable label) can be used to assist in determining the location of one or more modified peptides described herein. For example, molecule described herein that is labelled can be used in vivo to monitor anti-tumor therapy and/or to detect cancer cells (e.g., cancer cells expressing a modified peptide described herein) in a mammal. Examples of labels that can be attached to a molecule described herein include, without limitation, radionuclides, chromophores, enzymes, and fluorescent molecules (e.g., green fluorescent protein).

A molecule including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be attached (e.g., covalently or non-covalently attached) to a therapeutic agent. A therapeutic agent can be any therapeutic agent. In some cases, a therapeutic agent can be an anti-cancer agent. Examples of therapeutic agents that can be attached to a molecule described herein include, without limitation, anti-cancer agents such as monomethyl auristatin E (MMAE), monomethyl auristatin F (MMAF), maytansine, mertansine/emtansine (DM1), ravtansine/soravtansine (DM4), SN-38, calicheamicin, D6.5, dimeric pyrrolobenzodiazepines (PBDs), ricin, *pseudomonas* exotoxin A, diphtheria toxin, and gelonin.

This document also provides methods for using one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32). For example, one or more molecules including one or more antigen-binding domains (e.g., scFvs) that can target (e.g., bind to) one or more modified peptides can be used to assess a mammal having cancer or suspected of having cancer and/or to treat a mammal having a cancer (e.g., a cancer expressing one or more modified peptides). In some cases, one or more molecules includes one or more antigen-binding domains that can bind to a modified peptide can be used to detect the presence or absence of one or more modified peptides in a sample obtained from a mammal having cancer or suspected of having cancer. In some cases, one or more molecules including one or more antigen-binding domains that can bind to a modified peptide can be administered to a mammal having a cancer (e.g., a cancer expressing the modified peptide) to treat the mammal. Administration of one or more molecules including one or more antigen-binding domains that can bind to a modified peptide described herein to a mammal (e.g., human) having a cancer can be effective to treat the mammal.

Any type of mammal can be assessed and/or treated as described herein. Examples of mammals that can be assessed and/or treated as described herein include, without limitation, primates (e.g., humans and non-human primates such as chimpanzees, baboons, or monkeys), dogs, cats, pigs, sheep, rabbits, mice, and rats. In some cases, a mammal can be a human.

A mammal can be assessed and/or treated for any appropriate cancer. In some cases, a cancer can express one or more modified peptides (e.g., one or more MANAs) described herein. A cancer can be a primary cancer. A cancer can be a metastatic cancer. A cancer can include one or more solid tumors. A cancer can include one or more non-solid tumors. Examples of cancers that can be assessed as described herein (e.g., based at least in part on the presence of one or more modified peptides described herein) and/or treated as described herein (e.g, by administering one or more molecules including one or more antigen-binding domains (e.g., scFvs) that can bind to a modified peptide described herein) include, without limitation, blood cancers (e.g., Hodgkin's lymphoma, non-Hodgkin's lymphoma, leukemia such as acute myeloid leukemia (AML), and myeloma), lung cancers, pancreatic cancers, gastric cancers, colon cancers (e.g., colorectal cancers), ovarian cancers, endometrial cancers, biliary tract cancers, liver cancers, bone and soft tissue cancers, breast cancers, prostate cancers, esophageal cancers, stomach cancers, kidney cancers, head and neck cancers, and brain cancers (e.g., glioblastoma multiforme and astrocytomas).

When assessing a mammal having cancer or suspected of having cancer, one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be used to assess for the presence or absence of one or more modified peptides described herein. For example, the presence, absence, or level of one or more modified peptides described herein in a sample obtained from a human can be used to determine whether or not the human has a cancer. In some cases, the presence of one or more modified peptides described herein in a sample obtained from a mammal can be used to identify the mammal as having a cancer. For example, a mammal can be identified as having a cancer when a sample obtained from the mammal has one or more modified peptides described herein.

Any appropriate sample obtained from a mammal can be assessed for the presence, absence, or level of one or more modified peptides described herein. For example, biological samples such as tissue samples (e.g., breast tissue), and fluid samples (e.g., blood, serum, plasma, or urine) can be obtained from a mammal and assessed for the presence, absence, or level of one or more modified peptides described herein. Any appropriate method can be used to detect the presence, absence, or level of one or more modified peptides described herein. For example, sequencing techniques including, but not limited to, Sanger sequencing, chemical sequencing, nanopore sequencing, sequencing by ligation (SOLiD sequencing), and sequencing with mass spectrometry can be used to determine the presence, absence, or level of one or more modified peptides described herein in a sample obtained from a mammal.

When treating a mammal having cancer, one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be administered to a mammal having cancer to treat the mammal. In some cases, a mammal can have a cancer expressing one or more modified peptides described herein. For example, one or more molecules including one or more antigen-binding domains that can bind to a modified peptide described herein can be administered to a mammal having a cancer expressing that modified peptide to treat the mammal. For example, one or more molecules including one or more scFvs that can bind to a modified peptide described herein (e.g., one or more CARs and/or one or more scDbs) can be administered to a mammal having a cancer expressing that modified peptide to treat the mammal.

In some cases, one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be administered to a mammal (e.g., a mammal having a cancer) once or multiple times over a period of time ranging from days to weeks. In some cases, one or more molecules including one or more antigen-binding domains (e.g., scFvs) that can bind to a modified peptide described herein can be formulated into a pharmaceutically acceptable composition for administration to a mammal. For example, an effective amount of one or more molecules including one or more antigen-binding domains (e.g., scFvs) that can bind to a modified peptide described herein can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules. Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A composition containing one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be designed for oral, parenteral (including subcutaneous, intramuscular, intravenous, and intradermal), or intratumoral administration. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

A composition containing one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be administered using any appropriate technique and to any appropriate location. A composition including one or more molecules including one or more antigen-binding domains (e.g., scFvs) that can bind to a modified peptide described herein can be administered locally (e.g., intratumorally) or systemically. For example, a composition provided herein can be administered locally by intratumoral administration (e.g., injection into tumors) or by administration into biological spaces infiltrated by tumors (e.g. intraspinal administration, intracerebellar administration, intraperitoneal administration and/or pleural administration). For example, a composition provided herein can be administered systemically by oral administration or by intravenous administration (e.g., injection or infusion) to a mammal (e.g., a human).

Effective doses can vary depending on the risk and/or the severity of the cancer, the route of administration, the age and general health condition of the subject, excipient usage, the possibility of co-usage with other therapeutic treatments such as use of other agents, and the judgment of the treating physician. An effective amount of a composition containing one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be any amount that treats a cancer present within the subject without producing significant toxicity to the subject. If a particular subject fails to respond to a particular amount, then the amount of one or more molecules including one or more antigen-binding domains (e.g., scFvs) that can bind to a modified peptide described herein can be increased (e.g., by two-fold, three-fold, four-fold, or more). After receiving this higher amount, the mammal can be monitored for both responsiveness to the treatment and toxicity symptoms, and adjustments made accordingly. The effective amount can remain constant or can be adjusted as a sliding scale or variable dose depending on the subject's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be any frequency that effectively treats a mammal having a cancer without producing significant toxicity to the mammal. For example, the frequency of administration of one or more molecules including one or more antigen-binding domains (e.g., scFvs) that can bind to a modified peptide described herein can be from about two to about three times a week to about two to about three times a year. In some cases, a subject having cancer can receive a single administration of one or more antibodies described herein. The frequency of administration of one or more molecules including one or more antigen-binding domains (e.g., scFvs) that can bind to a modified peptide described herein can remain constant or can be variable during the duration of treatment. A course of treatment with a composition containing one or more molecules including one or more antigen-binding domains (e.g., scFvs) that can bind to a modified peptide described herein can include rest periods. For example, a composition containing one or more molecules including one or more antigen-binding domains (e.g., scFvs) that can bind to a modified peptide described herein can be administered every other month over a two-year period followed by a six-month rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be any duration that effectively treats a cancer present within the mammal without producing significant toxicity to the mammal. In some cases, the effective duration can vary from several months to several years. In general, the effective duration for treating a mammal having a cancer can range in duration from about one or two months to five or more years. Multiple factors can influence the actual effective duration used for a particular treatment. For example, an effective duration can vary with the frequency of administration, effective amount, use of multiple treatment agents, route of administration, and severity of the condition being treated.

In certain instances, a cancer within a mammal can be monitored to evaluate the effectiveness of the cancer treatment. Any appropriate method can be used to determine whether or not a mammal having cancer is treated. For example, imaging techniques or laboratory assays can be used to assess the number of cancer cells and/or the size of a tumor present within a mammal. For example, imaging techniques or laboratory assays can be used to assess the location of cancer cells and/or a tumor present within a mammal.

In some cases, one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be administered to a mammal having a cancer as a combination therapy with one or more additional cancer treatments (e.g., anti-cancer agents). A cancer treatment can include any appropriate cancer treatments. In some cases, a cancer treatment can include surgery. In some cases, a cancer treatment can include radiation therapy. In some cases, a cancer treatment can include administration of one or more therapeutic agents (e.g., one or more anti-cancer agents). Examples of anti-cancer agents include, without limitation, platinum compounds (e.g., a cisplatin or carboplatin), taxanes (e.g., paclitaxel, docetaxel, or an albumin bound paclitaxel such as nab-paclitaxel), altretamine, capecitabine, cyclophosphamide, etoposide (vp-16), gemcitabine, ifosfamide, irinotecan (cpt-11), liposomal doxorubicin, melphalan, pemetrexed, topotecan, vinorelbine, luteinizing-hormone-releasing hormone (LHRH) agonists (e.g., goserelin and leuprolide), anti-estrogens (e.g., tamoxifen), aromatase inhibitors (e.g., letrozole, anastrozole, and exemestane), angiogenesis inhibitors (e.g., bevacizumab), poly(ADP)-ribose polymerase (PARP) inhibitors (e.g., olaparib, rucaparib, and niraparib), radioactive phosphorus, anti-CTLA-4 antibodies, anti-PD-1 antibodies, anti-PD-L1 antibodies, IL-2 and other cytokines, and any combinations thereof. In cases where one or more molecules including one or more antigen-binding domains (e.g., scFvs) that can bind to a modified peptide described herein are used in combination with one or more additional cancer treatments, the one or more additional cancer treatments can be administered at the same time or independently. For example, a composition including one or more molecules including one or more antigen-binding domains (e.g., scFvs) that can bind to a modified peptide described herein can be administered first, and the one or more additional cancer treatments administered second, or vice versa.

Also provided herein are kits that include one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32). For example, a kit can include a composition (e.g., a pharmaceutically acceptable composition) containing one or more molecules including one or more antigen-binding domains (e.g., scFvs) that can bind to a modified peptide described herein. In some cases, a kit can include instructions for performing any of the methods described herein. In some cases, a kit can include at least one dose of any of the compositions (e.g., pharmaceutical compositions) described herein. In some cases, a kit can provide a means (e.g., a syringe) for administering any of the compositions (e.g., pharmaceutical compositions) described herein.

The invention is further described in the following examples, which do not limit the scope of the invention described in the claims.

EXAMPLES

Example 1: Identification of Additional MANAbody Clones and Conversion of MANAbody Clones into T Cell-Based Therapeutic Formats In this study, two phage display libraries were designed and built, both of which displayed a single chain variable fragment (scFv) on the phage surface. The scFvs present in both libraries were based on the humanized 4D5 (trastuzumab) framework with amino acid variability introduced at key positions of the scFv's complementarity determining regions (CDRs).

Phage display libraries were used to identify scFvs that specifically recognized mutation-containing peptides folded into a complex with a recombinant HLA allele alpha chain and beta-2 microglobulin (b2M). These complexes, also referred to herein as monomers, mimic the natural peptide/HLA complexes on a cancer cell surface.

Peptide-HLA targets can include mutant peptides (e.g., Mutation-Associated Neo-Antigens (MANAs)) shown in Table 1. Complementarity-determining regions (CDRs) that can specifically bind to peptide-HLA targets in Table 1 are shown in Table 2. scFvs that can specifically bind to peptide-HLA targets in Table 1 are shown in Table 3. These scFvs can also be referred to as MANAbodies for their ability to bind to Mutation-Associated Neo-Antigens.

TABLE 2

MANAbody complementarity-determining region (CDR) sequences of light (L) chains and heavy (H) chains.

| Target Peptide(s) | Target HLA Allele | CDR L1 | CDR L2 | CDR L3 | CDR H1 | CDR H2 | CDR H3 |
|---|---|---|---|---|---|---|---|
| \multicolumn{8}{c}{1) EGFR T790M(789-797)-A2} |
| IMQLMPFGC (SEQ ID NO: 13) | HLA-A2 | QDVNTA (SEQ ID NO: 33) | SAS | QQYDYAPIT (SEQ ID NO: 34) | GFNISWYQ (SEQ ID NO: 41) | VTPYSGYT (SEQ ID NO: 48) | SRSYTDGFDY (SEQ ID NO: 55) |
| IMQLMPFGC (SEQ ID NO: 13) | HLA-A2 | QDVNTA (SEQ ID NO: 33) | SAS | QQSPYYYLPIT (SEQ ID NO: 35) | GFNVSWSY (SEQ ID NO: 42) | IYGDSGYT (SEQ ID NO: 49) | SRGQWEASYYAMDY (SEQ ID NO: 56) |
| IMQLMPFGC (SEQ ID NO: 13) | HLA-A2 | QDVNTA (SEQ ID NO: 33) | SAS | QQYYYSPVT (SEQ ID NO: 36) | GFNISWNQ (SEQ ID NO: 43) | VSPYSGYT (SEQ ID NO: 50) | SRSDYYAMDY (SEQ ID NO: 57) |
| IMQLMPFGC (SEQ ID NO: 13) | HLA-A2 | QDVNTA (SEQ ID NO: 33) | SAS | QQHYGNPFT (SEQ ID NO: 37) | GFNVGYYG (SEQ ID NO: 44) | VSGMEGYT (SEQ ID NO: 51) | SRDIYGYAMDV (SEQ ID NO: 58) |
| IMQLMPFGC (SEQ ID NO: 13) | HLA-A2 | QDVNTA (SEQ ID NO: 33) | SAS | QQSYYSPPT (SEQ ID NO: 38) | GFNITSSY (SEQ ID NO: 45) | ISPADGYN (SEQ ID NO: 52) | SRTDSTAYTAMDV (SEQ ID NO: 59) |
| IMQLMPFGC (SEQ ID NO: 13) | HLA-A2 | QDVNTA (SEQ ID NO: 33) | SAS | QQYYSYPPT (SEQ ID NO: 39) | GFNINSSY (SEQ ID NO: 46) | ISPTDGYY (SEQ ID NO: 53) | SRTSDTSYAAMDV (SEQ ID NO: 60) |
| IMQLMPFGC (SEQ ID NO: 13) | HLA-A2 | QDVNTA (SEQ ID NO: 33) | SAS | QQYYYYPPT (SEQ ID NO: 40) | GFNISTSY (SEQ ID NO: 47) | IDPNDGYS (SEQ ID NO: 54) | SRTNNTAADAMDV (SEQ ID NO: 61) |
| \multicolumn{8}{c}{2) IDH2 R140Q(134-143)-B7} |
| SPNGTIQNIL (SEQ ID NO: 1) | HLA-B7 | QDVNTA (SEQ ID NO: 33) | SAS | QQYSYSPPT (SEQ ID NO: 62) | GFNISDTY (SEQ ID NO: 67) | ISPRTGYN (SEQ ID NO: 72) | SRAYYSYAYAMDV (SEQ ID NO: 77) |

TABLE 2-continued

MANAbody complementarity-determining region (CDR) sequences of light (L) chains and heavy (H) chains.

| Target Peptide(s) | Target HLA Allele | CDR L1 | CDR L2 | CDR L3 | CDR H1 | CDR H2 | CDR H3 |
|---|---|---|---|---|---|---|---|
| SPNGTIQNIL (SEQ ID NO: 1) | HLA-B7 | QDVNTA (SEQ ID NO: 33) | SAS | QQGKAYWPAT (SEQ ID NO: 63) | GFNVGHYR (SEQ ID NO: 68) | VSPNGYYT (SEQ ID NO: 73) | SRGYSSYAFDY (SEQ ID NO: 78) |
| SPNGTIQNIL (SEQ ID NO: 1) | HLA-B7 | QDVNTA (SEQ ID NO: 33) | SAS | QQVYSSPFT (SEQ ID NO: 64) | GFNVKYYM (SEQ ID NO: 69) | ISPGYDYT (SEQ ID NO: 74) | SRSYWRYSVDV (SEQ ID NO: 79) |
| SPNGTIQNIL (SEQ ID NO: 1) | HLA-B7 | QDVNTA (SEQ ID NO: 33) | SAS | QQYSLYSPMT (SEQ ID NO: 65) | GFNSFLS (SEQ ID NO: 70) | IFPSSDYT (SEQ ID NO: 75) | SRGKHSSDSNYYMDY (SEQ ID NO: 80) |
| SPNGTIQNIL (SEQ ID NO: 1) | HLA-B7 | QDVNTA (SEQ ID NO: 33) | SAS | QQSYYMPFT (SEQ ID NO: 66) | GFNIFRGY (SEQ ID NO: 71) | ISPHSDYT (SEQ ID NO: 76) | SRSYGWAAFDY (SEQ ID NO: 81) |
| 3) p53 R248Q/W(245-254)-A2 | | | | | | | |
| GMNQRPILTI (SEQ ID NO: 15) | HLA-A2 | QDVNTA (SEQ ID NO: 33) | SAS | QQSGYAPIT (SEQ ID NO: 82) | GFNISYYS (SEQ ID NO: 89) | VDPDSDYT (SEQ ID NO: 96) | SRSWIHMFSMDY (SEQ ID NO: 103) |
| GMNWRPILTI (SEQ ID NO: 16) | HLA-A2 | QDVNTA (SEQ ID NO: 33) | SAS | QQYSYAPIT (SEQ ID NO: 83) | GFNIGYYT (SEQ ID NO: 90) | VSPWSYST (SEQ ID NO: 97) | SRDHWDEAFDV (SEQ ID NO: 104) |
| GMNQRPILTI (SEQ ID NO: 15) | HLA-A2 | QDVNTA (SEQ ID NO: 33) | SAS | QQSLYGPFT (SEQ ID NO: 84) | GFNIAYEY (SEQ ID NO: 91) | IGPDSGYT (SEQ ID NO: 98) | SRVWYYSTYGMDY (SEQ ID NO: 105) |
| GMNWRPILTI (SEQ ID NO: 16) | HLA-A2 | QDVNTA (SEQ ID NO: 33) | SAS | QQYSYSPIT (SEQ ID NO: 85) | GFNLFGYG (SEQ ID NO: 92) | IGPYYYYT (SEQ ID NO: 99) | SRENYDMAMDY (SEQ ID NO: 106) |
| GMNWRPILTI (SEQ ID NO: 16) | HLA-A2 | QDVNTA (SEQ ID NO: 33) | SAS | QQSGYQPDT (SEQ ID NO: 86) | GFNISWYA (SEQ ID NO: 93) | IWPDSDWT (SEQ ID NO: 100) | SRYYYSSAFDV (SEQ ID NO: 107) |
| GMNQRPILTI (SEQ ID NO: 15), GMNWRPILTI (SEQ ID NO: 16) | HLA-A2 | QDVNTA (SEQ ID NO: 33) | SAS | QQYLYQPWT (SEQ ID NO: 87) | GFNIDYYG (SEQ ID NO: 94) | LYGGSDST (SEQ ID NO: 101) | SRQYSAYFDY (SEQ ID NO: 108) |
| GMNQRPILTI (SEQ ID NO: 15), GMNWRPILTI (SEQ ID NO: 16) | HLA-A2 | QDVNTA (SEQ ID NO: 33) | SAS | QQGLYYPWT (SEQ ID NO: 88) | GFNV SYS S (SEQ ID NO: 95) | IWPD SGQT (SEQ ID NO: 102) | SRSSYFDAMDY (SEQ ID NO: 109) |
| 4) KRAS G12V(6-14)-A2 | | | | | | | |
| LVVVGAVGV (SEQ ID NO: 18) | HLA-A2 | QDVNTA (SEQ ID NO: 33) | SAS | QQWYSSPVT (SEQ ID NO: 110) | GFNINWAN (SEQ ID NO: 112) | ISPPYDYT (SEQ ID NO: 115) | SRSYSYYFDY (SEQ ID NO: 118) |
| LVVVGAVGV (SEQ ID NO: 18) | HLA-A2 | QDVNTA (SEQ ID NO: 33) | SAS | QQYYSRPVT (SEQ ID NO: 111) | GFNIYLHD (SEQ ID NO: 113) | IIPAIDYT (SEQ ID NO: 116) | SRRDGYYFDY (SEQ ID NO: 119) |
| LVVVGAVGV (SEQ ID NO: 18) | HLA-A2 | QDVNTA (SEQ ID NO: 33) | SAS | QQWYSSPVT (SEQ ID NO: 110) | GFNIYWSH (SEQ ID NO: 114) | ISSFEGYT (SEQ ID NO: 117) | SRSYSYYMDY (SEQ ID NO: 120) |
| 5) KRAS G12C/D/V(7-16)-A3 | | | | | | | |
| VVVGACGVGK (SEQ ID NO: 20), VVVGAVGVGK (SEQ ID NO: 22) | HLA-A3 | QDVNTA (SEQ ID NO: 33) | SAS | QQSYGSGSPWT (SEQ ID NO: 121) | GFNIVGGG (SEQ ID NO: 124) | IYPQGDYT (SEQ ID NO: 127) | SRDSSYLAFDY (SEQ ID NO: 129) |
| VVVGACGVGK (SEQ ID NO: 20), VVVGADGVGK (SEQ ID NO: 21), | HLA-A3 | QDVNTA (SEQ ID NO: 33) | SAS | QQTYYSPWT (SEQ ID NO: 122) | GFNIRSYA (SEQ ID NO: 125) | VGPGKGYT (SEQ ID NO: 128) | SRNFQSTSHAFDY (SEQ ID NO: 130) |

TABLE 2-continued

MANAbody complementarity-determining region (CDR) sequences of light (L) chains and heavy (H) chains.

| Target Peptide(s) | Target HLA Allele | CDR L1 | CDR L2 | CDR L3 | CDR H1 | CDR H2 | CDR H3 |
|---|---|---|---|---|---|---|---|
| VVVGAVGVGK (SEQ ID NO: 22) | | | | | | | |
| VVVGACGVGK (SEQ ID NO: 20), VVVGADGVGK (SEQ ID NO: 21), VVVGAVGVGK (SEQ ID NO: 22) | HLA-A3 | QDVNTA (SEQ ID NO: 33) | SAS | QQYYYPPIT (SEQ ID NO: 123) | GFNVSHTG (SEQ ID NO: 126) | VGPGKGYT (SEQ ID NO: 128) | SRKTYYAFDY (SEQ ID NO: 131) |

6) KRAS G12V(7-16)-A3

| Target Peptide(s) | Target HLA Allele | CDR L1 | CDR L2 | CDR L3 | CDR H1 | CDR H2 | CDR H3 |
|---|---|---|---|---|---|---|---|
| VVVGAVGVGK (SEQ ID NO: 22) | HLA-A3 | QDVNTA (SEQ ID NO: 33) | SAS | QQSYYYFRPIT (SEQ ID NO: 132) | GFNLSYSD (SEQ ID NO: 137) | VMPDSGHT (SEQ ID NO: 142) | SRATNIPVYAFDY (SEQ ID NO: 147) |
| VVVGAVGVGK (SEQ ID NO: 22) | HLA-A3 | QDVNTA (SEQ ID NO: 33) | SAS | QQASYYYPLT (SEQ ID NO: 133) | GFNISASG (SEQ ID NO: 138) | IHPLKPYT (SEQ ID NO: 143) | SRYSSMYYYFDY (SEQ ID NO: 148) |
| VVVGAVGVGK (SEQ ID NO: 22) | HLA-A3 | QDVNTA (SEQ ID NO: 33) | SAS | QQKSEYSPWT (SEQ ID NO: 134) | GFNIYRYG (SEQ ID NO: 139) | LYPYGYST (SEQ ID NO: 144) | SRSYAYGYFAY (SEQ ID NO: 149) |
| VVVGAVGVGK (SEQ ID NO: 22) | HLA-A3 | QDVNTA (SEQ ID NO: 33) | SAS | QQSGYIPFT (SEQ ID NO: 135) | GFNIYGTM (SEQ ID NO: 140) | FKPDSYNT (SEQ ID NO: 145) | SRGEVYHYYAFDY (SEQ ID NO: 150) |
| VVVGAVGVGK (SEQ ID NO: 22) | HLA-A3 | QDVNTA (SEQ ID NO: 33) | SAS | QQGAYYRPFT (SEQ ID NO: 136) | GFNISYSY (SEQ ID NO: 141) | LLPYDGNT (SEQ ID NO: 146) | SRAAYSSMDV (SEQ ID NO: 151) |

7) KRAS G12D(7-16)-A3

| Target Peptide(s) | Target HLA Allele | CDR L1 | CDR L2 | CDR L3 | CDR H1 | CDR H2 | CDR H3 |
|---|---|---|---|---|---|---|---|
| VVVGADGVGK (SEQ ID NO: 21) | HLA-A3 | QDVNTA (SEQ ID NO: 33) | SAS | QQYMYSPVT (SEQ ID NO: 152) | GFNVSAYW (SEQ ID NO: 156) | IYGGSGYT (SEQ ID NO: 160) | SRTHSYWSAFDY (SEQ ID NO: 164) |
| VVVGADGVGK (SEQ ID NO: 21) | HLA-A3 | QDVNTA (SEQ ID NO: 33) | SAS | QQSSSSPIT (SEQ ID NO: 153) | GFNISGYG (SEQ ID NO: 157) | LYGGSDYT (SEQ ID NO: 161) | SRTVRYAFDY (SEQ ID NO: 165) |
| VVVGADGVGK (SEQ ID NO: 21) | HLA-A3 | QDVNTA (SEQ ID NO: 33) | SAS | QQSSASPLT (SEQ ID NO: 154) | GFNVSSVG (SEQ ID NO: 158) | IYGTSDYT (SEQ ID NO: 162) | SRSSRYSMDY (SEQ ID NO: 166) |
| VVVGADGVGK (SEQ ID NO: 21) | HLA-A3 | QDVNTA (SEQ ID NO: 33) | SAS | QQYAYSPLT (SEQ ID NO: 155) | GFNVSSYG (SEQ ID NO: 159) | IAPRRDYT (SEQ ID NO: 163) | SRKSSYYFDY (SEQ ID NO: 167) |

8) KRAS G12D(7-16)-A11

| Target Peptide(s) | Target HLA Allele | CDR L1 | CDR L2 | CDR L3 | CDR H1 | CDR H2 | CDR H3 |
|---|---|---|---|---|---|---|---|
| VVVGADGVGK (SEQ ID NO: 21) | HLA-A11 | QDVNTA (SEQ ID NO: 33) | SAS | QQYSYYPIT (SEQ ID NO: 168) | GFNFSYGY (SEQ ID NO: 173) | ISGYTGNT (SEQ ID NO: 178) | SRAASLSSSYYSAFDV (SEQ ID NO: 183) |
| VVVGADGVGK (SEQ ID NO: 21) | HLA-A11 | QDVNTA (SEQ ID NO: 33) | SAS | QQYSYTPVT (SEQ ID NO: 169) | GFNVWGPG (SEQ ID NO: 174) | IHPFSGNT (SEQ ID NO: 179) | SRGYSYSAMDY (SEQ ID NO: 184) |
| VVVGADGVGK (SEQ ID NO: 21) | HLA-A11 | QDVNTA (SEQ ID NO: 33) | SAS | QQYSYEPVT (SEQ ID NO: 170) | GFNVSGSQ (SEQ ID NO: 175) | IPGWSGYT (SEQ ID NO: 180) | SRGYSYFAMDY (SEQ ID NO: 185) |
| VVVGADGVGK (SEQ ID NO: 21) | HLA-A11 | QDVNTA (SEQ ID NO: 33) | SAS | QQYAYYSPVT (SEQ ID NO: 171) | GFNIYGQM (SEQ ID NO: 176) | LSPFSGNT (SEQ ID NO: 181) | SRNISYEQSSAFDY (SEQ ID NO: 186) |
| VVVGADGVGK (SEQ ID NO: 21) | HLA-A11 | QDVNTA (SEQ ID NO: 33) | SAS | QQYEYYPMT (SEQ ID NO: 172) | GFNVMYST (SEQ ID NO: 177) | IYSWSDYT (SEQ ID NO: 182) | SRGYAHNSFDY (SEQ ID NO: 187) |

TABLE 2-continued

MANAbody complementarity-determining region (CDR) sequences of light (L) chains and heavy (H) chains.

| Target Peptide(s) | Target HLA Allele | CDR L1 | CDR L2 | CDR L3 | CDR H1 | CDR H2 | CDR H3 |
|---|---|---|---|---|---|---|---|
| 9) KRAS G12D(8-16)-A11 | | | | | | | |
| VVGADGVGK (SEQ ID NO: 24) | HLA-A11 | QDVNTA (SEQ ID NO: 33) | SAS | QQYSFYPFT (SEQ ID NO: 188) | GFNFGSY (SEQ ID NO: 196) | ISGYSGNT (SEQ ID NO: 207) | SRSNQSAYSYMDY (SEQ ID NO: 218) |
| VVGADGVGK (SEQ ID NO: 24) | HLA-A11 | QDVNTA (SEQ ID NO: 33) | SAS | QQYSYSPIT (SEQ ID NO: 85) | GFNISDSY (SEQ ID NO: 197) | FSPYSSNT (SEQ ID NO: 208) | SRSQFTFYQYFDY (SEQ ID NO: 219) |
| VVGADGVGK (SEQ ID NO: 24) | HLA-A11 | QDVNTA (SEQ ID NO: 33) | SAY | QQYSAYYQPIT (SEQ ID NO: 189) | GFNIFSDQ (SEQ ID NO: 198) | FMPYDSYYT (SEQ ID NO: 209) | SRMSVRNAFDY (SEQ ID NO: 220) |
| VVGADGVGK (SEQ ID NO: 24) | HLA-A11 | QDVNTA (SEQ ID NO: 33) | SAS | QQYSYYPIT (SEQ ID NO: 168) | GFNLSYSY (SEQ ID NO: 199) | ISGFSGNT (SEQ ID NO: 210) | SRSDSYYTAMDY (SEQ ID NO: 221) |
| VVGADGVGK (SEQ ID NO: 24) | HLA-A11 | QDVNTA (SEQ ID NO: 33) | SAS | QQYEYVPHT (SEQ ID NO: 190) | GFNISYGY (SEQ ID NO: 200) | FHYGSGNT (SEQ ID NO: 211) | SRSNYYYLDY (SEQ ID NO: 222) |
| VVGADGVGK (SEQ ID NO: 24) | HLA-A11 | QDVNTA (SEQ ID NO: 33) | SAS | QQYSYMPIT (SEQ ID NO: 191) | GFNISYQH (SEQ ID NO: 201) | FMPYQGST (SEQ ID NO: 212) | SRANIYSSHSFFDY (SEQ ID NO: 223) |
| VVGADGVGK (SEQ ID NO: 24) | HLA-A11 | QDVNTA (SEQ ID NO: 33) | SAS | QQYAYYPVT (SEQ ID NO: 192) | GFNLSGYY (SEQ ID NO: 202) | FSPYSGYT (SEQ ID NO: 213) | SRTHSSIYHSFDY (SEQ ID NO: 224) |
| VVGADGVGK (SEQ ID NO: 24) | HLA-A11 | QDVNTA (SEQ ID NO: 33) | SAS | QQYSYMPIT (SEQ ID NO: 191) | GFNVSGQY (SEQ ID NO: 203) | ISPVSGNT (SEQ ID NO: 214) | SRPMKTSYYGAFDY (SEQ ID NO: 225) |
| VVGADGVGK (SEQ ID NO: 24) | HLA-A11 | QDVNTA (SEQ ID NO: 33) | SAS | QQYDYRPVT (SEQ ID NO: 193) | GFNVSTSG (SEQ ID NO: 204) | IYGAYSGT (SEQ ID NO: 215) | SRSQSYTYWSAMDY (SEQ ID NO: 226) |
| VVGADGVGK (SEQ ID NO: 24) | HLA-A11 | QDVNTA (SEQ ID NO: 33) | SAS | QQYDFTPMT (SEQ ID NO: 194) | GFNISYAK (SEQ ID NO: 205) | LTYWGGYT (SEQ ID NO: 216) | SRGEYGTYMDY (SEQ ID NO: 227) |
| VVGADGVGK (SEQ ID NO: 24) | HLA-A11 | QDVNTA (SEQ ID NO: 33) | SAS | QQYSSSSPVT (SEQ ID NO: 195) | GFNFSSYV (SEQ ID NO: 206) | VYPDSGGT (SEQ ID NO: 217) | SRTSSYYAFDY (SEQ ID NO: 228) |
| 10) KRAS G12V(7-16)-A11 | | | | | | | |
| VVVGAVGVGK (SEQ ID NO: 22) | HLA-A11 | QDVNTA (SEQ ID NO: 33) | SAS | QQSSYTPIT (SEQ ID NO: 229) | GFNISQGG (SEQ ID NO: 234) | VYPGGGQT (SEQ ID NO: 240) | SRGYDYSAFDY (SEQ ID NO: 246) |
| VVVGAVGVGK (SEQ ID NO: 22) | HLA-A11 | QDVNTA (SEQ ID NO: 33) | SAS | QQYAYYPIT (SEQ ID NO: 230) | GFNISSTG (SEQ ID NO: 235) | LLGGSGNT (SEQ ID NO: 241) | SRGLQYSAMDY (SEQ ID NO: 247) |
| VVVGAVGVGK (SEQ ID NO: 22) | HLA-A11 | QDVNTA (SEQ ID NO: 33) | SAS | QQYEYYPIT (SEQ ID NO: 231) | GFNFFSTV (SEQ ID NO: 236) | IYPWSGST (SEQ ID NO: 242) | SRSRSSNYYFDV (SEQ ID NO: 248) |
| VVVGAVGVGK (SEQ ID NO: 22) | HLA-A11 | QDVNTA (SEQ ID NO: 33) | SAS | QQYTYYPIT (SEQ ID NO: 232) | GFNLHGYL (SEQ ID NO: 237) | IYPPNGYT (SEQ ID NO: 243) | SRGVDYAYLDY (SEQ ID NO: 249) |
| VVVGAVGVGK (SEQ ID NO: 22) | HLA-A11 | QDVNTA (SEQ ID NO: 33) | SAS | QQYSYYPIT (SEQ ID NO: 168) | GFNLSTHV (SEQ ID NO: 238) | FYPYVGYT (SEQ ID NO: 244) | SRGYRYQYMDV (SEQ ID NO: 250) |
| VVVGAVGVGK (SEQ ID NO: 22) | HLA-A11 | QDVNTA (SEQ ID NO: 33) | SAS | QQSSVEPWT (SEQ ID NO: 233) | GFNVSYYS (SEQ ID NO: 239) | IYPWNDYT (SEQ ID NO: 245) | SRGSYYSFDY (SEQ ID NO: 251) |

TABLE 2-continued

MANAbody complementarity-determining region (CDR) sequences of light (L) chains and heavy (H) chains.

| Target Peptide(s) | Target HLA Allele | CDR L1 | CDR L2 | CDR L3 | CDR H1 | CDR H2 | CDR H3 |
|---|---|---|---|---|---|---|---|
| 11) CTNNB S45F(41-49)-A3 | | | | | | | |
| TTAPFLSGK (SEQ ID NO: 26) | HLA-A3 | QDVNTA (SEQ ID NO: 33) | SAS | QQSYYSPPT (SEQ ID NO: 38) | GFNINNTY (SEQ ID NO: 256) | IYPTDGYT (SEQ ID NO: 260) | SRTYYSYYSAMDV (SEQ ID NO: 265) |
| TTAPFLSGK (SEQ ID NO: 26) | HLA-A3 | QDVNTA (SEQ ID NO: 33) | SAY | QQIYTSPIT (SEQ ID NO: 252) | GFNFITTG (SEQ ID NO: 257) | IGPGSDYT (SEQ ID NO: 261) | SRYYYASALDY (SEQ ID NO: 266) |
| TTAPFLSGK (SEQ ID NO: 26) | HLA-A3 | QDVNTA (SEQ ID NO: 33) | SAS | QQRAYFPIT (SEQ ID NO: 253) | GFNFSDYG (SEQ ID NO: 258) | LIPASGYT (SEQ ID NO: 262) | SRGWSYYMDY (SEQ ID NO: 267) |
| TTAPFLSGK (SEQ ID NO: 26) | HLA-A3 | QDVNTA (SEQ ID NO: 33) | SAS | QQQYAYTPIT (SEQ ID NO: 254) | GFNVWSYG (SEQ ID NO: 259) | VTPDGSYT (SEQ ID NO: 263) | SRSYGWAMDY (SEQ ID NO: 268) |
| TTAPFLSGK (SEQ ID NO: 26) | HLA-A3 | QDVNTA (SEQ ID NO: 33) | SAY | QQIHYKPLT (SEQ ID NO: 255) | GFNVAWYS (SEQ ID NO: 260) | VYGGSSYT (SEQ ID NO: 264) | SRDFYSSGMDY (SEQ ID NO: 269) |
| 12) KRAS G12V(11-19)-B7 | | | | | | | |
| AVGVGKSAL (SEQ ID NO: 11) | HLA-B7 | QDVNTA (SEQ ID NO: 33) | SAS | QQEWRLPIT (SEQ ID NO: 270) | GFNVYGNQ (SEQ ID NO: 275) | IYPYSGST (SEQ ID NO: 278) | SRSAYVAYSYFDY (SEQ ID NO: 283) |
| AVGVGKSAL (SEQ ID NO: 11) | HLA-B7 | QDVNTA (SEQ ID NO: 33) | SAS | QQGTSTPFT (SEQ ID NO: 271) | GFNLSYYG (SEQ ID NO: 402) | IYPDSGYT (SEQ ID NO: 279) | SRAYLYYYLAY (SEQ ID NO: 284) |
| AVGVGKSAL (SEQ ID NO: 11) | HLA-B7 | QDVNTA (SEQ ID NO: 33) | SAS | QQSWRYPMT (SEQ ID NO: 272) | GFNISRYG (SEQ ID NO: 276) | FYPSSSYT (SEQ ID NO: 280) | SRKYYEAMDY (SEQ ID NO: 285) |
| AVGVGKSAL (SEQ ID NO: 11) | HLA-B7 | QDVNTA (SEQ ID NO: 33) | SAS | QQSYSYPVT (SEQ ID NO: 273) | GFNIYSSW (SEQ ID NO: 277) | FQPYSGYT (SEQ ID NO: 281) | SREYTYYFDY (SEQ ID NO: 286) |
| AVGVGKSAL (SEQ ID NO: 11) | HLA-B7 | QDVNTA (SEQ ID NO: 33) | SAS | QQGWLYSPFT (SEQ ID NO: 274) | GFNISGYG (SEQ ID NO: 157) | VYGGSGYT (SEQ ID NO: 282) | SRAHSSYYVDY (SEQ ID NO: 287) |
| 13) H/K/N RAS Q61H(55-64)-A1 | | | | | | | |
| ILDTAGHEEY (SEQ ID NO: 28) | HLA-A1 | QDVNTA (SEQ ID NO: 33) | SAS | QQGYFYYPNT (SEQ ID NO: 288) | GFNIGYYG (SEQ ID NO: 289) | VYPGGGYT (SEQ ID NO: 290) | SRYYYYGFDY (SEQ ID NO: 291) |
| 14) H/K/N RAS Q61K(55-64)-A1 | | | | | | | |
| ILDTAGKEEY (SEQ ID NO: 30) | HLA-A1 | QDVNTA (SEQ ID NO: 33) | SAS | QQHYYSPVT (SEQ ID NO: 292) | GFNIFYQD (SEQ ID NO: 293) | IYPDYDYT (SEQ ID NO: 294) | SRTYSVYMDY (SEQ ID NO: 295) |
| 15) H/K/N Q61L(55-64)-A1 | | | | | | | |
| ILDTAGLEEY (SEQ ID NO: 31) | HLA-A1 | QDVNTA (SEQ ID NO: 33) | SAS | QQYAYAPFT (SEQ ID NO: 296) | GFNVSYSM (SEQ ID NO: 297) | VWGDGGVT (SEQ ID NO: 298) | SRGSYYAFDY (SEQ ID NO: 299) |
| 16) H/K/N RAS Q61R(55-64)-A1 | | | | | | | |
| ILDTAGREEY (SEQ ID NO: 32) | HLA-A1 | QDVNTA (SEQ ID NO: 33) | SAS | QQAHMIPIT (SEQ ID NO: 300) | GFNFSFPG (SEQ ID NO: 305) | FVGYDGYT (SEQ ID NO: 310) | SRDYYSFSMDY (SEQ ID NO: 316) |
| ILDTAGREEY (SEQ ID NO: 32) | HLA-A1 | QDVNTA (SEQ ID NO: 33) | SAS | QQSVYDPIT (SEQ ID NO: 301) | GFNISGSW (SEQ ID NO: 306) | LYPDSDYT (SEQ ID NO: 311) | SRAHTYAFDY (SEQ ID NO: 317) |

TABLE 2-continued

MANAbody complementarity-determining region (CDR) sequences of light (L) chains and heavy (H) chains.

| Target Peptide(s) | Target HLA Allele | CDR L1 | CDR L2 | CDR L3 | CDR H1 | CDR H2 | CDR H3 |
|---|---|---|---|---|---|---|---|
| ILDTAGREEY (SEQ ID NO: 32) | HLA-A1 | QDVNTA (SEQ ID NO: 33) | SAS | QQSYTSPLT (SEQ ID NO: 302) | GFNIYYGV (SEQ ID NO: 307) | IYPDSSWT (SEQ ID NO: 312) | SRDQDFHYMNYYLSYALDY (SEQ ID NO: 318) |
| ILDTAGREEY (SEQ ID NO: 32) | HLA-A1 | QDVNTA (SEQ ID NO: 33) | SAS | QQGQYSPFT (SEQ ID NO: 303) | GFNVSYEY (SEQ ID NO: 308) | IYGGSDNT (SEQ ID NO: 313) | SRPLGSYFDY (SEQ ID NO: 319) |
| ILDTAGREEY (SEQ ID NO: 32) | HLA-A1 | QDVNTA (SEQ ID NO: 33) | SAS | QQYWYLPTT (SEQ ID NO: 320) | GFNISWYD (SEQ ID NO: 321) | IEPSVGYT (SEQ ID NO: 322) | SRSYPYYYFDY (SEQ ID NO: 323) |

TABLE 3

MANAbody scFv sequences.

| Target Peptide(s) | Target HLA Allele | ScFc clone name | scFv sequence | SEQ ID NO: |
|---|---|---|---|---|
| 1) EGFR T790M(789-797)-A2 | | | | |
| IMQLMPFGC (SEQ ID NO: 13) | HLA-A2 | EGFR_T790M_A2_cl1 | DIQMTQSPSSLSASVGDRVTITCRASQDVNTAVAWYQQKPGKAPKLLIYSASFLYSGVPSRFSGSRSGTDFTLTISSLQPEDFATYYCQQYDYAPITFGQGTKVEIKRTGGGSGGGGSGGGGASEVQLVESGGGLVQPGGSLRLSCAASGFNISWYQMHWVRQAPGKGLEWVALVTPYSGYTYYADSVKGRFTISADTSKNTAYLQMNSLRAEDTAVYYCSRSYTDGFDYWGQGTLVTVSS | 324 |
| IMQLMPFGC (SEQ ID NO: 13) | HLA-A2 | EGFR_T790M_A2_cl5 | DIQMTQSPSSLSASVGDRVTITCRASQDVNTAVAWYQQKPGKAPKLLIYSASFLYSGVPSRFSGSRSGTDFTLTISSLQPEDFATYYCQQSPYYYLPITFGQGTKVEIKRTGGGSGGGGSGGGGASEVQLVESGGGLVQPGGSLRLSCAASGFNVSWSYMHWVRQAPGKGLEWVANIYGDSGYTHYADSVKGRFTISADTSKNTAYLQMNSLRAEDTAVYYCSRGQWEASYYAMDYWGQGTLVTVSS | 325 |
| IMQLMPFGC (SEQ ID NO: 13) | HLA-A2 | EGFR_T790M_A2_cl18 | DIQMTQSPSSLSASVGDRVTITCRASQDVNTAVAWYQQKPGKAPKLLIYSASFLYSGVPSRFSGSRSGTDFTLTISSLQPEDFATYYCQQYYYSPVTFGQGTKVEIKRTGGGSGGGGSGGGGASEVQLVESGGGLVQPGGSLRLSCAASGFNISWNQMHWVRQAPGKGLEWVALVSPYSGYTYYADSVKGRFTISADTSKNTAYLQMNSLRAEDTAVYYCSRSDYYAMDYWGQGTLVTVSS | 326 |
| IMQLMPFGC (SEQ ID NO: 13) | HLA-A2 | EGFR_T790M_A2_cl23 | DIQMTQSPSSLSASVGDRVTITCRASQDVNTAVAWYQQKPGKAPKLLIYSASFLYSGVPSRFSGSRSGTDFTLTISSLQPEDFATYYCQQHYGNPFTFGQGTKVEIKRTGGGSGGGGSGGGGASEVQLVESGGGLVQPGGSLRLSCAASGFNVGYYGMHWVRQAPGKGLEWVAFVSGMEGYTSYADSVKGRFTISADTSKNTAYLQMNSLRAEDTAVYYCSRDIYGYAMDVWGQGTLVTVSS | 327 |
| IMQLMPFGC (SEQ ID NO: 13) | HLA-A2 | EGFR_T790M_A2_D2D6 | DIQMTQSPSSLSASVGDRVTITCRASQDVNTAVAWYQQKPGKAPKLLIYSASFLYSGVPSRFSGSRSGTDFTLTISSLQPEDFATYYCQQSYYSPPTFGQGTKVEIKRTGGGSGGGGSGGGGASEVQLVESGGGLVQPGGSLRLSCAASGFNITSSYIHWVRQAPGKGLEWVAYISPADGYNRYADSVKGRFTISADTSKNTAYLQMNSLRAEDTAVYYCSRTDSTAYTAMDVWGQGTLVTVSS | 328 |
| IMQLMPFGC (SEQ ID NO: 13) | HLA-A2 | EGFR_T790M_A2_D2D8 | DIQMTQSPSSLSASVGDRVTITCRASQDVNTAVAWYQQKPGKAPKLLIYSASFLYSGVPSRFSGSRSGTDFTLTISSLQPEDFATYYCQQYYSPPTFGQGTKVEIKRTGGGSGGGGSGGGGASEVQLVESGGGLVQPGGSLRLSCAASGFNINSSYIHWVRQAPGKGLEWVAYISPTDGYYRYADSVKGRFTISADTSKNTAYLQMNSLRAEDTAVYYCSRTSDTSYAAMDVWGQGTLVTVSS | 329 |

TABLE 3-continued

MANAbody scFv sequences.

| Target Peptide(s) | Target HLA Allele | ScFc clone name | scFv sequence | SEQ ID NO: |
|---|---|---|---|---|
| IMQLMPFGC (SEQ ID NO: 13) | HLA-A2 | EGFR_T790M_A2_D3E6 | DIQMTQSPSSLSASVGDRVTITCRASQDVNTAVAWYQQKPGKAPKLLIYSASFLYSGVPSRFSGSRSGTDFTLTISSLQPEDFATYYCQQYYYYPPTFGQGTKVEIKRTGGGSGGGSGGGASEVQLVESGGGLVQPGGSLRLSCAASGFNISTSYIHWVRQAPGKGLEWVATIDPNDGYSRYADSVKGRFTISADTSKNTAYLQMNSLRAEDTAVYYCSRTNNTAADAMDVWGQGTLVTVSS | 330 |
| 2) IDH2 R140Q(134-143)-B7 | | | | |
| SPNGTIQNIL (SEQ ID NO: 1) | HLA-B7 | IDH2_R140Q_B7_D4 | DIQMTQSPSSLSASVGDRVTITCRASQDVNTAVAWYQQKPGKAPKLLIYSASFLYSGVPSRFSGSRSGTDFTLTISSLQPEDFATYYCQQYSYSPPTFGQGTKVEIKRTGGGSGGGSGGGASEVQLVESGGGLVQPGGSLRLSCAASGFNISDTYIHWVRQAPGKGLEWVASISPRTGYNRYADSVKGRFTISADTSKNTAYLQMNSLRAEDTAVYYCSRAYYSYAYAMDVWGQGTLVTVSS | 3 |
| SPNGTIQNIL (SEQ ID NO: 1) | HLA-B7 | IDH2_R140Q_B7_cl29 | DIQMTQSPSSLSASVGDRVTITCRASQDVNTAVAWYQQKPGKAPKLLIYSASFLYSGVPSRFSGSRSGTDFTLTISSLQPEDFATYYCQQGKAYWPATFGQGTKVEIKRTGGGSGGGGSGGGASEVQLVESGGGLVQPGGSLRLSCAASGFNVGHYRMHWVRQAPGKGLEWVAMVSPNGYYTYYADSVKGRFTISADTSKNTAYLQMNSLRAEDTAVYYCSRGYSSYAFDYWGQGTLVTVSS | 4 |
| SPNGTIQNIL (SEQ ID NO: 1) | HLA-B7 | IDH2_R140Q_B7_cl1 | DIQMTQSPSSLSASVGDRVTITCRASQDVNTAVAWYQQKPGKAPKLLIYSASFLYSGVPSRFSGSRSGTDFTLTISSLQPEDFATYYCQQVYSSPFTFGQGTKVEIKRTGGGSGGGSGGGASEVQLVESGGGLVQPGGSLRLSCAASGFNVKYYMMHWVRQAPGKGLEWVAAISPGYDYTYYADSVKGRFTISADTSKNTAYLQMNSLRAEDTAVYYCSRSYWRYSVDVWGQGTLVTVSS | 5 |
| SPNGTIQNIL (SEQ ID NO: 1) | HLA-B7 | IDH2_R140Q_B7_cl3 | DIQMTQSPSSLSASVGDRVTITCRASQDVNTAVAWYQQKPGKAPKLLIYSASFLYSGVPSRFSGSRSGTDFTLTISSLQPEDFATYYCQQYSLYSPMTFGQGTKVEIKRTGGGSGGGGSGGGASEVQLVESGGGLVQPGGSLRLSCAASGFNSFLSIHWVRQAPGKGLEWVAHIFPSSDYTSYADSVKGRFTISADTSKNTAYLQMNSLRAEDTAVYYCSRGKHSSDSNYYMDYWGQGTLVTVSS | 6 |
| SPNGTIQNIL (SEQ ID NO: 1) | HLA-B7 | IDH2_R140Q_B7_cl8 | DIQMTQSPSSLSASVGDRVTITCRASQDVNTAVAWYQQKPGKAPKLLIYSASFLYSGVPSRFSGSRSGTDFTLTISSLQPEDFATYYCQQSYYMPFTFGQGTKVEIKRTGGGSGGGSGGGASEVQLVESGGGLVQPGGSLRLSCAASGFNIFRGYMHWVRQAPGKGLEWVAMISPHSDYTSYADSVKGRFTISADTSKNTAYLQMNSLRAEDTAVYYCSRSYGWAAFDYWGQGTLVTVSS | 8 |
| 3) p53 R248Q/W(245-254)-A2 | | | | |
| GMNQRPILTI (SEQ ID NO: 15) | HLA-A2 | p53_R248Q_A2_cl0 | DIQMTQSPSSLSASVGDRVTITCRASQDVNTAVAWYQQKPGKAPKLLIYSASFLYSGVPSRFSGSRSGTDFTLTISSLQPEDFATYYCQQSGYAPITFGQGTKVEIKRTGGGSGGGSGGGASEVQLVESGGGLVQPGGSLRLSCAASGFNISYYSMHWVRQAPGKGLEWVADVDPDSDYTEYADSVKGRFTISADTSKNTAYLQMNSLRAEDTAVYYCSRSWIHMFSMDYWGQGTLVTVSS | 331 |
| GMNWRPILTI (SEQ ID NO: 16) | HLA-A2 | p53_R248W_A2_cl2 | DIQMTQSPSSLSASVGDRVTITCRASQDVNTAVAWYQQKPGKAPKLLIYSASFLYSGVPSRFSGSRSGTDFTLTISSLQPEDFATYYCQQYSYAPITFGQGTKVEIKRTGGGSGGGSGGGASEVQLVESGGGLVQPGGSLRLSCAASGFNIGYYTMHWVRQAPGKGLEWVAEVSPWSYSTSYADSVKGRFTISADTSKNTAYLQMNSLRAEDTAVYYCSRDHWDEAFDVWGQGTLVTVSS | 332 |

TABLE 3-continued

MANAbody scFv sequences.

| Target Peptide(s) | Target HLA Allele | ScFc clone name | scFv sequence | SEQ ID NO: |
|---|---|---|---|---|
| GMNQRPILTI (SEQ ID NO: 15) | HLA-A2 | p53_R248Q_A2_cl4 | DIQMTQSPSSLSASVGDRVTITCRASQDVNTAVAWYQQKPGKAPKLLIYSASFLYSGVPSRFSGSRSGTDFTLTISSLQPEDFATYYCQQSLYGPFTFGQGTKVEIKRTGGGSGGGGSGGGASEVQLVESGGGLVQPGGSLRLSCAASGFNIAYEYMHWVRQAPGKGLEWVALIGPDSGYTYYADSVKGRFTISADTSKNTAYLQMNSLRAEDTAVYYCSRVWYYSTYGMDYWGQGTLVTVSS | 333 |
| GMNWRPILTI (SEQ ID NO: 16) | HLA-A2 | p53_R248W_A2_cl8 | DIQMTQSPSSLSASVGDRVTITCRASQDVNTAVAWYQQKPGKAPKLLIYSASFLYSGVPSRFSGSRSGTDFTLTISSLQPEDFATYYCQQYSYSPITFGQGTKVEIKRTGGGSGGGGSGGGASEVQLVESGGGLVQPGGSLRLSCAASGFNLFGYGMHWVRQAPGKGLEWVAEIGPYYYYTSYADSVKGRFTISADTSKNTAYLQMNSLRAEDTAVYYCSRENYDMAMDYWGQGTLVTVSS | 334 |
| GMNWRPILTI (SEQ ID NO: 16) | HLA-A2 | p53_R248W_A2_cl11 | DIQMTQSPSSLSASVGDRVTITCRASQDVNTAVAWYQQKPGKAPKLLIYSASFLYSGVPSRFSGSRSGTDFTLTISSLQPEDFATYYCQQSGYQPDTFGQGTKVEIKRTGGGSGGGGSGGGASEVQLVESGGGLVQPGGSLRLSCAASGFNISWYAMHWVRQAPGKGLEWVAEIWPDSDWTYYADSVKGRFTISADTSKNTAYLQMNSLRAEDTAVYYCSRYYYSSAFDVWGQGTLVTVSS | 335 |
| GMNQRPILTI (SEQ ID NO: 15), GMNWRPILTI (SEQ ID NO: 16) | HLA-A2 | p53_R248QW_A2_cl14 | DIQMTQSPSSLSASVGDRVTITCRASQDVNTAVAWYQQKPGKAPKLLIYSASFLYSGVPSRFSGSRSGTDFTLTISSLQPEDFATYYCQQYLYQPWTFGQGTKVEIKRTGGGSGGGGSGGGASEVQLVESGGGLVQPGGSLRLSCAASGFNIDYYGMHWVRQAPGKGLEWVASLYGGSDSTDYADSVKGRFTISADTSKNTAYLQMNSLRAEDTAVYYCSRQYSAYFDYWGQGTLVTVSS | 336 |
| GMNQRPILTI (SEQ ID NO: 15), GMNWRPILTI (SEQ ID NO: 16) | HLA-A2 | p53_R248QW_A2_cl17 | DIQMTQSPSSLSASVGDRVTITCRASQDVNTAVAWYQQKPGKAPKLLIYSASFLYSGVPSRFSGSRSGTDFTLTISSLQPEDFATYYCQQGLYYPWTFGQGTKVEIKRTGGGSGGGGSGGGASEVQLVESGGGLVQPGGSLRLSCAASGFNVSYSSIHWVRQAPGKGLEWVAEIWPDSGQTWYADSVKGRFTISADTSKNTAYLQMNSLRAEDTAVYYCSRSSYFDAMDYWGQGTLVTVSS | 337 |
| 4) KRAS G12V(6-14)-A2 | | | | |
| LVVVGAVGV (SEQ ID NO: 18) | HLA-A2 | KRAS_G12V_A2_A1 | DIQMTQSPSSLSASVGDRVTITCRASQDVNTAVAWYQQKPGKAPKLLIYSASFLYSGVPSRFSGSRSGTDFTLTISSLQPEDFATYYCQQWYSSPVTFGQGTKVEIKRTGGGSGGGGSGGGASEVQLVESGGGLVQPGGSLRLSCAASGFNINWANMHWVRQAPGKGLEWVAQISPPYDYTNYADSVKGRFTISADTSKNTAYLQMNSLRAEDTAVYYCSRSYSYYFDYWGQGTLVTVSS | 338 |
| LVVVGAVGV (SEQ ID NO: 18) | HLA-A2 | KRAS_G12V_A2_C1 | DIQMTQSPSSLSASVGDRVTITCRASQDVNTAVAWYQQKPGKAPKLLIYSASFLYSGVPSRFSGSRSGTDFTLTISSLQPEDFATYYCQQYYSRPVTFGQGTKVEIKRTGGGSGGGGSGGGASEVQLVESGGGLVQPGGSLRLSCAASGFNIYLHDMHWVRQAPGKGLEWVAQIIPAIDYTNYADSVKGRFTISADTSKNTAYLQMNSLRAEDTAVYYCSRRDGYYFDYWGQGTLVTVSS | 339 |
| LVVVGAVGV (SEQ ID NO: 18) | HLA-A2 | KRAS_G12V_A2_A5 | DIQMTQSPSSLSASVGDRVTITCRASQDVNTAVAWYQQKPGKAPKLLIYSASFLYSGVPSRFSGSRSGTDFTLTISSLQPEDFATYYCQQWYSSPVTFGQGTKVEIKRTGGGSGGGGSGGGASEVQLVESGGGLVQPGGSLRLSCAASGFNIYWSHMHWVRQAPGKGLEWVAIISSFEGYTYYADSVKGRFTISADTSKNTAYLQMNSLRAEDTAVYYCSRSYSYYMDYWGQGTLVTVSS | 340 |

TABLE 3-continued

MANAbody scFv sequences.

| Target Peptide(s) | Target HLA Allele | ScFc clone name | scFv sequence | SEQ ID NO: |
|---|---|---|---|---|
| 5) KRAS G12C/D/V(7-16)-A3 ||||||
| VVVGACGVGK (SEQ ID NO: 20), VVVGAVGVGK (SEQ ID NO: 22) | HLA-A3 | KRAS_G12CV_A3_cl5 | DIQMTQSPSSLSASVGDRVTITCRASQDVNTAVAWYQQ KPGKAPKLLIYSASFLYSGVPSRFSGSRSGTDFTLTIS SLQPEDFATYYCQQSYGSGSPWTFGQGTKVEIKRTGGG SGGGGSGGGASEVQLVESGGGLVQPGGSLRLSCAASGF NIVGGGIHWVRQAPGKGLEWVAKIYPQGDYTYYADSVK GRFTISADTSKNTAYLQMNSLRAEDTAVYYCSRDSSYL AFDYWGQGTLVTVSS | 341 |
| VVVGACGVGK (SEQ ID NO: 20), VVVGADGVGK (SEQ ID NO: 21), VVVGAVGVGK (SEQ ID NO: 22) | HLA-A3 | KRAS_G12CDV_A3_cl9 | DIQMTQSPSSLSASVGDRVTITCRASQDVNTAVAWYQQ KPGKAPKLLIYSASFLYSGVPSRFSGSRSGTDFTLTIS SLQPEDFATYYCQQTYYSPWTFGQGTKVEIKRTGGGSG GGGSGGGASEVQLVESGGGLVQPGGSLRLSCAASGFNI RSYAMHWVRQAPGKGLEWVAQVGPGKGYTYYADSVKGR FTISADTSKNTAYLQMNSLRAEDTAVYYCSRNFQSTSH AFDYWGQGTLVTVSS | 342 |
| VVVGACGVGK (SEQ ID NO: 20), VVVGADGVGK (SEQ ID NO: 21), VVVGAVGVGK (SEQ ID NO: 22) | HLA-A3 | KRAS_G12CDV_A3_cl18 | DIQMTQSPSSLSASVGDRVTITCRASQDVNTAVAWYQQ KPGKAPKLLIYSASFLYSGVPSRFSGSRSGTDFTLTIS SLQPEDFATYYCQQYYYPPITFGQGTKVEIKRTGGGSG GGGSGGGASEVQLVESGGGLVQPGGSLRLSCAASGFNV SHTGMHWVRQAPGKGLEWVAVVGPGKGYTYYADSVKGR FTISADTSKNTAYLQMNSLRAEDTAVYYCSRKTYYAFD YWGQGTLVTVSS | 343 |
| 6) KRAS G12V(7-16)-A3 ||||||
| VVVGAVGVGK (SEQ ID NO: 22) | HLA-A3 | KRAS_G12VA3_cl2 | DIQMTQSPSSLSASVGDRVTITCRASQDVNTAVAWYQQ KPGKAPKLLIYSASFLYSGVPSRFSGSRSGTDFTLTIS SLQPEDFATYYCQQSYYYFRPITFGQGTKVEIKRTGGG SGGGGSGGGASEVQLVESGGGLVQPGGSLRLSCAASGF NLSYSDIHWVRQAPGKGLEWVAVVMPDSGHTNYADSVK GRFTISADTSKNTAYLQMNSLRAEDTAVYYCSRATNIP VYAFDYWGQGTLVTVSS | 344 |
| VVVGAVGVGK (SEQ ID NO: 22) | HLA-A3 | KRAS_G12V_A3_V12 | DIQMTQSPSSLSASVGDRVTITCRASQDVNTAVAWYQQ KPGKAPKLLIYSASFLYSGVPSRFSGSRSGTDFTLTIS SLQPEDFATYYCQQASYYYPLTFGQGTKVEIKRTGGGS GGGGSGGGASEVQLVESGGGLVQPGGSLRLSCAASGFN ISASGMHWVRQAPGKGLEWVADIHPLKPYTNYADSVKG RFTISADTSKNTAYLQMNSLRAEDTAVYYCSRYSSMYY YYFDYWGQGTLVTVSS | 345 |
| VVVGAVGVGK (SEQ ID NO: 22) | HLA-A3 | KRAS_G12V_A3_cl20 | DIQMTQSPSSLSASVGDRVTITCRASQDVNTAVAWYQQ KPGKAPKLLIYSASFLYSGVPSRFSGSRSGTDFTLTIS SLQPEDFATYYCQQKSEYSPWTFGQGTKVEIKRTGGGS GGGGSGGGASEVQLVESGGGLVQPGGSLRLSCAASGFN IYRYGIHWVRQAPGKGLEWVAVLYPYGYSTSYADSVKG RFTISADTSKNTAYLQMNSLRAEDTAVYYCSRSYAYGY FAYWGQGTLVTVSS | 346 |
| VVVGAVGVGK (SEQ ID NO: 22) | HLA-A3 | KRAS_G12V_A3_cl21 | DIQMTQSPSSLSASVGDRVTITCRASQDVNTAVAWYQQ KPGKAPKLLIYSASFLYSGVPSRFSGSRSGTDFTLTIS SLQPEDFATYYCQQSGYIPFTFGQGTKVEIKRTGGGSG GGGSGGGASEVQLVESGGGLVQPGGSLRLSCAASGFNI YGTMMHWVRQAPGKGLEWVAQFKPDSYNTYYADSVKGR FTISADTSKNTAYLQMNSLRAEDTAVYYCSRGEVYHYY AFDYWGQGTLVTVSS | 347 |
| VVVGAVGVGK (SEQ ID NO: 22) | HLA-A3 | KRAS_G12V_A3_cl22 | DIQMTQSPSSLSASVGDRVTITCRASQDVNTAVAWYQQ KPGKAPKLLIYSASFLYSGVPSRFSGSRSGTDFTLTIS SLQPEDFATYYCQQGAYYRPFTFGQGTKVEIKRTGGGS GGGGSGGGASEVQLVESGGGLVQPGGSLRLSCAASGFN ISYSYMHWVRQAPGKGLEWVATLLPYDGNTYYADSVKG RFTISADTSKNTAYLQMNSLRAEDTAVYYCSRAAYSSM DVWGQGTLVTVSS | 348 |
| 7) KRAS G12D(7-16)-A3 ||||||
| VVVGADGVGK (SEQ ID NO: 21) | HLA-A3 | KRAS_G12D_A3_cl11 | DIQMTQSPSSLSASVGDRVTITCRASQDVNTAVAWYQQ KPGKAPKLLIYSASFLYSGVPSRFSGSRSGTDFTLTIS SLQPEDFATYYCQQYMYSPVTFGQGTKVEIKRTGGGSG GGGSGGGASEVQLVESGGGLVQPGGSLRLSCAASGFNV | 349 |

TABLE 3-continued

MANAbody scFv sequences.

| Target Peptide(s) | Target HLA Allele | ScFc clone name | scFv sequence | SEQ ID NO: |
|---|---|---|---|---|
| | | | SAYWNIHWVRQAPGKGLEWVAQIYGGSGYTMYADSVKG RFTISADTSKNTAYLQMNSLRAEDTAVYYCSRTHSYWS AFDYWGQGTLVTVSS | |
| VVVGADGVGK (SEQ ID NO: 21) | HLA-A3 | KRAS_G12D_A3_D12 | DIQMTQSPSSLSASVGDRVTITCRASQDVNTAVAWYQQ KPGKAPKLLIYSASFLYSGVPSRFSGSRSGTDFTLTIS SLQPEDFATYYCQQSSSSPITFGQGTKVEIKRTGGGSG GGGSGGGASEVQLVESGGGLVQPGGSLRLSCAASGFNI SGYGMHWVRQAPGKGLEWVAYLYGGSDYTNYADSVKGR FTISADTSKNTAYLQMNSLRAEDTAVYYCSRTVRYAFD YWGQGTLVTVSS | 350 |
| VVVGADGVGK (SEQ ID NO: 21) | HLA-A3 | KRAS_G12D_A3_D15 | DIQMTQSPSSLSASVGDRVTITCRASQDVNTAVAWYQQ KPGKAPKLLIYSASFLYSGVPSRFSGSRSGTDFTLTIS SLQPEDFATYYCQQSSASPLTFGQGTKVEIKRTGGGSG GGGSGGGASEVQLVESGGGLVQPGGSLRLSCAASGFNV SSVGNIHWVRQAPGKGLEWVAYIYGTSDYTYYADSVKG RFTISADTSKNTAYLQMNSLRAEDTAVYYCSRSSRYSM DYWGQGTLVTVSS | 351 |
| VVVGADGVGK (SEQ ID NO: 21) | HLA-A3 | KRAS_G12D_A3_D26 | DIQMTQSPSSLSASVGDRVTITCRASQDVNTAVAWYQQ KPGKAPKLLIYSASFLYSGVPSRFSGSRSGTDFTLTIS SLQPEDFATYYCQQYAYSPLTFGQGTKVEIKRTGGGSG GGGSGGGASEVQLVESGGGLVQPGGSLRLSCAASGFNV SSYGMHWVRQAPGKGLEWVAFIAPRRDYTSYADSVKGR FTISADTSKNTAYLQMNSLRAEDTAVYYCSRKSSYYFD YWGQGTLVTVSS | 352 |
| | | 8) KRAS G12D(7-16)-A11 | | |
| VVVGADGVGK (SEQ ID NO: 21) | HLA-A11 | KRAS_G12D_A11_D3 | DIQMTQSPSSLSASVGDRVTITCRASQDVNTAVAWYQQ KPGKAPKLLIYSASFLYSGVPSRFSGSRSGTDFTLTIS SLQPEDFATYYCQQYSYYPITFGQGTKVEIKRTGGGSG GGGSGGGASEVQLVESGGGLVQPGGSLRLSCAASGFNF SYGYMHWVRQAPGKGLEWVAWISGYTGNTYYADSVKGR FTISADTSKNTAYLQMNSLRAEDTAVYYCSRAASLSSS YYSAFDVWGQGTLVTVSS | 353 |
| VVVGADGVGK (SEQ ID NO: 21) | HLA-A11 | KRAS_G12D_A11_D14 | DIQMTQSPSSLSASVGDRVTITCRASQDVNTAVAWYQQ KPGKAPKLLIYSASFLYSGVPSRFSGSRSGTDFTLTIS SLQPEDFATYYCQQYSYTPVTFGQGTKVEIKRTGGGSG GGGSGGGASEVQLVESGGGLVQPGGSLRLSCAASGFNV WGPGMHWVRQAPGKGLEWVARIHPFSGNTYYADSVKGR FTISADTSKNTAYLQMNSLRAEDTAVYYCSRGYSYSAM DYWGQGTLVTVSS | 354 |
| VVVGADGVGK (SEQ ID NO: 21) | HLA-A11 | KRAS_G12D_A11_D18 | DIQMTQSPSSLSASVGDRVTITCRASQDVNTAVAWYQQ KPGKAPKLLIYSASFLYSGVPSRFSGSRSGTDFTLTIS SLQPEDFATYYCQQYSYEPVTFGQGTKVEIKRTGGGSG GGGSGGGASEVQLVESGGGLVQPGGSLRLSCAASGFNV SGSQMHWVRQAPGKGLEWVARIPGWSGYTYYADSVKGR FTISADTSKNTAYLQMNSLRAEDTAVYYCSRGYSYFAM DYWGQGTLVTVSS | 355 |
| VVVGADGVGK (SEQ ID NO: 21) | HLA-A11 | KRAS_G12D_A11_D21 | DIQMTQSPSSLSASVGDRVTITCRASQDVNTAVAWYQQ KPGKAPKLLIYSASFLYSGVPSRFSGSRSGTDFTLTIS SLQPEDFATYYCQQYAYYSPVTFGQGTKVEIKRTGGGS GGGGSGGGASEVQLVESGGGLVQPGGSLRLSCAASGFN IYGQMMHWVRQAPGKGLEWVAFLSPFSGNTYYADSVKG RFTISADTSKNTAYLQMNSLRAEDTAVYYCSRNISYEQ SSAFDYWGQGTLVTVSS | 356 |
| VVVGADGVGK (SEQ ID NO: 21) | HLA-A11 | KRAS_G12D_A11_D22 | DIQMTQSPSSLSASVGDRVTITCRASQDVNTAVAWYQQ KPGKAPKLLIYSASFLYSGVPSRFSGSRSGTDFTLTIS SLQPEDFATYYCQQYEYYPMTFGQGTKVEIKRTGGGSG GGGSGGGASEVQLVESGGGLVQPGGSLRLSCAASGFNV MYSTMHWVRQAPGKGLEWVASIYSWSDYTYYADSVKGR FTISADTSKNTAYLQMNSLRAEDTAVYYCSRGYAHNSF DYWGQGTLVTVSS | 357 |

TABLE 3-continued

MANAbody scFv sequences.

| Target Peptide(s) | Target HLA Allele | ScFc clone name | scFv sequence | SEQ ID NO: |
|---|---|---|---|---|
| 9) KRAS G12D(8-16)-A11 | | | | |
| VVGADGVGK (SEQ ID NO: 24) | HLA-A11 | KRAS_G12D_A11_cl4 | DIQMTQSPSSLSASVGDRVTITCRASQDVNTAVAWYQQKPGKAPKLLIYSASFLYSGVPSRFSGSRSGTDFTLTISSLQPEDFATYYCQQYSFYPFTFGQGTKVEIKRTGGGSGGGSGGGASEVQLVESGGGLVQPGGSLRLSCAASGFNFGSYIHWVRQAPGKGLEWVAIISGYSGNTYYADSVKGRFTISADTSKNTAYLQMNSLRAEDTAVYYCSRSNQSAYSYMDYWGQGTLVTVSS | 358 |
| VVGADGVGK (SEQ ID NO: 24) | HLA-A11 | KRAS_G12D_A11_cl6 | DIQMTQSPSSLSASVGDRVTITCRASQDVNTAVAWYQQKPGKAPKLLIYSASFLYSGVPSRFSGSRSGTDFTLTISSLQPEDFATYYCQQYSYSPITFGQGTKVEIKRTGGGSGGGSGGGASEVQLVESGGGLVQPGGSLRLSCAASGFNISDSYMHWVRQAPGKGLEWVATFSPYSSNTWYADSVKGRFTISADTSKNTAYLQMNSLRAEDTAVYYCSRSQFTFYQYFDYWGQGTLVTVSS | 359 |
| VVGADGVGK (SEQ ID NO: 24) | HLA-A11 | KRAS_G12D_A11_cl7 | DIQMTQSPSSLSASVGDRVTITCRASQDVNTAVAWYQQKPGKAPKLLIYSAYFLYSGVPSRFSGSRSGTDFTLTISSLQPEDFATYYCQQYSAYYQPITFGQGTKVEIKRTGGGSGGGGSGGGASEVQLVESGGGLVQPGGSLRLSCAASGFNIFSDQMHWVRQAPGKGLEWVAGFMPYDSYTNYADSVKGRFTISADTSKNTAYLQMNSLRAEDTAVYYCSRMSVRNAFDYWGQGTLVTVSS | 360 |
| VVGADGVGK (SEQ ID NO: 24) | HLA-A11 | KRAS_G12D_A11_cl9 | DIQMTQSPSSLSASVGDRVTITCRASQDVNTAVAWYQQKPGKAPKLLIYSASFLYSGVPSRFSGSRSGTDFTLTISSLQPEDFATYYCQQYSYYPITFGQGTKVEIKRTGGGSGGGSGGGASEVQLVESGGGLVQPGGSLRLSCAASGFNLSYSYNIHWVRQAPGKGLEWVAVISGFSGNTYYADSVKGRFTISADTSKNTAYLQMNSLRAEDTAVYYCSRSDSYYTAMDYWGQGTLVTVSS | 361 |
| VVGADGVGK (SEQ ID NO: 24) | HLA-A11 | KRAS_G12D_A11_cl10 | DIQMTQSPSSLSASVGDRVTITCRASQDVNTAVAWYQQKPGKAPKLLIYSASFLYSGVPSRFSGSRSGTDFTLTISSLQPEDFATYYCQQYEYVPHTFGQGTKVEIKRTGGGSGGGSGGGASEVQLVESGGGLVQPGGSLRLSCAASGFNISYGYMHWVRQAPGKGLEWVAKFHYGSGNTYYADSVKGRFTISADTSKNTAYLQMNSLRAEDTAVYYCSRSNYYYLDYWGQGTLVTVSS | 362 |
| VVGADGVGK (SEQ ID NO: 24) | HLA-A11 | KRAS_G12D_A11_cl12 | DIQMTQSPSSLSASVGDRVTITCRASQDVNTAVAWYQQKPGKAPKLLIYSASFLYSGVPSRFSGSRSGTDFTLTISSLQPEDFATYYCQQYSYMPITFGQGTKVEIKRTGGGSGGGSGGGASEVQLVESGGGLVQPGGSLRLSCAASGFNISYQHIHWVRQAPGKGLEWVAVFMPYQGSTYYADSVKGRFTISADTSKNTAYLQMNSLRAEDTAVYYCSRANIYSSHSFFDYWGQGTLVTVSS | 363 |
| VVGADGVGK (SEQ ID NO: 24) | HLA-A11 | KRAS_G12D_A11_cl14 | DIQMTQSPSSLSASVGDRVTITCRASQDVNTAVAWYQQKPGKAPKLLIYSASFLYSGVPSRFSGSRSGTDFTLTISSLQPEDFATYYCQQYAYYPVTFGQGTKVEIKRTGGGSGGGSGGGASEVQLVESGGGLVQPGGSLRLSCAASGFNLSGYYMHWVRQAPGKGLEWVAWFSPYSGYTYYADSVKGRFTISADTSKNTAYLQMNSLRAEDTAVYYCSRTHSSIYHSFDYWGQGTLVTVSS | 364 |
| VVGADGVGK (SEQ ID NO: 24) | HLA-A11 | KRAS_G12D_A11_cl15 | DIQMTQSPSSLSASVGDRVTITCRASQDVNTAVAWYQQKPGKAPKLLIYSASFLYSGVPSRFSGSRSGTDFTLTISSLQPEDFATYYCQQYSYMPITFGQGTKVEIKRTGGGSGGGSGGGASEVQLVESGGGLVQPGGSLRLSCAASGFNVSGQYMHWVRQAPGKGLEWVAVISPVSGNTYYADSVKGRFTISADTSKNTAYLQMNSLRAEDTAVYYCSRPMKTSYYGAFDYWGQGTLVTVSS | 365 |
| VVGADGVGK (SEQ ID NO: 24) | HLA-A11 | KRAS_G12D_A11_cl17 | DIQMTQSPSSLSASVGDRVTITCRASQDVNTAVAWYQQKPGKAPKLLIYSASFLYSGVPSRFSGSRSGTDFTLTISSLQPEDFATYYCQQYDYRPVTFGQGTKVEIKRTGGGSGGGSGGGASEVQLVESGGGLVQPGGSLRLSCAASGFNVSTSGMHWVRQAPGKGLEWVAFIYGAYSGTYYADSVKGRFTISADTSKNTAYLQMNSLRAEDTAVYYCSRSQSYTYWSAMDYWGQGTLVTVSS | 366 |

TABLE 3-continued

MANAbody scFv sequences.

| Target Peptide(s) | Target HLA Allele | ScFc clone name | scFv sequence | SEQ ID NO: |
|---|---|---|---|---|
| VVGADGVGK (SEQ ID NO: 24) | HLA-A11 | KRAS_G12D_A11_c118 | DIQMTQSPSSLSASVGDRVTITCRASQDVNTAVAWYQQ KPGKAPKLLIYSASFLYSGVPSRFSGSRSGTDFTLTIS SLQPEDFATYYCQQYDFTPMTFGQGTKVEIKRTGGGSG GGGSGGGASEVQLVESGGGLVQPGGSLRLSCAASGFNI SYAKMHWVRQAPGKGLEWVAYLTYWGGYTNYADSVKGR FTISADTSKNTAYLQMNSLRAEDTAVYYCSRGEYGTYM DYWGQGTLVTVSS | 367 |
| VVGADGVGK (SEQ ID NO: 24) | HLA-A11 | KRAS_G12D_A11_c119 | DIQMTQSPSSLSASVGDRVTITCRASQDVNTAVAWYQQ KPGKAPKLLIYSASFLYSGVPSRFSGSRSGTDFTLTIS SLQPEDFATYYCQQYSSSSPVTFGQGTKVEIKRTGGGS GGGGSGGGASEVQLVESGGGLVQPGGSLRLSCAASGFN FSSYVMHWVRQAPGKGLEWVAVVYPDSGGTYYADSVKG RFTISADTSKNTAYLQMNSLRAEDTAVYYCSRTSSYYA FDYWGQGTLVTVSS | 368 |

10) KRAS G12V(7-16)-A11

| Target Peptide(s) | Target HLA Allele | ScFc clone name | scFv sequence | SEQ ID NO: |
|---|---|---|---|---|
| VVVGAVGVGK (SEQ ID NO: 22) | HLA-A11 | KRAS_G12V_A11_V3 | DIQMTQSPSSLSASVGDRVTITCRASQDVNTAVAWYQQ KPGKAPKLLIYSASFLYSGVPSRFSGSRSGTDFTLTIS SLQPEDFATYYCQQSSYTPITFGQGTKVEIKRTGGGSG GGGSGGGASEVQLVESGGGLVQPGGSLRLSCAASGFNI SQGGIHWVRQAPGKGLEWVAYVYPGGGQTNYADSVKGR FTISADTSKNTAYLQMNSLRAEDTAVYYCSRGYDYSAF DYWGQGTLVTVSS | 369 |
| VVVGAVGVGK (SEQ ID NO: 22) | HLA-A11 | KRAS_G12_VA11_V9 | DIQMTQSPSSLSASVGDRVTITCRASQDVNTAVAWYQQ KPGKAPKLLIYSASFLYSGVPSRFSGSRSGTDFTLTIS SLQPEDFATYYCQQYAYYPITFGQGTKVEIKRTGGGSG GGGSGGGASEVQLVESGGGLVQPGGSLRLSCAASGFNI SSTGMHWVRQAPGKGLEWVAELLGGSGNTNYADSVKGR FTISADTSKNTAYLQMNSLRAEDTAVYYCSRGLQYSAM DYWGQGTLVTVSS | 370 |
| VVVGAVGVGK (SEQ ID NO: 22) | HLA-A11 | KRAS_G12V_A11V10 | DIQMTQSPSSLSASVGDRVTITCRASQDVNTAVAWYQQ KPGKAPKLLIYSASFLYSGVPSRFSGSRSGTDFTLTIS SLQPEDFATYYCQQYEYYPITFGQGTKVEIKRTGGGSG GGGSGGGASEVQLVESGGGLVQPGGSLRLSCAASGFNF FSTVIHWVRQAPGKGLEWVAEIYPWSGSTYYADSVKGR FTISADTSKNTAYLQMNSLRAEDTAVYYCSRSRSSNYY FDVWGQGTLVTVSS | 371 |
| VVVGAVGVGK (SEQ ID NO: 22) | HLA-A11 | KRAS_G12V_A11_V21 | DIQMTQSPSSLSASVGDRVTITCRASQDVNTAVAWYQQ KPGKAPKLLIYSASFLYSGVPSRFSGSRSGTDFTLTIS SLQPEDFATYYCQQYTYYPITFGQGTKVEIKRTGGGSG GGGSGGGASEVQLVESGGGLVQPGGSLRLSCAASGFNL HGYLMHWVRQAPGKGLEWVAFIYPPNGYTYYADSVKGR FTISADTSKNTAYLQMNSLRAEDTAVYYCSRGVDYAYL DYWGQGTLVTVSS | 372 |
| VVVGAVGVGK (SEQ ID NO: 22) | HLA-A11 | KRAS_G12V_A11_V23 | DIQMTQSPSSLSASVGDRVTITCRASQDVNTAVAWYQQ KPGKAPKLLIYSASFLYSGVPSRFSGSRSGTDFTLTIS SLQPEDFATYYCQQYSYYPITFGQGTKVEIKRTGGGSG GGGSGGGASEVQLVESGGGLVQPGGSLRLSCAASGFNL STHVMHWVRQAPGKGLEWVAEFYPYVGYTYYADSVKGR FTISADTSKNTAYLQMNSLRAEDTAVYYCSRGYRYQYM DVWGQGTLVTVSS | 373 |
| VVVGAVGVGK (SEQ ID NO: 22) | HLA-A11 | KRAS_G12V_A11_V24 | DIQMTQSPSSLSASVGDRVTITCRASQDVNTAVAWYQQ KPGKAPKLLIYSASFLYSGVPSRFSGSRSGTDFTLTIS SLQPEDFATYYCQQSSVEPWTFGQGTKVEIKRTGGGSG GGGSGGGASEVQLVESGGGLVQPGGSLRLSCAASGFNV SYYSIHWVRQAPGKGLEWVAYIYPWNDYTYYADSVKGR FTISADTSKNTAYLQMNSLRAEDTAVYYCSRGSYYSFD YWGQGTLVTVSS | 374 |

TABLE 3-continued

MANAbody scFv sequences.

| Target Peptide(s) | Target HLA Allele | ScFc clone name | scFv sequence | SEQ ID NO: |
|---|---|---|---|---|
| 11) CTNNB S45F(41-49)-A3 | | | | |
| TTAPFLSGK (SEQ ID NO: 26) | HLA-A3 | CTNNB_S45F_A3_E10 | DIQMTQSPSSLSASVGDRVTITCRASQDVNTAVAWYQQ KPGKAPKLLIYSASFLYSGVPSRFSGSRSGTDFTLTIS SLQPEDFATYYCQQSYYSPPTFGQGTKVEIKRTGGGSG GGASEVQLVESGGGLVQPGGSLRLSCAASGFNINNTYI HWVRQAPGKGLEWVASIYPTDGYTRYADSVKGRFTISA DTSKNTAYLQMNSLRAEDTAVYYCSRTYYSYYSAMDVW GQGTLVTVSS | 375 |
| TTAPFLSGK (SEQ ID NO: 26) | HLA-A3 | CTNNB_S45_FA3_cl3 | DIQMTQSPSSLSASVGDRVTITCRASQDVNTAVAWYQQ KPGKAPKLLIYSAYFLYSGVPSRFSGSRSGTDFTLTIS SLQPEDFATYYCQQIYTSPITFGQGTKVEIKRTGGGSG GGSGGGASEVQLVESGGGLVQPGGSLRLSCAASGFNF ITTGMHWVRQAPGKGLEWVARIGPGSDYTNYADSVKGR FTISADTSKNTAYLQMNSLRAEDTAVYYCSRYYYASAL DYWGQGTLVTVSS | 376 |
| TTAPFLSGK (SEQ ID NO: 26) | HLA-A3 | CTNNB_S45_FA3_cl4 | DIQMTQSPSSLSASVGDRVTITCRASQDVNTAVAWYQQ KPGKAPKLLIYSASFLYSGVPSRFSGSRSGTDFTLTIS SLQPEDFATYYCQQRAYFPITFGQGTKVEIKRTGGGSG GGSGGGASEVQLVESGGGLVQPGGSLRLSCAASGFNF SDYGMHWVRQAPGKGLEWVAMLIPASGYTNYADSVKGR FTISADTSKNTAYLQMNSLRAEDTAVYYCSRGWSYYMD YWGQGTLVTVSS | 377 |
| TTAPFLSGK (SEQ ID NO: 26) | HLA-A3 | CTNNB_S45_FA3_cl7 | DIQMTQSPSSLSASVGDRVTITCRASQDVNTAVAWYQQ KPGKAPKLLIYSASFLYSGVPSRFSGSRSGTDFTLTIS SLQPEDFATYYCQQQYAYTPITFGQGTKVEIKRTGGGS GGGGSGGGASEVQLVESGGGLVQPGGSLRLSCAASGFN VWSYGIHWVRQAPGKGLEWVAGVTPDGSYTYYADSVKG RFTISADTSKNTAYLQMNSLRAEDTAVYYCSRSYGWAM DYWGQGTLVTVSS | 378 |
| TTAPFLSGK (SEQ ID NO: 26) | HLA-A3 | CTNNB_S45_FA3_cl9 | DIQMTQSPSSLSASVGDRVTITCRASQDVNTAVAWYQQ KPGKAPKLLIYSAYFLYSGVPSRFSGSRSGTDFTLTIS SLQPEDFATYYCQQIHYKPLTFGQGTKVEIKRTGGGSG GGSGGGASEVQLVESGGGLVQPGGSLRLSCAASGFNV AWYSIHWVRQAPGKGLEWVAQVYGSSYTYYADSVKGR FTISADTSKNTAYLQMNSLRAEDTAVYYCSRDFYSSGM DYWGQGTLVTVSS | 379 |
| 12) KRAS G12V(11-19)-B7 | | | | |
| AVGVGKSAL (SEQ ID NO: 11) | HLA-B7 | KRAS_G12VB7_cl1 | DIQMTQSPSSLSASVGDRVTITCRASQDVNTAVAWYQQ KPGKAPKLLIYSASFLYSGVPSRFSGSRSGTDFTLTIS SLQPEDFATYYCQQEWRLPITFGQGTKVEIKRTGGGSG GGSGGGASEVQLVESGGGLVQPGGSLRLSCAASGFNV YGNQIHWVRQAPGKGLEWVARIYPYSGSTYYADSVKGR FTISADTSKNTAYLQMNSLRAEDTAVYYCSRSAYVAYS YFDYWGQGTLVTVSS | 380 |
| AVGVGKSAL (SEQ ID NO: 11) | HLA-B7 | KRAS_G12VB7_cl2 | DIQMTQSPSSLSASVGDRVTITCRASQDVNTAVAWYQQ KPGKAPKLLIYSASFLYSGVPSRFSGSRSGTDFTLTIS SLQPEDFATYYCQQGTSTPFTFGQGTKVEIKRTGGGSG GGSGGGASEVQLVESGGGLVQPGGSLRLSCAASGFNL SYYGMHWVRQAPGKGLEWVATIYPDSGYTKYADSVKGR FTISADTSKNTAYLQMNSLRAEDTAVYYCSRAYLYYYL AYWGQGTLVTVSS | 390 |
| AVGVGKSAL (SEQ ID NO: 11) | HLA-B7 | KRAS_G12VB7_cl3 | DIQMTQSPSSLSASVGDRVTITCRASQDVNTAVAWYQQ KPGKAPKLLIYSASFLYSGVPSRFSGSRSGTDFTLTIS SLQPEDFATYYCQQSWRYPMTFGQGTKVEIKRTGGGSG GGSGGGASEVQLVESGGGLVQPGGSLRLSCAASGFNI SRYGMHWVRQAPGKGLEWVAVFYPSSSYTYYADSVKGR FTISADTSKNTAYLQMNSLRAEDTAVYYCSRKYYEAMD YWGQGTLVTVSS | 391 |

TABLE 3-continued

MANAbody scFv sequences.

| Target Peptide(s) | Target HLA Allele | ScFc clone name | scFv sequence | SEQ ID NO: |
|---|---|---|---|---|
| AVGVGKSAL (SEQ ID NO: 11) | HLA-B7 | KRAS_G12VB7_cl5 | DIQMTQSPSSLSASVGDRVTITCRASQDVNTAVAWYQQ KPGKAPKLLIYSASFLYSGVPSRFSGSRSGTDFTLTIS SLQPEDFATYYCQQSYSYPVTFGHGTKVEIKRTGGGSG GGGSGGGASEVQLVESGGGLVQPGGSLRLSCAASGFNI YSSWMHWVRQAPGKGLEWVAYFQPYSGYTKYADSVKGR FTISADTSKNTAYLQMNSLRAEDTAVYYCSREYTYYFD YWGQGTLVTVSS | 392 |
| AVGVGKSAL (SEQ ID NO: 11) | HLA-B7 | KRAS_G12VB7_cl6 | DIQMTQSPSSLSASVGDRVTITCRASQDVNTAVAWYQQ KPGKAPKLLIYSASFLYSGVPSRFSGSRSGTDFTLTIS SLQPEDFATYYCQQGWLYSPFTFGQGTKVEIKRTGGGS GGGGSGGGASEVQLVESGGGLVQPGGSLRLSCAASGFN ISGYGMHWVRQAPGKGLEWVARVYGGSGYTYYADSVKG RFTISADTSKNTAYLQMNSLRAEDTAVYYCSRAHSSYY VDYWGQGTLVTVSS | 393 |

13) H/K/N RAS Q61H(55-64)-A1

| ILDTAGHEEY (SEQ ID NO: 28) | HLA-A1 | H/K/N RAS Q61H_A1_cl0 | DIQMTQSPSSLSASVGDRVTITCRASQDVNTAVAWYQQ KPGKAPKLLIYSASFLYSGVPSRFSGSRSGTDFTLTIS SLQPEDFATYYCQQGYFYYPNTFGQGTKVEIKRTGGGS GGGGSGGGASEVQLVESGGGLVQPGGSLRLSCAASGFN IGYYGMHWVRQAPGKGLEWVATVYPGGGYTSYADSVKG RFTISADTSKNTAYLQMNSLRAEDTAVYYCSRYYYYGF DYWGQGTLVTVSS | 394 |

14) H/K/N RAS Q61K(55-64)-A1

| ILDTAGKEEY (SEQ ID NO: 30) | HLA-A1 | H/K/N RAS Q61K_A1_cl6 | DIQMTQSPSSLSASVGDRVTITCRASQDVNTAVAWYQQ KPGKAPKLLIYSASFLYSGVPSRFSGSRSGTDFTLTIS SLQPEDFATYYCQQHYYSPVTFGQGTKVEIKRTGGGSG GGGSGGGASEVQLVESGGGLVQPGGSLRLSCAASGFNI FYQDMHWVRQAPGKGLEWVAMIYPDYDYTYYADSVKGR FTISADTSKNTAYLQMNSLRAEDTAVYYCSRTYSVYMD YWGQGTLVTVSS | 395 |

15) H/K/N RAS Q61L(55-64)-A1

| ILDTAGLEEY (SEQ ID NO: 31) | HLA-A1 | H/K/N RAS Q61K_A1_cl8 | DIQMTQSPSSLSASVGDRVTITCRASQDVNTAVAWYQQ KPGKAPKLLIYSASFLYSGVPSRFSGSRSGTDFTLTIS SLQPEDFATYYCQQYAYAPFTFGQGTKVEIKRTGGGSG GGGSGGGASEVQLVESGGGLVQPGGSLRLSCAASGFNV SYSMIHWVRQAPGKGLEWVARVWGDGGVTYYADSVKGR FTISADTSKNTAYLQMNSLRAEDTAVYYCSRGSYYAFD YWGQGTLVTVSS | 396 |

16) H/K/N RAS Q61R(55-64)-A1

| ILDTAGREEY (SEQ ID NO: 32) | HLA-A1 | H/R/N RAS Q61R_A1_cl16 | DIQMTQSPSSLSASVGDRVTITCRASQDVNTAVAWYQQ KPGKAPKLLIYSASFLYSGVPSRFSGSRSGTDFTLTIS SLQPEDFATYYCQQAHMIPITFGQGTKVEIKRTGGGSG GGGSGGGASEVQLVESGGGLVQPGGSLRLSCAASGFNF SFPGMEIWVRQAPGKGLEWVAWFVGYDGYTYYADSVKG RFTISADTSKNTAYLQMNSLRAEDTAVYYCSRDYYSFS MDYWGQGTLVTVSS | 397 |
| ILDTAGREEY (SEQ ID NO: 32) | HLA-A1 | H/R/N RAS Q61R_A1_cl17 | DIQMTQSPSSLSASVGDRVTITCRASQDVNTAVAWYQQ KPGKAPKLLIYSASFLYSGVPSRFSGSRSGTDFTLTIS SLQPEDFATYYCQQSVYDPITFGQGTKVEIKRTGGGSG GGGSGGGASEVQLVESGGGLVQPGGSLRLSCAASGFNI SGSWIHWVRQAPGKGLEWVAWLYPDSDYTYYADSVKGR FTISADTSKNTAYLQMNSLRAEDTAVYYCSRAHTYAFD YWGQGTLVTVSS | 398 |
| ILDTAGREEY (SEQ ID NO: 32) | HLA-A1 | H/R/N RAS Q61R_A1_cl18 | DIQMTQSPSSLSASVGDRVTITCRASQDVNTAVAWYQQ KPGKAPKLLIYSASFLYSGVPSRFSGSRSGTDFTLTIS SLQPEDFATYYCQQSYTSPLTFGQGTKVEIKRTGGGSG GGGSGGGASEVQLVESGGGLVQPGGSLRLSCAASGFNI YYGVMHWVRQAPGKGLEWVAMIYPDSSWTYYADSVKGR FTISADTSKNTAYLQMNSLRAEDTAVYYCSRDQDFHYM NYYLSYALDYWGQGTLVTVSS | 399 |

TABLE 3-continued

MANAbody scFv sequences.

| Target Peptide(s) | Target HLA Allele | ScFc clone name | scFv sequence | SEQ ID NO: |
|---|---|---|---|---|
| ILDTAGREEY (SEQ ID NO: 32) | HLA-A1 | H/R/N RAS Q61R_A1_cl19 | DIQMTQSPSSLSASVGDRVTITCRASQDVNTAVAWYQQ KPGKAPKLLIYSASFLYSGVPSRFSGSRSGTDFTLTIS SLQPEDFATYYCQQGQYSPFTFGQGTKVEIKRTGGGSG GGGSGGGASEVQLVESGGGLVQPGGSLRLSCAASGFNV SYEYMHWVRQAPGKGLEWVAEIYGGSDNTYYADSVKGR FTISADTSKNTAYLQMNSLRAEDTAVYYCSRPLGSYFD YWGQGTLVTVSS | 400 |
| ILDTAGREEY (SEQ ID NO: 32) | HLA-A1 | H/R/N RAS Q61R_A1_cl22 | DIQMTQSPSSLSASVGDRVTITCRASQDVNTAVAWYQQ KPGKAPKLLIYSASFLYSGVPSRFSGSRSGTDFTLTIS SLQPEDFATYYCQQYWYLPTTFGQGTKVEIKRTGGGSG GGGSGGGASEVQLVESGGGLVQPGGSLRLSCAASGFNI SWYDIHWVRQAPGKGLEWVADIEPSVGYTYYADSVKGR FTISADTSKNTAYLQMNSLRAEDTAVYYCSRSYPYYYF DYWGQGTLVTVSS | 401 |

Representative ELISA data for a scFvs that specifically recognized an IDH2 peptide containing the R140Q mutation in complex with HLA-B7 (SPNGTIQNIL; SEQ ID NO: 1) are shown in FIG. 1. The scFvs did not recognize the wt version of the peptide of interest in complex with the same HLA allele. The scFvs did not recognize other control peptides in complex with the HLA allele when tested for binding to a monomer-coated ELISA plate.

Further flow cytometry using showed that MANAbody scFv clones specifically stain the HLA allele-matched cell lines when these cells are pulsed with the mutant peptide, but not the wt peptide or other control peptides (FIGS. 2-14).

Figure 15A:
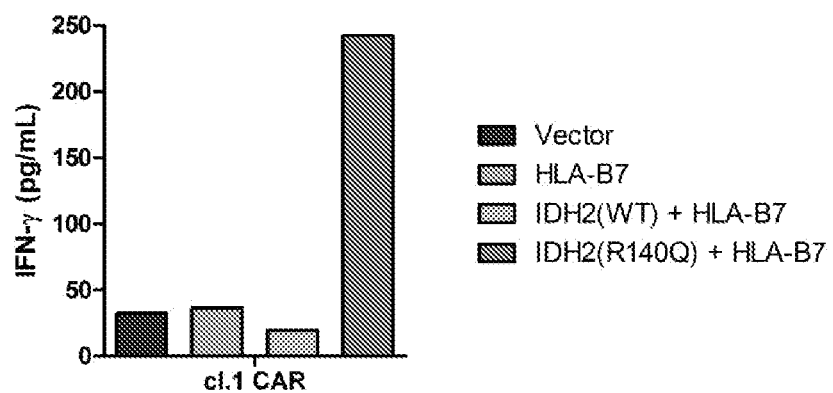
FIGS. 15A-15B show that MANAbody clones can be converted into CAR-T cells.
Figure 15B:
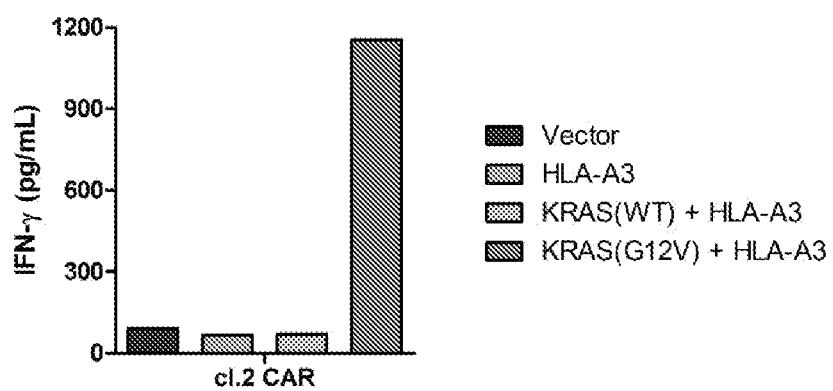

To demonstrate that MANAbody clones can be utilized as a therapeutic modality, selected MANAbody clones were engineered into CAR-T cells. Chimeric antigen receptor (CAR) T cells (CARTs) capable of recognizing and killing cells expressing oncogenic mutation-containing peptides in the context of HLA molecules via their endogenous processing and presentation machinery were engineered. Specifically, CARTs targeting a mutant KRAS G12V peptide presented in the context of HLA-A3 were engineered, and CARTs targeting a mutant IDH2 R140Q peptide presented in the context of HLA-B7 were engineered. MANAbody scFvs targeting either mutant peptide were grafted onto a 3$^{rd}$ Generation CAR construct, and CAR receptors were expressed in CD3+ T cells by mRNA electroporation. CAR-T cells were subsequently co-cultured with COS-7 cells co-transfected with plasmids encoding KRAS/IDH2 mutant and wt proteins in combination with their respective HLA. As T cells, including CAR-T cells, produce cytokines following activation by cognate antigen on target cells, the release of IFNγ in the co-culture media supernatant was measured by ELISA. Only when COS-7 cells were co-transfected with the mutant and cognate HLA plasmids was there significant release of IFNγ over background (FIG. 15). CAR-T cells co-cultured with COS-7 cells co-transfected with the wt and cognate HLA released only background levels of IFNγ. Together, these findings suggest that CAR-T cells expressing MANAbody clones can target tumor cells expressing MANAs presented in the context of HLA molecules.

To demonstrate that MANAbody clones can be utilized as a therapeutic modality, selected MANAbody clones were engineered into bispecific antibodies. A bispecific antibody having one antibody-fragment binding to a target cancer cell and having one antibody-fragment binding to a CD3 protein on the T cell surface was engineered. There are a number of different anti-CD3 scFv clones targeting human CD3 epsilon, delta, and/or gamma molecules. Examples of such clones are listed in Table 4.

Bispecific antibodies having one antibody-fragment binding to a mutant KRAS G12V peptide presented in the context of HLA-A3 and having one antibody-fragment binding to a CD3 protein on the T cell surface were engineered. Specifically, bispecific antibodies targeting a mutant KRAS G12V peptide presented in the context of HLA-A3 and CD3 were engineered, and bispecific antibodies targeting a mutant IDH2 R140Q peptide presented in the context of HLA-B7 and CD3 were engineered.

TABLE 4

Anti-human CD3 scFv sequences.

| Clone Name | Clone scFv Sequence | SEQ ID NO: |
|---|---|---|
| humanized UCHT1 (hUCHT1v9) | DIQMTQSPSSLSASVGDRVTITCRASQDIRNYLNWYQQKPGKAPKLLIYYTSRLESGVPSRFSGSGSGTDYT LTISSLQPEDFATYYCQQGNTLPWTFGQGTKVEIKGGGGSGGGGSGGGGSEVQLVESGGGLVQPGGSLRLSC AASGYSFTGYTMNWVRQAPGKGLEWVALINPYKGVSTYNQKFKDRFTISVDKSKNTAYLQMNSLRAEDTAVY YCARSGYYGDSDWYFDVWGQGTLVTVSS | 404 |
| murine UCHT1 (mUCHT1) | DIQMTQTTSSLSASLGDRVTISCRASQDIRNYLNWYQQKPDGTVKLLIYYTSRLHSGVPSKFSGSGSGTDYS LTISNLEQEDIATYFCQQGNTLPWTFAGGTKLEIKGGGGSGGGGSGGGGSEVQLQQSGPELVKPGASMKISC KASGYSFTGYTMNWVKQSHGKNLEWMGLINPYKGVSTYNQKFKDKATLTVDKSSSTAYMELLSLTSEDSAVY YCARSGYYGDSDWYFDVWGAGTTVTVSS | 405 |

TABLE 4-continued

Anti-human CD3 scFv sequences.

| Clone Name | Clone scFv Sequence | SEQ ID NO: |
|---|---|---|
| diL2K | DIVLTQSPATLSLSPGERATLSCRASQSVSYMNWYQQKPGKAPKRWIYDTSKVASGVPARFSGSGSGTDYSL TINSLEAEDAATYYCQQWSSNPLTFGGGTKVEIKGGGGSGGGGSGGGGSDVQLVQSGAEVKKPGASVKVSCK ASGYTFTRYTMHWVRQAPGQGLEWIGYINPSRGYTNYADSVKGRFTITTDKSTSTAYMELSSLRSEDTATYY CARYYDDHYCLDYWGQGTTVTVSS | 406 |
| hXR32 | QAVVTQEPSLTVSPGGTVTLTCRSSTGAVTTSNYANWVQQKPGQAPRGLIGGTNKRAPWTPARFSGSLLGGK AALTITGAQAEDEADYYCALWYSNLWVFGGGTKLTVLGGGGSGGGGSGGGGSEVQLVESGGGLVQPGGSLRL SCAASGFTFNTYAMNWVRQAPGKGLEWVARIRSKYNNYATYYADSVKDRFTISRDDSKNSLYLQMNSLKTED TAVYYCVRHGNFGNSYVSWFAYWGQGTLVTVSS | 407 |
| L2K-07 | DIQLTQSPAIMSASPGEKVTMTCRASSSVSYMNWYQQKSGTSPKRWIYDTSKVASGVPYRFSGSGSGTSYSL TISSMEAEDAATYYCQQWSSNPLTFGAGTKLELKGGGGSGGGGSGGGGSDIKLQQSGAELARPGASVKMSCK TSGYTFTRYTMHWVKQRPGQGLEWIGYINPSRGYTNYNQKFKDKATLTTDKSSSTAYMQLSSLTSEDSAVYY CARYYDDHYCLDYWGQGTTLTVSS | 408 |
| OKT3 | QIVLTQSPAIMSASPGEKVTMTCSASSSVSYMNWYQQKSGTSPKRWIYDTSKLASGVPAHFRGSGSGTSYSL TISGMEAEDAATYYCQQWSSNPFTFGSGTKLEINGGGGSGGGGSGGGGSQVQLQQSGAELARPGASVKMSCK ASGYTFTRYTMHWVKQRPGQGLEWIGYINPSRGYTNYNQKFKDKATLTTDKSSSTAYMQLSSLTSEDSAVYY CARYYDDHYCLDYWGQGTTLTVSS | 409 |
| PSMA-CD3 | QTVVTQEPSLTVSPGGTVTLTCGSSTGAVTSGNYPNWVQQKPGQAPRGLIGGTKFLAPGTPARFSGSLLGGK AALTLSGVQPEDEAEYYCVLWYSNRWVFGGGTKLTVLGGGGSGGGGSGGGGSEVQLVESGGGLVQPGGSLKL SCAASGFTFNKYAMNWVRQAPGKGLEWVARIRSKYNNYATYYADSVKDRFTISRDDSKNTAYLQMNNLKTED TAVYYCVRHGNFGNSYISYWAYWGQGTLVTVSS | 410 |
| 28F11 | EIVLTQSPATLSLSPGERATLSCRASQSVSSYLAWYQQKPGQAPRLLIYDASNRATGIPARFSGSGSGTDFT LTISSLEPEDFAVYYCQQRSNWPPLTFGGGTKVEIKGGGGSGGGGSGGGGSQVQLVESGGGVVQPGRSLRLS CAASGFKFSGYGMHWVRQAPGKGLEWVAVIWYDGSKKYYVDSVKGRFTISRDNSKNTLYLQMNSLRAEDTAV YYCARQMGYWHFDLWGRGTLVTVSS | 411 |
| 27H5-VL1 | EIVLTQSPRTLSLSPGERATLSCRASQSVSSSYLAWYQQKPGQAPRLLIYGASSRATGIPDRFSGSGSGTDF TLTISRLDPEDFAVYYCQQYGSSPITFGQGTRLEIKGGGGSGGGGSGGGGSQVQLVESGGGVVQPGRSLRLS CAASGFTFRSYGMHWVRQAPGKGLEWVAIIWYDGSKKNYADSVKGRFTISRDNSKNTLYLQMNSLRAEDTAV YYCARGTGYNWFDPWGQGTLVTVSS | 412 |
| 27H5-VL2 | DILMTQSPSSLSASVGDRVTITCRASQGISSALAWYQQKPGKAPKLLIYYASSLQSGVPSRFSGSGSGTDYT LTISSLQPEDFATYYCQQYYSTLTFGGGTKVEIKGGGGSGGGGSGGGGSQVQLVESGGGVVQPGRSLRLSCA ASGFTFRSYGMHWVRQAPGKGLEWVAIIWYDGSKKNYADSVKGRFTISRDNSKNTLYLQMNSLRAEDTAVYY CARGTGYNWFDPWGQGTLVTVSS | 413 |
| 23F10 | EIVLTQSPATLSLSPGERATLSCRASQSVSSYLAWYQQKPGQAPRLLIYDASNRATGIPARFSGSGSGTDFT LTISSLEPEDFAVYYCQQRSNWPPLTFGGGTKVEIKGGGGSGGGGSGGGGSQVQLVQSGGGVVQSGRSLRLS CAASGFKFSGYGMHWVRQAPGKGLEWVAVIWYDGSKKYYVDSVKGRFTISRDNSKNTLYLQMNSLRGEDTAV YYCARQMGYWHFDLWGRGTLVTVSS | 414 |
| 15C3-VL1 | EIVLTQSPATLSLSPGERATLSCRASQSVSSYLAWYQQKPGQAPRLLIYDASNRATGIPARFSGSGSGTDFT LTISSLEPEDFAVYYCQQRSNWPWTFGQGTKVEIKGGGGSGGGGSGGGGSQVQLVQSGGGVVQPGRSLRLSC VASGFTFSSYGMHWVRQAPGKGLEWVAAIWYNGRKQDYADSVKGRFTISRDNSKNTLYLQMNSLRAEDTAVY YCTRGTGYNWFDPWGQGTLVTVSS | 415 |
| 15C3-VL2 | AIQLTQSPSSLSASVGDRVTITCRASQGISSALAWYQQKPGKAPKLLIYDASSLESGVPSRFSGSGSGTDFT LTISSLQPEDFATYYCQQFNSYPITFGQGTRLEIKGGGGSGGGGSGGGGSQVQLVQSGGGVVQPGRSLRLSC VASGFTFSSYGMHWVRQAPGKGLEWVAAIWYNGRKQDYADSVKGRFTISRDNSKNTLYLQMNSLRAEDTAVY YCTRGTGYNWFDPWGQGTLVTVSS | 416 |
| hu 12F6 | QIVLSQSPAILSASPGEKVTMTCRASSSVSYMHWYQQKPGSSPKPWIYATSNLASGVPARFSGSGSGTSYSL TISRVEAEDAATYYCQQWSSNPPTFGGGTKLETKRGGGGSGGGGSGGGGSQVQLQQSGAELARPGASVKMSC KASGYTFTSYTMHWVKQRPGQGLEWIGYINPSSGYTKYNQKFKDKATLTADKSSSTAYMQLSSLTSEDSAVY YCARWQDYDVYFDYWGQGTTLTVSS | 417 |

Figure 16A:
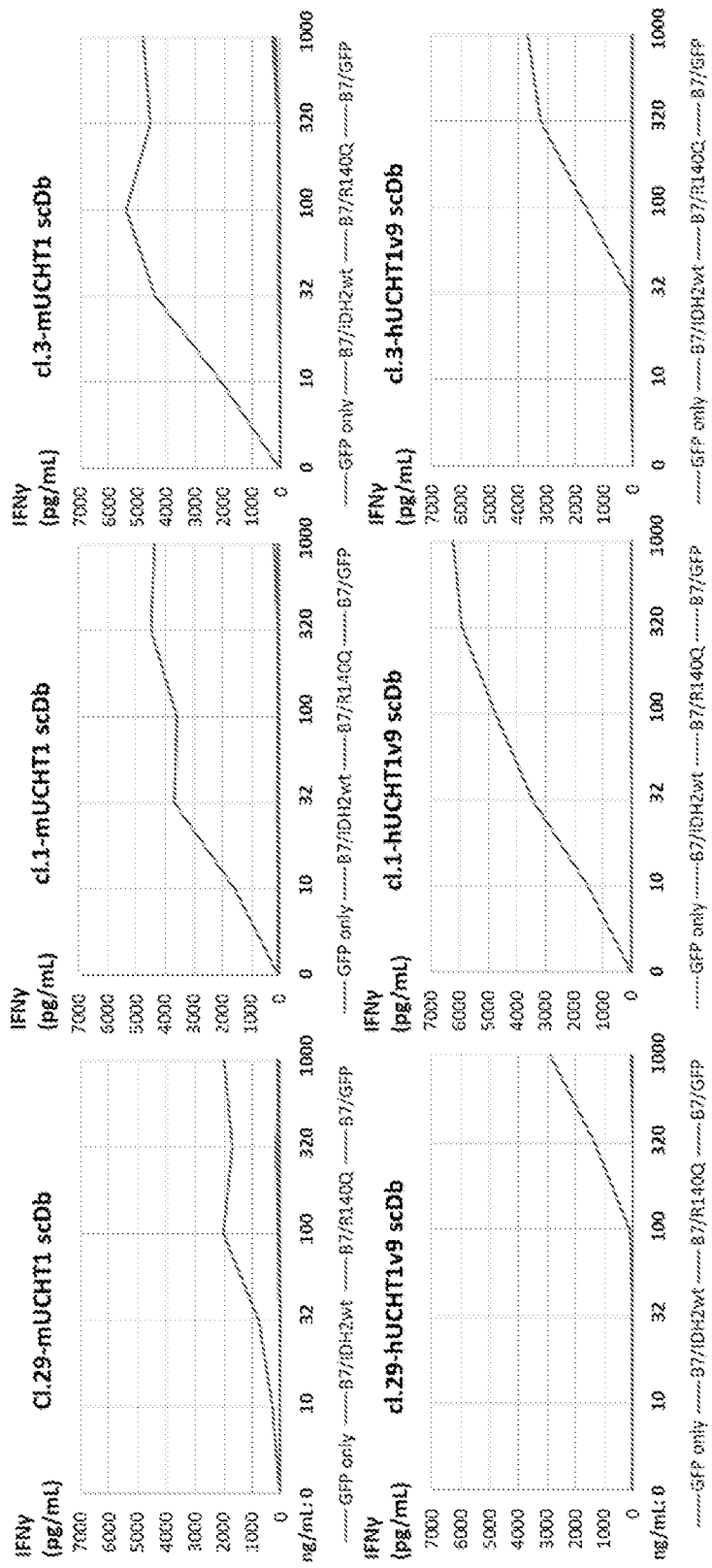
FIGS. 16A-16B show that MANAbody clones can be converted into single-chain diabodies (scDbs).
Figure 16B:
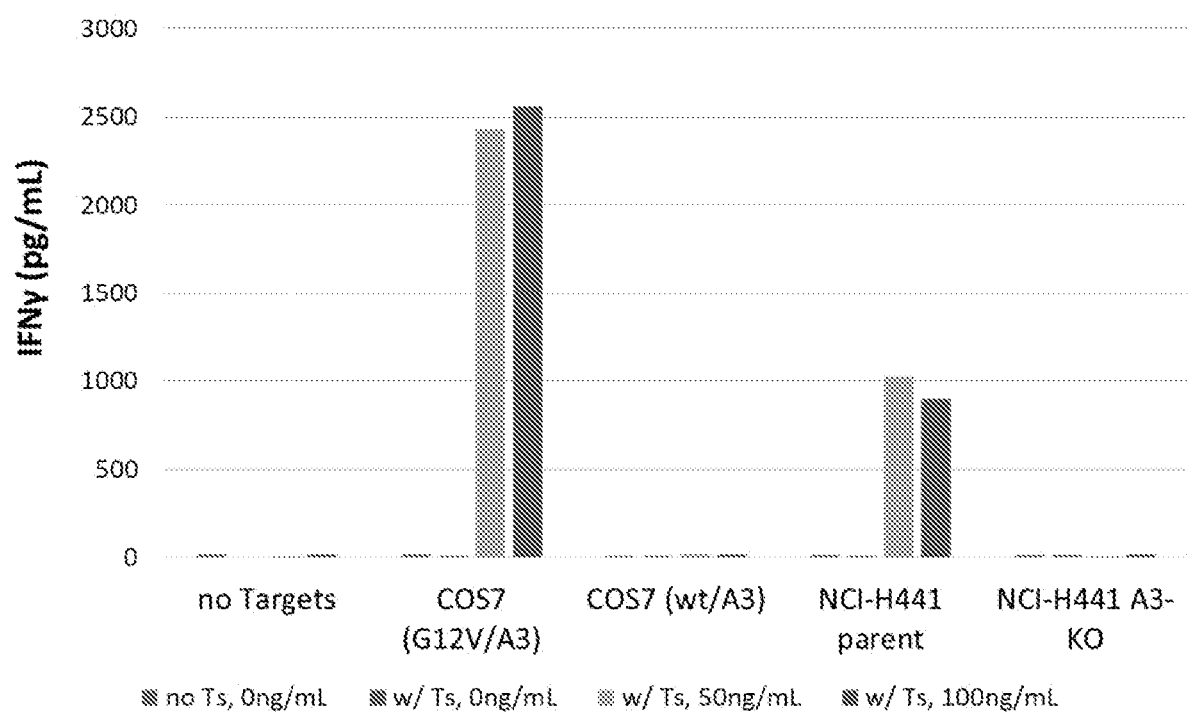

Representative scDb co-culture results are shown in FIG. 16A for three IDH2 R140Q HLA-B7 MANAbody scFv clones combined with two different anti-CD3 scFv clones. T cells were co-cultured with COS-7 cells co-transfected with plasmids encoding HLA-B7, full-length IDH2 variants, and/or GFP in the presence of the specified concentration of scDb. As a read out of T cell activation by cognate antigen on target cells, the release of IFNγ in the co-culture media supernatant was measured by ELISA. Only when COS-7 cells were co-transfected with HLA-B7 and mutant IDH2 R140Q plasmids was there significant T cell release of IFNγ over background, with the level of IFNγ dependent on the concentration of scDb included in the well. T cells co-cultured with COS-7 cells co-transfected with HLA-B7 and wt IDH2 released only background levels of IFNγ. Representative scDb co-culture results are shown in FIG. 16B for a KRAS G12V HLA-A3 MANAbody scFv clone combined with an anti-CD3 clone into a single chain diabody. In this co-culture, the single chain diabody was tested at concentrations of 0, 50, and 100 ng/mL. Only when COS-7 cells were co-transfected with HLA-A3 and mutant KRAS G12V plasmids was there significant T cell release of IFNγ over background. T cells co-cultured with COS-7 cells co-transfected with HLA-A3 and wt KRAS released only background levels of IFNγ, similar to the levels of IFNγ seen in no T cell, no target cell, and no scDb wells. An endogenous KRAS G12V HLA-A3 positive cell line NCI-H441 as a target cell line along with its isogenic HLA-A3 knockout control. IFNγ release was only seen against the parental NCI-H441 cell line but not the HLA-A3 knockout NCI-H441. Together, these findings suggest that bispecific antibodies containing MANAbody clones that target tumor cells expressing MANAs presented in the context of HLA molecules.

Figure 17:
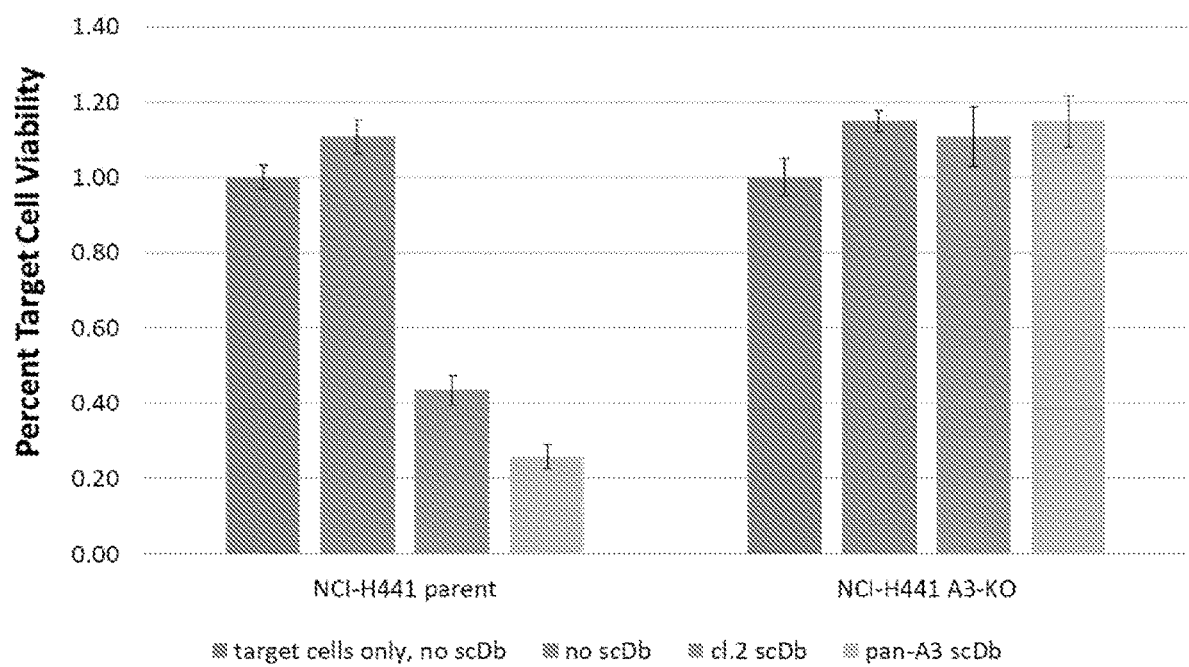
FIG. 17 shows that a MANAbody clone converted into a scDb can kill target cells. KRAS G12V(7-16)-A3 cl.2 mUCHT1 scDb and a pan-HLA-A3 scDb were incubated at 0 or 50 ng/mL with or without T cells and with NCI-H441 parental or HLA-A3 knockout cells for 24 hours at 37° C. Following co-culture, CellTiter-Glo® was used to assay viable cells in each well. Percent target cell viability was calculated by subtracting the value from T cell only wells and normalizing to the value from target cell only wells.

To evaluate the efficacy of using MANAbody clones as a therapeutic modality, target cell viability of a KRAS G12V HLA-A3 single-chain diabody was assayed using PROMEGA® CellTiter-Glo® reagent (FIG. 17). CellTiter-Glo® measures ATP concentration in a well, which is proportional to the number of viable cells. Percent target cell viability was measured by subtracting the CellTiter-Glo® value from T cell only wells and normalizing to target cell only wells. Only when NCI-H441 parent cells were incubated with T cells in the presence of the KRAS G12V-A3 scDb or a pan-HLA-A3 scDb positive control, was there significant target cell death. No target cell death was observed in the absence of scDb or among the NCI-H441 HLA-A3 knockout wells.

Together, these findings demonstrate that MANAbodies can be used to redirect and activate T cells to kill tumor cells expressing particular mutant protein and HLA allele pairs (e.g., IDH2 R140Q with HLA-B7 and KRAS G12V with HLA-A3).

Materials and Methods
Cells and Cell Lines.

RPMI-6666 cells (ATCC, Manassas, VA) was cultured in RPMI-1640 (ATCC) with 20% FBS (GE Hyclone, Logan, Utah, USA), and 1% penicillin streptomycin (Life Technologies). T2 cells (ATCC) and MINO cells (ATCC) were cultured in RPMI-1640 (ATCC) with 10% FBS (GE Hyclone), and 1% penicillin streptomycin (Thermo Fisher). T2A3 cells (gifted from Dr. Eric Lutz) were cultured in RPMI-1640 (ATCC) with 10% FBS (GE Hyclone), 1% penicillin streptomycin (Thermo Fisher), 0.1 mM MEM Non-Essential Amino Acids (NEAA, Thermo Fisher), and 500 µg/mL geneticin (Thermo Fisher). SigM5 cells (DSMZ, Brunswick, Germany) were cultured in Iscove's MDM (ATCC) with 20% FBS (GE Hyclone), and 1% penicillin streptomycin (Thermo Fisher). Hs611.T cells (ATCC) was cultured in Dulbecco's Modified Eagle's Medium (ATCC) with 10% FBS (GE Hyclone), and 1% penicillin streptomycin (Thermo Fisher). NCI-H441 cells (ATCC) and COS-7 cells (ATCC) was cultured in McCoy's 5A (Modified) Medium (Thermo Fisher) with 10% FBS (GE Hyclone), and 1% penicillin streptomycin (Thermo Fisher). COS-7 cells (ATCC, CRL-1651™) were cultured in DMEM (high glucose, pyruvate; Thermo Fisher) with 10% FBS (GE Hyclone), and 1% Penicillin-Streptomycin (Thermo Fisher). 293FT cells (Thermo Fisher) were cultured in high-glucose D-MEM (Thermo Fisher), with 10% FBS (GE Hyclone), 0.1 mM MEM Non-Essential Amino Acids (NEAA, Thermo Fisher), 6 mM L-glutamine (Thermo Fisher), 1 mM MEM Sodium Pyruvate (Thermo Fisher), 500 µg/ml geneticin (Thermo Fisher), and 1% Penicillin-Streptomycin (Thermo Fisher). All cell lines were maintained at 37° C. under 5% $CO_2$.

PBMCs were obtained by Ficoll-Paque PLUS (GE Healthcare) gradient centrifugation of whole blood from healthy volunteer donors. CD3+ cells were positively selected with CD3 MicroBeads (Miltenyi Biotec) from PBMCs, and were activated and expanded with Dynabeads® Human T-Activator CD3/CD28 (Life Technologies). Unless otherwise noted, primary CD3+ T cells were cultured in RPMI-1640 (ATCC) with 10% FBS (GE Hyclone), 1% Penicillin-Streptomycin (Life Technologies), and 100 IU/mL recombinant human inteuleukin-2 (Proleukin®) at 37° C. under 5% $CO_2$.

Phage Display Library Construction.

For the 1st generation phage library, oligonucleotides were synthesized at DNA 2.0 (Menlo Park, CA) using mixed and split pool degenerate oligonucleotide syntheses. For the 2nd generation phage library, oligonucleotides were synthesized at GeneArt (Thermo Fisher, Halethorpe, MD) using trinucleotide mutagenesis (TRIM) technology. For both libraries, the oligonucleotides were incorporated into the pADL-10b phagemid (Antibody Design Labs, San Diego, CA). This phagemid contains an F1 origin, a transcriptional repressor to limit uninduced expression, a lac operator, and a lac repressor. The scFv was synthesized with a pelB periplasmic secretion signal and was subcloned downstream of the lac operator. For the 1st generation library, a myc epitope tag followed by a TEV protease cleavage recognition sequence was placed immediately downstream of the variable heavy chain, while in the 2nd generation library, the scFv was followed by a FLAG tag. Following the scFv, tag, and cleavage site, was the full length, in-frame M13 pIII coat protein sequence.

To transform the phagemid DNA into bacteria, 10-20 ng of the ligation product was mixed on ice with 10 µL of electrocompetent SS320 cells (Lucigen, Middleton, WI) and 14 µL of double-distilled water. This mixture was electroporated using a Gene Pulser electroporation system (Bio-Rad, Hercules, CA) and allowed to recover in Recovery Media (Lucigen) for 60 min at 37° C. Cells transformed with 60 ng of ligation product were pooled and plated on a 24-cm×24-cm plate containing 2×YT medium supplemented with carbenicillin (100 µg/mL) and 2% glucose. Cells were grown at 37° C. for 6 hours and placed at 4° C. overnight. To determine the transformation efficiency for each series of electroporations, aliquots were taken and titered by serial dilution. Cells grown on plates were scraped into 850 mL of 2×YT medium with carbenicillin (100 µg/mL) plus 2% glucose for a final OD600 of 5-15. Two mL of the 850 mL culture were taken and diluted ~1:200 to reach a final OD600 of 0.05-0.07. To the remaining culture, 150 mL of sterile glycerol were added before snap freezing to produce glycerol stocks. The diluted bacteria were grown to an OD600 of 0.2-0.4, infected with M13K07 Helper phage (Antibody Design Labs, San Diego, CA) and allowed to shake at 37° C. for 1 hour. The culture was centrifuged and the cells were resuspended in 2×YT medium with carbenicillin (100 µg/mL) and kanamycin (50 µg/mL) and grown overnight at 30° C. for phage production. The following morning, the bacterial culture was aliquoted into 50 mL Falcon tubes and pelleted twice at high speed to obtain clarified supernatant. The phage-laden supernatant was precipitated on ice for 40 min with a 20% PEG-8000/2.5M NaCl solution at a 4:1 ratio of PEG/NaCl to supernatant. After precipitation, phage was centrifuged at 12,000 g for 40 minutes and resuspended in a 1 mL vol 1×TBS, 2 mM EDTA. Phage from multiple tubes was pooled, re-precipitated, and resuspended to an average titer of $1 \times 10^{13}$ cfu/mL. For the 1st generation library, the total number of transformants obtained was $5.5 \times 10^9$. For the 2nd generation library, the total number of transformants obtained was $3.6 \times 10^{10}$. Each library was aliquoted and stored in 15% glycerol at −80° C.

Next-Generation Sequencing of the Complete Phage Library.

DNA from the libraries was amplified using primers that flank the CDR-H3 region. The sequences at the 5'-ends of these primers incorporated molecular barcodes to facilitate unambiguous enumeration of distinct phage sequences. The protocols for PCR-amplification and sequencing are described in Kinde et al. Sequences processed and translated using a custom SQL database and both the nucleotide sequences and amino acid translations were analyzed using Microsoft Excel.

Peptides and HLA Monomers.

Mutant, wt, and control peptides (listed in Table 1) were predicted to bind to HLA alleles using NetMHC version 4.0. All peptides were synthesized at a purity of >90% by Peptide 2.0 (Chantilly, VA). Peptides were resuspended in DMSO or DMF at 10 mg/mL and stored at −20° C. HLA monomers were synthesized by refolding recombinant HLA with peptide and beta-2 microglobulin, purified by gel-filtration, and biotinylated (Fred Hutchinson Immune Monitoring Lab, Seattle, WA). Monomers were confirmed to be folded prior to selection by performing an ELISA using W6/32 antibody (BioLegend, San Diego, CA).

Selection for Phage Binding to Mutant Peptide-HLA Monomers.

Biotinylated monomers containing HLA and beta-2-microglobulin proteins were conjugated to MyOne™ T1 streptavidin magnetic beads (Life Technologies, Carlsbad, CA). The biotinylated monomers were incubated with 30 µL of MyOne™ T1 beads (per 1 kg of monomer) in blocking buffer (PBS, 0.5% BSA, 0.1% Na-azide) for 1 hour at room temperature (RT). After the initial incubation, the complexes were washed 3 times with 1ml blocking buffer and resuspended in 1 ml blocking buffer.

Enrichment Phase.

In the enrichment phase of selection (round 1), phage representing 1000-fold coverage of the library was incubated with naked, washed MyOne™ T1 beads and heat-denatured, bead-conjugated HLA monomer overnight at 4° C. on a rotator. This step was necessary to remove any phage recognizing either streptavidin or denatured monomer, present to a small extent in every preparation of biotinylated monomer. After negative selection, beads were isolated with a DynaMag-2 magnet (Life Technologies) and the supernatant containing unbound phage was transferred for positive selection against 1 µg of the mutant peptide-HLA monomer conjugated to MyOne™ T1 streptavidin magnetic beads. Prior to elution, beads were washed 10 times with 1 ml, 1×TBS containing 0.5% Tween®-20 using a magnet. Phage was eluted by resuspending the beads in 1 mL of 0.2 M glycine, pH 2.2. After a 10-minute incubation, the solution was neutralized by the addition of 150 µL of 1 M Tris, pH 9.0. Neutralized phage was used to infect 10 ml cultures of mid-log-phase SS320s, with the addition of M13K07 helper phage (MOI of 4) and 2% glucose. After shaking for 1 hour at 37° C., bacteria was resuspended in 2×YT medium with carbenicillin (100 µg/mL), kanamycin (50 µg/mL), and 50 uM of IPTG and grown overnight at 30° C. for phage production. Phage was precipitated the next morning with PEG/NaCl as previously described.

Final Selection Phase.

Three to five rounds of final selection were performed with phage resulting from the enrichment phase. For each round of final selection, the first negative selection was performed using 10-0.1% of the precipitated phage against HLA-allele matched cells lacking the mutated protein of interest. The unbound phage was then negatively selected against native wt peptide-HLA monomer and unrelated HLA-allele matched monomer. After negative selection, beads were isolated with a Dynamag 2 magnet (Life Technologies) and the supernatant containing unbound phage was transferred for positive selection with 250 ng to 1 µg of mutant peptide-HLA monomer, as described for the enrichment phase above.

ELISA.

Streptavidin-coated, 96-well plates (R&D Systems, Minneapolis, MN) were coated with 50 ng (in 50 uL) of biotinylated mutant or wt peptide-HLA monomers in blocking buffer (PBS with 0.5% BSA, 2 mM EDTA, and 0.1% sodium azide) at 4° C. overnight. Plates were briefly washed with 1×TBST (TBS+0.05% Trition-X 100). Phage was serially diluted to the specified concentrations in blocking buffer and 50 uL was added to each well. Phage were incubated for 2 hrs at RT, followed by washing (6 washes with 1×TBS-0.05% Tween®-20 (TBST) using an ELISA plate washer (BioTek, Winooski, VT). The bound phage were incubated with 50 µL of rabbit anti-M13 antibody (Pierce, Rockford, IL) diluted 1:3000 in 1×TBST for 1 hr at room temperature, followed by washing an additional 6× times and incubation with 50 µL of anti-Rabbit HRP (Thermo Fisher) diluted 1:10,000 in 1×TBST for 1 hour at room temperature. After a final 6 washes with 1×TBST, 50 µL of TMB substrate (BioLegend, San Diego, CA) was added to the well and the reaction was quenched with 1N sulfuric acid. Absorbance at 450 nm was measured with a Synergy H1 Multi-Mode Reader (BioTek, Winooski, VT).

Monoclonal phage ELISA was performed by selecting individual colonies of SS320 cells transformed with a limiting dilution of phage obtained from the final selection. Individual colonies were inoculated into 200 µl of 2×YT medium containing 100 µg/mL carbenicillin and 2% glucose and grown for three hours at 37° C. The cells were then infected with $1.6 \times 10^7$ M13K07 helper phage (Antibody Design Labs, San Diego, CA) and incubated for at 37° C. with shaking. The cells were pelleted, resuspended in 300 µL of 2×YT medium containing carbenicillin (100 µg/mL), kanamycin (50 µg/mL), and 50 µM IPTG, and grown overnight at 30° C. Cells were pelleted and the phage-laden supernatant was used for ELISA as described above.

Peptide Pulsing and Flow Cytometry.

For peptide pulsing, HLA-matched cells were washed once with PBS and once with serum-free RPMI-1640 before incubation at $10^6$ cells per mL in serum-free RPMI-1640 containing 50 µg/mL peptide and 10 µg/mL human beta-2 microglobulin (ProSpec, East Brunswick, NJ) overnight at 37° C. The pulsed cells were pelleted, washed once in cold stain buffer (PBS containing 0.5% BSA, 2 mM EDTA, and 0.1% sodium azide), and resuspended in 100 µL of stain buffer. Phage staining was performed on ice with 10 uL (approximately $1 \times 10^9$) phage for 1 hour in 100 uL total volume, followed by one 4 mL wash in cold stain buffer. Cells were then stained with 1 uL of rabbit anti-M13 antibody (Pierce, Rockford, IL) in 100 uL total volume on ice for 1 hour and washed once with 4 mL of cold stain buffer. Cells were stained with anti-rabbit-PE (Biolegend) on ice for 1 hour in 100 uL total volume, followed by incubation with LIVE/DEAD Fixable Near-IR Dead Cell Stain (Thermo Fisher) for 10 min at room temperature per manufacturer's instructions. Cells were washed once in 4 mL of stain buffer followed by resuspension in 300 uL of stain buffer before analysis. Stained cells were analyzed using an LSRII flow cytometer (Becton Dickinson, Mansfield, MA).

CAR Construction and Generation.

A third-generation Chimeric Antigen Receptor (CAR) construct, containing the MANAbody scFv, a CD28 transmembrane domain, and 4-1BB and CD3ζ intracellular domains, was synthesized (GeneArt®) and cloned into the mammalian expression vector pCI (PROMEGA®). mRNA was synthesized with the T7 mScript™ Standard mRNA Production System Kit (CellScript™) per manufacturer's instructions. CAR mRNA was electroporated into primary CD3+ T cells with the BTX ECM 2001 Electro Cell Manipulator (Harvard Apparatus) to generate CAR-T cells.

CAR-T Activation Co-Culture Assay.

COS-7 cells were transfected with various combinations of pcDNA3.1 (Life Technologies) plasmids encoding HLA-A3, HLA-B7, IDH2(WT), IDH2(R140Q), KRAS(WT), and KRAS(G12V) with Lipofectamine 3000 (Life Technologies) per manufacturer's instructions in a T75 flask. 50,000 T cells were combined with transfected 30,000 COS-7 cells or 10,000 NCI-H441 cells and the specified concentration of bispecific antibody in a 96-well plate, and the co-culture was allowed to incubate for 24 hours at 37° C. under 5% $CO_2$. Following co-culture, the 96-well plate was snap frozen and conditioned media lysate was collected and assayed for secreted IFNγ by ELISA (Quantikine®, R&D Systems). Alternatively, following coculture, target cell viability was measured using CellTiter-Glo® (PROMEGA®).

Bispecific Antibody Production.

gBLOCKs encoding bispecific antibodies were ordered from IDT (Skokie, Illinois). gBLOCKs were topo-cloned into the pcDNA3.4 plasmid (Thermo Fisher) following the manufacturer's protocol. 293FT cells (Thermo Fisher) were transfected with the bispecific antibody pcDNA3.4 plasmids using Lipofectamine 3000 (Life Technologies) per manufacturer's instructions in a T75 flask. Following a 5-7 day incubation, media was harvest and centrifuged at 3,000 g for 10 min at 4 C. Bispecific antibody protein was purified using a Clontech Capturem™ His-Tagged Purification Miniprep Kit (Takara, Mountain View, CA) per manufacturer's instructions. Bispecific antibody protein was desalted into PBS using Zeba spin 7k MWCO desalting columns per manufacturer's instructions. Bispecific antibody concentration was quantified using Mini-PROTEAN® TGX Stain-Free™ Precast Gels (Biorad, Hercules, California) using a standard curve of protein of known concentration. Stain-free gels were imaged using the ChemiDoc XRS+ Imager (Biorad).

Bispecific Antibody Co-Culture Assay.

COS-7 cells were transfected with various combinations of pcDNA3.1 (Life Technologies) plasmids encoding HLA-A3, HLA-B7, IDH2(WT), IDH2(R140Q), KRAS(WT), and KRAS(G12V) with Lipofectamine 3000 (Life Technologies) per manufacturer's instructions in a T75 flask. 50,000 T cells were combined with transfected 30,000 COS-7 cells or 10,000 NCI-H441 cells and the specified concentration of bispecific antibody in a 96-well plate, and the co-culture was allowed to incubate for 24 hours at 37° C. under 5% $CO_2$. Following co-culture, the 96-well plate was snap frozen and conditioned media lysate was collected and assayed for secreted IFNγ by ELISA (Quantikine®, R&D Systems). Alternatively, following coculture, target cell viability was measured using CellTiter-Glo (Promega).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A molecule comprising an antigen-binding domain that can bind to a peptide-human leukocyte antigen (HLA)-beta-2 microglobulin complex, wherein said antigen-binding domain is selected from the group consisting of:
   (i) an antigen-binding domain comprising a complementarity determining region (CDR)-VL1 comprising the amino acid sequence QDVNTA (SEQ ID NO:33); a CDR-VL2 comprising the amino acid sequence SAS; a CDR-VL3 comprising the amino acid sequence QQSGYAPIT (SEQ ID NO:82), a CDR-VH1 comprising the amino acid sequence GFNISYYS (SEQ ID NO:89), a CDR-VH2 comprising the amino acid sequence VDPDSDYT (SEQ ID NO:96); and a CDR-VH3 comprising the amino acid sequence SRSWIHMFSMDY (SEQ ID NO:103);
   (ii) an antigen-binding domain comprising comprises a CDR-VL1 comprising the amino acid sequence QDVNTA (SEQ ID NO:33); a CDR-VL2 comprising the amino acid sequence SAS; a CDR-VL3 comprising the amino acid sequence QQSLYGPFT (SEQ ID NO:84); a CDR-VH1 comprising the amino acid sequence GFNIAYEY (SEQ ID NO:91); a CDR-VH2 comprising the amino acid sequence IGPDSGYT (SEQ ID NO:98); and a CDR-VH3 comprising the amino acid sequence SRVWYYSTYGMDY (SEQ ID NO:105);
   (iii) an antigen-binding domain comprising a CDR-VL1 comprising the amino acid sequence QDVNTA (SEQ ID NO:33); a CDR-VL2 comprising the amino acid sequence SAS; a CDR-VL3 comprising the amino acid sequence QQYLYQPWT (SEQ ID NO:87); a CDR-VH1 comprising the amino acid sequence GFNIDYYG (SEQ ID NO:94); a CDR-VH2 comprising the amino acid sequence LYGGSDST (SEQ ID NO:101); and a CDR-VH3 comprising the amino acid sequence SRQYSAYFDY (SEQ ID NO:108); and
   (iv) an antigen-binding domain comprising a CDR-VL1 comprising the amino acid sequence QDVNTA (SEQ ID NO:33); a CDR-VL2 comprising the amino acid sequence SAS; a CDR-VL3 comprising the amino acid sequence QQGLYYPWT (SEQ ID NO: 88); a CDR-VH1 comprising the amino acid sequence GFNVSYSS (SEQ ID NO: 95); a CDR-VH2 comprising the amino acid sequence IWPDSGQT (SEQ ID NO: 102); and a CDR-VH3 comprising the amino acid sequence SRSSYFDAMDY (SEQ ID NO: 109);
wherein said peptide comprises a modified peptide derived from a p53 polypeptide, wherein said modified peptide comprises the amino acid sequence SEQ ID NO:15, wherein said HLA is a class I HLA, and wherein said antigen-binding domain does not bind to a complex that includes a wild-type version of the modified peptide.

2. The molecule of any one of claim 1, wherein said modified peptide comprises from 10 amino acids to 15 amino acids.

3. The molecule of claim 1, wherein said class I HLA is an HLA-A2, and wherein said antigen binding domain comprises an amino acid sequence selected from the group consisting of SEQ ID NO:331, SEQ ID NO:333, SEQ ID NO:336, and SEQ ID NO:337.

4. The molecule of claim 1, wherein said molecule is selected from the group consisting of an antibody, an antibody fragment, a single chain variable fragment (scFv), a chimeric antigen receptor (CAR), a T cell receptor (TCR), a TCR mimic, a tandem scFv, a bispecific T cell engager, a diabody, a single-chain diabody, an scFv-Fc, a bispecific antibody, and a dual-affinity re-targeting antibody (DART).

5. The molecule of claim 1, wherein said molecule further comprises a second antigen-binding domain that can bind to an effector cell receptor selected from the group consisting of CD3, CD28, CD4, CD8, CD16a, NKG2D, PD-1, CTLA-4, 4-1 BB, OX40, ICOS, and CD27.

6. The molecule of claim 5, wherein said second antigen-binding domain that can bind to an effector cell can bind to CD3, wherein said second antigen-binding domain comprises an amino acid sequence selected from the group consisting of SEQ ID NO:404, SEQ ID NO:405, SEQ ID NO:406, SEQ ID NO:407, SEQ ID NO:408, SEQ ID NO:409, SEQ ID NO:410, SEQ ID NO:411, SEQ ID NO:412, SEQ ID NO:413, SEQ ID NO:414, SEQ ID NO:415, SEQ ID NO:416, and SEQ ID NO:417.

7. A chimeric antigen receptor (CAR), said CAR comprising:
   an extracellular domain comprising the antigen binding domain of claim 1;
   a transmembrane domain; and
   an intracellular domain.

8. The CAR of claim 7, wherein said transmembrane domain comprises a transmembrane domain of CD4, CD8, or CD28.

9. The CAR of claim 7, wherein said intracellular domain comprises one or more costimulatory domains from CD28, DAP10, ICOS, OX40, and/or 4-1BB.

10. The CAR of claim 7, wherein said intracellular domain comprises a signaling domain from CD3-zeta.

11. A T cell expressing the CAR of claim 7.

12. A method for treating a mammal having a cancer, said method comprising:
   administering to said mammal the molecule of claim 3, wherein said cancer comprises cancer cells expressing said modified peptide.

13. A method for treating a mammal having a cancer, said method comprising:
   administering to said mammal a T cell expressing a CAR comprising:
   an extracellular domain comprising the antigen binding domain of claim 9;

a transmembrane domain; and
an intracellular domain,
wherein said cancer comprises cancer cells expressing said modified peptide.

14. The method of claim 12, wherein said mammal is a human.

15. The method of claim 12, wherein said cancer is selected from the group consisting of Hodgkin's lymphoma, non-Hodgkin's lymphoma, acute myeloid leukemia, lung cancer, pancreatic cancer, gastric cancer, colorectal cancer, ovarian cancer, endometrial cancer, biliary tract cancer, liver cancer, myeloma, breast cancer, prostate cancer, esophageal cancer, stomach cancer, kidney cancer, bone cancer, soft tissue cancer, head and neck cancer, glioblastoma multiforme, and astrocytomas.

* * * * *